US009439923B2

(12) United States Patent
Benkirane et al.

(10) Patent No.: US 9,439,923 B2
(45) Date of Patent: Sep. 13, 2016

(54) COMPOSITIONS AND METHODS FOR TREATING RETROVIRUS INFECTIONS

(75) Inventors: Monsef Benkirane, Saint Gely du Fesc (FR); Robinson Triboulet, Paris (FR); Christine Chable-Bessia, Vailauques (FR); Yamina Bennasser, Montpellier (FR); Daniel Latreille, Montpellier (FR); Oussama Meziane, Montpellier (FR); Pascal Barbry, Nice (FR); Bernard Mari, Nice (FR); Jacques Reynes, Saint Gely du Fesc (FR)

(73) Assignee: CENTRE NATIONAL DE LA RECHERCHE SCIENTIFIQUE (C.N.R.S), Paris (FR)

( * ) Notice: Subject to any disclaimer, the term of this patent is extended or adjusted under 35 U.S.C. 154(b) by 226 days.

(21) Appl. No.: 13/131,313

(22) PCT Filed: Nov. 26, 2009

(86) PCT No.: PCT/EP2009/065929
§ 371 (c)(1),
(2), (4) Date: Nov. 15, 2011

(87) PCT Pub. No.: WO2010/060967
PCT Pub. Date: Jun. 3, 2010

(65) Prior Publication Data

US 2012/0053223 A1 Mar. 1, 2012

(30) Foreign Application Priority Data

Nov. 26, 2008 (EP) .................................... 08305842

(51) Int. Cl.
*A61P 31/18* (2006.01)
*A61K 31/7105* (2006.01)

(52) U.S. Cl.
CPC ................................ *A61K 31/7105* (2013.01)

(58) Field of Classification Search
USPC ......... 435/6, 91.1, 91.31, 455, 6.1; 514/1, 2, 514/44; 536/23.1, 24.5
See application file for complete search history.

(56) References Cited

U.S. PATENT DOCUMENTS

| | | | | |
|---|---|---|---|---|
| 8,222,221 | B2 * | 7/2012 | Corey et al. | 514/44 A |
| 2005/0182005 | A1 * | 8/2005 | Tuschl et al. | 514/44 |
| 2007/0087335 | A1 * | 4/2007 | Brahmachari et al. | 435/5 |
| 2009/0004668 | A1 * | 1/2009 | Chen et al. | 435/6 |
| 2010/0010073 | A1 | 1/2010 | Thum et al. | |

FOREIGN PATENT DOCUMENTS

| | | | |
|---|---|---|---|
| JP | 2007-536242 | A | 12/2007 |
| JP | 2008239596 | | 10/2008 |
| WO | WO 02/44321 | * | 6/2002 |
| WO | 2005107816 | A2 | 11/2005 |
| WO | WO2007/042899 | | 4/2007 |
| WO | WO 2007/092181 | * | 8/2007 |
| WO | 2008043521 | A2 | 4/2008 |
| WO | 2008088858 | A2 | 7/2008 |
| WO | WO2009/029681 | | 3/2009 |

OTHER PUBLICATIONS

Doench et al., Genes & Development, vol. 18, No. 5, pp. 504-511 (2004).*
Holen et al., Nuvleic Acids Res., vol. 30, No. 8, pp. 1757-1766 (2002).*
Opalinska et al., Nature Rev., vol. 1, pp. 503-514 (2002).*
Peracchi et al., Rev. Med. Virol., vol. 14, pp. 47-64 (2004).*
Triboulet et al, Science, vol. 315, pp. 1579-1582 (2007).*
Corbeau, P., PLoS Pathogens, vol. 4, Issue 9, pp. 1-7 (2008).*
Provost et al, Virus Research, vol. 121, pp. 107-115 (2006).*
Hammer et al, JAMA, vol. 300, No. 5, pp. 555-570 (Aug. 2008).*
Esau et al., "Therapeutic potential for microRNAs," *Advanced Drug Delivery Reviews*, vol. 59, pp. 101-114 92007).
Griffiths-Jones, "The microRNA Registry," *Nucleic Acids Research*, vol. 32, pp. D109-D111 (2004).
Griffiths-Jones et al., "miRBase: tools for microRNA genomics," *Nucleic Acids Research*, vol. 36, pp. D154-D158 (2008).
Hammer et al., "Antiretroviral Treatment of Adult HIV Infection," *JAMA*, vol. 300, No. 5, pp. 555-570 (2008).
Provost et al., "HIV-1 and the microRNA-guided silencing pathway: An intricate and multifaceted encounter," *Virus Research*, vol. 121, pp. 107-115 (2006).
P. Corbeau, Interfering RNA and HIV: Reciprocal Interferences, PLOS Pathogens, Sep. 2008, vol. 4, Issue 9, pp. 1-6.
R. Triboulet, et al., Suppression of MicroRNA-Silencing Pathway by HIV-1 During Virus Replication, Science, vol. 315, Mar. 16, 2007, pp. 1579-1582.
Y. P. Liu, et al., Inhibition of HIV-1 by multiple siRNAs expressed from a single microRNA polycistron, Nucleic Acid Research, Mar. 16, 2008, vol. 36, No. 9, pp. 2811-2824.
H. S. Christensen, et al., Small Interfering RNAs against the TAR RNA Binding Protein, TRBP, a Dicer Cofactor, Inhibit Human Immunodeficiency Virus Type 1 Long Terminal Repeat Expression and Viral Production, Journal of Virology, May 2007, vol. 81, No. 10, pp. 5121-5131.
English translation of an Office Action, mailed Jan. 28, 2014, which issued during the prosecution of Japanese Application No. 2011-536905, which corresponds to the present application.

* cited by examiner

*Primary Examiner* — Jane Zara
(74) *Attorney, Agent, or Firm* — Blank Rome LLP

(57) ABSTRACT

The present invention relates to at least one nucleic acid (i) comprising or consisting of or (ii) encoding a nucleic acid comprising or consisting of, a sequence selected from the group consisting of: 1) SEQ ID NO: 1, SEQ ID NO: 2, SEQ ID NO: 3, and SEQ ID NO: 4, and 2) a sequence derived from SEQ ID NO: 1 to 4 by substitution deletion or insertion of at least one nucleotide, provided that a nucleic acid consisting of the sequence derived from SEQ ID NO: 1 to 4 is liable to induce HIV-1 expression in latent HIV-1-infected cells, for use as a medicament, in particular for treating retrovirus infections.

10 Claims, 9 Drawing Sheets

COMPOSITIONS AND METHODS FOR TREATING RETROVIRUS INFECTIONS

The present invention relates to compositions and methods for treating retrovirus infections, in particular in asymptomatic individuals in whom the retrovirus is in a latent state.

Retroviruses, such as Human Immunodeficiency Virus (HIV), are able to stay in infected cells in a latent state. The mechanisms which are responsible for latency and reactivation of the virus are poorly understood. It seems that the replication of the virus in CD4+ T lymphocyte cells is dependent in part upon the cell cycle of the host cell. HIV entry into activated CD4+ lymphocytes generally leads to a productive infection whereas no infective production is generally obtained after entry into non-activated CD4+ lymphocytes.

Some patients referred as to Elite HIV-1 Controllers are infected individuals who are able to maintain their virus at undetectable levels for many years in absence of treatment (Goudsmit et al. (2002) *AIDS*16:791-793). This capacity has today no clear explanation and concerns have been expressed regarding the ability of these individuals to manage long-term control of the infection.

Besides, HIV latency is a major problem for the current HIV antiviral therapies. In fact, these therapies do not eradicate the infection because of the latent, resistant reservoir of viruses. For example, Highly Active Anti-Retroviral Therapy (HAART), in which a cocktail of anti-retroviral drugs is administered to HIV-1 infected patients, fails to eradicate definitively HIV-1 infection because of this HAART refractory latent viral reservoirs (Marcello (2006) *Retrovirology* 3:7). Accordingly, the risk is always present, in such patients, that the infection reactivates, for instance upon a decrease of the efficiency of the administered drugs.

Accordingly, there is a need to fully eradicate the latent retrovirus reservoir in these patients.

One of the therapeutic strategies which has been suggested for achieving such a goal consists in reactivating latent retroviruses in infected cells, thereby inducing retroviral particles production and restoring sensitivity to medication. Such a strategy could thus lead to a complete recovery of infected patients.

Some molecules promoting reactivation of retroviruses are known. Prostratin, for instance, was shown to be able to up-regulate HIV expression in the CD8+ T lymphocytes of an infected patient undergoing HAART. Prostatin was thus, proposed to be a good candidate for the elimination of the persistent viral repertoire. However, the results obtained with prostratin are somewhat heterogeneous and a need for other molecules still exists (Kulkosky (2001) *Blood* 98:3006-3015, Korin et al. (2002) *Virology* 76:8118-8123).

MicroRNAs (miRNAs) are a newly discovered class of RNAs generally 20-25 nucleotides in length. They are involved in gene expression regulation at the post-transcriptional level by degrading or blocking translation of specific messenger RNAs mRNAs. The miRNA pathway, from synthesis to action, has been well described in terms of components of the pathway, which notably comprise, among others, the proteins known as Drosha, DGCR8, Dicer, RCK/p54, LSm-1, GW182, and XRN1 (Bartel (2004) *Cell* 116: 281-297). It has been recently shown that 2'-O-methyl-oligoribonucleotide antisense inhibitors of five miRNA, namely mir-28, mir-125b, mir-150, mir-223 and mir-382, could induce HIV-1 infectious particles production from CD4+ T cells obtained HIV-1 infected individuals under HAART (Huang et al. (2007) *Nat. Med.* 13:1241-1247). It was thus proposed to such anti-miRNA inhibitors to reverse HIV-1 latency in vivo. However, concerns were raised regarding the potential toxicity of these inhibitors (Zhang (2008) *Int J Biochem Cell*).

Accordingly, it is an object of the present invention to provide alternative compounds and methods useful for reactivating latent retroviral reservoirs in infected individuals.

SUMMARY OF THE INVENTION

In this regard, the present invention arises from the unexpected finding by the inventors that contacting latent cells infected by HIV-1 with particular miRNAs, namely miR-34a, miR-122, miR-206 and miR-210 (respectively represented by SEQ ID NO: 1 to 4), induced HIV-1 expression by these cells. Unexpectedly also, the same inventors have found that inhibiting the expression of components of the miRNA pathway, such as Drosha, DGCR8, Dicer, RCK/p54, LSm-1, GW182, and XRN1, induced HIV-1 expression in latent infected cells.

The present invention thus relates to at least one nucleic acid (i) comprising or consisting of, or (ii) encoding a nucleic acid comprising or consisting of, a sequence selected from the group consisting of:

1) SEQ ID NO: 1, SEQ ID NO: 2, SEQ ID NO: 3, and SEQ ID NO: 4, and
2) a sequence derived from SEQ ID NO: 1 to 4 by substitution, deletion or insertion of at least one nucleotide, provided that a nucleic acid consisting of the sequence derived from SEQ ID NO: 1 to 4 is liable to induce HIV-1 expression in latent HIV-1-infected cells, for use as a medicament, in particular for treating retrovirus infections.

The present invention also relates to at least one compound inhibiting the activity of at least one component of the miRNA pathway for use in the treatment of retrovirus infections.

The present invention also relates to a method for treating retrovirus infections in an individual comprising administering said individual with a therapeutically effective amount of at least one nucleic acid as defined above or at least one compound as defined above.

In an embodiment of the above-defined nucleic acid, compound or method, the nucleic acid or compound is used in combination with at least one other anti-retroviral compound.

The present invention also relates to the in vitro use of a nucleic acid as defined above or of a compound inhibiting a component of the miRNA pathway selected from the group consisting of DGCR8, RCK/p54, LSm-1, GW182, and XRN1, for the production of retroviral particles from cells harbouring a retroviral vector.

The present invention also relates to an in vitro method for the production of retroviral particles, comprising:

- contacting cells harbouring a retroviral vector with a nucleic acid as defined above or of a compound inhibiting a component of the miRNA pathway selected from the group consisting of DGCR8, RCK/p54, LSm-1, GW182, and XRN1;
- letting the cells express the retroviral vector;

whereby retroviral particles are produced from the cells.

In an embodiment of the invention, the above-defined in vitro use and in vitro method involve no step of culturing the cells with T cells.

The inventors have also identified 51 genes which are targeted by miR-34a, miR-206, miR-210 and miR-122, and which inhibition of the expression by siRNAs or shRNAs activates viral replication of HIV-1.

The present invention thus also relates to a modulator of the activity of a gene selected from the group consisting of DGUOK, MIR16, PPP1R11, ARHGAP1, TEDDM1, QDPR, C14orf32, C1orf19, ATP1B3, FLJ10241, ANP32E, TAGLN2, ARF3, PTMA, PPIB, PRCP, PTPRK, OBSL1, SLC44A1, PPIAL4, SERP1, EBPL, CBX6, ZBED3, NP, PRSS21, PPIA, C5orf13, E2F2, CACYBP, TROAP, APOBEC3A, C7orf44, ORC6L, WNT10B, VIM, CDC6, MCRS1, NAG18, PPP1CC, DULLARD, ASF1B, PLP2, MTHFD2, PIGS, KIF2C, NRM, PEG10, C22orf9, COL4A2, and SNX26, for use as a medicament, in particular for treating retrovirus infections.

The present invention also relates to a method for treating retrovirus infections in an individual, comprising administering the individual with at least one modulator of the activity of a gene selected from the group consisting of DGUOK, MIR16, PPP1R11, ARHGAP1, TEDDM1, QDPR, C14orf32, C1orf19, ATP1B3, FLJ10241, ANP32E, TAGLN2, ARF3, PTMA, PPIB, PRCP, PTPRK, OBSL1, SLC44A1, PPIAL4, SERP1, EBPL, CBX6, ZBED3, NP, PRSS21, PPIA, C5orf13, E2F2, CACYBP, TROAP, APOBEC3A, C7orf44, ORC6L, WNT10B, VIM, CDC6, MCRS1, NAG18, PPP1CC, DULLARD, ASF1B, PLP2, MTHFD2, PIGS, KIF2C, NRM, PEG10, C22orf9, COL4A2, and SNX26.

In an embodiment of the above defined modulator for use as a medicament or method of treatment involving the modulator, modulators of the expression of each one of DGUOK, MIR16, PPP1R11, ARHGAP1, TEDDM1, QDPR, C14orf32, C1orf19, ATP1B3, FLJ10241, ANP32E, TAGLN2, ARF3, PTMA, PPIB, PRCP, PTPRK, OBSL1, SLC44A1, PPIAL4, SERP1, EBPL, CBX6, ZBED3, NP, PRSS21, PPIA, C5orf13, E2F2, CACYBP, TROAP, APOBEC3A, C7orf44, ORC6L, WNT10B, VIM, CDC6, MCRS1, NAG18, PPP1CC, DULLARD, ASF1B, PLP2, MTHFD2, PIGS, KIF2C, NRM, PEG10, C22orf9, COL4A2, and SNX26, are used.

In an embodiment of the above-defined modulator for use a medicament or method of treatment involving the modulator, the modulator is used in combination with at least one other anti-retroviral compound.

DETAILED DESCRIPTION OF THE INVENTION

Nucleic Acid

As intended herein the nucleic acid of the invention can be of any type, it can notably be natural or synthetic, DNA or RNA, single or double stranded. In particular, where the nucleic acid is synthetic, it can comprise non-natural modifications of the bases or bonds, in particular for increasing the resistance to degradation of the nucleic acid. Where the nucleic acid is RNA the modifications notably encompass capping its ends or modifying the 2' position of the ribose backbone so as to decrease the reactivity of the hydroxyl moiety, for instance by suppressing the hydroxyl moiety (to yield a 2'-deoxyribose or a 2'-deoxyribose-2'-fluororibose), or substituting the hydroxyl moiety with an alkyl group, such as a methyl group (to yield a 2'-O-methyl-ribose).

SEQ ID NO: 1, 2, 3 and 4 respectively represent the sequences of miRNAs miR-34a, miR-122, miR-206 and miR-210. These miRNAS are notably described in Griffiths-Jones (2004) *Nucleic Acids Res* 32:D109-D111; Griffiths-Jones et al. (2008) *Nucleic Acids Res* 36:D154-D158; and the miRBase database available at http://microrna.sanger.ac.uk.

Where the nucleic acid of the invention comprises or consists of SEQ ID NO: 1, 2, 3 or 4, or of the sequences derived therefrom, the nucleic acid of the invention is intended to directly exert its effect on its cellular targets. In this case, the nucleic acid is preferably a RNA molecule.

Where the nucleic acid of the invention encodes a nucleic acid comprising or consisting of SEQ ID NO: 1, 2, 3 or 4, or of the sequences derived therefrom, the nucleic acid of the invention is intended to be expressed within cells where the nucleic acid it encodes, in particular a RNA molecule, will exert its effect on its cellular targets. In this case the nucleic acid of the invention is preferably a DNA molecule, more preferably a double stranded DNA molecule. Besides, as will be clear to one of skill in the art, the nucleic acid according to the invention preferably also comprises genetic elements ensuring expression of the encoded nucleic acid, in particular a promoter sequence of RNA polymerase II or III.

Methods for delivering nucleic acids into cells in vitro or in vivo are well known to one of skill in the art and are notably described in Nguyen et al. (2008) *Curr Opin Mol Ther* 10:158-67 and Dykxhoorn et al. (2006) *Gene Therapy* 13:541-552 which are incorporated herein by reference.

Preferably, where the nucleic acid of the invention comprises SEQ ID NO: 1, 2, 3, or 4, or a sequence derived therefrom, it is less than 1000 nucleotides long, more preferably less than 100 nucleotides long, and most preferably less than 50 nucleotides long.

Preferably, the sequence derived from SEQ ID NO: 1 to 4 by substitution deletion or insertion of at least one nucleotide presents at least 85%, more preferably at least 90%, and most preferably at least 95% identity with the sequence from which it is derived. As intended herein, the percentage of identity between two sequences is obtained by aligning the two sequences so as to maximize the number of positions of each sequence for which the nucleotides are identical and dividing the number of positions of each sequence for which the nucleotides are identical by the number of nucleotides of the longer of the two sequences.

As intended herein "latent HIV-1-infected cells" are cells in which HIV-1 sequences can be found integrated in one of their chromosomes and which do not express HIV-1 encoded RNAs or proteins. Such cells, in particular peripheral blood multinuclear cells, more particularly T cells, even more particularly CD4+ T cells, can notably be obtained from asymptomatic patients infected by HIV-1, such as HAART treated patients or elite HIV-1 controller patients. Determining whether HIV-1 sequences can be found integrated in one of the chromosomes of said cells can be carried out by numerous methods well known to one of skill in the art, such as Polymerase Chain Reaction (PCR) experiments conducted with HIV-1 specific primers. Determining whether said cells are latent can be carried out by measuring the expression of a HIV-1 encoded RNA or protein (e.g. the p24 antigen), by said cells, in particular using respectively quantitative Reverse-Transcriptase Polymerase Chain Reaction (qRT-PCR) or immunological methods, such as Enzyme-Linked Immunosorbent Assays (ELISA) as is notably described in the Examples. Latent cells express essentially no HIV-1-encoded RNAs and proteins, which can be defined as a level of expression which is undetectable (e.g. lower than 40 HIV-1 RNA copies/ml when using quantitative RT-PCR) or which is not significantly different from that of control cells, for instance non-HIV-1 infected cells.

As intended herein, establishing whether a nucleic acid is liable to induce HIV-1 expression in latent HIV-1-infected cells can be determined by comparing the expression level of a HIV-1 encoded protein, such as the p24 antigen, in cells contacted with a nucleic acid according to the invention with identical control cells which have not been contacted with the nucleic acid of the invention. If the contacted cells present a significantly altered level of expression of the HIV-1-encoded protein with respect to the control cells, the nucleic acid will be said liable to induce HIV-1 expression in latent HIV-1-infected cells.

In a preferable embodiment of the invention, a RNA molecule consisting of SEQ ID NO: 1, a RNA molecule consisting of SEQ ID NO: 2, a RNA molecule consisting of SEQ ID NO: 3, and a RNA molecule consisting of SEQ ID NO: 4 are administered to a patient in need thereof in combination or are present together in a same medicament or pharmaceutical composition.

Compound

As intended herein a "component of the miRNA pathway" relates to any one of the cellular proteins involved in the synthesis, the maturation, and the action of microRNAs (miRNAs). The components of the miRNA pathway are well known by one of skill in the art and are notably described in Bartel (2004) *Cell* 116:281-97 and Beckham and Parker (2008) *Cell Host Microbe* 3:206-12, which are incorporated herein by reference. In particular, the components of the miRNA pathway are selected from Drosha, DGCR8 (which are involved in the maturation pre-miRNAs upon their synthesis by RNA polymerases II or III), Dicer (which is involved in the maturation of pre-miRNAs to miRNAs), RCK/p54, LSm-1, GW182, and XRN1 (which are involved in the degradation of targeted mRNAs). More preferably, the components of the miRNA pathway are selected from the group consisting of DGCR8, RCK/p54, LSm-1, GW182, and XRN1.

More preferably, the components of the miRNA pathway are selected from the group consisting of DGCR8, RCK/p54, LSm-1, GW182, and XRN1.

By way of example Drosha is represented by SEQ ID NO: 6, DGCR8 is represented by SEQ ID NO: 8, Dicer is represented by SEQ ID NO: 10, RCK/p54 is represented by SEQ ID NO: 12, LSm-1 is represented by SEQ ID NO: 14, GW182 is represented by SEQ ID NO: 16, and XRN1 is represented by SEQ ID NO: 18.

As intended herein, the compound of the invention can be of any type. In particular, the compound of the invention may have the ability to directly interfere with the activity of a component of the miRNA pathway. The compound can also interfere with the expression of the component of the miRNA pathway at the transcriptional or the translational level. Where the compound interferes with the expression of the component of the miRNA pathway at the translational level, it can notably be an effector nucleic acid targeting a mRNA encoding a component of the miRNA pathway or a nucleic acid encoding said effector nucleic acid, such as a viral vector. In particular, the effector nucleic acid can be a DNA or RNA antisense oligonucleotide or a small interfering RNA (sRNA).

The effector nucleic acid of the invention can comprise non-natural modifications of the bases or bonds, in particular for increasing their resistance to degradation. Where the nucleic acid is RNA, Modifications notably encompass capping its ends or modifying the 2' position of the ribose backbone so as to decrease the reactivity of the hydroxyl moiety, for instance by suppressing the hydroxyl moiety (to yield a 2'-deoxyribose or a 2'-deoxyribose-2'-fluororibose), or substituting the hydroxyl moiety with an alkyl group, such as a methyl group (to yield a 2'-O-methyl-ribose).

Preferably, effector nucleic acids according to the invention are less than 50 nucleotides long, more preferably less than 40 nucleotides long, and most preferably less than 30 nucleotides long. Preferably also, effector nucleic acids according to the invention are at least 10 nucleotides long, more preferably at least 15 nucleotides long, and most preferably at least 20 nucleotides long.

The siRNAs of the invention are preferably double-stranded.

As intended herein the term "siRNA" encompasses "small hairpin RNA (shRNA)". shRNAs are formed of a self-hybridizing single stranded RNA molecule liable to yield a double-stranded siRNA upon processing of the single-stranded part of the shRNA linking the hybridized parts of the shRNA. As is well known to one of skill in the art, shRNAs transcribed from a nucleic acid which has been delivered into a target cell are the precursors of choice for siRNAs where the production of the siRNAs is to occur within a cell. As will be clear to one of skill in the art, the preferred length given above for the effector nucleic acids apply to shRNAs considered in their hybridized conformation and should be doubled if the shRNAs are considered in their unhybridized conformation.

It is well within the reach of one of skill in the art to devise a siRNA intended to target a specific mRNA where the sequence of the mRNA is known either partially or in totality and to deliver siRNAs, or nucleic acids encoding siRNAs and shRNAs into cells in vitro or in vivo, as is notably reported by Dykxhoorn et al. (op. cit.) and Nguyen et al (op. cit.)

By way of example, siRNAs targeting Drosha, DGCR8, Dicer, RCK/p54, LSm-1, GW182, and XRN1 are respectively represented by SEQ ID NO: 19, 20, 21, 22, 23, 24 and 25.

Modulator

As intended herein, the modulator of the invention can be of any type. Besides, as will be clear to one of skill in the art, the modulator of the invention may either activate or inhibit (i.e. interfere with) the activity of a gene selected from the group consisting of DGUOK, MIR16, PPP1R11, ARHGAP1, TEDDM1, QDPR, C14orf32, C1orf19, ATP1B3, FLJ10241, ANP32E, TAGLN2, ARF3, PTMA, PPIB, PRCP, PTPRK, OBSL1, SLC44A1, PPIAL4, SERP1, EBPL, CBX6, ZBED3, NP, PRSS21, PPIA, C5orf13, E2F2, CACYBP, TROAP, APOBEC3A, C7orf44, ORC6L, WNT10B, VIM, CDC6, MCRS1, NAG18, PPP1CC, DULLARD, ASF1B, PLP2, MTHFD2, PIGS, KIF2C, NRM, PEG10, C22orf9, COL4A2, and SNX26.

Advantageously, a modulator of the invention inhibiting the activity of one of the above genes is useful to activate the viral replication of a retrovirus, thereby enabling to eradicate a latent retrovirus reservoir in an individual.

Equally advantageously, a modulator of the invention activating the activity of one of the above genes is useful to inhibit the viral replication of a retrovirus.

In particular, the modulator of the invention may have the ability to directly activate or inhibit the activity of the genes selected from the group consisting of DGUOK, MIR16, PPP1R11, ARHGAP1, TEDDM1, QDPR, C14orf32, C1orf19, ATP1B3, FLJ10241, ANP32E, TAGLN2, ARF3, PTMA, PPIB, PRCP, PTPRK, OBSL1, SLC44A1, PPIAL4, SERP1, EBPL, CBX6, ZBED3, NP, PRSS21, PPIA, C5orf13, E2F2, CACYBP, TROAP, APOBEC3A, C7orf44, ORC6L, WNT10B, VIM, CDC6, MCRS1, NAG18, PPP1CC, DULLARD, ASF1B, PLP2, MTHFD2, PIGS, KIF2C, NRM, PEG10, C22orf9, COL4A2, and SNX26. The modulator can also activate or inhibit the expression of these genes at the transcriptional or the translational level.

Where the modulator interferes with the expression of the genes selected from the group consisting of DGUOK, MIR16, PPP1R11, ARHGAP1, TEDDM1, QDPR, C14orf32, C1orf19, ATP1B3, FLJ10241, ANP32E, TAGLN2, ARF3, PTMA, PPIB, PRCP, PTPRK, OBSL1, SLC44A1, PPIAL4, SERP1, EBPL, CBX6, ZBED3, NP, PRSS21, PPIA, C5orf13, E2F2, CACYBP, TROAP, APOBEC3A, C7orf44, ORC6L, WNT10B, VIM, CDC6, MCRS1, NAG18, PPP1CC, DULLARD, ASF1B, PLP2, MTHFD2, PIGS, KIF2C, NRM, PEG10, C22orf9, COL4A2, and SNX26, at the translational level, it can notably be an effector nucleic acid targeting a mRNA encoding one of these genes or a nucleic acid encoding said effector nucleic acid, such as a viral vector. In particular, the effector nucleic acid can be a DNA or RNA antisense oligonucleotide or a small interfering RNA (siRNA).

The effector nucleic acid of the invention can comprise non-natural modifications of the bases or bonds, in particular for increasing their resistance to degradation. Where the nucleic acid is RNA, Modifications notably encompass capping its ends or modifying the 2' position of the ribose backbone so as to decrease the reactivity of the hydroxyl moiety, for instance by suppressing the hydroxyl moiety (to yield a 2'-deoxyribose or a 2'-deoxyribose-2'-fluororibose), or substituting the hydroxyl moiety with an alkyl group, such as a methyl group (to yield a 2'-O-methyl-ribose).

Preferably, effector nucleic acids according to the invention are less than 50 nucleotides long, more preferably less than 40 nucleotides long, and most preferably less than 30 nucleotides long. Preferably also, effector nucleic acids according to the invention are at least 10 nucleotides long, more preferably at least 15 nucleotides long, and most preferably at least 20 nucleotides long.

The siRNAs of the invention are preferably double-stranded.

As intended herein the term “siRNA” encompasses “small hairpin RNA (shRNA)”. shRNAs are formed of a self-hybridizing single stranded RNA molecule liable to yield a double-stranded siRNA upon processing of the single-stranded part of the shRNA linking the hybridized parts of the shRNA. As is well known to one of skill in the art, shRNAs transcribed from a nucleic acid which has been delivered into a target cell are the precursors of choice for siRNAs where the production of the siRNAs is to occur within a cell. As will be clear to one of skill in the art, the preferred length given above for the effector nucleic acids apply to shRNAs considered in their hybridized conformation and should be doubled if the shRNAs are considered in their unhybridized conformation.

It is well within the reach of one of skill in the art to devise a siRNA intended to target a specific mRNA where the sequence of the mRNA is known either partially or in totality and to deliver siRNAs, or nucleic acids encoding siRNAs and shRNAs into cells in vitro or in vivo, as is notably reported by Dykxhoorn et al. (op. cit.) and Nguyen et al (op. cit.)

Where the modulator activates the activity of the genes selected from the group consisting of DGUOK, MIR16, PPP1R11, ARHGAP1, TEDDM1, QDPR, C14orf32, C1orf19, ATP1B3, FLJ10241, ANP32E, TAGLN2, ARF3, PTMA, PPIB, PRCP, PTPRK, OBSL1, SLC44A1, PPIAL4, SERP1, EBPL, CBX6, ZBED3, NP, PRSS21, PPIA, C5orf13, E2F2, CACYBP, TROAP, APOBEC3A, C7orf44, ORC6L, WNT10B, VIM, CDC6, MCRS1, NAG18, PPP1CC, DULLARD, ASF1B, PLP2, MTHFD2, PIGS, KIF2C, NRM, PEG10, C22orf9, COL4A2, and SNX26, it can notably a nucleic acid expressing one of these genes, such as an expression vector, in particular a viral vector, harbouring a sequence of one of these genes.

The above genes are well known to one of skill in the art and are notably represented by the NCBI accession numbers or the SEQ ID NOs listed in the following table. The NCBI accession numbers and the SEQ ID NOs refer to the sequences of the mRNAs or to the coding sequences (CDS) of the listed genes.

| Gene Symbol | Gene Name | Accession number (NCBI) | SEQ ID NO: |
|---|---|---|---|
| DGUOK | deoxyguanosine kinase | NM_080916 | 26 |
| MIR16 | membrane interacting protein of RGS16 | AY463154 | 27 |
| PPP1R11 | protein phosphatase 1, regulatory (inhibitor) subunit 11 | NM_021959 | 28 |
| ARHGAP1 | Rho GTPase activating protein 1 | NM_004308 | 29 |
| TEDDM1 | transmembrane epididymal protein 1 | NM_172000 | 30 |
| QDPR | quinoid dihydropteridine reductase | NM_000320 | 31 |
| C14orf32 | mitogen-activated protein kinase 1 interacting protein 1-like | NM_144578 | 32 |
| C1orf19 | homolog of *S. cerevisiae* tRNA splicing endonuclease 15 | NM_052965 | 33 |
| ATP1B3 | ATPase, Na+/K+ transporting, beta 3 polypeptide | NM_001679 | 34 |
| FLJ10241 | ATP5S-like | NM_018035 | 35 |
| ANP32E | acidic (leucine-rich) nuclear phosphoprotein 32 family, member E | NM_030920 | 36 |
| TAGLN2 | transgelin 2 | NM_003564 | 37 |
| ARF3 | ADP-ribosylation factor 3 | NM_001659 | 38 |
| PTMA | prothymosin alpha | NM_002823 | 39 |
| PPIB | peptidylprolyl isomerase B (cyclophilin B) | NM_000942 | 40 |
| PRCP | prolylcarboxypeptidase (angiotensinase C) | NM_005040 | 41 |
| PTPRK | protein tyrosine phosphatase, receptor type, K | NM_002844 | 42 |
| OBSL1 | obscurin-like 1 | NM_015311 | 43 |
| SLC44A1 | solute carrier family 44, member 1 | NM_080546 | 44 |
| PPIAL4 | peptidylprolyl isomerase A (cyclophilin A)-like 4A | NM_178230 | 45 |
| SERP1 | stress-associated endoplasmic reticulum protein 1 | NM_014445 | 46 |

-continued

| Gene Symbol | Gene Name | Accession number (NCBI) | SEQ ID NO: |
|---|---|---|---|
| EBPL | emopamil binding protein-like | NM_032565 | 47 |
| CBX6 | chromobox homolog 6 | NM_014292 | 48 |
| ZBED3 | zinc finger, BED-type containing 3 | NM_032367 | 49 |
| NP | nucleoside phosphorylase | NM_000270 | 50 |
| PRSS21 | protease, serine, 21 (testisin) | NM_144956 | 51 |
| PPIA | peptidylprolyl isomerase A (cyclophilin A) | NM_021130 | 52 |
| C5orf13 | chromosome 5 open reading frame 13 | NM_004772 | 53 |
| E2F2 | E2F transcription factor 2 | NM_004091 | 54 |
| CACYBP | calcyclin binding protein | NM_014412 | 55 |
| TROAP | trophinin associated protein (tastin) | NM_005480 | 56 |
| APOBEC3A | apolipoprotein B mRNA editing enzyme, catalytic polypeptide-like 3A | NM_145699 | 57 |
| C7orf44 | chromosome 7 open reading frame 44 | NM_018224 | 58 |
| ORC6L | origin recognition complex, subunit 6 like (yeast) | NM_014321 | 59 |
| WNT10B | wingless-type MMTV integration site family, member 10B | NM_003394 | 60 |
| VIM | vimentin | EF445046 | 61 |
| CDC6 | homolog of *S. cerevisiae* cell division cycle 6 | NM_001254 | 62 |
| MCRS1 | microspherule protein 1 | NM_006337 | 63 |
| NAG18 | NAG18 | AF210651 | 64 |
| PPP1CC | protein phosphatase 1, catalytic subunit, gamma isoform | NM_002710 | 65 |
| DULLARD | homolog of *Xenopus laevis* dullard | NM_015343 | 66 |
| ASF1B | homolog B of *S. cerevisiae* ASF1 anti-silencing function 1 | NM_018154 | 67 |
| PLP2 | proteolipid protein 2 (colonic epithelium-enriched) | NM_002668 | 68 |
| MTHFD2 | methylenetetrahydrofolate dehydrogenase (NADP+ dependent) 2, methenyltetrahydrofolate cyclohydrolase | NM_006636 | 69 |
| PIGS | phosphatidylinositol glycan anchor biosynthesis, class S | NM_033198 | 70 |
| KIF2C | kinesin family member 2C | NM_006845 | 71 |
| NRM | nurim (nuclear envelope membrane protein) | NM_007243 | 72 |
| PEG10 | paternally expressed 10 | NM_015068 | 73 |
| C22orf9 | chromosome 22 open reading frame 9 | NM_015264 | 74 |
| COL4A2 | collagen, type IV, alpha 2 | NM_001846 | 75 |
| SNX26 | sorting nexin 26 | NM_052948 | 76 |

Administration

Where a therapeutic use of: the nucleic acid of the invention, the compound of the invention, or the modulator of the invention, or a medicament or a pharmaceutical composition comprising the nucleic acid of the invention, the compound of the invention, or the modulator of the invention, is contemplated, the nucleic acid, the compound, and the modulator can be associated to one or more pharmaceutically acceptable carriers. In particular, it is preferred that the pharmaceutically acceptable carrier be suitable for delivering nucleic acid into cells. Carriers suitable for delivering nucleic acid into cells are well known to one of skill in the art and notably comprise cationic lipids or peptides, nanoparticles and liposomes, optionally linked to moieties, such as antibodies or antibody fragments, having a specificity towards a specific receptor of the target cells, notably T cells.

Either local or systemic routes can be used for administering the nucleic acid of the invention, the compound of the invention or the modulator of the invention. Examples of administration procedures for nucleic acids are notably described in Nguyen et al. (op. cit.) nad Dykxhoorn et al. (op. cit.)

Anti-Retroviral compound

Preferably, the other anti-retroviral compound as defined above is selected from the group consisting of a reverse-transcriptase inhibitor and a protease inhibitor, such as described in Hammer et al. (2008) *JAMA* 300:555-70, which is incorporated herein by reference.

Reverse-transcriptase inhibitors are a well-known class of anti-retroviral compounds targeting the retroviral enzyme which catalyses reverse-transcription of the RNA genome of the retrovirus to DNA. Reverse-transcriptase inhibitors notably comprise:

- Nucleoside analogs reverse transcriptase inhibitors (NRTIs), such as Zidovudine (i.e. AZT), Didanosine, Zalcitabine, Stavudine, Lamivudine, Abacavir, and Emtricitabine;
- Nucleotide analogs reverse transcriptase inhibitors (NtRTIs, such as Tenofovir and Adefovir;
- Non-nucleoside reverse transcriptase inhibitors (NNRTIs), such as Efavirenz, Nevirapine, Delavirdine, Etravirine.

Protease inhibitors are a well-known class of anti-retroviral compounds targeting the retroviral enzyme which catalyses cleavage of polyproteins expressed by retroviral genomes. Protease inhibitors notably comprise: Saquinavir, Ritonavir, Indinavir, Nelfinavir, Amprenavir, Lopinavir, Atazanavir, Fosamprenavir, Tipranavir, and Darunavir.

Anti-retroviral compounds are often used in combinations. For instance, in the frame of Highly Active Antiretroviral Therapy (HAART), two or more different anti-retroviral compounds are used in combination, for instance 2 NRTIs and a protease inhibitor or 2 NRTIs and a NNTI. The definition of combinations suited for a particular retrovirus-infected patient are within the ordinary skills of one skilled in the art.

Retrovirus Infection

As intended herein the terms "retrovirus" or "retroviral" relate to viruses of the Retroviridae family, more particularly of the Lentivirus genus. The retroviruses of the invention notably encompass the Human Immunodeficiency Virus (HIV), in particular HIV-1 and HIV-2, the Simian Immunodeficiency Virus (SIV), and the Feline Immunodeficiency Virus (FIV).

Preferably, the nucleic acid of the invention and the compound of the invention, or medicaments or pharmaceutical compositions comprising the nucleic acid of the invention or the compound of the invention, are intended to treat asymptomatic patients infected by a retrovirus.

As intended herein, the expression "asymptomatic patients infected by a retrovirus" refers to individuals harbouring cells in which retroviral sequences can be found integrated in one of their chromosomes but who do not express the retroviral sequences. Identification of such individuals is well within the common skills of one of skill in the art and notably involves measuring blood, serum or plasma levels of retrovirus RNAs or antigens (e.g. the p24 antigen of HIV-1) using respectively qRT-PCR and immunological techniques for instance. In particular, patients are said to be asymptomatic if the retroviral sequences expression products (i.e. RNAs and proteins) are undetectable.

Where the asymptomatic patients are infected by HIV-1, they can notably be under Highly Active Antiretroviral Therapy (HAART) or elite HIV-1 controllers.

Production of Retroviral Particles

As intended herein a "retroviral particle" or a "retroviral vector" relate to particles or vectors derived from viruses the Retroviridae family, more particularly of the Lentivirus genus, which notably encompass the Human Immunodeficiency Virus (HIV), in particular HIV-1 and HIV-2, the Simian Immunodeficiency Virus (SIV), and the Feline Immunodeficiency Virus (FIV).

The retroviral particle or vector of the invention can respectively comprise and encode elements (e.g. nucleic acids and proteins) which are not of a retroviral origin. The retroviral particles can notably harbour envelope proteins intended to target it to specific cells and tissues, in particular to deliver transgenes. Such particles and vectors are well known in the art, as reported by Cronin et al. (2005) *Curr. Gene Ther.* 5:387-398 which is incorporated herein by reference, and are generally referred to as pseudotyped retroviral particles and vectors.

Methods for producing retroviral particles from retroviral vectors are well known to one of skill in the art and the method of the invention can be easily implemented, in particular in view of the following examples.

Advantageously, the above-defined in vitro use and in vitro method can be carried out without culturing the cells with T cells.

Sequence Description

| Sequence description | SEQ ID NO: |
|---|---|
| miR-34a | 1 |
| miR-122 | 2 |
| miR-206 | 3 |
| miR-210 | 4 |
| Drosha nucleotide sequence | 5 |
| Drosha amino acid sequence | 6 |
| DGCR8 nucleotide sequence | 7 |
| DGCR8 amino acid sequence | 8 |
| Dicer nucleotide sequence | 9 |
| Dicer amino acid sequence | 10 |
| RCK/p54 nucleotide sequence | 11 |
| RCK/p54 amino acid sequence | 12 |
| LSm-1 nucleotide sequence | 13 |
| LSm-1 amino acid sequence | 14 |
| GW182 nucleotide sequence | 15 |
| GW182 amino acid sequence | 16 |
| XRN1 nucleotide sequence | 17 |
| XRN1 amino acid sequence | 18 |
| siRNA targeting Drosha | 19 |
| siRNA targeting DGCR8 | 20 |
| siRNA targeting Dicer | 21 |
| siRNA targeting RCK/p54 | 22 |
| siRNA targeting LSm-1 | 23 |
| siRNA targeting GW182 | 24 |
| siRNA targeting XRN1 | 25 |
| DGUOK | 26 |
| MIR16 | 27 |
| PPP1R11 | 28 |
| ARHGAP1 | 29 |
| TEDDM1 | 30 |
| QDPR | 31 |
| C14orf32 | 32 |
| C1orf19 | 33 |
| ATP1B3 | 34 |
| FLJ10241 | 35 |
| ANP32E | 36 |
| TAGLN2 | 37 |
| ARF3 | 38 |
| PTMA | 39 |
| PPIB | 40 |
| PRCP | 41 |
| PTPRK | 42 |
| OBSL1 | 43 |
| SLC44A1 | 44 |
| PPIAL4 | 45 |
| SERP1 | 46 |
| EBPL | 47 |
| CBX6 | 48 |
| ZBED3 | 49 |
| NP | 50 |
| PRSS21 | 51 |
| PPIA | 52 |
| C5orf13 | 53 |
| E2F2 | 54 |
| CACYBP | 55 |
| TROAP | 56 |
| APOBEC3A | 57 |
| C7orf44 | 58 |
| ORC6L | 59 |
| WNT10B | 60 |
| VIM | 61 |
| CDC6 | 62 |
| MCRS1 | 63 |
| NAG18 | 64 |
| PPP1CC | 65 |
| DULLARD | 66 |
| ASF1B | 67 |
| PLP2 | 68 |
| MTHFD2 | 69 |
| PIGS | 70 |
| KIF2C | 71 |
| NRM | 72 |
| PEG10 | 73 |
| C22orf9 | 74 |
| COL4A2 | 75 |
| SNX26 | 76 |

EXAMPLES

Example 1

MiRNA Effectors Are Repressors of HIV-1 Gene Expression

To investigate whether RNAi effectors regulate HIV-1 replication, virus replication was analyzed in cells where expression of RNAi effectors was reduced using specific siRNA.

Methods

HeLa cells were transfected with siRNA as indicated in Triboulet et al. (2007) *Science* 315 (5818):1579-82 which is incorporated herein by reference. 48 hours post transfection, cells were analyzed for RCK/p54, LSm-1, GW182, XRN1, DGCR8, DROSHA and CDK9 expression by western blot, or infected with a single round infectious virus (HIV-1-VSV-luc) and cell extracts were measured for luciferase activity 48 hrs after infection. RCK/p54 restricts HIV-1 mRNA association with polysomes. Cytoplasmic extracts from HeLa cells that were transfected with the indicated siRNA and infected with HIV-1-VSVG-luc were run on glycerol gradient (7% to 47%). Fractions were collected and their RNA contents were monitored by measuring absorbance (OD) at 254 nm. HIV-1 mRNA and Hdm2 mRNA were quantified in all the fractions by Q-RT-PCR using specific oligonucleotides.

Results

Figure 1:
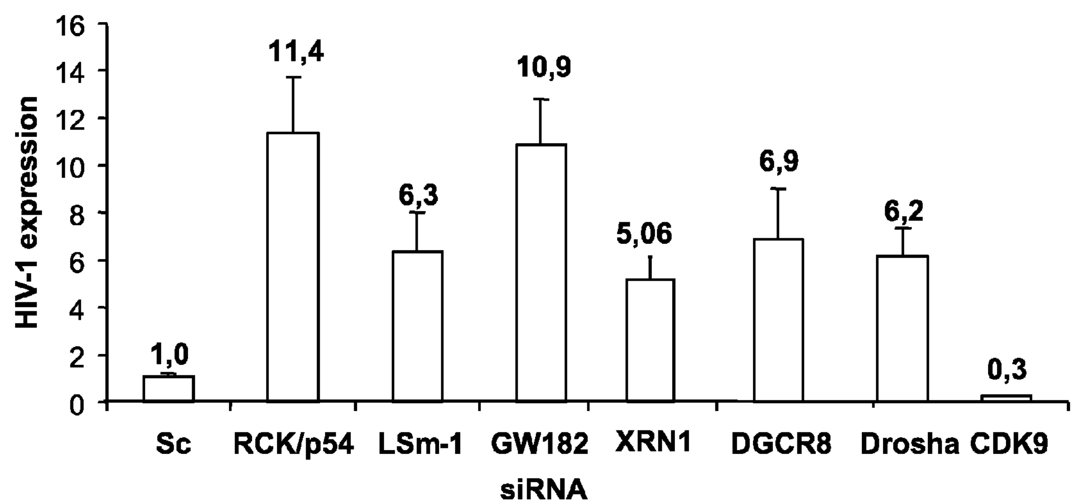
FIG. 1 depicts the effect of knockdown of RCK/p54, LSm-1, GW182, XRN1, DGCR8, Drosha or control protein CDK9 by transfection with specific siRNA (horizontal axes), on virus production (vertical axes), compared to virus production after transfection with scramble siRNA (sc).

HeLa cells were transfected with siRNA specific to RCK/p54, LSm-1, GW182 XRN1 or DGCR8. As controls, HeLa cells were transfected with scrambled siRNA (Scr) or CDK9 specific siRNA. Knockdown of RCK/p54, LSm-1, GW182 and XRN1 enhanced virus replication by up to 10 fold (FIG. 1). As previously shown, (Triboulet et al) knockdown of DROSHA and DGCR8 (FIG. 1), the two subunits of the microprocessor complex, increased virus production while knockdown of CDK9 subunit of the PTEFb complex that is known to be required for viral gene expression, reduced it (FIG. 1). Interestingly, analysis of HIV-1 cytoplasmic mRNA distribution on glycerol gradient shows that knockdown of RCK/p54 shifted HIV-1 mRNA from the non-polysomal fraction to polysomes as compared to control siRNA transfected cells. Knockdown of RCK/p54 did not affect endogenous Hdm2 mRNA distribution.

These experiments show that GW182, RCK/p54, LSm-1 and XRN1 required for RNAi are repressors of HIV-1 gene expression by preventing HIV-1 mRNA translation.

Example 2

HIV-1mRNA is Physically Associated with Argonaute2 and Co-Localizes With Protein Required for miRNA-Mediated Silencing The physical interaction between RNAi effectors and HIV-1 mRNA was investigated.

Methods

HeLa cells were transfected with HIV-1 molecular clone pNL4-3, Myc-Ago2 or Myc-AgoPAZ9 as indicated. 48 hrs later cells were harvested and cytoplasmic extracts were prepared. Total RNA was purified from a fraction of harvested cells while the rest was subjected to immunoprecipitation using anti-Myc antibody. After washing, a fraction was used to analyze the amount of Myc-Ago2 and Myc-AgoPAZ9 immunoprecipitated by western blot and the rest of the Myc-IPs was used for RNA extraction. HIV-1 mRNAs (TAR and unspliced), Hdm2 and GAPDH mRNA were quantified from total RNA or from Myc immunoprecipitated mRNPs by RT-PCR using specific oligonucleotides. The experiment was also performed using 32P-labelled nucleotides in the PCR reaction. PCR products were visualized by autoradiography.

Results

HeLa cells were mock transfected or transfected with combinations of pNL4-3, Myc-Ago2, a central component of the RISC complex, or its RNA binding mutant Myc-Ago2PAZ9. First, the fact that Myc-Ago2 and Myc-Ago2DPAZ9 were equally expressed was verified. Second, cytoplasmic extracts were prepared and a fraction was used for total RNA extraction while the rest was subjected to immunoprecipitation using anti-Myc antibody to purify myc-Ago2 associated mRNP. Both total RNA and Myc-Ago2 associated RNA were reverse transcribed and subjected to PCR amplification using oligonucleotides specific for HIV-1 TAR RNA (a 5' structure associated with all HIV-1 mRNA) or HIV-1 unspliced mRNA, Hdm2 mRNA or GAPDH mRNA. PCR analysis of total RNA shows that equal amount of HIV-1, Hdm2 and GAPDH mRNAs were present in all samples. HIV-1 mRNAs (both TAR and unspliced) were associated with Myc-Ago2 but not with Myc-Ago2PAZ9 mutant. Hdm2 mRNA was absent in Myc-Ago2 mRNPs suggest that, under these conditions, Hdm2 is not regulated by RNAi. A similar experiment was performed to analyze the association of HIV-1 multispliced mRNA with Myc-Ago2 mRNPs. The RT-PCR reactions were performed in presence of ATP-32P and analyzed by autoradiography. HIV-1 multispliced mRNAs associate with Myc-Ago2 and weakly with Myc-Ago2PAZ9. Co-localisation of HIV-1 mRNA and effectors of RNAi such as Ago2, RCK/p54 and DCP1 within the P-Bodies was also observed by immunofluorescence using HIV-1 containing MS2 binding sites and MS2-GFP constructs.

The inventors show that HIV-1 mRNAs physically associate with Ago2, a central component of RISC, and co-localize with cellular proteins required for miRNA-mediated silencing such as RCK/p54 and DCP1/DCP2 in P-bodies. The fact that all HIV-1 mRNA species associate with the RISC suggest that cellular miRNA(s) target a sequence common to all of these mRNAs. Accordingly, Huang et al. (op cit.) identified 5 cellular miRNAs able to target the 3'UTR sequence present in all HIV-1 mRNAs. However, the fact that other cellular miRNA(s) able to target regions outside the 3'UTR may participate can not be ruled out.

Example 3

Accumulation of HIV-1 mRNA in P-Bodies Limits Virus Replication and is Independent of A3G-Mediated HIV-1 Repression Methods HeLa CD4+ cells were transfected with sRNA as indicated. 48 hrs post transfection cells were analyzed for RCK/p54 and LSm-1 expression by western blot or infected with equal amount of HIV-1. Virus production was monitored 48 hrs post infection by measuring p24 antigen in culture supernatant. To analyze the infectivity of the virions produced from the different sRNA transfected HeLa cells, equal volumes of supernatant from sRNA transfected Hela CD4+ were used to re-infect HeLa CD4+ cells. P24 antigen was measured in culture supernatant 48 hrs post infection. APOBEC3G and RNAi effectors-mediated HIV-1 inhibition involves different mechanisms. HeLa CD4+ cells were transfected with the indicated sRNA. 48 hrs later cells were analyzed for RCK/p54 and LSm-1 expression or co-transfected with pNL4-3Dvif (lacking vif gene) and pcDNA or expression vectors for wild-type APOBEC3G or APOBEC3G double mutant lacking both deaminase and antiviral activity. HIV-1 production was measured 24 hrs post transfection in culture supernatant by quantifying p24 antigen. Infectivity assay was performed using equal amounts of p24 antigen to infect HeLa CD4+ cells. HIV-1 p24 antigen was measured 24 hrs post infection.

Results

Emerging evidence suggests physical and functional interactions between P-bodies and viral life cycles. Viral mRNA trafficking through P-bodies may represent a pool of translationally repressed viral transcripts for efficient packaging or formation of viral-replication complexes. Indeed, yeast retrotransposons Ty1 and Ty3 mRNA associate with P-bodies and this association is required for efficient retrotransposition. In case of BMV (Brome Mosaic Virus), formation of the virus replication complex occurs in P-bodies. In addition, P-bodies may also function in host defenses against viruses and transposable elements. Indeed, the cellular factors APOBEC 3G and 3F, which are viral restriction factors, are found to accumulate in P-bodies. It has been suggested that 3G and 3F mediated HIV-1 restriction may involve viral mRNA targeting to P-bodies leading to their translational inhibition.

First, it was asked whether P-bodies are positive or negative regulators of HIV-1 replication. HeLa CD4+ cells were transfected with RCK/p54 or LSm-1 specific siRNA or control siRNA. Forty eight hours later cells were infected with equal amount of HIV-1. HIV-1 p24 antigen was measured in cell culture supernatant 48 hrs post-infection. Knockdown of RCK/p54 and LSm-1 results in enhanced virus production as compared to infection of control siRNA transfected cells. To assess the infectivity of produced viruses, an equal volume of supernatant from Scr, RCK/p54 and LSm-1 siRNA transfected cells was used to infect HeLa CD4+ cells, and p24 in the culture supernatant was measured 48 hrs later. Virus infectivity correlates with the amount of p24 produced showing that virions produced in RCK/p54 and LSm-1 knocked down cells are fully competent for replication and have no defect such as RNA packaging. Since knockdown of RCK/p54 and LSm-1 were shown to result in P-bodies disruption, it was concluded from these experiments that accumulation of HIV-1 mRNA in P-bodies limits virus replication.

Second, it was asked whether APOBEC3G-mediated HIV-1 restriction requires effectors of miRNA-mediated mRNA translational inhibition associated and needed for P-bodies formation. Thus, APOBEC3G-mediated HIV-1 restriction in cells where RCK/p54 or LSm-1 expression is reduced was compared to control cells. HeLa cells were transfected with control sRNA or with sRNA specific for RCK/p54 or LSm-1.

Forty eight hours later, cells were transfected with an HIV-1 molecular clone lacking the vif gene (pNL4-3Dvif) either alone or with wild-type A3G or A3G mutant lacking antiviral activity (A3Gdm). HIV-1 p24 antigen was measured in culture supernatant 48 hrs post-transfection. Interestingly, knock down of RCK/p54 or LSm-1 enhanced HIV-1 production regardless of A3G. Similarly, A3G but not A3Gdm reduced virus production regardless of RCK/p54 or LSm-1 expression. These results suggest that RCK/p54 or LSm-1 and A3G mediated HIV-1 repression involve different mechanisms. Next, the infectivity of HIV-1 produced from sRNA transfected cells was analyzed. Equal amount of p24 was used to infected HeLa CD4+ cells and HIV-1 p24 antigen was measured in culture supernatant 48 hrs post-infection. Virus produced in Scr sRNA transfected cells in presence of A3G show low infectivity than those produced in absence or in presence of A3Gdm. Similar HIV-1 restriction activity of A3G was observed when virus was produced in RCK/p54 or LSm-1 knocked down cells.

This experiment shows that accumulation of HIV-1 mRNA in P-bodies limits virus replication and that A3G-mediated HIV-1 restriction is independent of RNAi effectors RCK/p54 and LSm-1 and does not require P-bodies.

Example 4

Endogenous Levels of Drosha, DGCR8 and RCK/p54 Contribute to HIV-1 Latency in Infected Patients Taken together, these results show a physical repressive interaction between RNAi effectors and HIV-1 mRNA. Since cellular miRNAs were shown to play role in HIV-1 latency, it was asked whether RCK/p54, which is required for miRNA-mediated mRNA translational inhibition, contributes to HIV-1 silencing in vivo.

Methods

Figure 2:
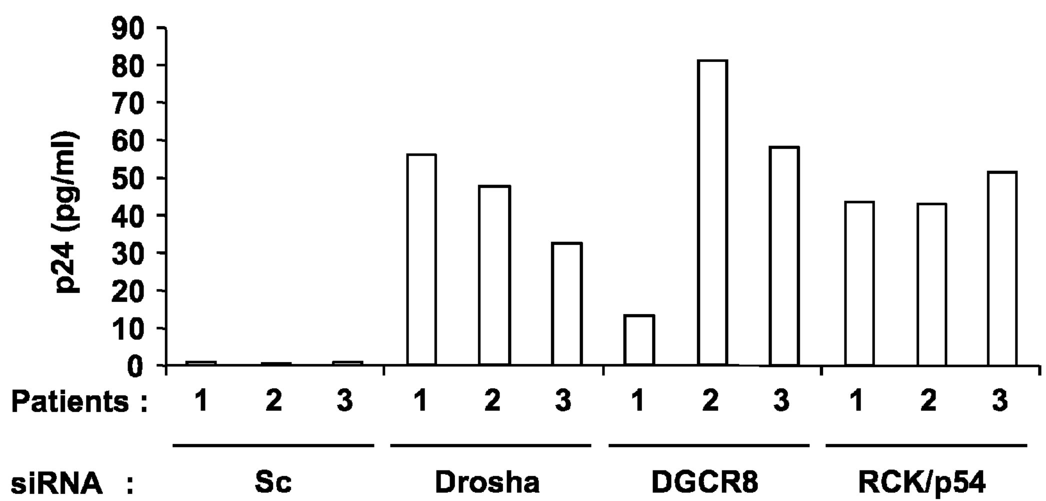
FIG. 2 shows virus production estimated by the quantity of p24 antigen (vertical axes) present in PBMCs isolated from healthy donor in contact with PBMCs isolated from HAART-treated HIV-1 from three patients (1, 2, 3) transfected with scramble sRNA (sc) or with Drosha, DGCR8 or RCK/p54 specific sRNA (horizontal axes).

Implication of RNAi in HIV-1 latency. PBMCs were isolated from 3 patients undergoing active HAART. Isolated PBMCs were transfected with the indicated sRNA and either analyzed for RCK/p54, DGCR8 and DROSHA expression by western blot 48 hrs after transfection or co-cultured with activated PBMCs obtained from healthy donor. Virus replication was monitored every 3 to 4 days post co-culture by measuring p24 antigen in culture supernatant. Shown is the amount of p24 antigen at day 15 post co-culture. No virus was isolated from Sc transfected-PBMCs for up to 27 days Results PBMCs isolated from 3 HAART-treated HIV-1 infected patients with undetectable viremia were transfected with control sRNA or with sRNA specific for Drosha, DGCR8 or RCK/p54. Transfected cells were co-cultured with PHA/IL2-activated PBMCs isolated from healthy donors. Virus production was monitored every 3 days by measuring p24 antigen in the culture supernatant. Knockdown of Drosha results in virus reactivation in PBMCs isolated from HAART-treated HIV-1 infected patients (FIG. 2). HIV-1 reactivation is also seen when DGCR8, another component of the microprocessor complex, was knocked down using specific sRNA. Interestingly, knockdown of RCK/p54 lead to virus reactivation in naturally infected latent HIV-1 cells.

These results show that endogenous levels of Drosha, DGCR8 and RCK/p54 contribute to HIV-1 latency in infected patients.

Example 5

Figure 3:
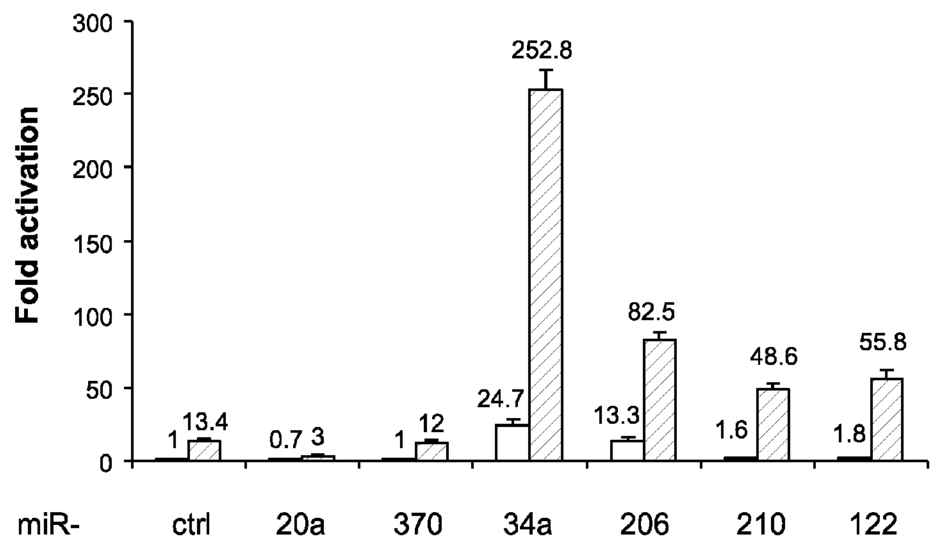
FIG. 3 shows the effects of different miRNA or of control miRNA (ctrl) (horizontal axes) on the LTR activity (vertical axes), in HeLa cells containing an integrated LTR-luciferase construct with an empty vector (white bars) or with a Tat expressing vector (hatched bars).
Figure 4:
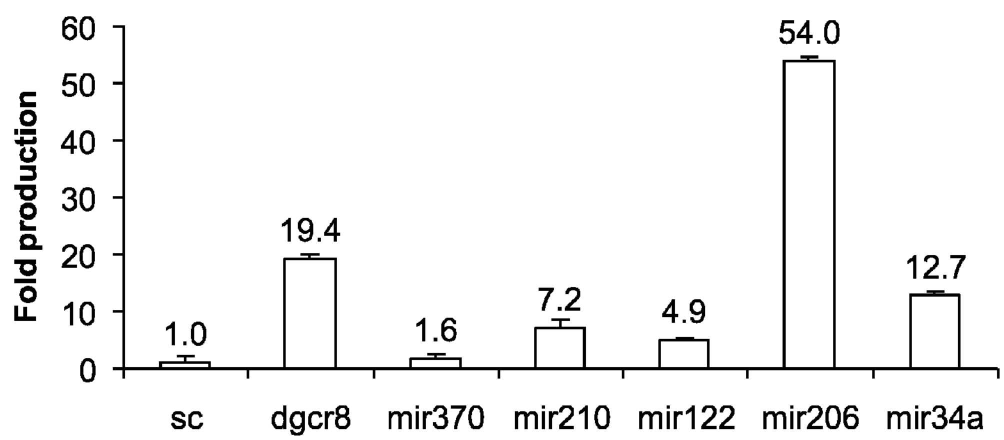
FIG. 4 shows the HIV production (vertical axes) in HeLa cells transfected with sRNA specific for different miRNA, with scramble sRNA (sc), or with DGCR8 specific sRNA (horizontal axes) and infected with HIV-1 harbouring the luciferase gene.
Figure 5:
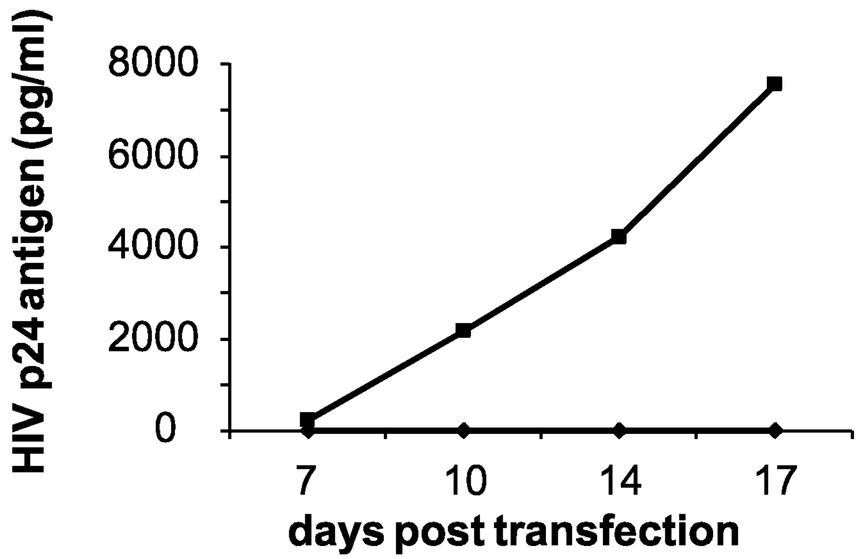
FIG. 5 shows HIV reactivation (vertical axes), in PBMCs isolated from a first patient Elite HIV-1 Controller with undetectable viremia, after transfection with control miRNA (diamonds) or with a mix of miRNA: miR-34a, miR-206, miR-122 and miR-210 (squares) in function of time (in days, horizontal axes).
Figure 6:
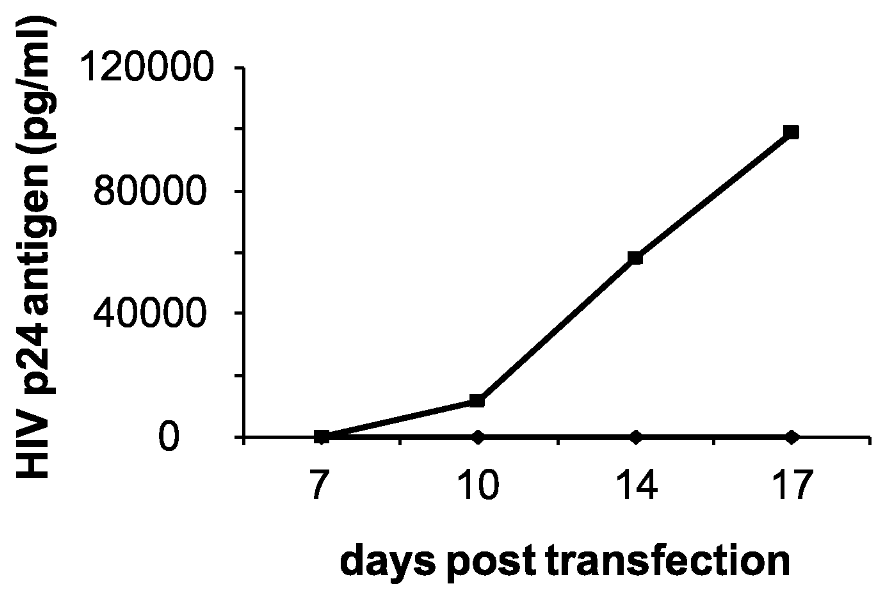
FIG. 6 shows HIV reactivation (vertical axes), in PBMCs isolated from a second patient Elite HIV-1 Controller with undetectable viremia, after transfection with control miRNA (diamonds) or with a mix of miRNA: miR-34a, miR-206, miR-122 and miR-210 (squares) in function of time (in days, horizontal axes).
Figure 7:
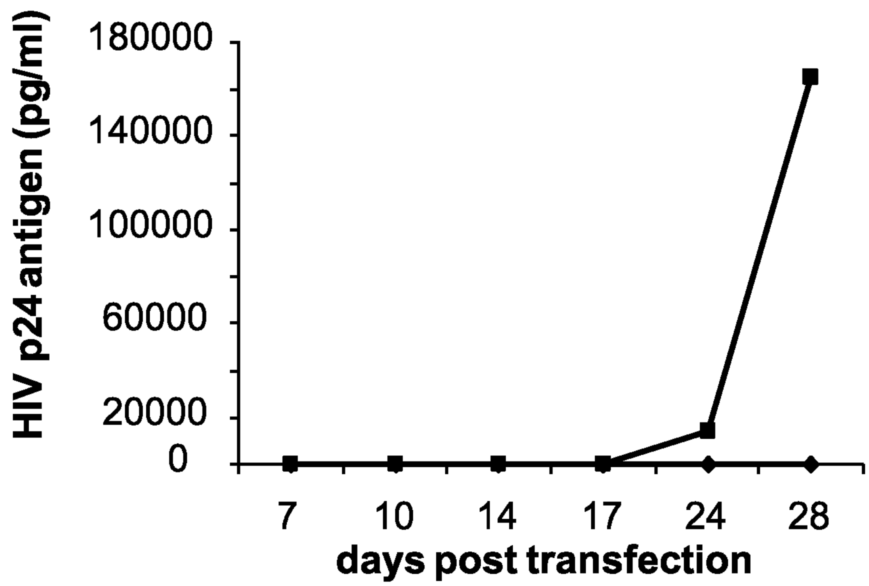
FIG. 7 shows HIV reactivation (vertical axes), in PBMCs isolated from a third patient Elite HIV-1 Controller with undetectable viremia, after transfection with control miRNA (diamonds) or with a mix of miRNA: miR-34a, miR-206, miR-122 and miR-210 (squares) in function of time (in days, horizontal axes).
Figure 8:
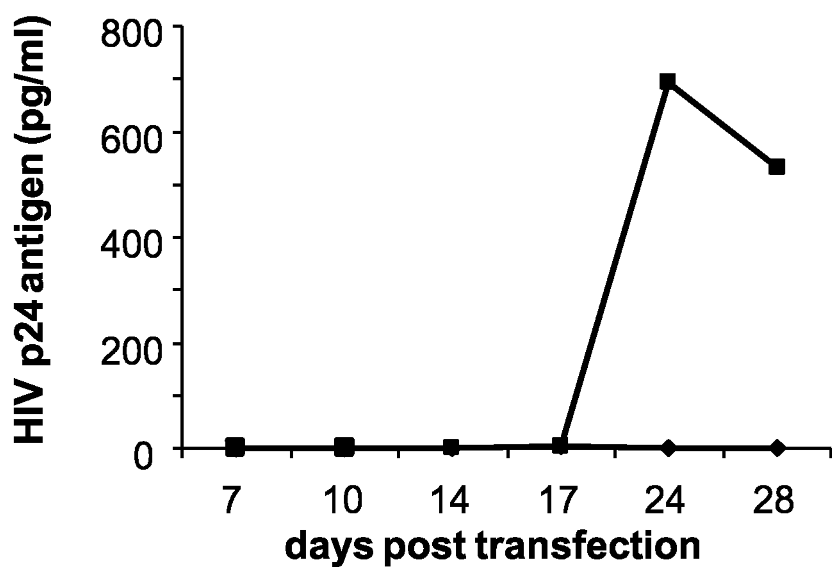
FIG. 8 shows HIV reactivation (vertical axes), in PBMCs isolated from a fourth patient Elite HIV-1 Controller with undetectable viremia, after transfection with control miRNA (diamonds) or with a mix of miRNA: miR-34a, miR-206, miR-122 and miR-210 (squares) in function of time (in days, horizontal axes).
Figure 9:
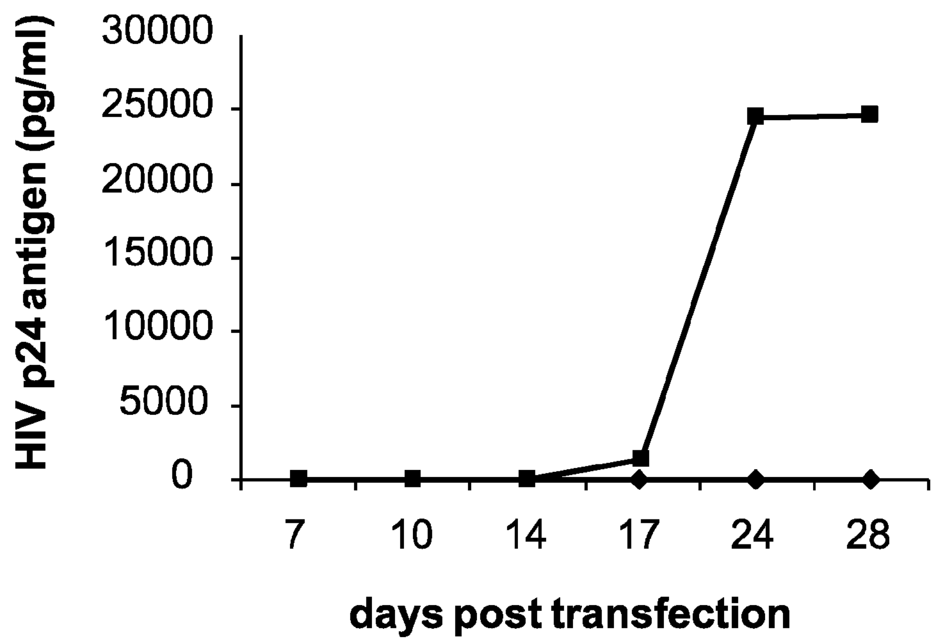
FIG. 9 shows HIV reactivation (vertical axes), in PBMCs isolated from a fifth patient Elite HIV-1 Controller with undetectable viremia, after transfection with control miRNA (diamonds) or with a mix of miRNA: miR-34a, miR-206, miR-122 and miR-210 (squares) in function of time (in days, horizontal axes).
Figure 10:
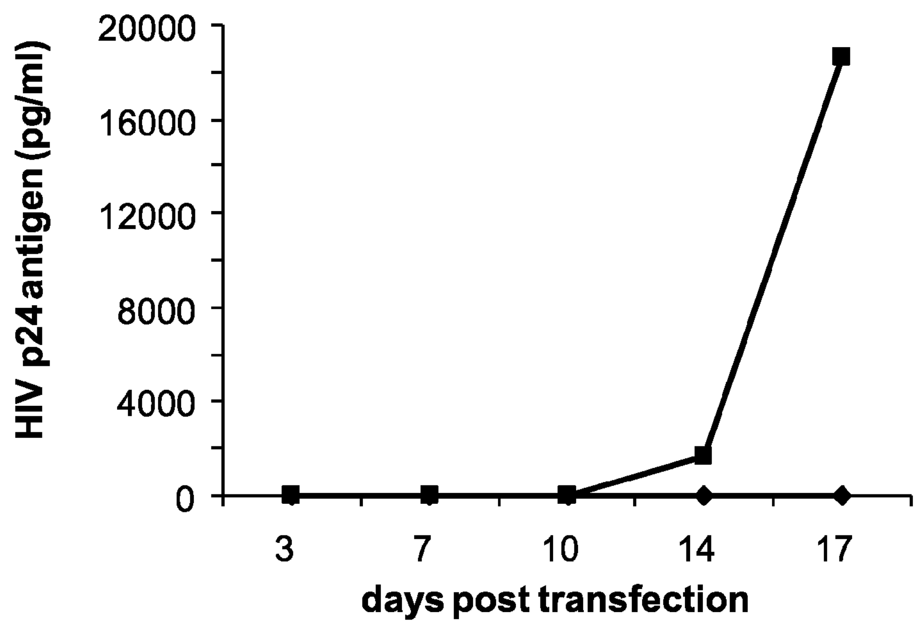
FIG. 10 shows HIV reactivation (vertical axes), in PBMCs isolated from a first HAART-treated infected patient, with undetectable viremia, after transfection with control miRNA (diamonds) or with a mix of miRNA: miR-34a, miR-206, miR-122 and miR-210 (squares) in function of time (in days, horizontal axes).
Figure 11:
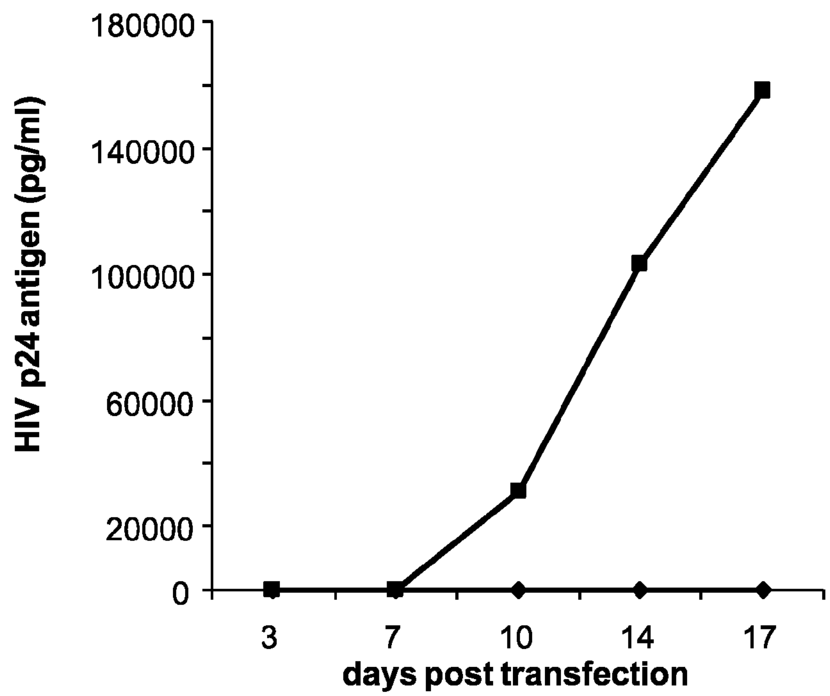
FIG. 11 shows HIV reactivation (vertical axes), in PBMCs isolated from a second HAART-treated infected patient, with undetectable viremia, after transfection with control miRNA (diamonds) or with a mix of miRNA: miR-34a, miR-206, miR-122 and miR-210 (squares) in function of time (in days, horizontal axes).
Figure 12:
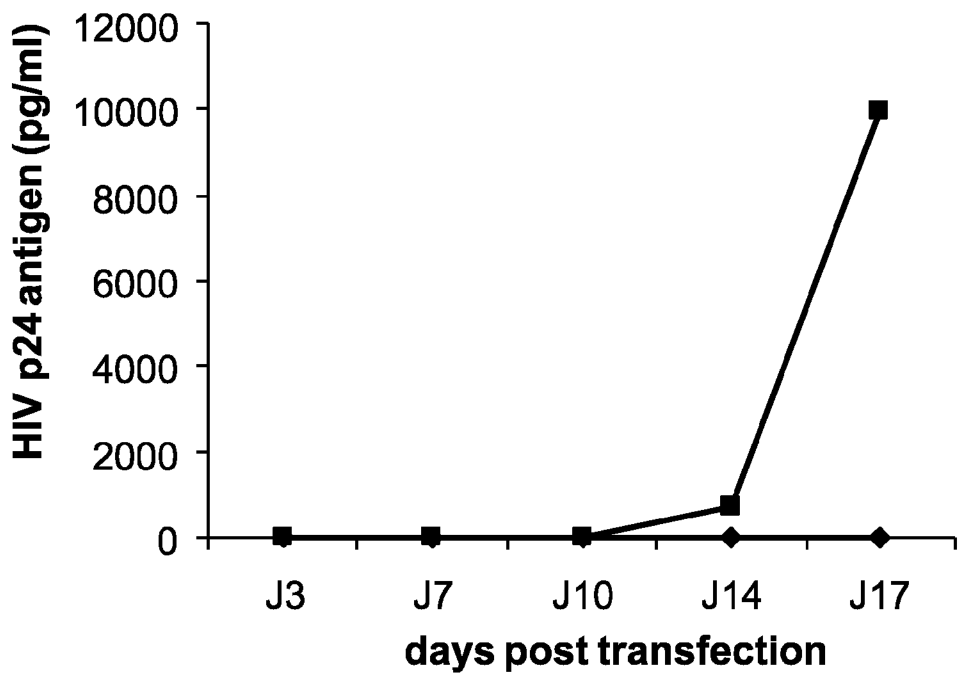
FIG. 12 shows HIV reactivation (vertical axes), in PBMCs isolated from a third HAART-treated infected patient, with undetectable viremia, after transfection with control miRNA (diamonds) or with a mix of miRNA: miR-34a, miR-206, miR-122 and miR-210 (squares) in function of time (in days, horizontal axes).
Figure 13:
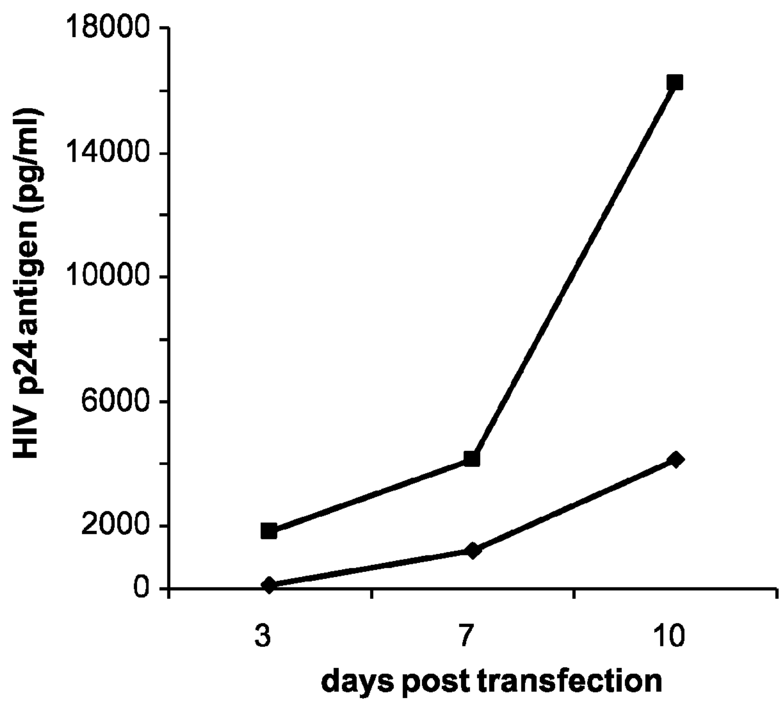
FIG. 13 shows HIV reactivation (vertical axes), in PBMCs isolated from a fourth HAART-treated infected patient, with undetectable viremia, after transfection with control miRNA (diamonds) or with a mix of miRNA: miR-34a, miR-206, miR-122 and miR-210 (squares) in function of time (in days, horizontal axes).
Figure 14:
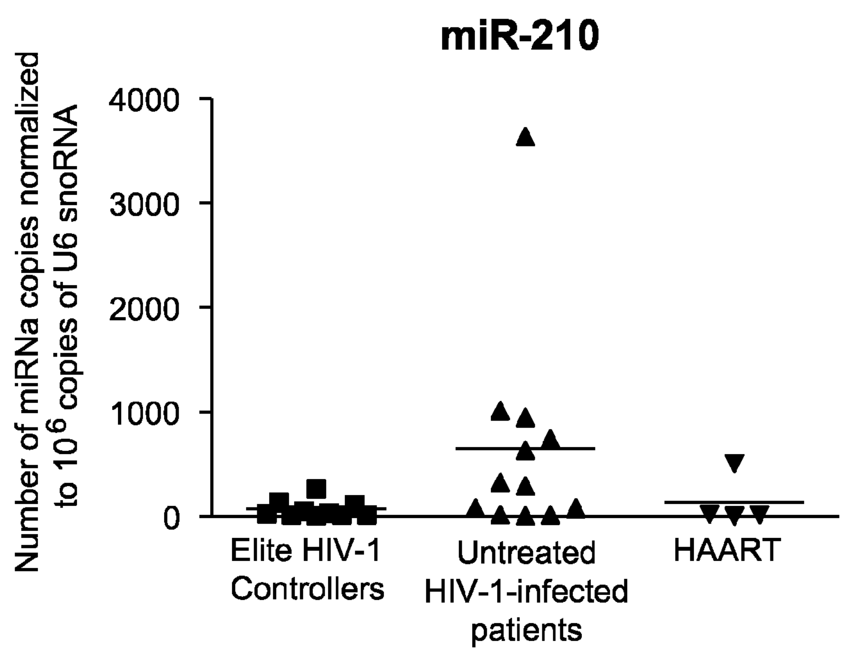
FIG. 14 shows the expression of miR-210 by RT-PCR (vertical axes), in PBMCs isolated from Elite HIV-1 Controllers (squares), untreated HIV-1-infected patients (triangles) and HAART-treated HIV-1-infected patients (upside down triangles).
Figure 15:
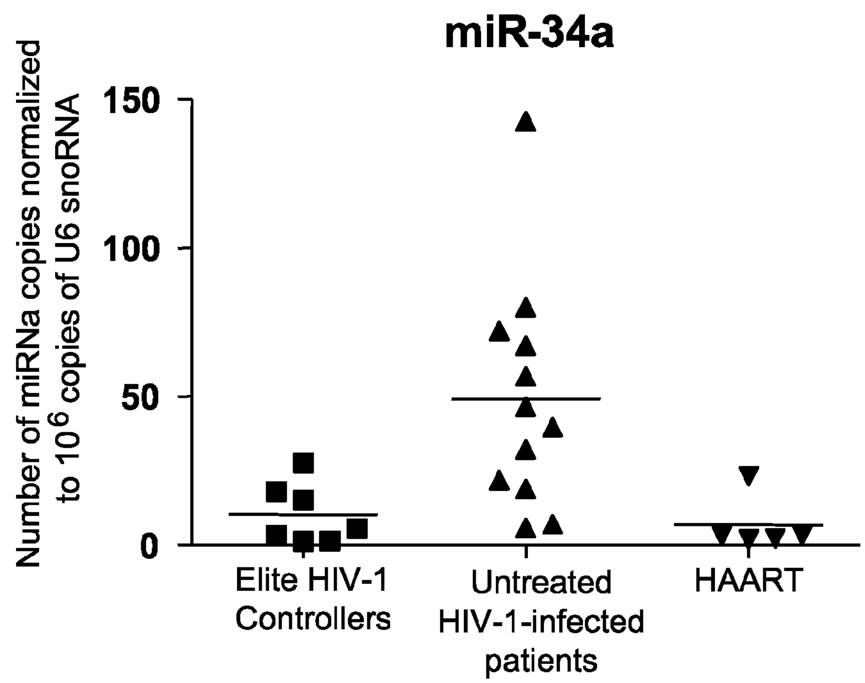
FIG. 15 shows the expression of miR-34a by RT-PCR (vertical axes), in PBMCs isolated from Elite HIV-1 Controller (squares), untreated HIV-1-infected patients (triangles) and HAART-treated HIV-1-infected patients (upside down triangles).
Figure 16:
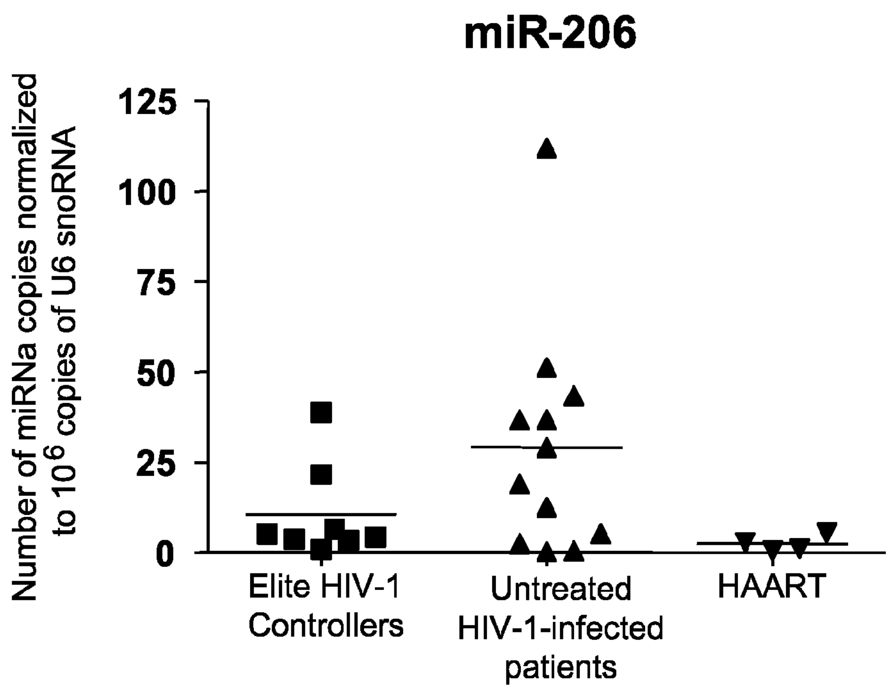
FIG. 16 shows the expression of miR-206 by RT-PCR (vertical axes), in PBMCs isolated from Elite HIV-1 Controllers (squares), untreated HIV-1-infected patients (triangles) and HAART-treated HIV-1-infected patients (upside down triangles).
Figure 17:
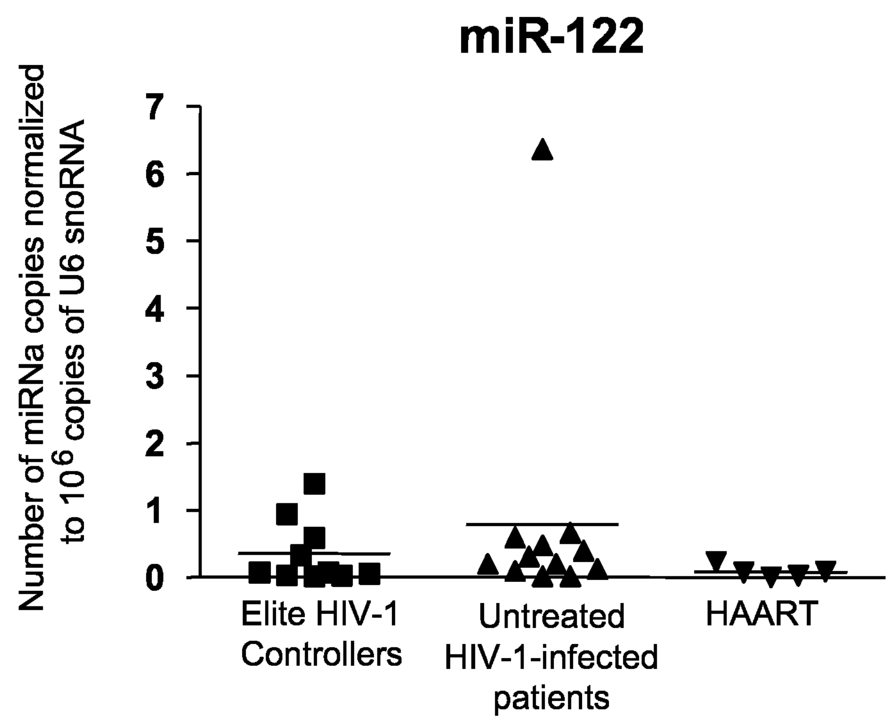
FIG. 17 shows the expression of miR-122 by RT-PCR (vertical axes), in PBMCs isolated from Elite HIV-1 Controllers (squares), untreated HIV-1-infected patients (triangles) and HAART-treated HIV-1-infected patients (upside down triangles).

MiR-34a, miR-206, miR-122 and miR-210 Enhance Virus Expression in HeLa Cells and in Naturally Isolated Silent HIV-1 Reservoirs Methods HIV-1 up-regulated cellular miRNA (Triboulet et al. (2007) *Science* 315 (5818):1579-82) were overexpressed in HeLa cells containing an integrated LTR-luciferase reporter construct. 24 hrs later, cells were transfected with empty or Tat-expressing vector. Luciferase activity was measured 24 hrs post-transfection (FIG. 3). HeLa CD4+ cells were transfected with the indicated miRNA or DGCR8 specific sRNA. 48 hrs post transfection cells were infected with HIV-1 expressing luciferase gene in nef frame and luciferase activity was measured 24 hrs later (FIG. 4). PBMCs were isolated from 5 Elite HIV Controllers patients (FIG. 5 to FIG. 9) or 4 HIV-1-infected HAART-treated patients (FIG. 10 to FIG. 13). Isolated PBMCs were transfected with a mix of miR-34a, miR-206, miR-210 and miR-122 (miRmix) or with control miRNA (miR-32) as indicated. Transfected PBMCs were co-cultured with activated PBMCs obtained from healthy donors. Virus replication was monitored every 3 to 4 days post co-culture by measuring p24 antigen in culture supernatant. Small RNAs were purified from PBMCs isolated from healthy donors, HIV-1-infected HAART-treated, Elite HIV Controllers or HIV-1 infected untreated patients. miR-210, miR206, miR34a, miR-125 and U6 snoRNA were quantified by QRT-PCR using specific oligonucleotides. Results were normalized to U6 snoRNA.

Results miRNA, through regulation of gene expression, play important role in the modulation of almost every cellular process investigated (cell differentiation, proliferation, apoptosis . . . ) In particular, miRNA were found to play an important role in immune system development and in the adaptive immune response. It is tempting to hypothesize that HIV-1 may use cellular miRNA to regulate genes important for its replication. Indeed, it was previously shown that infection of Jurkat cells with HIV-1 alters the miRNA expression profile with some miRNA being down-regulated while others were up-regulated (Triboulet et al. (2007) *Science* 315:1579-1582). Two miRNAs (miR-17 and miR-20) of the down regulated miRNA cluster 17/92 target the histone acetyltrasferase PCAF known to be required for Tat-mediated HIV-1 gene activation (Triboulet et al. op. cit.). In the present study, the function of HIV-1 up-regulated miRNA in virus replication was analyzed. In silico analysis show that none of HIV-1 induced miRNA can target viral mRNA suggesting that if HIV-1 induced miRNA play a role in virus replication, this effect will be mediated through targeting of HIV-1 repressive cellular genes. Among HIV-1 induced miRNAs, it was screened for those able to modulate HIV-1 promoter activity. HeLa cells containing integrated LTR-luciferase construct were transfected with the indicated miRNA either alone, to measure their effect on basal LTR activity, or cotransfected with Tat expression plasmid to analyse their effect on Tat-mediated transactivation of the LTR. While miR-34a and miR-206 enhanced basal LTR activity with no effect on Tat-mediated transactivation of the LTR, miR-210 and miR-122 had no effect on basal expression level but enhanced Tat-mediated transcriptional activity toward the LTR (FIG. 3). miR-370 had no effect. As a control, miR-20a, which targets PCAF, reduced the ability of Tat to activate the LTR. This experiment suggests that miR-34a and miR-206 target a cellular gene involved in the repression of basal LTR activity while miR-122 and miR-210 target cellular (s) factor (s) that repress Tat transcriptional activity. Then, the effect of these miRNAs was analyzed on HIV-1 production using a single round infectious pNL4-3 molecular clone expressing luciferase inserted in nef open reading frame. Interestingly, miR-34a, miR-206, miR-122 and miR-210 enhanced virus expression in this assay with an impressive effect of miR-206 which enhanced virus production by 54 fold (FIG. 4). miR-370 had no significant effect on virus production in this assay.

In HIV-1 infected patients, there are two situations where HIV-1 is silenced at the gene expression level. First, HAART-treatment revealed the presence of silent HIV-1 reservoir which consists of memory CD4+ T cells containing integrated silent provirus. Second, HIV-infected individuals who are able to control their virus to undetectable levels for many years in the absence of treatment have been recently identified and referred to Elite HIV Controllers. The fact that miR-34a, miR-206, miR-122 and miR-210 enhanced viral LTR activity lead us to ask whether these miRNA may play role in HIV-1 silencing observed in infected patients. Thus, PBMCs isolated from 5 HIV-1 Elite Controllers and 4 HAART-treated HIV-1-infected patients with undetectable viremia were transfected with either control miRNA (miR-32) or a mix of miR-34a, miR-206, miR-122 and miR-210. Transfected PBMCs were co-cultured with PHA/IL2-activated PBMCs from healthy donors and p24 antigen in culture supernatant was measured every 3 to 4 days. Over expression of miRmix lead to virus reactivation in PBMCs from 5 Elite Controllers out of five tested (FIG. 5 to FIG. 9) and in 4 HAART-treated HIV-1-infected out of 4 tested (FIG. 10 to FIG. 13). miR control had no effect. These experiments show that miR-34a, miR-206, miR-122 and miR-210 are able to reactivate HIV-1 replication in naturally isolated silent HIV-1 reservoirs. Quantitative real time RT-PCR was then used to analyze the expression levels of these miRNAs in PBMCs from Elite Controllers, HAART-treated and HIV-1-infected untreated patients (FIG. 14 to FIG. 17). Expression of miR-34a, miR-206 and miR-210 is low in PBMCs isolated from Elite HIV Controllers and HAART-treated HIV-1-infected patients compared to untreated HIV-1-infected patients. Expression of miR-122 was low in all the patients tested. Expression level of miR-125b, which is not regulated by HIV-1, was similar in all PBMCs tested. Interestingly, as in Elite Controllers and HAART-treated patients, expression level of miR34a, miR-206 and miR-210 was low in healthy donors. These experiments suggest a correlation between the expression of miR34a, miR-206, miR-210 and HIV-1 replication.

Example 4

Identification of Genes Involved in the Activation of HIV Replication

Among 135 putative target genes of miR-34a, miR-206, miR-210 and miR-122, the inventors have identified 51 genes (Table 1) which inhibition of the expression by siRNAs or shRNAs activates viral replication of HIV-1.

Briefly, a siRNA library specifically targeting the 135 putative target genes of miR-34a, miR-206, miR-210 and miR-122 has been generated. Each gene was thus specifically targeted by a pool of 4 siRNAs. The siRNAs were obtained from siGenome, Dharmacon.

HeLa cells were first transfected by siRNA pools with oligofectamine (Invitrogen). 48 h later, the cells were infected by a HIV virus pseudotyped a VSV-G envelope and expressing a luciferase report gene replacing the nef gene (HIV-VSVG-Luc). 48 h post-infection, cells were collected and the luciferase activity quantified (Luciferase assay kit, Promega). Luciferase activity was normalized with respect to the quantity of proteins in the cellular lysate measured by a Bradford assay.

51 genes could thus be identified which specific inhibition leads to an increase of viral replication in HeLa cells by a factor 5.

The above analysis was also carried out in other in vitro cell models closer to the physiological conditions of infection:

- HeLa CD4 cells, which express the CD4 receptor and the CCR5 and CXCR4 coreceptors; siRNAs were transfected according to the above procedure but the infected virus carried a HIV envelope (pNL4-3-Luc);
- Jurkat T cells, peripheral blood mononuclear cells (PBMCs) from non-infected individuals as well as human macrophages; in these cases, genes are inhibited following transduction of shRNA-expressing lentiviral particles (TRC clones).

TABLE 1

| Gene Symbol | Accession number (NCBI) | Gene ID |
|---|---|---|
| DGUOK | NM_080916 | 1716 |
| MIR16 | AY463154 | 53591 |
| PPP1R11 | NM_021959 | 6992 |
| ARHGAP1 | NM_004308 | 392 |
| TEDDM1 | NM_172000 | 127670 |
| QDPR | NM_000320 | 5860 |
| C14orf32 | NM_144578 | 93487 |
| C1orf19 | NM_052965 | 116461 |
| ATP1B3 | NM_001679 | 483 |
| FLJ10241 | NM_018035 | 55101 |
| ANP32E | NM_030920 | 81611 |
| TAGLN2 | NM_003564 | 8407 |
| ARF3 | NM_001659 | 377 |
| PTMA | NM_002823 | 5757 |
| PPIB | NM_000942 | 5479 |
| PRCP | NM_005040 | 5547 |
| PTPRK | NM_002844 | 6745 |
| OBSL1 | NM_015311 | 23363 |
| SLC44A1 | NM_080546 | 23446 |
| PPIAL4 | NM_178230 | 164022 |
| SERP1 | NM_014445 | 27230 |
| EBPL | NM_032565 | 84650 |
| CBX6 | NM_014292 | 23466 |
| ZBED3 | NM_032367 | 84327 |
| NP | NM_000270 | 4860 |
| PRSS21 | NM_144956 | 10942 |
| PPIA | NM_021130 | 5478 |
| C5orf13 | NM_004772 | 9315 |
| E2F2 | NM_004091 | 1870 |
| CACYBP | NM_014412 | 27101 |
| TROAP | NM_005480 | 10024 |
| APOBEC3A | NM_145699 | 200315 |
| C7orf44 | NM_018224 | 55744 |
| ORC6L | NM_014321 | 23594 |
| WNT10B | NM_003394 | 7480 |
| VIM | EF445046 | 7431 |
| CDC6 | NM_001254 | 990 |
| MCRS1 | NM_006337 | 10445 |

TABLE 1-continued

| Gene Symbol | Accession number (NCBI) | Gene ID |
|---|---|---|
| NAG18 | AF210651 | 57051 |
| PPP1CC | NM_002710 | 5501 |
| DULLARD | NM_015343 | 23399 |
| ASF1B | NM_018154 | 55723 |
| PLP2 | NM_002668 | 5355 |
| MTHFD2 | NM_006636 | 10797 |
| PIGS | NM_033198. | 94005 |

TABLE 1-continued

| Gene Symbol | Accession number (NCBI) | Gene ID |
|---|---|---|
| KIF2C | NM_006845 | 11004 |
| NRM | NM_007243 | 11270 |
| PEG10 | NM_015068 | 23089 |
| C22orf9 | NM_015264 | 23313 |
| COL4A2 | NM_001846 | 1284 |
| SNX26 | NM_052948 | 115703 |

The invention claimed is:

1. A method for inducing HIV-1 expression in latent HIV-1-infected cells in an individual in need thereof comprising administering to the individual a therapeutically effective amount of at least one nucleic acid comprising or encoding a nucleic acid comprising:

a sequence selected from the group consisting of: SEQ ID NO:1, SEQ ID NO:2, SEQ ID NO:3; SEQ ID NO:4, and a combination thereof.

2. The method according to claim 1, wherein the at least one nucleic acid consists of a RNA molecule.

3. The method according to claim 1, wherein the at least one nucleic acid comprises a RNA molecule consisting of SEQ ID NO: 1, a RNA molecule consisting of SEQ ID NO: 2, a RNA molecule consisting of SEQ ID NO: 3, and a RNA molecule consisting of SEQ ID NO: 4.

4. The method according to claim 1, wherein the at least one nucleic acid is used in combination with at least one other anti-retroviral compound.

5. The method according to claim 1, wherein the individual is an asymptomatic patient infected by HIV-1.

6. The method according to claim 4, wherein the at least one other anti-viral compound is selected from the group consisting of a reverse transcriptase inhibitor and a protease inhibitor.

7. The method according to claim 5, wherein the individual is under Highly Active Antiretroviral Therapy (HAART).

8. The method according to claim 5, wherein the individual is an elite HIV-1 controller.

9. An in vitro method for the production of retroviral particles, comprising:

contacting cells harbouring a retroviral vector with a nucleic acid as defined in claim 1;

letting the cells express the retroviral vector;

whereby retroviral particles are produced from the cells.

10. The in vitro method of claim 9, involving no step of culturing the cells with T cells.

* * * * *

SEQUENCE LISTING

```
<160> NUMBER OF SEQ ID NOS: 76

<210> SEQ ID NO 1
<211> LENGTH: 22
<212> TYPE: RNA
<213> ORGANISM: Homo sapiens

<400> SEQUENCE: 1

uggcagugu c uuagcugguu gu                                        22


<210> SEQ ID NO 2
<211> LENGTH: 22
<212> TYPE: RNA
<213> ORGANISM: Homo sapiens

<400> SEQUENCE: 2

uggaguguga caaugguguu ug                                         22


<210> SEQ ID NO 3
<211> LENGTH: 22
<212> TYPE: RNA
<213> ORGANISM: Homo sapiens

<400> SEQUENCE: 3

uggaauguaa ggaagugugu gg                                         22


<210> SEQ ID NO 4
<211> LENGTH: 22
<212> TYPE: RNA
<213> ORGANISM: Homo sapiens

<400> SEQUENCE: 4

cugugcgugu gacagcggcu ga                                         22


<210> SEQ ID NO 5
<211> LENGTH: 5424
<212> TYPE: DNA
<213> ORGANISM: Homo sapiens
<220> FEATURE:
<221> NAME/KEY: CDS
<222> LOCATION: (360)..(4484)

<400> SEQUENCE: 5

accgcgcaca aggccctgcg gtgggctgaa gagttttccc tcccttggcc cagctttctc     60

aggtttgctt tttaattccc tcggtttcct gttccggagg cgcgggcggt gccactgtct    120

tggtacctgc ggtagtagcc tggctttgct ctgacggcga tctcgcggcc cgagagcctt    180

ttataggttg cttttcccgg ggatgtgaag gatacagaaa tgactgtgaa tcaacccata    240

tcatcaagga gctgataatc tagtggaaga gttagacgtg tgcatacttc actatgatat    300

gaggcagtct ctgagcttat attctctgtg gaagatgtga catatccagg cggaacatc     359
```

-continued

```
atg atg cag gga aac aca tgt cac aga atg tcg ttc cac ccg gga cga      407
Met Met Gln Gly Asn Thr Cys His Arg Met Ser Phe His Pro Gly Arg
1               5                   10                  15

ggg tgt ccc cga gga cga gga gga cat gga gcc aga ccc tca gca cca      455
Gly Cys Pro Arg Gly Arg Gly Gly His Gly Ala Arg Pro Ser Ala Pro
            20                  25                  30

tcc ttt agg ccc caa aat ctg agg ctg ctt cac cct cag cag cct cct      503
Ser Phe Arg Pro Gln Asn Leu Arg Leu Leu His Pro Gln Gln Pro Pro
        35                  40                  45

gtg caa tat caa tat gaa cct cca agt gcc cct tcc acc act ttc tca      551
Val Gln Tyr Gln Tyr Glu Pro Pro Ser Ala Pro Ser Thr Thr Phe Ser
    50                  55                  60

aac tct cca gcc ccc aat ttt ctc cct cca cga cca gac ttt gta ccc      599
Asn Ser Pro Ala Pro Asn Phe Leu Pro Pro Arg Pro Asp Phe Val Pro
65                  70                  75                  80

ttc ccc cca ccc atg cct ccg tca gcg caa ggc cct ctt ccc ccc tgc      647
Phe Pro Pro Pro Met Pro Pro Ser Ala Gln Gly Pro Leu Pro Pro Cys
                85                  90                  95

cca atc agg ccg cct ttc ccc aac cac cag atg agg cac ccc ttc cca      695
Pro Ile Arg Pro Pro Phe Pro Asn His Gln Met Arg His Pro Phe Pro
            100                 105                 110

gtt cct cct tgt ttt cct ccc atg cca cca cca atg cct tgt cct aat      743
Val Pro Pro Cys Phe Pro Pro Met Pro Pro Pro Met Pro Cys Pro Asn
        115                 120                 125

aac ccc cca gtc cct ggg gca cct cct gga caa ggc act ttc ccc ttc      791
Asn Pro Pro Val Pro Gly Ala Pro Pro Gly Gln Gly Thr Phe Pro Phe
    130                 135                 140

atg atg ccc cct ccc tcc atg cct cat ccc ccg ccc cct cca gtc atg      839
Met Met Pro Pro Pro Ser Met Pro His Pro Pro Pro Pro Pro Val Met
145                 150                 155                 160

ccg cag cag gtt aat tat cag tac cct ccg ggc tat tct cac cac aac      887
Pro Gln Gln Val Asn Tyr Gln Tyr Pro Pro Gly Tyr Ser His His Asn
                165                 170                 175

ttc cca cct ccc agt ttt aat agt ttc cag aac aac cct agt tct ttc      935
Phe Pro Pro Pro Ser Phe Asn Ser Phe Gln Asn Asn Pro Ser Ser Phe
            180                 185                 190

ctg ccc agt gct aat aac agc agt agt cct cat ttc aga cat ctc cct      983
Leu Pro Ser Ala Asn Asn Ser Ser Ser Pro His Phe Arg His Leu Pro
        195                 200                 205

cca tac cca ctc cca aag gct ccc agt gag aga agg tcc cca gaa agg     1031
Pro Tyr Pro Leu Pro Lys Ala Pro Ser Glu Arg Arg Ser Pro Glu Arg
    210                 215                 220

ctg aaa cac tat gat gac cac agg cac cga gat cac agt cat ggg cga     1079
Leu Lys His Tyr Asp Asp His Arg His Arg Asp His Ser His Gly Arg
225                 230                 235                 240

ggt gag agg cat cgg tcc ctg gat cgg cgg gag cga ggc cgc agt ccc     1127
Gly Glu Arg His Arg Ser Leu Asp Arg Arg Glu Arg Gly Arg Ser Pro
                245                 250                 255

gac agg aga aga caa gac agc cgg tac aga tct gat tat gac cga ggg     1175
Asp Arg Arg Arg Gln Asp Ser Arg Tyr Arg Ser Asp Tyr Asp Arg Gly
            260                 265                 270

aga aca cca tct cgc cac cgc agc tac gaa cgg agc aga gag cga gaa     1223
Arg Thr Pro Ser Arg His Arg Ser Tyr Glu Arg Ser Arg Glu Arg Glu
        275                 280                 285

cgg gag aga cac agg cat cga gac aac cga aga tca cca tct ctg gaa     1271
Arg Glu Arg His Arg His Arg Asp Asn Arg Arg Ser Pro Ser Leu Glu
    290                 295                 300

agg tcc tac aaa aaa gag tat aag aga tct gga agg agt tac ggt tta     1319
Arg Ser Tyr Lys Lys Glu Tyr Lys Arg Ser Gly Arg Ser Tyr Gly Leu
305                 310                 315                 320
```

```
tcg gtt gtt cct gaa cct gct gga tgc aca cca gaa tta cct ggg gag      1367
Ser Val Val Pro Glu Pro Ala Gly Cys Thr Pro Glu Leu Pro Gly Glu
                325                 330                 335

att att aaa aat aca gat tct tgg gcc cca ccc ctg gag att gtg aat      1415
Ile Ile Lys Asn Thr Asp Ser Trp Ala Pro Pro Leu Glu Ile Val Asn
            340                 345                 350

cat cgc tcc cca agt agg gag aag aag aga gct cgt tgg gag gaa gaa      1463
His Arg Ser Pro Ser Arg Glu Lys Lys Arg Ala Arg Trp Glu Glu Glu
        355                 360                 365

aaa gac cgt tgg agt gac aac cag agt tct ggc aaa gac aag aac tat      1511
Lys Asp Arg Trp Ser Asp Asn Gln Ser Ser Gly Lys Asp Lys Asn Tyr
    370                 375                 380

acc tca atc aag gaa aaa gag ccc gag gag acc atg cct gac aag aat      1559
Thr Ser Ile Lys Glu Lys Glu Pro Glu Glu Thr Met Pro Asp Lys Asn
385                 390                 395                 400

gag gag gaa gaa gaa gaa ctt ctt aag cct gtg tgg att cga tgc act      1607
Glu Glu Glu Glu Glu Glu Leu Leu Lys Pro Val Trp Ile Arg Cys Thr
                405                 410                 415

cat tca gaa aac tac tac tcc agt gac ccc atg gat cag gtg gga gat      1655
His Ser Glu Asn Tyr Tyr Ser Ser Asp Pro Met Asp Gln Val Gly Asp
            420                 425                 430

tct aca gtg gtt gga acg agt agg ctt cgt gac tta tat gac aaa ttt      1703
Ser Thr Val Val Gly Thr Ser Arg Leu Arg Asp Leu Tyr Asp Lys Phe
        435                 440                 445

gag gag gag ttg ggg agc agg caa gaa aag gcc aaa gct gct cgg cct      1751
Glu Glu Glu Leu Gly Ser Arg Gln Glu Lys Ala Lys Ala Ala Arg Pro
    450                 455                 460

ccg tgg gaa cct cca aag acg aag ctc gat gaa gat tta gag agt tcc      1799
Pro Trp Glu Pro Pro Lys Thr Lys Leu Asp Glu Asp Leu Glu Ser Ser
465                 470                 475                 480

agt gaa tcc gag tgt gag tct gat gag gac agc acc tgt tct agc agc      1847
Ser Glu Ser Glu Cys Glu Ser Asp Glu Asp Ser Thr Cys Ser Ser Ser
                485                 490                 495

tca gac tct gaa gtt ttt gac gtt att gca gaa atc aaa cgc aaa aag      1895
Ser Asp Ser Glu Val Phe Asp Val Ile Ala Glu Ile Lys Arg Lys Lys
            500                 505                 510

gcc cac cct gac cga ctt cat gat gaa ctt tgg tac aac gat cca ggc      1943
Ala His Pro Asp Arg Leu His Asp Glu Leu Trp Tyr Asn Asp Pro Gly
        515                 520                 525

cag atg aat gat gga cca ctc tgc aaa tgc agc gca aag gca aga cgc      1991
Gln Met Asn Asp Gly Pro Leu Cys Lys Cys Ser Ala Lys Ala Arg Arg
    530                 535                 540

aca gga att agg cac agc att tat cct gga gaa gag gcc atc aag ccc      2039
Thr Gly Ile Arg His Ser Ile Tyr Pro Gly Glu Glu Ala Ile Lys Pro
545                 550                 555                 560

tgt cgt cct atg acc aac aat gct ggc aga ctt ttc cac tac cgg atc      2087
Cys Arg Pro Met Thr Asn Asn Ala Gly Arg Leu Phe His Tyr Arg Ile
                565                 570                 575

aca gtc tcc ccg cct acg aac ttt tta act gac agg cca act gtt ata      2135
Thr Val Ser Pro Pro Thr Asn Phe Leu Thr Asp Arg Pro Thr Val Ile
            580                 585                 590

gaa tac gat gat cac gag tat atc ttt gaa gga ttt tct atg ttt gca      2183
Glu Tyr Asp Asp His Glu Tyr Ile Phe Glu Gly Phe Ser Met Phe Ala
        595                 600                 605

cat gcc ccc ctg acc aat att cca ctg tgt aaa gta att aga ttc aac      2231
His Ala Pro Leu Thr Asn Ile Pro Leu Cys Lys Val Ile Arg Phe Asn
    610                 615                 620

ata gac tac acg att cat ttc att gaa gag atg atg ccg gag aat ttt      2279
Ile Asp Tyr Thr Ile His Phe Ile Glu Glu Met Met Pro Glu Asn Phe
```

-continued

```
625                 630                 635                 640

tgt gtg aaa ggg ctt gaa ctc ttt tca ctg ttc cta ttc aga gat att      2327
Cys Val Lys Gly Leu Glu Leu Phe Ser Leu Phe Leu Phe Arg Asp Ile
                645                 650                 655

ttg gaa tta tat gac tgg aat ctt aaa ggt cct ttg ttt gaa gac agc      2375
Leu Glu Leu Tyr Asp Trp Asn Leu Lys Gly Pro Leu Phe Glu Asp Ser
            660                 665                 670

cct ccc tgc tgc cca aga ttt cat ttc atg cca cgt ttt gta aga ttt      2423
Pro Pro Cys Cys Pro Arg Phe His Phe Met Pro Arg Phe Val Arg Phe
        675                 680                 685

ctt cca gat gga gga aag gaa gtg ctg tcc atg cac cag att ctc ctg      2471
Leu Pro Asp Gly Gly Lys Glu Val Leu Ser Met His Gln Ile Leu Leu
    690                 695                 700

tac ttg tta agg tgc agc aaa gcc ctg gtg cct gag gag gag att gcc      2519
Tyr Leu Leu Arg Cys Ser Lys Ala Leu Val Pro Glu Glu Glu Ile Ala
705                 710                 715                 720

aat atg ctt cag tgg gag gag ctg gag tgg cag aaa tat gca gaa gaa      2567
Asn Met Leu Gln Trp Glu Glu Leu Glu Trp Gln Lys Tyr Ala Glu Glu
                725                 730                 735

tgc aaa ggc atg att gtt acc aac cct ggg acg aaa cca agc tct gtc      2615
Cys Lys Gly Met Ile Val Thr Asn Pro Gly Thr Lys Pro Ser Ser Val
            740                 745                 750

cgt atc gat caa ctg gat cgt gaa cag ttc aac ccc gat gtg att act      2663
Arg Ile Asp Gln Leu Asp Arg Glu Gln Phe Asn Pro Asp Val Ile Thr
        755                 760                 765

ttt ccg att atc gtc cac ttt ggg ata cgc cct gca cag ttg agt tat      2711
Phe Pro Ile Ile Val His Phe Gly Ile Arg Pro Ala Gln Leu Ser Tyr
    770                 775                 780

gca gga gac cca cag tac caa aaa ctg tgg aag agt tat gtg aaa ctt      2759
Ala Gly Asp Pro Gln Tyr Gln Lys Leu Trp Lys Ser Tyr Val Lys Leu
785                 790                 795                 800

cgc cac ctc cta gca aat agt ccc aaa gtc aaa caa act gac aaa cag      2807
Arg His Leu Leu Ala Asn Ser Pro Lys Val Lys Gln Thr Asp Lys Gln
                805                 810                 815

aag ctg gca cag agg gag gaa gcc ctc caa aaa ata cgg cag aag aat      2855
Lys Leu Ala Gln Arg Glu Glu Ala Leu Gln Lys Ile Arg Gln Lys Asn
            820                 825                 830

aca atg aga cga gaa gta acg gtg gag cta agt agc caa gga ttc tgg      2903
Thr Met Arg Arg Glu Val Thr Val Glu Leu Ser Ser Gln Gly Phe Trp
        835                 840                 845

aaa act ggc atc cgt tct gat gtc tgt cag cat gca atg atg cta cct      2951
Lys Thr Gly Ile Arg Ser Asp Val Cys Gln His Ala Met Met Leu Pro
    850                 855                 860

gtt ctg acc cat cat atc cgc tac cac caa tgc cta atg cat ttg gac      2999
Val Leu Thr His His Ile Arg Tyr His Gln Cys Leu Met His Leu Asp
865                 870                 875                 880

aag ttg ata gga tat act ttc caa gat cgt tgt ctg ttg cag ctg gcc      3047
Lys Leu Ile Gly Tyr Thr Phe Gln Asp Arg Cys Leu Leu Gln Leu Ala
                885                 890                 895

atg act cat cca agt cat cat tta aat ttt gga atg aat cct gat cat      3095
Met Thr His Pro Ser His His Leu Asn Phe Gly Met Asn Pro Asp His
            900                 905                 910

gcc agg aat tca tta tct aac tgt gga att cgg cag ccc aaa tac gga      3143
Ala Arg Asn Ser Leu Ser Asn Cys Gly Ile Arg Gln Pro Lys Tyr Gly
        915                 920                 925

gac aga aaa gtt cat cac atg cac atg cgg aag aaa ggg att aac acc      3191
Asp Arg Lys Val His His Met His Met Arg Lys Lys Gly Ile Asn Thr
    930                 935                 940

ttg ata aat atc atg tca cgc ctt ggc caa gat gac cca act ccc tcg      3239
```

```
Leu Ile Asn Ile Met Ser Arg Leu Gly Gln Asp Asp Pro Thr Pro Ser
945                 950                 955                 960

agg att aac cac aat gaa cgg ttg gaa ttc ctg ggt gat gct gtt gtt     3287
Arg Ile Asn His Asn Glu Arg Leu Glu Phe Leu Gly Asp Ala Val Val
                965                 970                 975

gaa ttt ctg acc agc gtc cat ttg tac tat ttg ttt cct agt ctg gaa     3335
Glu Phe Leu Thr Ser Val His Leu Tyr Tyr Leu Phe Pro Ser Leu Glu
            980                 985                 990

gaa gga gga tta gca acc tat cgg  act gcc att gtt cag  aat cag cac   3383
Glu Gly Gly Leu Ala Thr Tyr Arg  Thr Ala Ile Val Gln  Asn Gln His
        995                 1000                1005

ctt gcc  atg cta gca aag aaa  ctt gaa ctg gat cga  ttt atg ctg     3428
Leu Ala  Met Leu Ala Lys Lys  Leu Glu Leu Asp Arg  Phe Met Leu
    1010                 1015                 1020

tat gct  cac ggg cct gac ctt  tgt aga gaa tcg gac  ctt cga cat     3473
Tyr Ala  His Gly Pro Asp Leu  Cys Arg Glu Ser Asp  Leu Arg His
    1025                 1030                 1035

gca atg  gcc aat tgt ttt gaa  gcg tta ata gga gct  gtt tac ttg     3518
Ala Met  Ala Asn Cys Phe Glu  Ala Leu Ile Gly Ala  Val Tyr Leu
    1040                 1045                 1050

gag gga  agc ctg gag gaa gcc  aag cag tta ttt gga  cgc ttg ctc     3563
Glu Gly  Ser Leu Glu Glu Ala  Lys Gln Leu Phe Gly  Arg Leu Leu
    1055                 1060                 1065

ttt aat  gat ccg gac ctg cgc  gaa gtc tgg ctc aat  tat cct ctc     3608
Phe Asn  Asp Pro Asp Leu Arg  Glu Val Trp Leu Asn  Tyr Pro Leu
    1070                 1075                 1080

cac cca  ctc caa cta caa gag  cca aat act gat cga  caa ctt att     3653
His Pro  Leu Gln Leu Gln Glu  Pro Asn Thr Asp Arg  Gln Leu Ile
    1085                 1090                 1095

gaa act  tct cca gtt cta caa  aaa ctt act gag ttt  gaa gaa gca     3698
Glu Thr  Ser Pro Val Leu Gln  Lys Leu Thr Glu Phe  Glu Glu Ala
    1100                 1105                 1110

att gga  gta att ttt act cat  gtt cga ctt ctg gca  agg gca ttc     3743
Ile Gly  Val Ile Phe Thr His  Val Arg Leu Leu Ala  Arg Ala Phe
    1115                 1120                 1125

aca ttg  aga act gtg gga ttt  aac cat ctg acc cta  ggc cac aat     3788
Thr Leu  Arg Thr Val Gly Phe  Asn His Leu Thr Leu  Gly His Asn
    1130                 1135                 1140

cag aga  atg gaa ttc cta ggt  gac tcc ata atg caa  ctg gta gcc     3833
Gln Arg  Met Glu Phe Leu Gly  Asp Ser Ile Met Gln  Leu Val Ala
    1145                 1150                 1155

aca gag  tac tta ttc att cat  ttc cca gat cat cat  gaa gga cac     3878
Thr Glu  Tyr Leu Phe Ile His  Phe Pro Asp His His  Glu Gly His
    1160                 1165                 1170

tta act  ttg ttg cga agc tct  ttg gtg aat aat aga  act cag gcc     3923
Leu Thr  Leu Leu Arg Ser Ser  Leu Val Asn Asn Arg  Thr Gln Ala
    1175                 1180                 1185

aag gta  gcg gag gag ctg ggc  atg cag gag tac gcc  ata acc aac     3968
Lys Val  Ala Glu Glu Leu Gly  Met Gln Glu Tyr Ala  Ile Thr Asn
    1190                 1195                 1200

gac aag  acc aag agg cct gtg  gcg ctt cgc acc aag  acc ttg gcg     4013
Asp Lys  Thr Lys Arg Pro Val  Ala Leu Arg Thr Lys  Thr Leu Ala
    1205                 1210                 1215

gac ctt  ttg gaa tca ttt att  gca gcg ctg tac att  gat aag gat     4058
Asp Leu  Leu Glu Ser Phe Ile  Ala Ala Leu Tyr Ile  Asp Lys Asp
    1220                 1225                 1230

ttg gaa  tat gtt cat act ttc  atg aat gtc tgc ttc  ttt cca cga     4103
Leu Glu  Tyr Val His Thr Phe  Met Asn Val Cys Phe  Phe Pro Arg
    1235                 1240                 1245
```

```
ttg aaa  gag ttc att ttg aat  cag gat tgg aat gac  ccc aaa tcc      4148
Leu Lys  Glu Phe Ile Leu Asn  Gln Asp Trp Asn Asp  Pro Lys Ser
    1250                 1255                 1260

cag ctt  cag cag tgt tgc ttg  aca ctt agg aca gaa  gga aaa gag      4193
Gln Leu  Gln Gln Cys Cys Leu  Thr Leu Arg Thr Glu  Gly Lys Glu
    1265                 1270                 1275

cca gac  att cct ctg tac aag  act ctg cag aca gtg  ggc cca tcc      4238
Pro Asp  Ile Pro Leu Tyr Lys  Thr Leu Gln Thr Val  Gly Pro Ser
    1280                 1285                 1290

cat gcc  cga acc tac act gtg  gct gtt tat ttc aag  gga gaa aga      4283
His Ala  Arg Thr Tyr Thr Val  Ala Val Tyr Phe Lys  Gly Glu Arg
    1295                 1300                 1305

ata ggc  tgt ggg aaa gga cca  agt att cag caa gcg  gaa atg gga      4328
Ile Gly  Cys Gly Lys Gly Pro  Ser Ile Gln Gln Ala  Glu Met Gly
    1310                 1315                 1320

gca gca  atg gat gcg ctt gaa  aaa tat aat ttt ccc  cag atg gcc      4373
Ala Ala  Met Asp Ala Leu Glu  Lys Tyr Asn Phe Pro  Gln Met Ala
    1325                 1330                 1335

cat cag  aag cgg ttc atc gaa  cgg aag tac aga caa  gag tta aaa      4418
His Gln  Lys Arg Phe Ile Glu  Arg Lys Tyr Arg Gln  Glu Leu Lys
    1340                 1345                 1350

gaa atg  agg tgg gaa aga gag  cat caa gag aga gag  cca gat gag      4463
Glu Met  Arg Trp Glu Arg Glu  His Gln Glu Arg Glu  Pro Asp Glu
    1355                 1360                 1365

act gaa  gac atc aag aaa taa aggagggcat gcaagtgtgg agtatttact       4514
Thr Glu  Asp Ile Lys Lys
    1370

tgctcagtaa ctgtgactgt tgtctattga gacctagcct agttttcctg cagacaatga   4574

atgaagtgtg ctcattgaaa taaaatacag agtcaaatcg ctattgttgt tttaatgatc   4634

tgtttttagc tggatggtct ttattacaaa gtattagatt tttcttctat ttaacggaaa   4694

acttgacttt ggtgaatgtg cattacttcc ttttattttg ctctttaaat aataaaattc   4754

aagaagcata ttctatgtgg aatagatcct gtttttccat ctgtgtccca gattgtgacc   4814

ctagactttc aattgacaag taaaaaattg actttactag acattttgac tgtgctctag   4874

taacatctat cctttttcaa atctctggat ttttaagtag attgttcagc tttcatccgg   4934

tggctgttca tcaagttatc agctgcaaat attgaactta cctctctcta agcagtgagt   4994

gttttgtaga aggaatccgt ttaacaatta attggctaat gggagaaggg gaaagactga   5054

tattcaagtc atacagattc tttgaatcat tagaatagga gagaaatcat gattctaagc   5114

caggccacac tttaaaccaa gtgctctcac cctggggtta gtggaacctt taagaagtta   5174

atgaacagac ttcaaggaag tcaaaaacct cccaatacta tattcaattt tctgtgtgtg   5234

tttgagattt gagagggcat ggggagcagg aaggaggagg gtttatagct tttatcagcc   5294

tctctaagtg ggccctgcag taaaaggcta acatgacatt caaagacata acattttaaa   5354

aaaagttatt ccaaactaaa catcactggt ttcttattaa taaaggcaaa acttctttgt   5414

aaaacaaaaa                                                          5424
```

<210> SEQ ID NO 6
<211> LENGTH: 1374
<212> TYPE: PRT
<213> ORGANISM: Homo sapiens

<400> SEQUENCE: 6

```
Met Met Gln Gly Asn Thr Cys His Arg Met Ser Phe His Pro Gly Arg
1               5                   10                  15
```

-continued

```
Gly Cys Pro Arg Gly Arg Gly Gly His Gly Ala Arg Pro Ser Ala Pro
            20                  25                  30

Ser Phe Arg Pro Gln Asn Leu Arg Leu Leu His Pro Gln Gln Pro Pro
        35                  40                  45

Val Gln Tyr Gln Tyr Glu Pro Pro Ser Ala Pro Ser Thr Thr Phe Ser
    50                  55                  60

Asn Ser Pro Ala Pro Asn Phe Leu Pro Pro Arg Pro Asp Phe Val Pro
65                  70                  75                  80

Phe Pro Pro Pro Met Pro Pro Ser Ala Gln Gly Pro Leu Pro Pro Cys
                85                  90                  95

Pro Ile Arg Pro Pro Phe Pro Asn His Gln Met Arg His Pro Phe Pro
            100                 105                 110

Val Pro Pro Cys Phe Pro Pro Met Pro Pro Pro Met Pro Cys Pro Asn
        115                 120                 125

Asn Pro Pro Val Pro Gly Ala Pro Pro Gly Gln Gly Thr Phe Pro Phe
    130                 135                 140

Met Met Pro Pro Pro Ser Met Pro His Pro Pro Pro Pro Pro Val Met
145                 150                 155                 160

Pro Gln Gln Val Asn Tyr Gln Tyr Pro Pro Gly Tyr Ser His His Asn
                165                 170                 175

Phe Pro Pro Pro Ser Phe Asn Ser Phe Gln Asn Asn Pro Ser Ser Phe
            180                 185                 190

Leu Pro Ser Ala Asn Asn Ser Ser Ser Pro His Phe Arg His Leu Pro
        195                 200                 205

Pro Tyr Pro Leu Pro Lys Ala Pro Ser Glu Arg Arg Ser Pro Glu Arg
    210                 215                 220

Leu Lys His Tyr Asp Asp His Arg His Arg Asp His Ser His Gly Arg
225                 230                 235                 240

Gly Glu Arg His Arg Ser Leu Asp Arg Arg Glu Arg Gly Arg Ser Pro
                245                 250                 255

Asp Arg Arg Arg Gln Asp Ser Arg Tyr Arg Ser Asp Tyr Asp Arg Gly
            260                 265                 270

Arg Thr Pro Ser Arg His Arg Ser Tyr Glu Arg Ser Arg Glu Arg Glu
        275                 280                 285

Arg Glu Arg His Arg His Arg Asp Asn Arg Arg Ser Pro Ser Leu Glu
    290                 295                 300

Arg Ser Tyr Lys Lys Glu Tyr Lys Arg Ser Gly Arg Ser Tyr Gly Leu
305                 310                 315                 320

Ser Val Val Pro Glu Pro Ala Gly Cys Thr Pro Glu Leu Pro Gly Glu
                325                 330                 335

Ile Ile Lys Asn Thr Asp Ser Trp Ala Pro Pro Leu Glu Ile Val Asn
            340                 345                 350

His Arg Ser Pro Ser Arg Glu Lys Lys Arg Ala Arg Trp Glu Glu Glu
        355                 360                 365

Lys Asp Arg Trp Ser Asp Asn Gln Ser Ser Gly Lys Asp Lys Asn Tyr
    370                 375                 380

Thr Ser Ile Lys Glu Lys Glu Pro Glu Glu Thr Met Pro Asp Lys Asn
385                 390                 395                 400

Glu Glu Glu Glu Glu Glu Leu Leu Lys Pro Val Trp Ile Arg Cys Thr
                405                 410                 415

His Ser Glu Asn Tyr Tyr Ser Ser Asp Pro Met Asp Gln Val Gly Asp
            420                 425                 430

Ser Thr Val Val Gly Thr Ser Arg Leu Arg Asp Leu Tyr Asp Lys Phe
```

```
        435                 440                 445

Glu Glu Glu Leu Gly Ser Arg Gln Glu Lys Ala Lys Ala Ala Arg Pro
    450                 455                 460

Pro Trp Glu Pro Pro Lys Thr Lys Leu Asp Glu Asp Leu Glu Ser Ser
465                 470                 475                 480

Ser Glu Ser Glu Cys Glu Ser Asp Glu Asp Ser Thr Cys Ser Ser Ser
                485                 490                 495

Ser Asp Ser Glu Val Phe Asp Val Ile Ala Glu Ile Lys Arg Lys Lys
            500                 505                 510

Ala His Pro Asp Arg Leu His Asp Glu Leu Trp Tyr Asn Asp Pro Gly
        515                 520                 525

Gln Met Asn Asp Gly Pro Leu Cys Lys Cys Ser Ala Lys Ala Arg Arg
    530                 535                 540

Thr Gly Ile Arg His Ser Ile Tyr Pro Gly Glu Glu Ala Ile Lys Pro
545                 550                 555                 560

Cys Arg Pro Met Thr Asn Asn Ala Gly Arg Leu Phe His Tyr Arg Ile
                565                 570                 575

Thr Val Ser Pro Pro Thr Asn Phe Leu Thr Asp Arg Pro Thr Val Ile
            580                 585                 590

Glu Tyr Asp Asp His Glu Tyr Ile Phe Glu Gly Phe Ser Met Phe Ala
        595                 600                 605

His Ala Pro Leu Thr Asn Ile Pro Leu Cys Lys Val Ile Arg Phe Asn
    610                 615                 620

Ile Asp Tyr Thr Ile His Phe Ile Glu Glu Met Met Pro Glu Asn Phe
625                 630                 635                 640

Cys Val Lys Gly Leu Glu Leu Phe Ser Leu Phe Leu Phe Arg Asp Ile
                645                 650                 655

Leu Glu Leu Tyr Asp Trp Asn Leu Lys Gly Pro Leu Phe Glu Asp Ser
            660                 665                 670

Pro Pro Cys Cys Pro Arg Phe His Phe Met Pro Arg Phe Val Arg Phe
        675                 680                 685

Leu Pro Asp Gly Gly Lys Glu Val Leu Ser Met His Gln Ile Leu Leu
    690                 695                 700

Tyr Leu Leu Arg Cys Ser Lys Ala Leu Val Pro Glu Glu Glu Ile Ala
705                 710                 715                 720

Asn Met Leu Gln Trp Glu Glu Leu Glu Trp Gln Lys Tyr Ala Glu Glu
                725                 730                 735

Cys Lys Gly Met Ile Val Thr Asn Pro Gly Thr Lys Pro Ser Ser Val
            740                 745                 750

Arg Ile Asp Gln Leu Asp Arg Glu Gln Phe Asn Pro Asp Val Ile Thr
        755                 760                 765

Phe Pro Ile Ile Val His Phe Gly Ile Arg Pro Ala Gln Leu Ser Tyr
    770                 775                 780

Ala Gly Asp Pro Gln Tyr Gln Lys Leu Trp Lys Ser Tyr Val Lys Leu
785                 790                 795                 800

Arg His Leu Leu Ala Asn Ser Pro Lys Val Lys Gln Thr Asp Lys Gln
                805                 810                 815

Lys Leu Ala Gln Arg Glu Glu Ala Leu Gln Lys Ile Arg Gln Lys Asn
            820                 825                 830

Thr Met Arg Arg Glu Val Thr Val Glu Leu Ser Ser Gln Gly Phe Trp
        835                 840                 845

Lys Thr Gly Ile Arg Ser Asp Val Cys Gln His Ala Met Met Leu Pro
    850                 855                 860
```

```
Val Leu Thr His His Ile Arg Tyr His Gln Cys Leu Met His Leu Asp
865                 870                 875                 880

Lys Leu Ile Gly Tyr Thr Phe Gln Asp Arg Cys Leu Leu Gln Leu Ala
                885                 890                 895

Met Thr His Pro Ser His His Leu Asn Phe Gly Met Asn Pro Asp His
            900                 905                 910

Ala Arg Asn Ser Leu Ser Asn Cys Gly Ile Arg Gln Pro Lys Tyr Gly
        915                 920                 925

Asp Arg Lys Val His His Met His Met Arg Lys Lys Gly Ile Asn Thr
    930                 935                 940

Leu Ile Asn Ile Met Ser Arg Leu Gly Gln Asp Asp Pro Thr Pro Ser
945                 950                 955                 960

Arg Ile Asn His Asn Glu Arg Leu Glu Phe Leu Gly Asp Ala Val Val
                965                 970                 975

Glu Phe Leu Thr Ser Val His Leu Tyr Tyr Leu Phe Pro Ser Leu Glu
            980                 985                 990

Glu Gly Gly Leu Ala Thr Tyr Arg  Thr Ala Ile Val Gln  Asn Gln His
        995                 1000                1005

Leu Ala  Met Leu Ala Lys Lys  Leu Glu Leu Asp Arg  Phe Met Leu
    1010                1015                1020

Tyr Ala  His Gly Pro Asp Leu  Cys Arg Glu Ser Asp  Leu Arg His
    1025                1030                1035

Ala Met  Ala Asn Cys Phe Glu  Ala Leu Ile Gly Ala  Val Tyr Leu
    1040                1045                1050

Glu Gly  Ser Leu Glu Glu Ala  Lys Gln Leu Phe Gly  Arg Leu Leu
    1055                1060                1065

Phe Asn  Asp Pro Asp Leu Arg  Glu Val Trp Leu Asn  Tyr Pro Leu
    1070                1075                1080

His Pro  Leu Gln Leu Gln Glu  Pro Asn Thr Asp Arg  Gln Leu Ile
    1085                1090                1095

Glu Thr  Ser Pro Val Leu Gln  Lys Leu Thr Glu Phe  Glu Glu Ala
    1100                1105                1110

Ile Gly  Val Ile Phe Thr His  Val Arg Leu Leu Ala  Arg Ala Phe
    1115                1120                1125

Thr Leu  Arg Thr Val Gly Phe  Asn His Leu Thr Leu  Gly His Asn
    1130                1135                1140

Gln Arg  Met Glu Phe Leu Gly  Asp Ser Ile Met Gln  Leu Val Ala
    1145                1150                1155

Thr Glu  Tyr Leu Phe Ile His  Phe Pro Asp His His  Glu Gly His
    1160                1165                1170

Leu Thr  Leu Leu Arg Ser Ser  Leu Val Asn Asn Arg  Thr Gln Ala
    1175                1180                1185

Lys Val  Ala Glu Glu Leu Gly  Met Gln Glu Tyr Ala  Ile Thr Asn
    1190                1195                1200

Asp Lys  Thr Lys Arg Pro Val  Ala Leu Arg Thr Lys  Thr Leu Ala
    1205                1210                1215

Asp Leu  Leu Glu Ser Phe Ile  Ala Ala Leu Tyr Ile  Asp Lys Asp
    1220                1225                1230

Leu Glu  Tyr Val His Thr Phe  Met Asn Val Cys Phe  Phe Pro Arg
    1235                1240                1245

Leu Lys  Glu Phe Ile Leu Asn  Gln Asp Trp Asn Asp  Pro Lys Ser
    1250                1255                1260
```

-continued

```
Gln Leu  Gln Gln Cys Cys Leu  Thr Leu Arg Thr Glu  Gly Lys Glu
    1265                 1270                 1275

Pro Asp  Ile Pro Leu Tyr Lys  Thr Leu Gln Thr Val  Gly Pro Ser
    1280                 1285                 1290

His Ala  Arg Thr Tyr Thr Val  Ala Val Tyr Phe Lys  Gly Glu Arg
    1295                 1300                 1305

Ile Gly  Cys Gly Lys Gly Pro  Ser Ile Gln Gln Ala  Glu Met Gly
    1310                 1315                 1320

Ala Ala  Met Asp Ala Leu Glu  Lys Tyr Asn Phe Pro  Gln Met Ala
    1325                 1330                 1335

His Gln  Lys Arg Phe Ile Glu  Arg Lys Tyr Arg Gln  Glu Leu Lys
    1340                 1345                 1350

Glu Met  Arg Trp Glu Arg Glu  His Gln Glu Arg Glu  Pro Asp Glu
    1355                 1360                 1365

Thr Glu  Asp Ile Lys Lys
    1370


<210> SEQ ID NO 7
<211> LENGTH: 4461
<212> TYPE: DNA
<213> ORGANISM: Homo sapiens
<220> FEATURE:
<221> NAME/KEY: CDS
<222> LOCATION: (351)..(2672)

<400> SEQUENCE: 7

ggcggtcggt cggtgaggct ttcccggctg tggtttggct gcgggcggct tgggcagccc     60

gcgggcgcct caggtagaag aagaaaggtg ccactccggc atgaagacag actcgcttag    120

tcgccagtca cttaagctga gtgcattgtg atttccaata attgaggcag tggttctaaa    180

agctgtctac attaatgaaa agagcaatgt ggccagcttg actaagccgc cagcgcacag    240

cgcggcagga cgcgcccggg tctcagcgga cttgtgcatg ttagctgtgt agatttatgt    300

gagggcttgt aaaactctgg tcttgtaaac tagtcttaag cgcttttaat atg gag      356
                                                       Met Glu
                                                       1

aca gat gag agc ccc tct ccg ctc ccg tgt ggg ccc gca gga gaa gcg      404
Thr Asp Glu Ser Pro Ser Pro Leu Pro Cys Gly Pro Ala Gly Glu Ala
        5                   10                  15

gtg atg gag agc cga gct cgc ccc ttc caa gcg ctg ccc cgt gag cag      452
Val Met Glu Ser Arg Ala Arg Pro Phe Gln Ala Leu Pro Arg Glu Gln
    20                  25                  30

tct cca cca cct ccc ctg caa acg tcc agt ggt gca gag gta atg gac      500
Ser Pro Pro Pro Pro Leu Gln Thr Ser Ser Gly Ala Glu Val Met Asp
35                  40                  45                  50

gtt ggc tct ggt ggt gat gga cag tcc gaa ctc cct gct gag gac ccc      548
Val Gly Ser Gly Gly Asp Gly Gln Ser Glu Leu Pro Ala Glu Asp Pro
                55                  60                  65

ttc aac ttc tac gga gct tct ctt ctc tcc aaa gga tcc ttc tct aag      596
Phe Asn Phe Tyr Gly Ala Ser Leu Leu Ser Lys Gly Ser Phe Ser Lys
            70                  75                  80

ggc cgc ctc ctc ata gac ccg aac tgt agt ggc cac agc ccg cgc acc      644
Gly Arg Leu Leu Ile Asp Pro Asn Cys Ser Gly His Ser Pro Arg Thr
        85                  90                  95

gcc cgg cac gca cct gcg gtc cgg aag ttc tcc cct gac ctt aag ttg      692
Ala Arg His Ala Pro Ala Val Arg Lys Phe Ser Pro Asp Leu Lys Leu
    100                 105                 110

ctt aag gat gta aag att agc gtg agc ttt acc gag agc tgc agg agt      740
Leu Lys Asp Val Lys Ile Ser Val Ser Phe Thr Glu Ser Cys Arg Ser
```

```
115                 120                 125                 130

aag gac agg aag gtg ctg tac aca gga gca gag cgc gac gtg cgg gcg      788
Lys Asp Arg Lys Val Leu Tyr Thr Gly Ala Glu Arg Asp Val Arg Ala
                135                 140                 145

gag tgc ggt ctg ctc ctt agc cct gtc agt ggg gac gtg cat gct tgt      836
Glu Cys Gly Leu Leu Leu Ser Pro Val Ser Gly Asp Val His Ala Cys
            150                 155                 160

ccc ttt ggc ggg agt gtt ggt gac ggg gta ggc ata ggg ggt gag agt      884
Pro Phe Gly Gly Ser Val Gly Asp Gly Val Gly Ile Gly Gly Glu Ser
        165                 170                 175

gct gat aag aag gat gag gag aat gag ctg gat cag gaa aag aga gtg      932
Ala Asp Lys Lys Asp Glu Glu Asn Glu Leu Asp Gln Glu Lys Arg Val
    180                 185                 190

gag tat gca gtg ctc gat gag tta gaa gat ttt act gac aat ttg gag      980
Glu Tyr Ala Val Leu Asp Glu Leu Glu Asp Phe Thr Asp Asn Leu Glu
195                 200                 205                 210

cta gat gaa gaa gga gca ggc ggg ttc acg gct aaa gca atc gtt cag     1028
Leu Asp Glu Glu Gly Ala Gly Gly Phe Thr Ala Lys Ala Ile Val Gln
                215                 220                 225

aga gac aga gtg gat gaa gag gcc ttg aat ttc ccc tac gag gat gac     1076
Arg Asp Arg Val Asp Glu Glu Ala Leu Asn Phe Pro Tyr Glu Asp Asp
            230                 235                 240

ttt gac aac gat gtg gat gct ctg ctg gaa gaa ggc ctt tgt gcc ccc     1124
Phe Asp Asn Asp Val Asp Ala Leu Leu Glu Glu Gly Leu Cys Ala Pro
        245                 250                 255

aaa aag agg cga aca gag gaa aaa tat ggc gga gac agc gac cat ccg     1172
Lys Lys Arg Arg Thr Glu Glu Lys Tyr Gly Gly Asp Ser Asp His Pro
    260                 265                 270

tcc gat gga gag aca agt gtg cag ccg atg atg acc aag att aaa aca     1220
Ser Asp Gly Glu Thr Ser Val Gln Pro Met Met Thr Lys Ile Lys Thr
275                 280                 285                 290

gtg ctc aaa agt cgt ggc cgc cca cct aca gag ccg ctg ccc gac ggg     1268
Val Leu Lys Ser Arg Gly Arg Pro Pro Thr Glu Pro Leu Pro Asp Gly
                295                 300                 305

tgg atc atg aca ttc cat aac tct gga gtc ccg gtg tac cta cac aga     1316
Trp Ile Met Thr Phe His Asn Ser Gly Val Pro Val Tyr Leu His Arg
            310                 315                 320

gag tct cgg gtg gtc acc tgg tcc agg cca tac ttc ttg gga acg gga     1364
Glu Ser Arg Val Val Thr Trp Ser Arg Pro Tyr Phe Leu Gly Thr Gly
        325                 330                 335

agc ata cgg aaa cac gac cct cct ctg agt agc atc cct tgt ctg cat     1412
Ser Ile Arg Lys His Asp Pro Pro Leu Ser Ser Ile Pro Cys Leu His
    340                 345                 350

tat aag aaa atg aag gac aac gag gaa cgg gag caa agc agt gac ctc     1460
Tyr Lys Lys Met Lys Asp Asn Glu Glu Arg Glu Gln Ser Ser Asp Leu
355                 360                 365                 370

acc cct agt ggg gat gtg tcc ccc gtc aag ccc ctg agc cga tct gca     1508
Thr Pro Ser Gly Asp Val Ser Pro Val Lys Pro Leu Ser Arg Ser Ala
                375                 380                 385

gag ctg gag ttt ccc ctg gat gag cct gac tct atg ggt gct gac ccg     1556
Glu Leu Glu Phe Pro Leu Asp Glu Pro Asp Ser Met Gly Ala Asp Pro
            390                 395                 400

ggg ccc ccg gac gag aaa gac cca cta ggg gct gag gca gcc cct ggg     1604
Gly Pro Pro Asp Glu Lys Asp Pro Leu Gly Ala Glu Ala Ala Pro Gly
        405                 410                 415

gcc ctg ggg cag gtg aag gcc aaa gtc gag gtg tgc aaa gat gaa tcc     1652
Ala Leu Gly Gln Val Lys Ala Lys Val Glu Val Cys Lys Asp Glu Ser
    420                 425                 430

gtt gat ctc gag gaa ttt cga agc tac ctg gag aag cgt ttt gac ttt     1700
```

-continued

```
Val Asp Leu Glu Glu Phe Arg Ser Tyr Leu Glu Lys Arg Phe Asp Phe
435                 440                 445                 450

gag caa gtt act gtg aaa aaa ttc agg act tgg gct gag cgg cgg caa      1748
Glu Gln Val Thr Val Lys Lys Phe Arg Thr Trp Ala Glu Arg Arg Gln
                455                 460                 465

ttc aat cgg gaa atg aag cgg aag cag gcg gag tcc gag agg ccc atc      1796
Phe Asn Arg Glu Met Lys Arg Lys Gln Ala Glu Ser Glu Arg Pro Ile
            470                 475                 480

ttg cca gcc aat cag aag ctc att act tta tca gtg caa gat gca ccc      1844
Leu Pro Ala Asn Gln Lys Leu Ile Thr Leu Ser Val Gln Asp Ala Pro
        485                 490                 495

aca aag aaa gag ttt gtt att aac ccc aac ggg aaa tcc gag gtc tgc      1892
Thr Lys Lys Glu Phe Val Ile Asn Pro Asn Gly Lys Ser Glu Val Cys
    500                 505                 510

atc ctg cac gag tac atg cag cgt gtc ctc aag gtc cgc cct gtc tat      1940
Ile Leu His Glu Tyr Met Gln Arg Val Leu Lys Val Arg Pro Val Tyr
515                 520                 525                 530

aat ttc ttt gaa tgt gag aac cca agt gag cct ttt ggt gcc tcg gtg      1988
Asn Phe Phe Glu Cys Glu Asn Pro Ser Glu Pro Phe Gly Ala Ser Val
                535                 540                 545

acc att gat ggt gtg act tac gga tct gga act gca agc agc aaa aaa      2036
Thr Ile Asp Gly Val Thr Tyr Gly Ser Gly Thr Ala Ser Ser Lys Lys
            550                 555                 560

ctt gcg aag aat aaa gct gcc cga gct aca ctg gaa atc ctc atc cct      2084
Leu Ala Lys Asn Lys Ala Ala Arg Ala Thr Leu Glu Ile Leu Ile Pro
        565                 570                 575

gac ttt gtt aaa cag acc tct gaa gag aag ccc aaa gac agt gaa gaa      2132
Asp Phe Val Lys Gln Thr Ser Glu Glu Lys Pro Lys Asp Ser Glu Glu
    580                 585                 590

ctc gag tat ttt aac cac atc agc atc gag gac tcg cgg gtc tac gag      2180
Leu Glu Tyr Phe Asn His Ile Ser Ile Glu Asp Ser Arg Val Tyr Glu
595                 600                 605                 610

ctg acc agc aag gct ggg ctg ttg tct cca tat cag atc ctc cac gag      2228
Leu Thr Ser Lys Ala Gly Leu Leu Ser Pro Tyr Gln Ile Leu His Glu
                615                 620                 625

tgc ctt aaa aga aac cat ggg atg ggt gac acg tct atc aag ttt gaa      2276
Cys Leu Lys Arg Asn His Gly Met Gly Asp Thr Ser Ile Lys Phe Glu
            630                 635                 640

gtg gtt cct ggg aaa aac cag aag agt gaa tac gtc atg gcg tgt ggc      2324
Val Val Pro Gly Lys Asn Gln Lys Ser Glu Tyr Val Met Ala Cys Gly
        645                 650                 655

aag cac aca gtg cgc ggg tgg tgt aag aac aag aga gtt gga aag cag      2372
Lys His Thr Val Arg Gly Trp Cys Lys Asn Lys Arg Val Gly Lys Gln
    660                 665                 670

tta gcc tca cag aag atc ctt cag ctg ctg cac cca cat gtc aag aac      2420
Leu Ala Ser Gln Lys Ile Leu Gln Leu Leu His Pro His Val Lys Asn
675                 680                 685                 690

tgg ggg tct tta ctg cgc atg tat ggc cgt gag agc agc aag atg gtc      2468
Trp Gly Ser Leu Leu Arg Met Tyr Gly Arg Glu Ser Ser Lys Met Val
                695                 700                 705

aag cag gag aca tcg gac aag agt gtg att gag ctg cag cag tat gcc      2516
Lys Gln Glu Thr Ser Asp Lys Ser Val Ile Glu Leu Gln Gln Tyr Ala
            710                 715                 720

aag aag aac aag ccc aac ctg cac atc ctc agc aag ctc caa gag gag      2564
Lys Lys Asn Lys Pro Asn Leu His Ile Leu Ser Lys Leu Gln Glu Glu
        725                 730                 735

atg aag agg cta gct gag gaa agg gag gag act cga aag aag ccc aag      2612
Met Lys Arg Leu Ala Glu Glu Arg Glu Glu Thr Arg Lys Lys Pro Lys
    740                 745                 750
```

```
atg tcc att gtg gcg tcc gcc cag cct ggc ggt gag ccc ctg tgc acc     2660
Met Ser Ile Val Ala Ser Ala Gln Pro Gly Gly Glu Pro Leu Cys Thr
755                 760                 765                 770

gtg gac gtg tga gggaggtggc acgggccagg gcgcgggggc cgccagccgc         2712
Val Asp Val

acttctgagg agaccagcag tcatgcatcg tgcaccacag tgtcaggcct ccaacccacg   2772

ctccttccct gtggccaacc tgtgggcccg gccttagggt ggaggcttta gtgtacaggg   2832

acagccatgg ccacacagca cacatgtgga gcagcggctc tccctggaaa gctccaggcc   2892

tgaatggatg gactcagcga ctgcaccagt ggcagctggt gactgtggac agtggtggac   2952

cctgcttctg tgcacctgct gcaggctctt tttatgaagg ctttcatgaa ttttagtatg   3012

taatacgcac tgacgacaca tgatgcttgg atgacagatg agaggggatg gctgagtcct   3072

gtggctggcc cgtgatgcca ggtggcccat gtgcccaggg cgcctgcagg gctgctacag   3132

ggacctggtc aggaggtgca catggtgccc tgccctcacc caccctctgt gtttcccctt   3192

ctttgaaaag gtagaagaga aaggaatatt ttaaaccttt ttggcttaaa cagaatttta   3252

gcatcagaac tagctttctg ggattggagg caaaccatca aggtggtccc tctccagtct   3312

ggacacgatg ccagcaagga tgacgtcctg ccacctcctg gagttaccct ggcctcctag   3372

ggtccctttt tctgatgaag tcttaattcc ctaaaagcgc ctctttggac actgaggccc   3432

tctctgcctt tcctggcctc cggcaacagt tttttacaaa gattttttgc agtcgagtcc   3492

atatgtccac ccattgattt ttaaagcttt tgtgatattt tagcattttg aaagactttc   3552

acagtgagag tagaaggtag atttggaatc atgcatttta gcaagtggac ttgttgaaac   3612

aggaagcaag ggccttcagt gtagcccatt cttgatccag agctgttgcc tgtgacagcg   3672

gtttctctgg atgtcaaagg cagctgcctg gtgcccagct tgcttctcga ctggtggccc   3732

ctatgggtgg gtgtgcgatg gaaatgtgtt cctgccggag tctgaggcac cagggtgtgc   3792

tcaaaggctg gccctggtgg tggactggca cctgtgcaga gtgccgtgtg cttgtggtgc   3852

gccatctgaa gcaagagtcc agcgttctgc cgtgtctgtc ccccaccatg ccccctacag   3912

gcggtactga tggcgctttt tttttttttt ctgtcaggaa aacaatgttg gcctgtgggc   3972

cgcccacaac atatccttcc ctcactacct gtgtgaccaa ggttggcttc tgttgacctt   4032

taaaaaagaa accctcaact caaattgcta taattagaca cttgcttctg tcttgcctcc   4092

tgtctgcagc tgtgaatagt catttgactg tgactgttgc ccttagccag ccagatgcgc   4152

ctgtgaacca aagcttcgtg cacatgtgtt cccctaaagg ttggggagcc tcgctgtgtc   4212

ttgctgttcc caggcaccac cacagcaggt gctgccatac tcttgtggtc tctgtgcgcc   4272

cccccccccc ccccacccgt ctgccaagca tgggtatgaa tcgtgcacac agccatgctt   4332

caaggccggg gcaggggagc ctgtgctgat gccatccagg gcactgggct gtgcctggaa   4392

ggcgagcctt gattgtctga acacataaag caaactgtcc agaagggaaa aaaaaaaaaa   4452

aaaaaaaaa                                                           4461


<210> SEQ ID NO 8
<211> LENGTH: 773
<212> TYPE: PRT
<213> ORGANISM: Homo sapiens

<400> SEQUENCE: 8

Met Glu Thr Asp Glu Ser Pro Ser Pro Leu Pro Cys Gly Pro Ala Gly
1               5                   10                  15

Glu Ala Val Met Glu Ser Arg Ala Arg Pro Phe Gln Ala Leu Pro Arg
```

```
            20                  25                  30

Glu Gln Ser Pro Pro Pro Pro Leu Gln Thr Ser Ser Gly Ala Glu Val
        35                  40                  45

Met Asp Val Gly Ser Gly Gly Asp Gly Gln Ser Glu Leu Pro Ala Glu
    50                  55                  60

Asp Pro Phe Asn Phe Tyr Gly Ala Ser Leu Leu Ser Lys Gly Ser Phe
65                  70                  75                  80

Ser Lys Gly Arg Leu Leu Ile Asp Pro Asn Cys Ser Gly His Ser Pro
                85                  90                  95

Arg Thr Ala Arg His Ala Pro Ala Val Arg Lys Phe Ser Pro Asp Leu
            100                 105                 110

Lys Leu Leu Lys Asp Val Lys Ile Ser Val Ser Phe Thr Glu Ser Cys
        115                 120                 125

Arg Ser Lys Asp Arg Lys Val Leu Tyr Thr Gly Ala Glu Arg Asp Val
    130                 135                 140

Arg Ala Glu Cys Gly Leu Leu Leu Ser Pro Val Ser Gly Asp Val His
145                 150                 155                 160

Ala Cys Pro Phe Gly Gly Ser Val Gly Asp Gly Val Gly Ile Gly Gly
                165                 170                 175

Glu Ser Ala Asp Lys Lys Asp Glu Glu Asn Glu Leu Asp Gln Glu Lys
            180                 185                 190

Arg Val Glu Tyr Ala Val Leu Asp Glu Leu Glu Asp Phe Thr Asp Asn
        195                 200                 205

Leu Glu Leu Asp Glu Glu Gly Ala Gly Gly Phe Thr Ala Lys Ala Ile
    210                 215                 220

Val Gln Arg Asp Arg Val Asp Glu Glu Ala Leu Asn Phe Pro Tyr Glu
225                 230                 235                 240

Asp Asp Phe Asp Asn Asp Val Asp Ala Leu Leu Glu Glu Gly Leu Cys
                245                 250                 255

Ala Pro Lys Lys Arg Arg Thr Glu Glu Lys Tyr Gly Gly Asp Ser Asp
            260                 265                 270

His Pro Ser Asp Gly Glu Thr Ser Val Gln Pro Met Met Thr Lys Ile
        275                 280                 285

Lys Thr Val Leu Lys Ser Arg Gly Arg Pro Pro Thr Glu Pro Leu Pro
    290                 295                 300

Asp Gly Trp Ile Met Thr Phe His Asn Ser Gly Val Pro Val Tyr Leu
305                 310                 315                 320

His Arg Glu Ser Arg Val Val Thr Trp Ser Arg Pro Tyr Phe Leu Gly
                325                 330                 335

Thr Gly Ser Ile Arg Lys His Asp Pro Pro Leu Ser Ser Ile Pro Cys
            340                 345                 350

Leu His Tyr Lys Lys Met Lys Asp Asn Glu Glu Arg Glu Gln Ser Ser
        355                 360                 365

Asp Leu Thr Pro Ser Gly Asp Val Ser Pro Val Lys Pro Leu Ser Arg
    370                 375                 380

Ser Ala Glu Leu Glu Phe Pro Leu Asp Glu Pro Asp Ser Met Gly Ala
385                 390                 395                 400

Asp Pro Gly Pro Pro Asp Glu Lys Asp Pro Leu Gly Ala Glu Ala Ala
                405                 410                 415

Pro Gly Ala Leu Gly Gln Val Lys Ala Lys Val Glu Val Cys Lys Asp
            420                 425                 430

Glu Ser Val Asp Leu Glu Glu Phe Arg Ser Tyr Leu Glu Lys Arg Phe
        435                 440                 445
```

```
Asp Phe Glu Gln Val Thr Val Lys Lys Phe Arg Thr Trp Ala Glu Arg
    450                 455                 460

Arg Gln Phe Asn Arg Glu Met Lys Arg Lys Gln Ala Glu Ser Glu Arg
465                 470                 475                 480

Pro Ile Leu Pro Ala Asn Gln Lys Leu Ile Thr Leu Ser Val Gln Asp
                485                 490                 495

Ala Pro Thr Lys Lys Glu Phe Val Ile Asn Pro Asn Gly Lys Ser Glu
            500                 505                 510

Val Cys Ile Leu His Glu Tyr Met Gln Arg Val Leu Lys Val Arg Pro
        515                 520                 525

Val Tyr Asn Phe Phe Glu Cys Glu Asn Pro Ser Glu Pro Phe Gly Ala
    530                 535                 540

Ser Val Thr Ile Asp Gly Val Thr Tyr Gly Ser Gly Thr Ala Ser Ser
545                 550                 555                 560

Lys Lys Leu Ala Lys Asn Lys Ala Ala Arg Ala Thr Leu Glu Ile Leu
                565                 570                 575

Ile Pro Asp Phe Val Lys Gln Thr Ser Glu Glu Lys Pro Lys Asp Ser
            580                 585                 590

Glu Glu Leu Glu Tyr Phe Asn His Ile Ser Ile Glu Asp Ser Arg Val
        595                 600                 605

Tyr Glu Leu Thr Ser Lys Ala Gly Leu Leu Ser Pro Tyr Gln Ile Leu
    610                 615                 620

His Glu Cys Leu Lys Arg Asn His Gly Met Gly Asp Thr Ser Ile Lys
625                 630                 635                 640

Phe Glu Val Val Pro Gly Lys Asn Gln Lys Ser Glu Tyr Val Met Ala
                645                 650                 655

Cys Gly Lys His Thr Val Arg Gly Trp Cys Lys Asn Lys Arg Val Gly
            660                 665                 670

Lys Gln Leu Ala Ser Gln Lys Ile Leu Gln Leu Leu His Pro His Val
        675                 680                 685

Lys Asn Trp Gly Ser Leu Leu Arg Met Tyr Gly Arg Glu Ser Ser Lys
    690                 695                 700

Met Val Lys Gln Glu Thr Ser Asp Lys Ser Val Ile Glu Leu Gln Gln
705                 710                 715                 720

Tyr Ala Lys Lys Asn Lys Pro Asn Leu His Ile Leu Ser Lys Leu Gln
                725                 730                 735

Glu Glu Met Lys Arg Leu Ala Glu Glu Arg Glu Glu Thr Arg Lys Lys
            740                 745                 750

Pro Lys Met Ser Ile Val Ala Ser Ala Gln Pro Gly Gly Glu Pro Leu
        755                 760                 765

Cys Thr Val Asp Val
    770
```

<210> SEQ ID NO 9
<211> LENGTH: 10323
<212> TYPE: DNA
<213> ORGANISM: Homo sapiens
<220> FEATURE:
<221> NAME/KEY: CDS
<222> LOCATION: (239)..(6007)

<400> SEQUENCE: 9

```
cggaggcgcg gcgcaggctg ctgcaggccc aggtgaatgg agtaacctga cagcggggac      60

gaggcgacgg cgagcgcgag gaaatggcgg cgggggcggc ggcgccgggc ggctccggga     120
```

-continued

```
ggcctgggct gtgacgcgcg cgccggagcg gggtccgatg gttctcgaag gcccgcggcg    180

ccccgtgctg cagtaagctg tgctagaaca aaaatgcaat gaaagaaaca ctggatga      238

atg aaa agc cct gct ttg caa ccc ctc agc atg gca ggc ctg cag ctc      286
Met Lys Ser Pro Ala Leu Gln Pro Leu Ser Met Ala Gly Leu Gln Leu
1               5                   10                  15

atg acc cct gct tcc tca cca atg ggt cct ttc ttt gga ctg cca tgg      334
Met Thr Pro Ala Ser Ser Pro Met Gly Pro Phe Phe Gly Leu Pro Trp
            20                  25                  30

caa caa gaa gca att cat gat aac att tat acg cca aga aaa tat cag      382
Gln Gln Glu Ala Ile His Asp Asn Ile Tyr Thr Pro Arg Lys Tyr Gln
        35                  40                  45

gtt gaa ctg ctt gaa gca gct ctg gat cat aat acc atc gtc tgt tta      430
Val Glu Leu Leu Glu Ala Ala Leu Asp His Asn Thr Ile Val Cys Leu
    50                  55                  60

aac act ggc tca ggg aag aca ttt att gca gta cta ctc act aaa gag      478
Asn Thr Gly Ser Gly Lys Thr Phe Ile Ala Val Leu Leu Thr Lys Glu
65                  70                  75                  80

ctg tcc tat cag atc agg gga gac ttc agc aga aat gga aaa agg acg      526
Leu Ser Tyr Gln Ile Arg Gly Asp Phe Ser Arg Asn Gly Lys Arg Thr
                85                  90                  95

gtg ttc ttg gtc aac tct gca aac cag gtt gct caa caa gtg tca gct      574
Val Phe Leu Val Asn Ser Ala Asn Gln Val Ala Gln Gln Val Ser Ala
            100                 105                 110

gtc aga act cat tca gat ctc aag gtt ggg gaa tac tca aac cta gaa      622
Val Arg Thr His Ser Asp Leu Lys Val Gly Glu Tyr Ser Asn Leu Glu
        115                 120                 125

gta aat gca tct tgg aca aaa gag aga tgg aac caa gag ttt act aag      670
Val Asn Ala Ser Trp Thr Lys Glu Arg Trp Asn Gln Glu Phe Thr Lys
    130                 135                 140

cac cag gtt ctc att atg act tgc tat gtc gcc ttg aat gtt ttg aaa      718
His Gln Val Leu Ile Met Thr Cys Tyr Val Ala Leu Asn Val Leu Lys
145                 150                 155                 160

aat ggt tac tta tca ctg tca gac att aac ctt ttg gtg ttt gat gag      766
Asn Gly Tyr Leu Ser Leu Ser Asp Ile Asn Leu Leu Val Phe Asp Glu
                165                 170                 175

tgt cat ctt gca atc cta gac cac ccc tat cga gaa att atg aag ctc      814
Cys His Leu Ala Ile Leu Asp His Pro Tyr Arg Glu Ile Met Lys Leu
            180                 185                 190

tgt gaa aat tgt cca tca tgt cct cgc att ttg gga cta act gct tcc      862
Cys Glu Asn Cys Pro Ser Cys Pro Arg Ile Leu Gly Leu Thr Ala Ser
        195                 200                 205

att tta aat ggg aaa tgt gat cca gag gaa ttg gaa gaa aag att cag      910
Ile Leu Asn Gly Lys Cys Asp Pro Glu Glu Leu Glu Glu Lys Ile Gln
    210                 215                 220

aaa cta gag aaa att ctt aag agt aat gct gaa act gca act gac ctg      958
Lys Leu Glu Lys Ile Leu Lys Ser Asn Ala Glu Thr Ala Thr Asp Leu
225                 230                 235                 240

gtg gtc tta gac agg tat act tct cag cca tgt gag att gtg gtg gat     1006
Val Val Leu Asp Arg Tyr Thr Ser Gln Pro Cys Glu Ile Val Val Asp
                245                 250                 255

tgt gga cca ttt act gac aga agt ggg ctt tat gaa aga ctg ctg atg     1054
Cys Gly Pro Phe Thr Asp Arg Ser Gly Leu Tyr Glu Arg Leu Leu Met
            260                 265                 270

gaa tta gaa gaa gca ctt aat ttt atc aat gat tgt aat ata tct gta     1102
Glu Leu Glu Glu Ala Leu Asn Phe Ile Asn Asp Cys Asn Ile Ser Val
        275                 280                 285

cat tca aaa gaa aga gat tct act tta att tcg aaa cag ata cta tca     1150
His Ser Lys Glu Arg Asp Ser Thr Leu Ile Ser Lys Gln Ile Leu Ser
    290                 295                 300
```

```
gac tgt cgt gcc gta ttg gta gtt ctg gga ccc tgg tgt gca gat aaa     1198
Asp Cys Arg Ala Val Leu Val Val Leu Gly Pro Trp Cys Ala Asp Lys
305                 310                 315                 320

gta gct gga atg atg gta aga gaa cta cag aaa tac atc aaa cat gag     1246
Val Ala Gly Met Met Val Arg Glu Leu Gln Lys Tyr Ile Lys His Glu
                325                 330                 335

caa gag gag ctg cac agg aaa ttt tta ttg ttt aca gac act ttc cta     1294
Gln Glu Glu Leu His Arg Lys Phe Leu Leu Phe Thr Asp Thr Phe Leu
            340                 345                 350

agg aaa ata cat gca cta tgt gaa gag cac ttc tca cct gcc tca ctt     1342
Arg Lys Ile His Ala Leu Cys Glu Glu His Phe Ser Pro Ala Ser Leu
        355                 360                 365

gac ctg aaa ttt gta act cct aaa gta atc aaa ctg ctc gaa atc tta     1390
Asp Leu Lys Phe Val Thr Pro Lys Val Ile Lys Leu Leu Glu Ile Leu
    370                 375                 380

cgc aaa tat aaa cca tat gag cga cag cag ttt gaa agc gtt gag tgg     1438
Arg Lys Tyr Lys Pro Tyr Glu Arg Gln Gln Phe Glu Ser Val Glu Trp
385                 390                 395                 400

tat aat aat aga aat cag gat aat tat gtg tca tgg agt gat tct gag     1486
Tyr Asn Asn Arg Asn Gln Asp Asn Tyr Val Ser Trp Ser Asp Ser Glu
                405                 410                 415

gat gat gat gag gat gaa gaa att gaa gaa aaa gag aag cca gag aca     1534
Asp Asp Asp Glu Asp Glu Glu Ile Glu Glu Lys Glu Lys Pro Glu Thr
            420                 425                 430

aat ttt cct tct cct ttt acc aac att ttg tgc gga att att ttt gtg     1582
Asn Phe Pro Ser Pro Phe Thr Asn Ile Leu Cys Gly Ile Ile Phe Val
        435                 440                 445

gaa aga aga tac aca gca gtt gtc tta aac aga ttg ata aag gaa gct     1630
Glu Arg Arg Tyr Thr Ala Val Val Leu Asn Arg Leu Ile Lys Glu Ala
    450                 455                 460

ggc aaa caa gat cca gag ctg gct tat atc agt agc aat ttc ata act     1678
Gly Lys Gln Asp Pro Glu Leu Ala Tyr Ile Ser Ser Asn Phe Ile Thr
465                 470                 475                 480

gga cat ggc att ggg aag aat cag cct cgc aac aaa cag atg gaa gca     1726
Gly His Gly Ile Gly Lys Asn Gln Pro Arg Asn Lys Gln Met Glu Ala
                485                 490                 495

gaa ttc aga aaa cag gaa gag gta ctt agg aaa ttt cga gca cat gag     1774
Glu Phe Arg Lys Gln Glu Glu Val Leu Arg Lys Phe Arg Ala His Glu
            500                 505                 510

acc aac ctg ctt att gca aca agt att gta gaa gag ggt gtt gat ata     1822
Thr Asn Leu Leu Ile Ala Thr Ser Ile Val Glu Glu Gly Val Asp Ile
        515                 520                 525

cca aaa tgc aac ttg gtg gtt cgt ttt gat ttg ccc aca gaa tat cga     1870
Pro Lys Cys Asn Leu Val Val Arg Phe Asp Leu Pro Thr Glu Tyr Arg
    530                 535                 540

tcc tat gtt caa tct aaa gga aga gca agg gca ccc atc tct aat tat     1918
Ser Tyr Val Gln Ser Lys Gly Arg Ala Arg Ala Pro Ile Ser Asn Tyr
545                 550                 555                 560

ata atg tta gcg gat aca gac aaa ata aaa agt ttt gaa gaa gac ctt     1966
Ile Met Leu Ala Asp Thr Asp Lys Ile Lys Ser Phe Glu Glu Asp Leu
                565                 570                 575

aaa acc tac aaa gct att gaa aag atc ttg aga aac aag tgt tcc aag     2014
Lys Thr Tyr Lys Ala Ile Glu Lys Ile Leu Arg Asn Lys Cys Ser Lys
            580                 585                 590

tcg gtt gat act ggt gag act gac att gat cct gtc atg gat gat gat     2062
Ser Val Asp Thr Gly Glu Thr Asp Ile Asp Pro Val Met Asp Asp Asp
        595                 600                 605

gac gtt ttc cca cca tat gtg ttg agg cct gac gat ggt ggt cca cga     2110
Asp Val Phe Pro Pro Tyr Val Leu Arg Pro Asp Asp Gly Gly Pro Arg
```

```
    610                 615                 620

gtc aca atc aac acg gcc att gga cac atc aat aga tac tgt gct aga     2158
Val Thr Ile Asn Thr Ala Ile Gly His Ile Asn Arg Tyr Cys Ala Arg
625                 630                 635                 640

tta cca agt gat ccg ttt act cat cta gct cct aaa tgc aga acc cga     2206
Leu Pro Ser Asp Pro Phe Thr His Leu Ala Pro Lys Cys Arg Thr Arg
                645                 650                 655

gag ttg cct gat ggt aca ttt tat tca act ctt tat ctg cca att aac     2254
Glu Leu Pro Asp Gly Thr Phe Tyr Ser Thr Leu Tyr Leu Pro Ile Asn
            660                 665                 670

tca cct ctt cga gcc tcc att gtt ggt cca cca atg agc tgt gta cga     2302
Ser Pro Leu Arg Ala Ser Ile Val Gly Pro Pro Met Ser Cys Val Arg
        675                 680                 685

ttg gct gaa aga gtt gta gct ctc att tgc tgt gag aaa ctg cac aaa     2350
Leu Ala Glu Arg Val Val Ala Leu Ile Cys Cys Glu Lys Leu His Lys
    690                 695                 700

att ggc gaa ctg gat gac cat ttg atg cca gtt ggg aaa gag act gtt     2398
Ile Gly Glu Leu Asp Asp His Leu Met Pro Val Gly Lys Glu Thr Val
705                 710                 715                 720

aaa tat gaa gag gag ctt gat ttg cat gat gaa gaa gag acc agt gtt     2446
Lys Tyr Glu Glu Glu Leu Asp Leu His Asp Glu Glu Glu Thr Ser Val
                725                 730                 735

cca gga aga cca ggt tcc acg aaa cga agg cag tgc tac cca aaa gca     2494
Pro Gly Arg Pro Gly Ser Thr Lys Arg Arg Gln Cys Tyr Pro Lys Ala
            740                 745                 750

att cca gag tgt ttg agg gat agt tat ccc aga cct gat cag ccc tgt     2542
Ile Pro Glu Cys Leu Arg Asp Ser Tyr Pro Arg Pro Asp Gln Pro Cys
        755                 760                 765

tac ctg tat gtg ata gga atg gtt tta act aca cct tta cct gat gaa     2590
Tyr Leu Tyr Val Ile Gly Met Val Leu Thr Thr Pro Leu Pro Asp Glu
    770                 775                 780

ctc aac ttt aga agg cgg aag ctc tat cct cct gaa gat acc aca aga     2638
Leu Asn Phe Arg Arg Arg Lys Leu Tyr Pro Pro Glu Asp Thr Thr Arg
785                 790                 795                 800

tgc ttt gga ata ctg acg gcc aaa ccc ata cct cag att cca cac ttt     2686
Cys Phe Gly Ile Leu Thr Ala Lys Pro Ile Pro Gln Ile Pro His Phe
                805                 810                 815

cct gtg tac aca cgc tct gga gag gtt acc ata tcc att gag ttg aag     2734
Pro Val Tyr Thr Arg Ser Gly Glu Val Thr Ile Ser Ile Glu Leu Lys
            820                 825                 830

aag tct ggt ttc atg ttg tct cta caa atg ctt gag ttg att aca aga     2782
Lys Ser Gly Phe Met Leu Ser Leu Gln Met Leu Glu Leu Ile Thr Arg
        835                 840                 845

ctt cac cag tat ata ttc tca cat att ctt cgg ctt gaa aaa cct gca     2830
Leu His Gln Tyr Ile Phe Ser His Ile Leu Arg Leu Glu Lys Pro Ala
    850                 855                 860

cta gaa ttt aaa cct aca gac gct gat tca gca tac tgt gtt cta cct     2878
Leu Glu Phe Lys Pro Thr Asp Ala Asp Ser Ala Tyr Cys Val Leu Pro
865                 870                 875                 880

ctt aat gtt gtt aat gac tcc agc act ttg gat att gac ttt aaa ttc     2926
Leu Asn Val Val Asn Asp Ser Ser Thr Leu Asp Ile Asp Phe Lys Phe
                885                 890                 895

atg gaa gat att gag aag tct gaa gct cgc ata ggc att ccc agt aca     2974
Met Glu Asp Ile Glu Lys Ser Glu Ala Arg Ile Gly Ile Pro Ser Thr
            900                 905                 910

aag tat aca aaa gaa aca ccc ttt gtt ttt aaa tta gaa gat tac caa     3022
Lys Tyr Thr Lys Glu Thr Pro Phe Val Phe Lys Leu Glu Asp Tyr Gln
        915                 920                 925

gat gcc gtt atc att cca aga tat cgc aat ttt gat cag cct cat cga     3070
```

```
Asp Ala Val Ile Ile Pro Arg Tyr Arg Asn Phe Asp Gln Pro His Arg
    930                 935                 940

ttt tat gta gct gat gtg tac act gat ctt acc cca ctc agt aaa ttt     3118
Phe Tyr Val Ala Asp Val Tyr Thr Asp Leu Thr Pro Leu Ser Lys Phe
945                 950                 955                 960

cct tcc cct gag tat gaa act ttt gca gaa tat tat aaa aca aag tac     3166
Pro Ser Pro Glu Tyr Glu Thr Phe Ala Glu Tyr Tyr Lys Thr Lys Tyr
                965                 970                 975

aac ctt gac cta acc aat ctc aac cag cca ctg ctg gat gtg gac cac     3214
Asn Leu Asp Leu Thr Asn Leu Asn Gln Pro Leu Leu Asp Val Asp His
            980                 985                 990

aca tct tca aga ctt aat ctt ttg  aca cct cga cat ttg  aat cag aag   3262
Thr Ser Ser Arg Leu Asn Leu Leu  Thr Pro Arg His Leu  Asn Gln Lys
        995                 1000                1005

ggg aaa  gcg ctt cct tta agc  agt gct gag aag agg  aaa gcc aaa      3307
Gly Lys  Ala Leu Pro Leu Ser  Ser Ala Glu Lys Arg  Lys Ala Lys
    1010                1015                1020

tgg gaa  agt ctg cag aat aaa  cag ata ctg gtt cca  gaa ctc tgt      3352
Trp Glu  Ser Leu Gln Asn Lys  Gln Ile Leu Val Pro  Glu Leu Cys
    1025                1030                1035

gct ata  cat cca att cca gca  tca ctg tgg aga aaa  gct gtt tgt      3397
Ala Ile  His Pro Ile Pro Ala  Ser Leu Trp Arg Lys  Ala Val Cys
    1040                1045                1050

ctc ccc  agc ata ctt tat cgc  ctt cac tgc ctt ttg  act gca gag      3442
Leu Pro  Ser Ile Leu Tyr Arg  Leu His Cys Leu Leu  Thr Ala Glu
    1055                1060                1065

gag cta  aga gcc cag act gcc  agc gat gct ggc gtg  gga gtc aga      3487
Glu Leu  Arg Ala Gln Thr Ala  Ser Asp Ala Gly Val  Gly Val Arg
    1070                1075                1080

tca ctt  cct gcg gat ttt aga  tac cct aac tta gac  ttc ggg tgg      3532
Ser Leu  Pro Ala Asp Phe Arg  Tyr Pro Asn Leu Asp  Phe Gly Trp
    1085                1090                1095

aaa aaa  tct att gac agc aaa  tct ttc atc tca att  tct aac tcc      3577
Lys Lys  Ser Ile Asp Ser Lys  Ser Phe Ile Ser Ile  Ser Asn Ser
    1100                1105                1110

tct tca  gct gaa aat gat aat  tac tgt aag cac agc  aca att gtc      3622
Ser Ser  Ala Glu Asn Asp Asn  Tyr Cys Lys His Ser  Thr Ile Val
    1115                1120                1125

cct gaa  aat gct gca cat caa  ggt gct aat aga acc  tcc tct cta      3667
Pro Glu  Asn Ala Ala His Gln  Gly Ala Asn Arg Thr  Ser Ser Leu
    1130                1135                1140

gaa aat  cat gac caa atg tct  gtg aac tgc aga acg  ttg ctc agc      3712
Glu Asn  His Asp Gln Met Ser  Val Asn Cys Arg Thr  Leu Leu Ser
    1145                1150                1155

gag tcc  cct ggt aag ctc cac  gtt gaa gtt tca gca  gat ctt aca      3757
Glu Ser  Pro Gly Lys Leu His  Val Glu Val Ser Ala  Asp Leu Thr
    1160                1165                1170

gca att  aat ggt ctt tct tac  aat caa aat ctc gcc  aat ggc agt      3802
Ala Ile  Asn Gly Leu Ser Tyr  Asn Gln Asn Leu Ala  Asn Gly Ser
    1175                1180                1185

tat gat  tta gct aac aga gac  ttt tgc caa gga aat  cag cta aat      3847
Tyr Asp  Leu Ala Asn Arg Asp  Phe Cys Gln Gly Asn  Gln Leu Asn
    1190                1195                1200

tac tac  aag cag gaa ata ccc  gtg caa cca act acc  tca tat tcc      3892
Tyr Tyr  Lys Gln Glu Ile Pro  Val Gln Pro Thr Thr  Ser Tyr Ser
    1205                1210                1215

att cag  aat tta tac agt tac  gag aac cag ccc cag  ccc agc gat      3937
Ile Gln  Asn Leu Tyr Ser Tyr  Glu Asn Gln Pro Gln  Pro Ser Asp
    1220                1225                1230
```

```
gaa tgt  act ctc ctg agt aat  aaa tac ctt gat gga  aat gct aac      3982
Glu Cys  Thr Leu Leu Ser Asn  Lys Tyr Leu Asp Gly  Asn Ala Asn
    1235                 1240                 1245

aaa tct  acc tca gat gga agt  cct gtg atg gcc gta  atg cct ggt      4027
Lys Ser  Thr Ser Asp Gly Ser  Pro Val Met Ala Val  Met Pro Gly
    1250                 1255                 1260

acg aca  gac act att caa gtg  ctc aag ggc agg atg  gat tct gag      4072
Thr Thr  Asp Thr Ile Gln Val  Leu Lys Gly Arg Met  Asp Ser Glu
    1265                 1270                 1275

cag agc  cct tct att ggg tac  tcc tca agg act ctt  ggc ccc aat      4117
Gln Ser  Pro Ser Ile Gly Tyr  Ser Ser Arg Thr Leu  Gly Pro Asn
    1280                 1285                 1290

cct gga  ctt att ctt cag gct  ttg act ctg tca aac  gct agt gat      4162
Pro Gly  Leu Ile Leu Gln Ala  Leu Thr Leu Ser Asn  Ala Ser Asp
    1295                 1300                 1305

gga ttt  aac ctg gag cgg ctt  gaa atg ctt ggc gac  tcc ttt tta      4207
Gly Phe  Asn Leu Glu Arg Leu  Glu Met Leu Gly Asp  Ser Phe Leu
    1310                 1315                 1320

aag cat  gcc atc acc aca tat  cta ttt tgc act tac  cct gat gcg      4252
Lys His  Ala Ile Thr Thr Tyr  Leu Phe Cys Thr Tyr  Pro Asp Ala
    1325                 1330                 1335

cat gag  ggc cgc ctt tca tat  atg aga agc aaa aag  gtc agc aac      4297
His Glu  Gly Arg Leu Ser Tyr  Met Arg Ser Lys Lys  Val Ser Asn
    1340                 1345                 1350

tgt aat  ctg tat cgc ctt gga  aaa aag aag gga cta  ccc agc cgc      4342
Cys Asn  Leu Tyr Arg Leu Gly  Lys Lys Lys Gly Leu  Pro Ser Arg
    1355                 1360                 1365

atg gtg  gtg tca ata ttt gat  ccc cct gtg aat tgg  ctt cct cct      4387
Met Val  Val Ser Ile Phe Asp  Pro Pro Val Asn Trp  Leu Pro Pro
    1370                 1375                 1380

ggt tat  gta gta aat caa gac  aaa agc aac aca gat  aaa tgg gaa      4432
Gly Tyr  Val Val Asn Gln Asp  Lys Ser Asn Thr Asp  Lys Trp Glu
    1385                 1390                 1395

aaa gat  gaa atg aca aaa gac  tgc atg ctg gcg aat  ggc aaa ctg      4477
Lys Asp  Glu Met Thr Lys Asp  Cys Met Leu Ala Asn  Gly Lys Leu
    1400                 1405                 1410

gat gag  gat tac gag gag gag  gat gag gag gag gag  agc ctg atg      4522
Asp Glu  Asp Tyr Glu Glu Glu  Asp Glu Glu Glu Glu  Ser Leu Met
    1415                 1420                 1425

tgg agg  gct ccg aag gaa gag  gct gac tat gaa gat  gat ttc ctg      4567
Trp Arg  Ala Pro Lys Glu Glu  Ala Asp Tyr Glu Asp  Asp Phe Leu
    1430                 1435                 1440

gag tat  gat cag gaa cat atc  aga ttt ata gat aat  atg tta atg      4612
Glu Tyr  Asp Gln Glu His Ile  Arg Phe Ile Asp Asn  Met Leu Met
    1445                 1450                 1455

ggg tca  gga gct ttt gta aag  aaa atc tct ctt tct  cct ttt tca      4657
Gly Ser  Gly Ala Phe Val Lys  Lys Ile Ser Leu Ser  Pro Phe Ser
    1460                 1465                 1470

acc act  gat tct gca tat gaa  tgg aaa atg ccc aaa  aaa tcc tcc      4702
Thr Thr  Asp Ser Ala Tyr Glu  Trp Lys Met Pro Lys  Lys Ser Ser
    1475                 1480                 1485

tta ggt  agt atg cca ttt tca  tca gat ttt gag gat  ttt gac tac      4747
Leu Gly  Ser Met Pro Phe Ser  Ser Asp Phe Glu Asp  Phe Asp Tyr
    1490                 1495                 1500

agc tct  tgg gat gca atg tgc  tat ctg gat cct agc  aaa gct gtt      4792
Ser Ser  Trp Asp Ala Met Cys  Tyr Leu Asp Pro Ser  Lys Ala Val
    1505                 1510                 1515

gaa gaa  gat gac ttt gtg gtg  ggg ttc tgg aat cca  tca gaa gaa      4837
Glu Glu  Asp Asp Phe Val Val  Gly Phe Trp Asn Pro  Ser Glu Glu
    1520                 1525                 1530
```

```
aac tgt  ggt gtt gac acg gga  aag cag tcc att tct  tac gac ttg      4882
Asn Cys  Gly Val Asp Thr Gly  Lys Gln Ser Ile Ser  Tyr Asp Leu
    1535                 1540                 1545

cac act  gag cag tgt att gct  gac aaa agc ata gcg  gac tgt gtg      4927
His Thr  Glu Gln Cys Ile Ala  Asp Lys Ser Ile Ala  Asp Cys Val
    1550                 1555                 1560

gaa gcc  ctg ctg ggc tgc tat  tta acc agc tgt ggg  gag agg gct      4972
Glu Ala  Leu Leu Gly Cys Tyr  Leu Thr Ser Cys Gly  Glu Arg Ala
    1565                 1570                 1575

gct cag  ctt ttc ctc tgt tca  ctg ggg ctg aag gtg  ctc ccg gta      5017
Ala Gln  Leu Phe Leu Cys Ser  Leu Gly Leu Lys Val  Leu Pro Val
    1580                 1585                 1590

att aaa  agg act gat cgg gaa  aag gcc ctg tgc cct  act cgg gag      5062
Ile Lys  Arg Thr Asp Arg Glu  Lys Ala Leu Cys Pro  Thr Arg Glu
    1595                 1600                 1605

aat ttc  aac agc caa caa aag  aac ctt tca gtg agc  tgt gct gct      5107
Asn Phe  Asn Ser Gln Gln Lys  Asn Leu Ser Val Ser  Cys Ala Ala
    1610                 1615                 1620

gct tct  gtg gcc agt tca cgc  tct tct gta ttg aaa  gac tcg gaa      5152
Ala Ser  Val Ala Ser Ser Arg  Ser Ser Val Leu Lys  Asp Ser Glu
    1625                 1630                 1635

tat ggt  tgt ttg aag att cca  cca aga tgt atg ttt  gat cat cca      5197
Tyr Gly  Cys Leu Lys Ile Pro  Pro Arg Cys Met Phe  Asp His Pro
    1640                 1645                 1650

gat gca  gat aaa aca ctg aat  cac ctt ata tcg ggg  ttt gaa aat      5242
Asp Ala  Asp Lys Thr Leu Asn  His Leu Ile Ser Gly  Phe Glu Asn
    1655                 1660                 1665

ttt gaa  aag aaa atc aac tac  aga ttc aag aat aag  gct tac ctt      5287
Phe Glu  Lys Lys Ile Asn Tyr  Arg Phe Lys Asn Lys  Ala Tyr Leu
    1670                 1675                 1680

ctc cag  gct ttt aca cat gcc  tcc tac cac tac aat  act atc act      5332
Leu Gln  Ala Phe Thr His Ala  Ser Tyr His Tyr Asn  Thr Ile Thr
    1685                 1690                 1695

gat tgt  tac cag cgc tta gaa  ttc ctg gga gat gcg  att ttg gac      5377
Asp Cys  Tyr Gln Arg Leu Glu  Phe Leu Gly Asp Ala  Ile Leu Asp
    1700                 1705                 1710

tac ctc  ata acc aag cac ctt  tat gaa gac ccg cgg  cag cac tcc      5422
Tyr Leu  Ile Thr Lys His Leu  Tyr Glu Asp Pro Arg  Gln His Ser
    1715                 1720                 1725

ccg ggg  gtc ctg aca gac ctg  cgg tct gcc ctg gtc  aac aac acc      5467
Pro Gly  Val Leu Thr Asp Leu  Arg Ser Ala Leu Val  Asn Asn Thr
    1730                 1735                 1740

atc ttt  gca tcg ctg gct gta  aag tac gac tac cac  aag tac ttc      5512
Ile Phe  Ala Ser Leu Ala Val  Lys Tyr Asp Tyr His  Lys Tyr Phe
    1745                 1750                 1755

aaa gct  gtc tct cct gag ctc  ttc cat gtc att gat  gac ttt gtg      5557
Lys Ala  Val Ser Pro Glu Leu  Phe His Val Ile Asp  Asp Phe Val
    1760                 1765                 1770

cag ttt  cag ctt gag aag aat  gaa atg caa gga atg  gat tct gag      5602
Gln Phe  Gln Leu Glu Lys Asn  Glu Met Gln Gly Met  Asp Ser Glu
    1775                 1780                 1785

ctt agg  aga tct gag gag gat  gaa gag aaa gaa gag  gat att gaa      5647
Leu Arg  Arg Ser Glu Glu Asp  Glu Glu Lys Glu Glu  Asp Ile Glu
    1790                 1795                 1800

gtt cca  aag gcc atg ggg gat  att ttt gag tcg ctt  gct ggt gcc      5692
Val Pro  Lys Ala Met Gly Asp  Ile Phe Glu Ser Leu  Ala Gly Ala
    1805                 1810                 1815

att tac  atg gat agt ggg atg  tca ctg gag aca gtc  tgg cag gtg      5737
Ile Tyr  Met Asp Ser Gly Met  Ser Leu Glu Thr Val  Trp Gln Val
```

```
    1820                1825                1830

tac tat  ccc atg atg cgg cca  cta ata gaa aag ttt  tct gca aat      5782
Tyr Tyr  Pro Met Met Arg Pro  Leu Ile Glu Lys Phe  Ser Ala Asn
    1835                1840                1845

gta ccc  cgt tcc cct gtg cga  gaa ttg ctt gaa atg  gaa cca gaa      5827
Val Pro  Arg Ser Pro Val Arg  Glu Leu Leu Glu Met  Glu Pro Glu
    1850                1855                1860

act gcc  aaa ttt agc ccg gct  gag aga act tac gac  ggg aag gtc      5872
Thr Ala  Lys Phe Ser Pro Ala  Glu Arg Thr Tyr Asp  Gly Lys Val
    1865                1870                1875

aga gtc  act gtg gaa gta gta  gga aag ggg aaa ttt  aaa ggt gtt      5917
Arg Val  Thr Val Glu Val Val  Gly Lys Gly Lys Phe  Lys Gly Val
    1880                1885                1890

ggt cga  agt tac agg att gcc  aaa tct gca gca gca  aga aga gcc      5962
Gly Arg  Ser Tyr Arg Ile Ala  Lys Ser Ala Ala Ala  Arg Arg Ala
    1895                1900                1905

ctc cga  agc ctc aaa gct aat  caa cct cag gtt ccc  aat agc tga      6007
Leu Arg  Ser Leu Lys Ala Asn  Gln Pro Gln Val Pro  Asn Ser
    1910                1915                1920

aaccgctttt taaaattcaa aacaagaaac aaaacaaaaa aaattaaggg gaaaattatt   6067

taaatcggaa aggaagactt aaagttgtta gtgagtggaa tgaattgaag gcagaattta   6127

aagtttggtt gataacagga tagataacag aataaaacat ttaacatatg tataaaattt   6187

tggaactaat tgtagtttta gttttttgcg caaacacaat cttatcttct ttcctcactt   6247

ctgctttgtt taaatcacaa gagtgcttta atgatgacat ttagcaagtg ctcaaaataa   6307

ttgacaggtt ttgttttttt tttttgagt ttatgtcagc tttgcttagt gttagaaggc    6367

catggagctt aaacctccag cagtccctag gatgatgtag attcttctcc atctctccgt   6427

gtgtgcagta gtgccagtcc tgcagtagtt gataagctga atagaaagat aaggttttcg   6487

agaggagaag tgcgccaatg ttgtcttttc tttccacgtt atactgtgta aggtgatgtt   6547

cccggtcgct gttgcacctg atagtaaggg acagattttt aatgaacatt ggctggcatg   6607

ttggtgaatc acattttagt tttctgatgc cacatagtct tgcataaaaa agggttcttg   6667

ccttaaaagt gaaaccttca tggatagtct ttaatctctg atctttttgg aacaaactgt   6727

tttacattcc tttcatttta ttatgcatta gacgttgaga cagcgtgata cttacaactc   6787

actagtatag ttgtaactta ttacaggatc atactaaaat ttctgtcata tgtatactga   6847

agacatttta aaaaccagaa tatgtagtct acggatattt tttatcataa aaatgatctt   6907

tggctaaaca ccccatttta ctaaagtcct cctgccaggt agttcccact gatggaaatg   6967

tttatggcaa ataattttgc cttctaggct gttgctctaa caaaataaac cttagacata   7027

tcacacctaa aatatgctgc agattttata attgattggt tacttattta agaagcaaaa   7087

cacagcacct ttacccttag tctcctcaca taaatttctt actatacttt tcataatgtt   7147

gcatgcatat ttcacctacc aaagctgtgc tgttaatgcc gtgaaagttt aacgtttgcg   7207

ataaactgcc gtaattttga tacatctgtg atttaggtca ttaatttaga taaactagct   7267

cattatttcc atctttggaa aaggaaaaaa aaaaaaactt ctttaggcat ttgcctaagt   7327

ttctttaatt agacttgtag gcactcttca cttaaatacc tcagttcttc ttttcttttg   7387

catgcatttt tcccctgttt ggtgctatgt ttatgtatta tgcttgaaat tttaattttt   7447

tttttttgc actgtaacta taatacctct taatttacct ttttaaaagc tgtgggtcag    7507

tcttgcactc ccatcaacat accagtagag gtttgctgca atttgccccg ttaattatgc   7567

ttgaagttta agaaagctga gcagaggtgt ctcatatttc ccagcacatg attctgaact   7627
```

-continued

```
tgatgcttcg tggaatgctg catttatatg taagtgacat ttgaatactg tccttcctgc   7687
tttatctgca tcatccaccc acagagaaat gcctctgtgc gagtgcaccg acagaaaact   7747
gtcagctctg ctttctaagg aaccctgagt gagggggta ttaagcttct ccagtgtttt    7807
ttgttgtctc caatcttaaa cttaaattga gatctaaatt attaaacgag tttttgagca   7867
aattaggtga cttgttttaa aaatatttaa ttccgatttg gaaccttaga tgtctatttg   7927
attttttaaa aaaccttaat gtaagatatg accagttaaa acaaagcaat tcttgaatta   7987
tataactgta aaagtgtgca gttaacaagg ctggatgtga attttattct gagggtgatt   8047
tgtgatcaag tttaatcaca aatctcttaa tatttataaa ctacctgatg ccaggagctt   8107
agggctttgc attgtgtcta atacattgat cccagtgtta cgggattctc ttgattcctg   8167
gcaccaaaat cagattgttt tcacagttat gattcccagt gggagaaaaa tgcctcaata   8227
tatttgtaac cttaagaaga gtattttttt gttaatacta agatgttcaa acttagacat   8287
gattaggtca tacattctca ggggttcaaa tttccttcta ccattcaaat gttttatcaa   8347
cagcaaactt cagccgtttc actttttgtt ggagaaaaat agtagatttt aatttgactc   8407
acagtttgaa gcattctgtg atcccctggt tactgagtta aaaaataaaa aagtacgagt   8467
tagacatatg aaatggttat gaacgctttt gtgctgctga tttttaatgc tgtaaagttt   8527
tcctgtgttt agcttgttga aatgttttgc atctgtcaat taaggaaaaa aaaaatcact   8587
ctatgttgcc ccactttaga gccctgtgtg ccaccctgtg ttcctgtgat tgcaatgtga   8647
gaccgaatgt aatatggaaa acctaccagt ggggtgtggt tgtgccctga gcacgtgtgt   8707
aaaggactgg ggaggcgtgt cttgaaaaag caactgcaga aattccttat gatgattgtg   8767
tgcaagttag ttaacatgaa ccttcatttg taaatttttt aaaatttctt ttataatatg   8827
ctttccgcag tcctaactat gctgcgtttt ataatagctt tttcccttct gttctgttca   8887
tgtagcacag ataagcattg cacttggtac catgctttac ctcatttcaa gaaaatatgc   8947
ttaacagaga ggaaaaaaat gtggtttggc cttgctgctg ttttgattta tggaatttga   9007
aaaagataat tataatgcct gcaatgtgtc atatactcgc acaacttaaa taggtcattt   9067
ttgtctgtgg catttttact gtttgtgaaa gtatgaaaca gatttgttaa ctgaactctt   9127
aattatgttt ttaaaatgtt tgttatattt cttttctttt ttcttttata ttacgtgaag   9187
tgatgaaatt tagaatgacc tctaacactc ctgtaattgt cttttaaaat actgatattt   9247
ttatttgtta ataatacttt gccctcagaa agattctgat accctgcctt gacaacatga   9307
aacttgaggc tgctttggtt catgaatcca ggtgttcccc cggcagtcgg cttcttcagt   9367
cgctccctgg aggcaggtgg gcactgcaga ggatcactgg aatccagatc gagcgcagtt   9427
catgcacaag gccccgttga tttaaaatat tggatcttgc tctgttaggg tgtctaatcc   9487
ctttacacaa gattgaagcc accaaactga gaccttgata ccttttttta actgcatctg   9547
aaattatgtt aagagtcttt aacccatttg cattatctgc agaagagaaa ctcatgtcat   9607
gtttattacc tatatggttg ttttaattac atttgaataa ttatattttt ccaaccactg   9667
attacttttc aggaatttaa ttatttccag ataaatttct ttattttata ttgtacatga   9727
aaagttttaa agatatgttt aagaccaaga ctattaaaat gatttttaaa gttgttggag   9787
acgccaatag caatatctag gaaatttgca ttgagaccat tgtattttcc actagcagtg   9847
aaaatgattt ttcacaacta acttgtaaat atattttaat cattacttct ttttttctag   9907
tccattttta tttggacatc aaccacagac aatttaaatt ttatagatgc actaagaatt   9967
```

```
cactgcagca gcaggttaca tagcaaaaat gcaaaggtga acaggaagta aatttctggc  10027

ttttctgctg taaatagtga aggaaaatta ctaaaatcaa gtaaaactaa tgcatattat  10087

ttgattgaca ataaaatatt taccatcaca tgctgcagct gttttttaag gaacatgatg  10147

tcattcattc atacagtaat catgctgcag aaatttgcag tctgcacctt atggatcaca  10207

attaccttta gttgtttttt ttgtaataat tgtagccaag taaatctcca ataaagttat  10267

cgtctgttca aaaaaaaaaa aaaaaaaaaa aaaaaaaaaa aaaaaaaaaa aaaaaa      10323
```

```
<210> SEQ ID NO 10
<211> LENGTH: 1922
<212> TYPE: PRT
<213> ORGANISM: Homo sapiens

<400> SEQUENCE: 10

Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

Asn Thr Gly Ser Gly Lys Thr Phe Ile Ala Val Leu Leu Thr Lys Glu
65                  70                  75                  80

Leu Ser Tyr Gln Ile Arg Gly Asp Phe Ser Arg Asn Gly Lys Arg Thr
                85                  90                  95

Val Phe Leu Val Asn Ser Ala Asn Gln Val Ala Gln Gln Val Ser Ala
            100                 105                 110

Val Arg Thr His Ser Asp Leu Lys Val Gly Glu Tyr Ser Asn Leu Glu
        115                 120                 125

Val Asn Ala Ser Trp Thr Lys Glu Arg Trp Asn Gln Glu Phe Thr Lys
    130                 135                 140

His Gln Val Leu Ile Met Thr Cys Tyr Val Ala Leu Asn Val Leu Lys
145                 150                 155                 160

Asn Gly Tyr Leu Ser Leu Ser Asp Ile Asn Leu Leu Val Phe Asp Glu
                165                 170                 175

Cys His Leu Ala Ile Leu Asp His Pro Tyr Arg Glu Ile Met Lys Leu
            180                 185                 190

Cys Glu Asn Cys Pro Ser Cys Pro Arg Ile Leu Gly Leu Thr Ala Ser
        195                 200                 205

Ile Leu Asn Gly Lys Cys Asp Pro Glu Glu Leu Glu Glu Lys Ile Gln
    210                 215                 220

Lys Leu Glu Lys Ile Leu Lys Ser Asn Ala Glu Thr Ala Thr Asp Leu
225                 230                 235                 240

Val Val Leu Asp Arg Tyr Thr Ser Gln Pro Cys Glu Ile Val Val Asp
                245                 250                 255

Cys Gly Pro Phe Thr Asp Arg Ser Gly Leu Tyr Glu Arg Leu Leu Met
            260                 265                 270

Glu Leu Glu Glu Ala Leu Asn Phe Ile Asn Asp Cys Asn Ile Ser Val
        275                 280                 285

His Ser Lys Glu Arg Asp Ser Thr Leu Ile Ser Lys Gln Ile Leu Ser
    290                 295                 300

Asp Cys Arg Ala Val Leu Val Val Leu Gly Pro Trp Cys Ala Asp Lys
305                 310                 315                 320
```

```
Val Ala Gly Met Met Val Arg Glu Leu Gln Lys Tyr Ile Lys His Glu
                325                 330                 335

Gln Glu Glu Leu His Arg Lys Phe Leu Leu Phe Thr Asp Thr Phe Leu
            340                 345                 350

Arg Lys Ile His Ala Leu Cys Glu Glu His Phe Ser Pro Ala Ser Leu
        355                 360                 365

Asp Leu Lys Phe Val Thr Pro Lys Val Ile Lys Leu Leu Glu Ile Leu
    370                 375                 380

Arg Lys Tyr Lys Pro Tyr Glu Arg Gln Gln Phe Glu Ser Val Glu Trp
385                 390                 395                 400

Tyr Asn Asn Arg Asn Gln Asp Asn Tyr Val Ser Trp Ser Asp Ser Glu
                405                 410                 415

Asp Asp Asp Glu Asp Glu Glu Ile Glu Glu Lys Glu Lys Pro Glu Thr
            420                 425                 430

Asn Phe Pro Ser Pro Phe Thr Asn Ile Leu Cys Gly Ile Ile Phe Val
        435                 440                 445

Glu Arg Arg Tyr Thr Ala Val Val Leu Asn Arg Leu Ile Lys Glu Ala
    450                 455                 460

Gly Lys Gln Asp Pro Glu Leu Ala Tyr Ile Ser Ser Asn Phe Ile Thr
465                 470                 475                 480

Gly His Gly Ile Gly Lys Asn Gln Pro Arg Asn Lys Gln Met Glu Ala
                485                 490                 495

Glu Phe Arg Lys Gln Glu Glu Val Leu Arg Lys Phe Arg Ala His Glu
            500                 505                 510

Thr Asn Leu Leu Ile Ala Thr Ser Ile Val Glu Glu Gly Val Asp Ile
        515                 520                 525

Pro Lys Cys Asn Leu Val Val Arg Phe Asp Leu Pro Thr Glu Tyr Arg
    530                 535                 540

Ser Tyr Val Gln Ser Lys Gly Arg Ala Arg Ala Pro Ile Ser Asn Tyr
545                 550                 555                 560

Ile Met Leu Ala Asp Thr Asp Lys Ile Lys Ser Phe Glu Glu Asp Leu
                565                 570                 575

Lys Thr Tyr Lys Ala Ile Glu Lys Ile Leu Arg Asn Lys Cys Ser Lys
            580                 585                 590

Ser Val Asp Thr Gly Glu Thr Asp Ile Asp Pro Val Met Asp Asp Asp
        595                 600                 605

Asp Val Phe Pro Pro Tyr Val Leu Arg Pro Asp Asp Gly Gly Pro Arg
    610                 615                 620

Val Thr Ile Asn Thr Ala Ile Gly His Ile Asn Arg Tyr Cys Ala Arg
625                 630                 635                 640

Leu Pro Ser Asp Pro Phe Thr His Leu Ala Pro Lys Cys Arg Thr Arg
                645                 650                 655

Glu Leu Pro Asp Gly Thr Phe Tyr Ser Thr Leu Tyr Leu Pro Ile Asn
            660                 665                 670

Ser Pro Leu Arg Ala Ser Ile Val Gly Pro Pro Met Ser Cys Val Arg
        675                 680                 685

Leu Ala Glu Arg Val Val Ala Leu Ile Cys Cys Glu Lys Leu His Lys
    690                 695                 700

Ile Gly Glu Leu Asp Asp His Leu Met Pro Val Gly Lys Glu Thr Val
705                 710                 715                 720

Lys Tyr Glu Glu Glu Leu Asp Leu His Asp Glu Glu Glu Thr Ser Val
                725                 730                 735
```

```
Pro Gly Arg Pro Gly Ser Thr Lys Arg Arg Gln Cys Tyr Pro Lys Ala
            740                 745                 750

Ile Pro Glu Cys Leu Arg Asp Ser Tyr Pro Arg Pro Asp Gln Pro Cys
        755                 760                 765

Tyr Leu Tyr Val Ile Gly Met Val Leu Thr Thr Pro Leu Pro Asp Glu
    770                 775                 780

Leu Asn Phe Arg Arg Arg Lys Leu Tyr Pro Pro Glu Asp Thr Thr Arg
785                 790                 795                 800

Cys Phe Gly Ile Leu Thr Ala Lys Pro Ile Pro Gln Ile Pro His Phe
                805                 810                 815

Pro Val Tyr Thr Arg Ser Gly Glu Val Thr Ile Ser Ile Glu Leu Lys
            820                 825                 830

Lys Ser Gly Phe Met Leu Ser Leu Gln Met Leu Glu Leu Ile Thr Arg
        835                 840                 845

Leu His Gln Tyr Ile Phe Ser His Ile Leu Arg Leu Glu Lys Pro Ala
    850                 855                 860

Leu Glu Phe Lys Pro Thr Asp Ala Asp Ser Ala Tyr Cys Val Leu Pro
865                 870                 875                 880

Leu Asn Val Val Asn Asp Ser Ser Thr Leu Asp Ile Asp Phe Lys Phe
                885                 890                 895

Met Glu Asp Ile Glu Lys Ser Glu Ala Arg Ile Gly Ile Pro Ser Thr
            900                 905                 910

Lys Tyr Thr Lys Glu Thr Pro Phe Val Phe Lys Leu Glu Asp Tyr Gln
        915                 920                 925

Asp Ala Val Ile Ile Pro Arg Tyr Arg Asn Phe Asp Gln Pro His Arg
    930                 935                 940

Phe Tyr Val Ala Asp Val Tyr Thr Asp Leu Thr Pro Leu Ser Lys Phe
945                 950                 955                 960

Pro Ser Pro Glu Tyr Glu Thr Phe Ala Glu Tyr Tyr Lys Thr Lys Tyr
                965                 970                 975

Asn Leu Asp Leu Thr Asn Leu Asn Gln Pro Leu Leu Asp Val Asp His
            980                 985                 990

Thr Ser Ser Arg Leu Asn Leu Leu  Thr Pro Arg His Leu  Asn Gln Lys
        995                 1000                1005

Gly Lys  Ala Leu Pro Leu Ser  Ser Ala Glu Lys Arg  Lys Ala Lys
    1010                 1015                 1020

Trp Glu  Ser Leu Gln Asn Lys  Gln Ile Leu Val Pro  Glu Leu Cys
    1025                 1030                 1035

Ala Ile  His Pro Ile Pro Ala  Ser Leu Trp Arg Lys  Ala Val Cys
    1040                 1045                 1050

Leu Pro  Ser Ile Leu Tyr Arg  Leu His Cys Leu Leu  Thr Ala Glu
    1055                 1060                 1065

Glu Leu  Arg Ala Gln Thr Ala  Ser Asp Ala Gly Val  Gly Val Arg
    1070                 1075                 1080

Ser Leu  Pro Ala Asp Phe Arg  Tyr Pro Asn Leu Asp  Phe Gly Trp
    1085                 1090                 1095

Lys Lys  Ser Ile Asp Ser Lys  Ser Phe Ile Ser Ile  Ser Asn Ser
    1100                 1105                 1110

Ser Ser  Ala Glu Asn Asp Asn  Tyr Cys Lys His Ser  Thr Ile Val
    1115                 1120                 1125

Pro Glu  Asn Ala Ala His Gln  Gly Ala Asn Arg Thr  Ser Ser Leu
    1130                 1135                 1140

Glu Asn  His Asp Gln Met Ser  Val Asn Cys Arg Thr  Leu Leu Ser
```

```
        1145                1150                1155

Glu Ser  Pro Gly Lys Leu His  Val Glu Val Ser Ala  Asp Leu Thr
    1160                1165                1170

Ala Ile  Asn Gly Leu Ser Tyr  Asn Gln Asn Leu Ala  Asn Gly Ser
    1175                1180                1185

Tyr Asp  Leu Ala Asn Arg Asp  Phe Cys Gln Gly Asn  Gln Leu Asn
    1190                1195                1200

Tyr Tyr  Lys Gln Glu Ile Pro  Val Gln Pro Thr Thr  Ser Tyr Ser
    1205                1210                1215

Ile Gln  Asn Leu Tyr Ser Tyr  Glu Asn Gln Pro Gln  Pro Ser Asp
    1220                1225                1230

Glu Cys  Thr Leu Leu Ser Asn  Lys Tyr Leu Asp Gly  Asn Ala Asn
    1235                1240                1245

Lys Ser  Thr Ser Asp Gly Ser  Pro Val Met Ala Val  Met Pro Gly
    1250                1255                1260

Thr Thr  Asp Thr Ile Gln Val  Leu Lys Gly Arg Met  Asp Ser Glu
    1265                1270                1275

Gln Ser  Pro Ser Ile Gly Tyr  Ser Ser Arg Thr Leu  Gly Pro Asn
    1280                1285                1290

Pro Gly  Leu Ile Leu Gln Ala  Leu Thr Leu Ser Asn  Ala Ser Asp
    1295                1300                1305

Gly Phe  Asn Leu Glu Arg Leu  Glu Met Leu Gly Asp  Ser Phe Leu
    1310                1315                1320

Lys His  Ala Ile Thr Thr Tyr  Leu Phe Cys Thr Tyr  Pro Asp Ala
    1325                1330                1335

His Glu  Gly Arg Leu Ser Tyr  Met Arg Ser Lys Lys  Val Ser Asn
    1340                1345                1350

Cys Asn  Leu Tyr Arg Leu Gly  Lys Lys Lys Gly Leu  Pro Ser Arg
    1355                1360                1365

Met Val  Val Ser Ile Phe Asp  Pro Pro Val Asn Trp  Leu Pro Pro
    1370                1375                1380

Gly Tyr  Val Val Asn Gln Asp  Lys Ser Asn Thr Asp  Lys Trp Glu
    1385                1390                1395

Lys Asp  Glu Met Thr Lys Asp  Cys Met Leu Ala Asn  Gly Lys Leu
    1400                1405                1410

Asp Glu  Asp Tyr Glu Glu Glu  Asp Glu Glu Glu Glu  Ser Leu Met
    1415                1420                1425

Trp Arg  Ala Pro Lys Glu Glu  Ala Asp Tyr Glu Asp  Asp Phe Leu
    1430                1435                1440

Glu Tyr  Asp Gln Glu His Ile  Arg Phe Ile Asp Asn  Met Leu Met
    1445                1450                1455

Gly Ser  Gly Ala Phe Val Lys  Lys Ile Ser Leu Ser  Pro Phe Ser
    1460                1465                1470

Thr Thr  Asp Ser Ala Tyr Glu  Trp Lys Met Pro Lys  Lys Ser Ser
    1475                1480                1485

Leu Gly  Ser Met Pro Phe Ser  Ser Asp Phe Glu Asp  Phe Asp Tyr
    1490                1495                1500

Ser Ser  Trp Asp Ala Met Cys  Tyr Leu Asp Pro Ser  Lys Ala Val
    1505                1510                1515

Glu Glu  Asp Asp Phe Val Val  Gly Phe Trp Asn Pro  Ser Glu Glu
    1520                1525                1530

Asn Cys  Gly Val Asp Thr Gly  Lys Gln Ser Ile Ser  Tyr Asp Leu
    1535                1540                1545
```

```
His Thr  Glu Gln Cys Ile Ala  Asp Lys Ser Ile Ala  Asp Cys Val
    1550                 1555                 1560

Glu Ala  Leu Leu Gly Cys Tyr  Leu Thr Ser Cys Gly  Glu Arg Ala
    1565                 1570                 1575

Ala Gln  Leu Phe Leu Cys Ser  Leu Gly Leu Lys Val  Leu Pro Val
    1580                 1585                 1590

Ile Lys  Arg Thr Asp Arg Glu  Lys Ala Leu Cys Pro  Thr Arg Glu
    1595                 1600                 1605

Asn Phe  Asn Ser Gln Gln Lys  Asn Leu Ser Val Ser  Cys Ala Ala
    1610                 1615                 1620

Ala Ser  Val Ala Ser Ser Arg  Ser Ser Val Leu Lys  Asp Ser Glu
    1625                 1630                 1635

Tyr Gly  Cys Leu Lys Ile Pro  Pro Arg Cys Met Phe  Asp His Pro
    1640                 1645                 1650

Asp Ala  Asp Lys Thr Leu Asn  His Leu Ile Ser Gly  Phe Glu Asn
    1655                 1660                 1665

Phe Glu  Lys Lys Ile Asn Tyr  Arg Phe Lys Asn Lys  Ala Tyr Leu
    1670                 1675                 1680

Leu Gln  Ala Phe Thr His Ala  Ser Tyr His Tyr Asn  Thr Ile Thr
    1685                 1690                 1695

Asp Cys  Tyr Gln Arg Leu Glu  Phe Leu Gly Asp Ala  Ile Leu Asp
    1700                 1705                 1710

Tyr Leu  Ile Thr Lys His Leu  Tyr Glu Asp Pro Arg  Gln His Ser
    1715                 1720                 1725

Pro Gly  Val Leu Thr Asp Leu  Arg Ser Ala Leu Val  Asn Asn Thr
    1730                 1735                 1740

Ile Phe  Ala Ser Leu Ala Val  Lys Tyr Asp Tyr His  Lys Tyr Phe
    1745                 1750                 1755

Lys Ala  Val Ser Pro Glu Leu  Phe His Val Ile Asp  Asp Phe Val
    1760                 1765                 1770

Gln Phe  Gln Leu Glu Lys Asn  Glu Met Gln Gly Met  Asp Ser Glu
    1775                 1780                 1785

Leu Arg  Arg Ser Glu Glu Asp  Glu Glu Lys Glu Glu  Asp Ile Glu
    1790                 1795                 1800

Val Pro  Lys Ala Met Gly Asp  Ile Phe Glu Ser Leu  Ala Gly Ala
    1805                 1810                 1815

Ile Tyr  Met Asp Ser Gly Met  Ser Leu Glu Thr Val  Trp Gln Val
    1820                 1825                 1830

Tyr Tyr  Pro Met Met Arg Pro  Leu Ile Glu Lys Phe  Ser Ala Asn
    1835                 1840                 1845

Val Pro  Arg Ser Pro Val Arg  Glu Leu Leu Glu Met  Glu Pro Glu
    1850                 1855                 1860

Thr Ala  Lys Phe Ser Pro Ala  Glu Arg Thr Tyr Asp  Gly Lys Val
    1865                 1870                 1875

Arg Val  Thr Val Glu Val Val  Gly Lys Gly Lys Phe  Lys Gly Val
    1880                 1885                 1890

Gly Arg  Ser Tyr Arg Ile Ala  Lys Ser Ala Ala Ala  Arg Arg Ala
    1895                 1900                 1905

Leu Arg  Ser Leu Lys Ala Asn  Gln Pro Gln Val Pro  Asn Ser
    1910                 1915                 1920
```

<210> SEQ ID NO 11
<211> LENGTH: 6246

```
<212> TYPE: DNA
<213> ORGANISM: Homo sapiens
<220> FEATURE:
<221> NAME/KEY: CDS
<222> LOCATION: (434)..(1885)

<400> SEQUENCE: 11

atcttgagtg gaggaggagc cgcggtcgcc gccatgcgga gaggcaggga aagagggagg      60

aggcggcggg cgggcgaacg ggcgagcgag ggagggggca gaggagccga gttagctcag     120

ccaggcggcg acttcggcgg cgccacgaga gcgggcagcg gaggagattg acgtgagtga     180

attcagatat aactcaagct tgttagaggg ctttttaaaa ataaaaagtt gattccgtgc     240

aagagagcaa gttactgctg cttaccgttc agagacttac aggtgcttgc ctgcattgca     300

ataaaggact catttattga gcaagactta tatttatctc ttcattttgg agagcctaat     360

aaactgttat tacagtttct ctactgactt tcaaaagttt tgaagtttga aagacctttg     420

caattaaaac agc atg agc acg gcc aga aca gag aac cct gtt ata atg        469
               Met Ser Thr Ala Arg Thr Glu Asn Pro Val Ile Met
               1               5                   10

ggt ctg tcc agt caa aat ggt cag ctg aga ggc cct gtg aaa ccc act       517
Gly Leu Ser Ser Gln Asn Gly Gln Leu Arg Gly Pro Val Lys Pro Thr
        15                  20                  25

ggt ggc cct gga gga ggg ggc aca cag aca cag caa cag atg aac cag       565
Gly Gly Pro Gly Gly Gly Gly Thr Gln Thr Gln Gln Gln Met Asn Gln
    30                  35                  40

ctg aaa aac acc aac aca atc aat aat ggc act cag cag caa gca cag       613
Leu Lys Asn Thr Asn Thr Ile Asn Asn Gly Thr Gln Gln Gln Ala Gln
45                  50                  55                  60

agt atg acc acc act att aaa cct ggt gat gac tgg aaa aag act tta       661
Ser Met Thr Thr Thr Ile Lys Pro Gly Asp Asp Trp Lys Lys Thr Leu
                65                  70                  75

aaa ctc cct cca aag gat cta aga atc aaa act tcg gat gtg acc tcc       709
Lys Leu Pro Pro Lys Asp Leu Arg Ile Lys Thr Ser Asp Val Thr Ser
            80                  85                  90

aca aaa gga aat gag ttt gaa gat tac tgt ttg aaa cgg gag tta ctg       757
Thr Lys Gly Asn Glu Phe Glu Asp Tyr Cys Leu Lys Arg Glu Leu Leu
        95                  100                 105

atg gga att ttt gaa atg ggc tgg gaa aag cca tct cct att cag gag       805
Met Gly Ile Phe Glu Met Gly Trp Glu Lys Pro Ser Pro Ile Gln Glu
    110                 115                 120

gag agc att ccc att gct tta tct ggt agg gat atc tta gct aga gca       853
Glu Ser Ile Pro Ile Ala Leu Ser Gly Arg Asp Ile Leu Ala Arg Ala
125                 130                 135                 140

aaa aat gga aca ggc aag agc ggt gcc tac ctc att ccc tta ctt gaa       901
Lys Asn Gly Thr Gly Lys Ser Gly Ala Tyr Leu Ile Pro Leu Leu Glu
                145                 150                 155

cgg cta gac ctg aag aag gac aat ata caa gca atg gtg att gtt ccc       949
Arg Leu Asp Leu Lys Lys Asp Asn Ile Gln Ala Met Val Ile Val Pro
            160                 165                 170

act aga gaa ctt gct cta cag gtc agt caa att tgc atc cag gtc agc       997
Thr Arg Glu Leu Ala Leu Gln Val Ser Gln Ile Cys Ile Gln Val Ser
        175                 180                 185

aaa cac atg gga ggg gcc aaa gtg atg gca acc aca gga gga acc aat      1045
Lys His Met Gly Gly Ala Lys Val Met Ala Thr Thr Gly Gly Thr Asn
    190                 195                 200

tta cga gat gac ata atg agg ctt gat gat aca gtg cac gtg gtg att      1093
Leu Arg Asp Asp Ile Met Arg Leu Asp Asp Thr Val His Val Val Ile
205                 210                 215                 220

gct acc cct ggg aga atc ctg gat ctt att aag aaa gga gta gca aag      1141
```

```
Ala Thr Pro Gly Arg Ile Leu Asp Leu Ile Lys Lys Gly Val Ala Lys
                225                 230                 235

gtt gat cat gtc cag atg ata gta ttg gat gag gca gat aag ttg ctg     1189
Val Asp His Val Gln Met Ile Val Leu Asp Glu Ala Asp Lys Leu Leu
            240                 245                 250

tca cag gat ttt gtg cag ata atg gag gat att att ctc acg cta cct     1237
Ser Gln Asp Phe Val Gln Ile Met Glu Asp Ile Ile Leu Thr Leu Pro
        255                 260                 265

aaa aac agg cag att tta cta tat tcc gct act ttc cct ctt agt gta     1285
Lys Asn Arg Gln Ile Leu Leu Tyr Ser Ala Thr Phe Pro Leu Ser Val
    270                 275                 280

cag aag ttc atg aat tcc cat ttg cag aaa ccc tat gag att aac ctg     1333
Gln Lys Phe Met Asn Ser His Leu Gln Lys Pro Tyr Glu Ile Asn Leu
285                 290                 295                 300

atg gag gaa cta act ctg aag gga gta acc cag tac tac gca tat gta     1381
Met Glu Glu Leu Thr Leu Lys Gly Val Thr Gln Tyr Tyr Ala Tyr Val
                305                 310                 315

act gag cgc caa aaa gta cac tgc ctc aac aca ctt ttc tcc agg ctt     1429
Thr Glu Arg Gln Lys Val His Cys Leu Asn Thr Leu Phe Ser Arg Leu
            320                 325                 330

cag ata aac cag tcg atc att ttc tgt aac tcc tct cag cga gtt gaa     1477
Gln Ile Asn Gln Ser Ile Ile Phe Cys Asn Ser Ser Gln Arg Val Glu
        335                 340                 345

ttg cta gcc aag aag att tct caa ctg ggt tat tct tgc ttc tat att     1525
Leu Leu Ala Lys Lys Ile Ser Gln Leu Gly Tyr Ser Cys Phe Tyr Ile
    350                 355                 360

cat gct aaa atg agg cag gaa cat cga aat cgt gta ttt cat gat ttc     1573
His Ala Lys Met Arg Gln Glu His Arg Asn Arg Val Phe His Asp Phe
365                 370                 375                 380

cga aat ggc tta tgc cgc aat ctt gtt tgc act gat ctg ttt acc cga     1621
Arg Asn Gly Leu Cys Arg Asn Leu Val Cys Thr Asp Leu Phe Thr Arg
                385                 390                 395

ggt att gat ata caa gct gtg aat gtg gta ata aac ttt gat ttc cca     1669
Gly Ile Asp Ile Gln Ala Val Asn Val Val Ile Asn Phe Asp Phe Pro
            400                 405                 410

aag ctg gca gag acc tat ctc cat cgt att gga aga tca ggt cgc ttt     1717
Lys Leu Ala Glu Thr Tyr Leu His Arg Ile Gly Arg Ser Gly Arg Phe
        415                 420                 425

ggt cat ctt ggc tta gcc atc aac ttg atc aca tat gat gat cgc ttc     1765
Gly His Leu Gly Leu Ala Ile Asn Leu Ile Thr Tyr Asp Asp Arg Phe
    430                 435                 440

aac ctg aaa agt att gag gag cag ctg gga aca gaa att aaa cct att     1813
Asn Leu Lys Ser Ile Glu Glu Gln Leu Gly Thr Glu Ile Lys Pro Ile
445                 450                 455                 460

ccg agc aac att gat aag agc ctg tat gtg gca gaa tac cac agc gag     1861
Pro Ser Asn Ile Asp Lys Ser Leu Tyr Val Ala Glu Tyr His Ser Glu
                465                 470                 475

cct gta gaa gat gag aaa cct taa caagcatgct ttgacaaatt acaaaaggct    1915
Pro Val Glu Asp Glu Lys Pro
            480

cgtttggatc tgtgacacat cgttttgggg ggaatgctcc tctctttgtg ggtttttcat   1975

cttttatttt ggaactatga agacttaaaa gagctcagac attttctttt tttaactggt   2035

gaagagaaaa aggctgaaaa gaaggaatat accttttttg ttccacttgt ttgcactgtg   2095

tgctgactga acattagttg cactaactgc tggtttttaa aaaatgtttt ctggggaaag   2155

gggacaagga aggaaaagaa agaagagaag gggagaaacc ctaaaaagag aagaatctta   2215

atgaacacac aagcttgtca atgatttcaa aattctccaa cagctgactc tcgtgcattt   2275
```

-continued

```
caacttctcc ctgattcctc atccgttttt taagcctgaa gagcttatta cttatttgtg   2335
cgaagtgcct tatgctatga gaccattcag aatatcatct tttagacaca gcccgaggaa   2395
tcaacaatag taactctttc tttccgtttt tttttctttt tcttttaaaa aatgtcttct   2455
tattttggtt tcaggttgaa gtctcttccc tttctaccca gtactcgagc ccagggctag   2515
aagttgaaac tcactagtaa tgttaaacac catttttttt ttctttttgg ggaggagttg   2575
atatgcaact gcagttcatc cgcactgtaa atacatgtat ttaaaaaaac aatcccaagt   2635
aaaaatttct tctgggctga gtagataaaa aacatcatcg ctcccaaagg aaagagcagt   2695
ctatcattgc aggagccata tgacaagcct ttgtgctcta tagcagacac taaagactgg   2755
gttacatatg cctccagtag tagtatggca cttgatgtgt agacatgtca gagcttggcc   2815
ctctttcctc tgtggcaaag cgtgtcccat agaaaattgg gtgtgtatac ttgtataact   2875
ttgtaaataa gttttttttc tgggttcata tatatatata tatatacata tatatatatt   2935
tttttttgga tgaaggttgc tgggattaag ggattagag tgattatggg agcagctaaa   2995
gatgagaggg gctcagtttt acgcaacact aaattctaga aagtactttg gcctcgtgct   3055
gtagagagca gatttctatg gtaccctgtg ttagtaaagg ggcccagaaa tctgggatgt   3115
actgtttgct gccacactgt ctcatctagt acctttggag taggtttacc agagagagca   3175
aggaagcttc aaaacattga taattcaaca tttattttga gaagctctga ttttgcttct   3235
tccccctttc taaaagtttg aggaatattt caagctctgc aacagggggc aaagattaat   3295
ctaccttgca gtgtaggaat tctattgagt ggcagtgtca ttgagcagta tatatataaa   3355
gcacagattt gcatttcaga atattagcca gtaccagctt tggtaatgtt agcagttctg   3415
gagcttaatt ttctgtggat catttcctgt agtgtgtaaa tgtgttgccc tctgcccgct   3475
ttgatacata aacttttgca ggaatgggca acctgagagc tgttaacttt catgctacag   3535
aaagctgctt gccattctct tgcattgtga caagaattgt tacctgtcat tttgcactgt   3595
aaattgctgg cagatgcttt acagtcaata gtgttgcttt aaattgtgcc cctcccaaca   3655
tgcttgatgt ttggcctgat ctccaggcaa aaggagtgag atgaatcaaa accagtgaac   3715
ttttttttt aatgttttta attccctttt aacccagtgt actaggtcaa tcaggaggca   3775
tctggaaagg gggggaaaaa agcaaaaaac aaaattaaaa aaaattgatt tccatatttt   3835
atttttcaaa accctaaaat attacaaaat aagtcccgca tatactttaa tgttttaact   3895
cttttggaca aaggaatcaa ttacttgaag ttgctttttt gactctgcct acttctgagc   3955
aaactatttg cgactcaccc acaattgcct tggagatcaa aatcctacag atgcctcctg   4015
atgggacata gccctaactc cttaacaact gtagcaagaa ctgcacggta caaacccaaa   4075
aaagaacaag ctcatctatt tggaacccaa gcctcatatt ttctgtccag tcaatgttgg   4135
ttactaaata gaaaacctaa ttaaggaagt aactttttc cagggagggg tgggagaggg   4195
aatttaaaag gtgtcaactt ttgaccaaaa aaattgtgcc cttgtaccga tgcagctctc   4255
tttctccccc acctcttgcg agataagagg gatcattcat gtagaagaaa agagtataaa   4315
tgcaattctg tatctcgcta gagaacgtgt gggtgactaa acaaaaagtg cagtctcctt   4375
caccaacttt agactgcgtg gtgccacatg cctgtgggtc cctcttaaag cacagactta   4435
aaatggaaag tattactgaa gtatagcctc taatgaggag tggcacttaa actatctggg   4495
acaccactac tggacacggt cttgtagagg cagctgtcca gttttggtgc ttgactcttg   4555
aataggaatt gttaaatgga aagatgctct gaggactagg tcaaagcctg gtcttttttt   4615
ttttttttt tttttcttt cttttttggg ccctcataat aagcattgtt actattggaa   4675
```

```
gttgttttca cattctttcc aatattaaat atgtattttt ttaagtaatg ataatatttt   4735

ccagtggctc atttggatga gaactaccct ctatttttaa tattaaaact acatccaact   4795

catcatttag cctttggttg tacagttgtg taatgggcta tggactgtta cacaccttac   4855

cacctctagg cctatgtttt ttctttcccc atatattctg atggggataa atactgtttt   4915

gcctctccca taggaatgga atacatttat tctaaaatga tctttcacag aagtaagaga   4975

gagggaaacc taaatatacc tctaaattgt ttgaagttgg tcccagcagc ataaaatggg   5035

ttggccccaa agggttggag ggtgggcttg gttatcagta tttgttttca gaatgagatg   5095

ggagcatctt tcctttgcca cgtgctttgt gcttgataac atcatgcttg gttcaaacga   5155

caactcagca caaagccttg agtataaatt gttggaatca aaacatctca ttctgatgac   5215

gtggtttaat tttttaattt ttttttttaa taggggtggg agggagggta ctttgcccca   5275

gaagggaggg tgtctgcact aaggatttag aaacactttg gaagctcata acctcatcag   5335

aaactgcctt tagccacact cctgaccttc tagatgagta acaaaaaaat gaaataagtt   5395

cttggaaatt aagccattta ttttaatttg ctattttttt caatgttcta ggtatcttta   5455

aatttgttat tgtggaatca ttttcctgcc agataccttt atcaaaatta ttggcctcat   5515

gagagctgaa gtaagtcagc tttttggtga actttagtgg acttctgtga gattgtagtt   5575

gtactttgta tctctaaatc taaagatagt tttttaaaac tcccaaagaa aatctgctct   5635

cctttctgat ctaaaaactc atctttgggg taaagagtta agtgtccaaa ggttgtcaca   5695

gttcatgagg tcagagggag ctagcctggc acctggactc tgcccatcca cagctgacag   5755

attccaacag aagtgtattt aaattctcca gtagacaatg ctgggtaagg gagggggtag   5815

ggctgggtta ttaagataca ggctgctgta ttttacattg gttgtgtggg aaggggagcc   5875

tggagaaaac aaagtcacta ttcccttttt tgaaacagga aaaaaaatta ttttttgttc   5935

agtaaaaatg gtagagaatt ccaatgtccc tagccacaag ggaccagttc cactgagaag   5995

tgaacagtgg gaactcaaaa tttcagaaac attgggggaa gggaaaattg gctttctctt   6055

aattggcaga tgttccagtg gggggggggg gggctctgtt tttgttggga tgtgttatgt   6115

tgtatgtacg catatatgga ccggagtctg ctgagtttat aaggttccaa aaatatggta   6175

aaatcttggt ttttgttaat ttatctcaat aaaagcccac tggaactcca aaaaaaaaaa   6235

aaaaaaaaaa a                                                        6246
```

<210> SEQ ID NO 12
<211> LENGTH: 483
<212> TYPE: PRT
<213> ORGANISM: Homo sapiens

<400> SEQUENCE: 12

```
Met Ser Thr Ala Arg Thr Glu Asn Pro Val Ile Met Gly Leu Ser Ser
1               5                   10                  15

Gln Asn Gly Gln Leu Arg Gly Pro Val Lys Pro Thr Gly Gly Pro Gly
            20                  25                  30

Gly Gly Gly Thr Gln Thr Gln Gln Gln Met Asn Gln Leu Lys Asn Thr
        35                  40                  45

Asn Thr Ile Asn Asn Gly Thr Gln Gln Gln Ala Gln Ser Met Thr Thr
    50                  55                  60

Thr Ile Lys Pro Gly Asp Asp Trp Lys Lys Thr Leu Lys Leu Pro Pro
65                  70                  75                  80

Lys Asp Leu Arg Ile Lys Thr Ser Asp Val Thr Ser Thr Lys Gly Asn
```

```
                85                  90                  95

Glu Phe Glu Asp Tyr Cys Leu Lys Arg Glu Leu Leu Met Gly Ile Phe
            100                 105                 110

Glu Met Gly Trp Glu Lys Pro Ser Pro Ile Gln Glu Glu Ser Ile Pro
        115                 120                 125

Ile Ala Leu Ser Gly Arg Asp Ile Leu Ala Arg Ala Lys Asn Gly Thr
    130                 135                 140

Gly Lys Ser Gly Ala Tyr Leu Ile Pro Leu Leu Glu Arg Leu Asp Leu
145                 150                 155                 160

Lys Lys Asp Asn Ile Gln Ala Met Val Ile Val Pro Thr Arg Glu Leu
                165                 170                 175

Ala Leu Gln Val Ser Gln Ile Cys Ile Gln Val Ser Lys His Met Gly
            180                 185                 190

Gly Ala Lys Val Met Ala Thr Thr Gly Gly Thr Asn Leu Arg Asp Asp
        195                 200                 205

Ile Met Arg Leu Asp Asp Thr Val His Val Val Ile Ala Thr Pro Gly
    210                 215                 220

Arg Ile Leu Asp Leu Ile Lys Lys Gly Val Ala Lys Val Asp His Val
225                 230                 235                 240

Gln Met Ile Val Leu Asp Glu Ala Asp Lys Leu Leu Ser Gln Asp Phe
                245                 250                 255

Val Gln Ile Met Glu Asp Ile Ile Leu Thr Leu Pro Lys Asn Arg Gln
            260                 265                 270

Ile Leu Leu Tyr Ser Ala Thr Phe Pro Leu Ser Val Gln Lys Phe Met
        275                 280                 285

Asn Ser His Leu Gln Lys Pro Tyr Glu Ile Asn Leu Met Glu Glu Leu
    290                 295                 300

Thr Leu Lys Gly Val Thr Gln Tyr Tyr Ala Tyr Val Thr Glu Arg Gln
305                 310                 315                 320

Lys Val His Cys Leu Asn Thr Leu Phe Ser Arg Leu Gln Ile Asn Gln
                325                 330                 335

Ser Ile Ile Phe Cys Asn Ser Ser Gln Arg Val Glu Leu Leu Ala Lys
            340                 345                 350

Lys Ile Ser Gln Leu Gly Tyr Ser Cys Phe Tyr Ile His Ala Lys Met
        355                 360                 365

Arg Gln Glu His Arg Asn Arg Val Phe His Asp Phe Arg Asn Gly Leu
    370                 375                 380

Cys Arg Asn Leu Val Cys Thr Asp Leu Phe Thr Arg Gly Ile Asp Ile
385                 390                 395                 400

Gln Ala Val Asn Val Val Ile Asn Phe Asp Phe Pro Lys Leu Ala Glu
                405                 410                 415

Thr Tyr Leu His Arg Ile Gly Arg Ser Gly Arg Phe Gly His Leu Gly
            420                 425                 430

Leu Ala Ile Asn Leu Ile Thr Tyr Asp Asp Arg Phe Asn Leu Lys Ser
        435                 440                 445

Ile Glu Glu Gln Leu Gly Thr Glu Ile Lys Pro Ile Pro Ser Asn Ile
    450                 455                 460

Asp Lys Ser Leu Tyr Val Ala Glu Tyr His Ser Glu Pro Val Glu Asp
465                 470                 475                 480

Glu Lys Pro


<210> SEQ ID NO 13
<211> LENGTH: 935
```

```
<212> TYPE: DNA
<213> ORGANISM: Homo sapiens
<220> FEATURE:
<221> NAME/KEY: CDS
<222> LOCATION: (189)..(590)

<400> SEQUENCE: 13

gaagtgggta agggtaatat ggaggagctt ccggcaggcc ccggcggctg aaagccgggg      60

cagaagtgct ggtctcggtc gggattccgg gcttggtccc accgaggcgg cgactgcggt     120

aggagggaag aggttttgga cgcgctggcc tcccgccgct gtgcattgca gcattatttc     180

agttcaaa atg aac tat atg cct ggc acc gcc agc ctc atc gag gac att     230
         Met Asn Tyr Met Pro Gly Thr Ala Ser Leu Ile Glu Asp Ile
         1               5                   10

gac aaa aag cac ttg gtt ctg ctt cga gat gga agg aca ctt ata ggc      278
Asp Lys Lys His Leu Val Leu Leu Arg Asp Gly Arg Thr Leu Ile Gly
15                  20                  25                  30

ttt tta aga agc att gat caa ttt gca aac tta gtg cta cat cag act      326
Phe Leu Arg Ser Ile Asp Gln Phe Ala Asn Leu Val Leu His Gln Thr
                35                  40                  45

gtg gag cgt att cat gtg ggc aaa aaa tac ggt gat att cct cga ggg      374
Val Glu Arg Ile His Val Gly Lys Lys Tyr Gly Asp Ile Pro Arg Gly
            50                  55                  60

att ttt gtg gtc aga gga gaa aat gtg gtc cta cta gga gaa ata gac      422
Ile Phe Val Val Arg Gly Glu Asn Val Val Leu Leu Gly Glu Ile Asp
        65                  70                  75

ttg gaa aag gag agt gac aca ccc ctc cag caa gta tcc att gaa gaa      470
Leu Glu Lys Glu Ser Asp Thr Pro Leu Gln Gln Val Ser Ile Glu Glu
    80                  85                  90

att cta gaa gaa caa agg gtg gaa cag cag acc aag ctg gaa gca gag      518
Ile Leu Glu Glu Gln Arg Val Glu Gln Gln Thr Lys Leu Glu Ala Glu
95                  100                 105                 110

aag ttg aaa gtg cag gcc ctg aag gac cga ggt ctt tcc att cct cga      566
Lys Leu Lys Val Gln Ala Leu Lys Asp Arg Gly Leu Ser Ile Pro Arg
                115                 120                 125

gca gat act ctt gat gag tac taa tcttttgccc agaggctgtt ggctcttgaa     620
Ala Asp Thr Leu Asp Glu Tyr
            130

gagtaggggc tgtcactgag tgaaagtgac atcctggcca cctcacgcat ttgatcacag     680

actgtagagt tttgaaaagt cacttttatt tttaattatt ttacatatgc aacatgaaga     740

aatcgtgtag gtgggttttt tttttaataa caaaatcact gtttaaagaa acagtggcat     800

agactccttc acacatcact gtggcaccag caactacttc tttatattgt tcttcatatc     860

ccaaattaga gtttacaggg acagtcttca tttacttgta aataaaatat gaatctcaaa     920

aaaaaaaaaa aaaaa                                                      935


<210> SEQ ID NO 14
<211> LENGTH: 133
<212> TYPE: PRT
<213> ORGANISM: Homo sapiens

<400> SEQUENCE: 14

Met Asn Tyr Met Pro Gly Thr Ala Ser Leu Ile Glu Asp Ile Asp Lys
1               5                   10                  15

Lys His Leu Val Leu Leu Arg Asp Gly Arg Thr Leu Ile Gly Phe Leu
            20                  25                  30

Arg Ser Ile Asp Gln Phe Ala Asn Leu Val Leu His Gln Thr Val Glu
        35                  40                  45
```

```
Arg Ile His Val Gly Lys Lys Tyr Gly Asp Ile Pro Arg Gly Ile Phe
    50                  55                  60

Val Val Arg Gly Glu Asn Val Val Leu Leu Gly Glu Ile Asp Leu Glu
65                  70                  75                  80

Lys Glu Ser Asp Thr Pro Leu Gln Gln Val Ser Ile Glu Glu Ile Leu
                85                  90                  95

Glu Glu Gln Arg Val Glu Gln Gln Thr Lys Leu Glu Ala Glu Lys Leu
            100                 105                 110

Lys Val Gln Ala Leu Lys Asp Arg Gly Leu Ser Ile Pro Arg Ala Asp
        115                 120                 125

Thr Leu Asp Glu Tyr
    130


<210> SEQ ID NO 15
<211> LENGTH: 8438
<212> TYPE: DNA
<213> ORGANISM: Homo sapiens
<220> FEATURE:
<221> NAME/KEY: CDS
<222> LOCATION: (115)..(5889)

<400> SEQUENCE: 15

gtgtagaaaa tggcgctggt gcagcggctc gggcctctcc ccgcggcgct gcggagggct      60

tgaggctcgc gagcctcctt cgccgcgccc cacttgctcg tgcactttac acac atg       117
                                                            Met
                                                            1

aga gaa ttg gaa gct aaa gct acc aaa gac gta gaa aga aat ctt agc       165
Arg Glu Leu Glu Ala Lys Ala Thr Lys Asp Val Glu Arg Asn Leu Ser
            5                   10                  15

agg gat tta gtg caa gaa gaa gaa cag ttg atg gaa gaa aag aaa aag       213
Arg Asp Leu Val Gln Glu Glu Glu Gln Leu Met Glu Glu Lys Lys Lys
        20                  25                  30

aaa aaa gac gac aag aaa aag aag gaa gct gct caa aag aag gcc act       261
Lys Lys Asp Asp Lys Lys Lys Lys Glu Ala Ala Gln Lys Lys Ala Thr
    35                  40                  45

gaa caa aaa atc aaa gtg cca gaa cag ata aag ccc agt gta agc cag       309
Glu Gln Lys Ile Lys Val Pro Glu Gln Ile Lys Pro Ser Val Ser Gln
50                  55                  60                  65

cct cag cct gcc aac tct aat aac ggc act tcc aca gca acc agc act       357
Pro Gln Pro Ala Asn Ser Asn Asn Gly Thr Ser Thr Ala Thr Ser Thr
                70                  75                  80

aat aat aat gcc aag cga gct aca gcc aac aat cag cag cca cag cag       405
Asn Asn Asn Ala Lys Arg Ala Thr Ala Asn Asn Gln Gln Pro Gln Gln
            85                  90                  95

cag cag caa cag cag cag ccg cag cag cag cag cca cag cag cag cca       453
Gln Gln Gln Gln Gln Gln Pro Gln Gln Gln Gln Pro Gln Gln Gln Pro
        100                 105                 110

cag ccg cag ccg cag cag cag cag cca cag cag cag cca cag gcc ttg       501
Gln Pro Gln Pro Gln Gln Gln Gln Pro Gln Gln Gln Pro Gln Ala Leu
    115                 120                 125

cct cgg tat cct cgt gaa gta cct cca cga ttt cgc cac cag gaa cac       549
Pro Arg Tyr Pro Arg Glu Val Pro Pro Arg Phe Arg His Gln Glu His
130                 135                 140                 145

aaa cag ctt cta aag agg ggt cag cat ttt cct gtt ata gca gca aac       597
Lys Gln Leu Leu Lys Arg Gly Gln His Phe Pro Val Ile Ala Ala Asn
                150                 155                 160

ctt gga tct gct gtt aag gtg tta aac agc cag tca gaa agc agt gct       645
Leu Gly Ser Ala Val Lys Val Leu Asn Ser Gln Ser Glu Ser Ser Ala
            165                 170                 175
```

```
tta aca aat caa cag cca caa aat aac gga gag gtg cag aac agc aaa      693
Leu Thr Asn Gln Gln Pro Gln Asn Asn Gly Glu Val Gln Asn Ser Lys
        180                 185                 190

aac cag tca gat ata aac cac agt act tca gga tcc cat tat gaa aat      741
Asn Gln Ser Asp Ile Asn His Ser Thr Ser Gly Ser His Tyr Glu Asn
    195                 200                 205

tcc cag cgg gga cct gtg tct tct aca agt gat tct agc aca aac tgt      789
Ser Gln Arg Gly Pro Val Ser Ser Thr Ser Asp Ser Ser Thr Asn Cys
210                 215                 220                 225

aag aat gct gtt gta agt gac ttg tcg gaa aaa gaa gca tgg ccc tca      837
Lys Asn Ala Val Val Ser Asp Leu Ser Glu Lys Glu Ala Trp Pro Ser
                230                 235                 240

gcc cct ggc agt gat ccg gag ttg gct tca gaa tgt atg gat gct gat      885
Ala Pro Gly Ser Asp Pro Glu Leu Ala Ser Glu Cys Met Asp Ala Asp
            245                 250                 255

tct gcc tcc agt tct gaa tca gag aga aac atc act atc atg gct tca      933
Ser Ala Ser Ser Ser Glu Ser Glu Arg Asn Ile Thr Ile Met Ala Ser
        260                 265                 270

ggg aac aca ggt ggt gaa aaa gat ggc ctt cgg aat agc act gga ctt      981
Gly Asn Thr Gly Gly Glu Lys Asp Gly Leu Arg Asn Ser Thr Gly Leu
    275                 280                 285

ggt tcc caa aac aag ttt gta gtt ggt agc agc agc aat aat gtg ggc     1029
Gly Ser Gln Asn Lys Phe Val Val Gly Ser Ser Ser Asn Asn Val Gly
290                 295                 300                 305

cat gga agt agt act ggg cca tgg ggt ttt tcc cat gga gcc ata ata     1077
His Gly Ser Ser Thr Gly Pro Trp Gly Phe Ser His Gly Ala Ile Ile
                310                 315                 320

agc aca tgt cag gtc tct gtg gat gct cct gaa agc aaa tct gaa agt     1125
Ser Thr Cys Gln Val Ser Val Asp Ala Pro Glu Ser Lys Ser Glu Ser
            325                 330                 335

agc aac aat aga atg aat gct tgg ggc act gta agt tct tca tca aat     1173
Ser Asn Asn Arg Met Asn Ala Trp Gly Thr Val Ser Ser Ser Ser Asn
        340                 345                 350

gga ggg tta aat cca agc act ttg aat tca gct agc aac cat ggt gcc     1221
Gly Gly Leu Asn Pro Ser Thr Leu Asn Ser Ala Ser Asn His Gly Ala
    355                 360                 365

tgg cca gta tta gag aac aat gga ctt gcc cta aaa ggg cct gta ggg     1269
Trp Pro Val Leu Glu Asn Asn Gly Leu Ala Leu Lys Gly Pro Val Gly
370                 375                 380                 385

agt ggt agt tct ggc att aat att cag tgc agt act ata ggc cag atg     1317
Ser Gly Ser Ser Gly Ile Asn Ile Gln Cys Ser Thr Ile Gly Gln Met
                390                 395                 400

cct aac aat cag agt att aac tct aaa gtg agt ggt ggt tct acc cat     1365
Pro Asn Asn Gln Ser Ile Asn Ser Lys Val Ser Gly Gly Ser Thr His
            405                 410                 415

ggt acc tgg gga agc ctt cag gaa act tgt gaa tct gaa gta agt ggt     1413
Gly Thr Trp Gly Ser Leu Gln Glu Thr Cys Glu Ser Glu Val Ser Gly
        420                 425                 430

aca cag aag gtt tca ttc agt ggt caa cct caa aat att acc act gaa     1461
Thr Gln Lys Val Ser Phe Ser Gly Gln Pro Gln Asn Ile Thr Thr Glu
    435                 440                 445

atg act gga cca aat aac act act aac ttt atg acc tct agt tta cca     1509
Met Thr Gly Pro Asn Asn Thr Thr Asn Phe Met Thr Ser Ser Leu Pro
450                 455                 460                 465

aac tcc ggt tca gtg cag aat aat gag ctg cct agt agt aac aca ggg     1557
Asn Ser Gly Ser Val Gln Asn Asn Glu Leu Pro Ser Ser Asn Thr Gly
                470                 475                 480

gcc tgg cgt gtg agc aca atg aat cat cct cag atg cag gct cca tca     1605
Ala Trp Arg Val Ser Thr Met Asn His Pro Gln Met Gln Ala Pro Ser
            485                 490                 495
```

```
ggt atg aat ggc act tcc ctt tct cac ctt agc aat gga gag tca aaa      1653
Gly Met Asn Gly Thr Ser Leu Ser His Leu Ser Asn Gly Glu Ser Lys
        500                 505                 510

agt gga ggc tct tat ggt act aca tgg ggt gcc tat ggt tct aat tac      1701
Ser Gly Gly Ser Tyr Gly Thr Thr Trp Gly Ala Tyr Gly Ser Asn Tyr
    515                 520                 525

tct gga gac aaa tgt tca ggc cct aat ggc caa gct aat ggt gac act      1749
Ser Gly Asp Lys Cys Ser Gly Pro Asn Gly Gln Ala Asn Gly Asp Thr
530                 535                 540                 545

gtg aat gca act cta atg cag cct ggc gta aat ggt cct atg ggc act      1797
Val Asn Ala Thr Leu Met Gln Pro Gly Val Asn Gly Pro Met Gly Thr
                550                 555                 560

aac ttt caa gtt aac aca aac aaa gga ggt ggt gtg tgg gaa tct ggt      1845
Asn Phe Gln Val Asn Thr Asn Lys Gly Gly Gly Val Trp Glu Ser Gly
            565                 570                 575

gca gca aac tcc cag agt aca tca tgg gga agt gga aat ggc gca aat      1893
Ala Ala Asn Ser Gln Ser Thr Ser Trp Gly Ser Gly Asn Gly Ala Asn
        580                 585                 590

tct gga gga agt cga aga gga tgg gga acc cct gca caa aac act ggc      1941
Ser Gly Gly Ser Arg Arg Gly Trp Gly Thr Pro Ala Gln Asn Thr Gly
    595                 600                 605

act aat tta ccc agc gtt gag tgg aac aaa ctg cct agc aat cag cat      1989
Thr Asn Leu Pro Ser Val Glu Trp Asn Lys Leu Pro Ser Asn Gln His
610                 615                 620                 625

tcc aat gat agt gca aat ggc aat ggt aag acg ttt aca aat gga tgg      2037
Ser Asn Asp Ser Ala Asn Gly Asn Gly Lys Thr Phe Thr Asn Gly Trp
                630                 635                 640

aaa tct act gag gaa gag gat cag ggt tct gcc aca tct cag aca aat      2085
Lys Ser Thr Glu Glu Glu Asp Gln Gly Ser Ala Thr Ser Gln Thr Asn
            645                 650                 655

gag caa agc agt gtg tgg gcc aaa aca gga ggt aca gtg gag agc gat      2133
Glu Gln Ser Ser Val Trp Ala Lys Thr Gly Gly Thr Val Glu Ser Asp
        660                 665                 670

ggt agt aca gaa agc act gga cgc ctt gag gaa aaa gga act ggg gaa      2181
Gly Ser Thr Glu Ser Thr Gly Arg Leu Glu Glu Lys Gly Thr Gly Glu
    675                 680                 685

agt cag agt aga gac aga aga aaa att gat cag cac aca tta ctc caa      2229
Ser Gln Ser Arg Asp Arg Arg Lys Ile Asp Gln His Thr Leu Leu Gln
690                 695                 700                 705

agc att gta aac aga act gac tta gat cca cgt gtc ctg tcc aac tct      2277
Ser Ile Val Asn Arg Thr Asp Leu Asp Pro Arg Val Leu Ser Asn Ser
                710                 715                 720

ggt tgg gga cag act cct att aag cag aat act gcc tgg gat aca gaa      2325
Gly Trp Gly Gln Thr Pro Ile Lys Gln Asn Thr Ala Trp Asp Thr Glu
            725                 730                 735

aca tca cct aga ggg gaa cga aag act gac aat ggg aca gag gcc tgg      2373
Thr Ser Pro Arg Gly Glu Arg Lys Thr Asp Asn Gly Thr Glu Ala Trp
        740                 745                 750

gga agc tct gca aca cag act ttt aac tca ggg gca tgt ata gat aag      2421
Gly Ser Ser Ala Thr Gln Thr Phe Asn Ser Gly Ala Cys Ile Asp Lys
    755                 760                 765

act agc cct aat ggt aat gat acc tca tct gta tca ggg tgg ggc gat      2469
Thr Ser Pro Asn Gly Asn Asp Thr Ser Ser Val Ser Gly Trp Gly Asp
770                 775                 780                 785

ccc aaa cct gct ctg agg tgg gga gat tcc aaa ggc tca aac tgc cag      2517
Pro Lys Pro Ala Leu Arg Trp Gly Asp Ser Lys Gly Ser Asn Cys Gln
                790                 795                 800

ggg ggg tgg gaa gat gat tct gct gct aca gga atg gtc aag agc aat      2565
Gly Gly Trp Glu Asp Asp Ser Ala Ala Thr Gly Met Val Lys Ser Asn
```

```
            805                 810                 815

cag tgg ggg aat tgc aaa gag gag aag gct gca tgg aat gac tcg caa     2613
Gln Trp Gly Asn Cys Lys Glu Glu Lys Ala Ala Trp Asn Asp Ser Gln
        820                 825                 830

aag aat aaa cag gga tgg ggt gat gga caa aaa tca agc caa ggg tgg     2661
Lys Asn Lys Gln Gly Trp Gly Asp Gly Gln Lys Ser Ser Gln Gly Trp
    835                 840                 845

tct gtt tct gcc agt gat aac tgg gga gaa act tca agg aat aac cat     2709
Ser Val Ser Ala Ser Asp Asn Trp Gly Glu Thr Ser Arg Asn Asn His
850                 855                 860                 865

tgg ggt gag gcc aat aag aaa tcc agc tca gga ggt agt gac agt gac     2757
Trp Gly Glu Ala Asn Lys Lys Ser Ser Ser Gly Gly Ser Asp Ser Asp
                870                 875                 880

agg tcc gtt tcc ggt tgg aac gaa ctt ggt aaa act agt tct ttc act     2805
Arg Ser Val Ser Gly Trp Asn Glu Leu Gly Lys Thr Ser Ser Phe Thr
            885                 890                 895

tgg gga aac aac ata aat cca aat aat tca tca gga tgg gat gaa tct     2853
Trp Gly Asn Asn Ile Asn Pro Asn Asn Ser Ser Gly Trp Asp Glu Ser
        900                 905                 910

tct aaa cct act cct tcc cag gga tgg gga gac cct cca aag tct aat     2901
Ser Lys Pro Thr Pro Ser Gln Gly Trp Gly Asp Pro Pro Lys Ser Asn
    915                 920                 925

cag tct cta ggt tgg gga gat tcg tca aag cca gtc agc tct cca gac     2949
Gln Ser Leu Gly Trp Gly Asp Ser Ser Lys Pro Val Ser Ser Pro Asp
930                 935                 940                 945

tgg aac aag caa caa gac att gtt gga tct tgg gga atc cca cca gct     2997
Trp Asn Lys Gln Gln Asp Ile Val Gly Ser Trp Gly Ile Pro Pro Ala
                950                 955                 960

aca ggc aaa cct cct ggt aca ggc tgg ctg ggg gga cct ata cca gcc     3045
Thr Gly Lys Pro Pro Gly Thr Gly Trp Leu Gly Gly Pro Ile Pro Ala
            965                 970                 975

cca gca aaa gaa gaa gaa ccc aca ggc tgg gag gaa cca tcc cca gaa     3093
Pro Ala Lys Glu Glu Glu Pro Thr Gly Trp Glu Glu Pro Ser Pro Glu
        980                 985                 990

tct ata cgt cgc aaa atg gag  att gat gat gga act  tca gct tgg gga   3141
Ser Ile Arg Arg Lys Met Glu  Ile Asp Asp Gly Thr  Ser Ala Trp Gly
    995                 1000                1005

gat  cca agc aaa tac aac  tac aaa aat gtg aac  atg tgg aac aaa      3186
Asp  Pro Ser Lys Tyr Asn  Tyr Lys Asn Val Asn  Met Trp Asn Lys
1010                 1015                 1020

aac  gtc cca aat ggc aac  agc cgt tca gac cag  caa gca cag gta      3231
Asn  Val Pro Asn Gly Asn  Ser Arg Ser Asp Gln  Gln Ala Gln Val
1025                 1030                 1035

cat  cag ctg cta acg cct  gca agt gcc atc tca  aac aaa gag gca      3276
His  Gln Leu Leu Thr Pro  Ala Ser Ala Ile Ser  Asn Lys Glu Ala
1040                 1045                 1050

agc  agt ggc tct ggc tgg  ggt gag ccc tgg ggg  gag cct tct act      3321
Ser  Ser Gly Ser Gly Trp  Gly Glu Pro Trp Gly  Glu Pro Ser Thr
1055                 1060                 1065

cca  gcc aca act gtg gat  aat ggt act tca gca  tgg ggt aag ccc      3366
Pro  Ala Thr Thr Val Asp  Asn Gly Thr Ser Ala  Trp Gly Lys Pro
1070                 1075                 1080

ata  gac agt ggt ccc agc  tgg ggg gaa ccc att  gct gcg gca tcc      3411
Ile  Asp Ser Gly Pro Ser  Trp Gly Glu Pro Ile  Ala Ala Ala Ser
1085                 1090                 1095

agc  aca tcc acg tgg ggc  tcc agc tct gtt ggt  cca caa gca tta      3456
Ser  Thr Ser Thr Trp Gly  Ser Ser Ser Val Gly  Pro Gln Ala Leu
1100                 1105                 1110

agc  aaa tct ggg cca aaa  tct atg caa gat ggc  tgg tgt ggt gat      3501
```

```
Ser  Lys Ser Gly Pro Lys  Ser Met Gln Asp Gly  Trp Cys Gly Asp
1115                1120                1125

gat  atg cca ttg cct gga  aat cgc ccc act ggc  tgg gaa gag gaa      3546
Asp  Met Pro Leu Pro Gly  Asn Arg Pro Thr Gly  Trp Glu Glu Glu
1130                1135                1140

gag  gat gtg gag att gga  atg tgg aat agt aat  tca tct caa gag      3591
Glu  Asp Val Glu Ile Gly  Met Trp Asn Ser Asn  Ser Ser Gln Glu
1145                1150                1155

ctt  aac tca tct tta aat  tgg cca cca tat aca  aag aaa atg tca      3636
Leu  Asn Ser Ser Leu Asn  Trp Pro Pro Tyr Thr  Lys Lys Met Ser
1160                1165                1170

tcg  aag ggt ctg agt ggc  aaa aaa agg aga agg  gaa agg gga atg      3681
Ser  Lys Gly Leu Ser Gly  Lys Lys Arg Arg Arg  Glu Arg Gly Met
1175                1180                1185

atg  aaa ggt gga aac aaa  caa gaa gaa gcg tgg  ata aat cca ttt      3726
Met  Lys Gly Gly Asn Lys  Gln Glu Glu Ala Trp  Ile Asn Pro Phe
1190                1195                1200

gtt  aaa cag ttt tca aac  atc agt ttt tcg aga  gac tca cca gag      3771
Val  Lys Gln Phe Ser Asn  Ile Ser Phe Ser Arg  Asp Ser Pro Glu
1205                1210                1215

gaa  aat gta caa agc aat  aag atg gac ctt tct  gga gga atg tta      3816
Glu  Asn Val Gln Ser Asn  Lys Met Asp Leu Ser  Gly Gly Met Leu
1220                1225                1230

caa  gac aaa cga atg gag  ata gat aaa cat agc  cta aat att ggt      3861
Gln  Asp Lys Arg Met Glu  Ile Asp Lys His Ser  Leu Asn Ile Gly
1235                1240                1245

gat  tac aat cga acg gtc  ggg aaa ggc cct ggt  tct cgg cct cag      3906
Asp  Tyr Asn Arg Thr Val  Gly Lys Gly Pro Gly  Ser Arg Pro Gln
1250                1255                1260

att  tcc aaa gag tct tcc  atg gag cgc aat cct  tat ttt gat aag      3951
Ile  Ser Lys Glu Ser Ser  Met Glu Arg Asn Pro  Tyr Phe Asp Lys
1265                1270                1275

gat  ggc att gta gca gat  gaa tcc caa aac atg  cag ttt atg tcc      3996
Asp  Gly Ile Val Ala Asp  Glu Ser Gln Asn Met  Gln Phe Met Ser
1280                1285                1290

agt  caa agc atg aag ctt  ccc cct tca aat agt  gca cta cct aac      4041
Ser  Gln Ser Met Lys Leu  Pro Pro Ser Asn Ser  Ala Leu Pro Asn
1295                1300                1305

cag  gcc ctt ggc tcc ata  gca ggg ctg ggt atg  caa aac ttg aat      4086
Gln  Ala Leu Gly Ser Ile  Ala Gly Leu Gly Met  Gln Asn Leu Asn
1310                1315                1320

tct  gtt aga cag aat ggc  aat ccc agt atg ttt  ggt gtt gga aac      4131
Ser  Val Arg Gln Asn Gly  Asn Pro Ser Met Phe  Gly Val Gly Asn
1325                1330                1335

aca  gca gca caa ccc cgg  ggc atg cag cag cct  cca gca caa cct      4176
Thr  Ala Ala Gln Pro Arg  Gly Met Gln Gln Pro  Pro Ala Gln Pro
1340                1345                1350

ctt  agt tca tct cag cct  aat ctc cgt gct caa  gtg cct cct cca      4221
Leu  Ser Ser Ser Gln Pro  Asn Leu Arg Ala Gln  Val Pro Pro Pro
1355                1360                1365

tta  ctc tcc cct cag gtt  cca gtt tca ttg ctg  aag tat gca cca      4266
Leu  Leu Ser Pro Gln Val  Pro Val Ser Leu Leu  Lys Tyr Ala Pro
1370                1375                1380

aac  aac ggt ggc ctg aat  cca ctc ttt ggc cct  caa cag gta gcc      4311
Asn  Asn Gly Gly Leu Asn  Pro Leu Phe Gly Pro  Gln Gln Val Ala
1385                1390                1395

atg  ctg aac cag cta tcc  cag cta aac cag ctt  tct cag atc tcc      4356
Met  Leu Asn Gln Leu Ser  Gln Leu Asn Gln Leu  Ser Gln Ile Ser
1400                1405                1410
```

-continued

```
cag  tta cag cga ttg tta  gcg cag cag caa agg  gcg cag agt cag      4401
Gln  Leu Gln Arg Leu Leu  Ala Gln Gln Gln Arg  Ala Gln Ser Gln
1415                 1420                 1425

aga  agc gtg cct tct ggg  aac cgg ccg cag caa  gac cag cag ggt      4446
Arg  Ser Val Pro Ser Gly  Asn Arg Pro Gln Gln  Asp Gln Gln Gly
1430                 1435                 1440

cga  cct ctt agt gtg cag  cag caa atg atg caa  caa tct cgt caa      4491
Arg  Pro Leu Ser Val Gln  Gln Gln Met Met Gln  Gln Ser Arg Gln
1445                 1450                 1455

ctt  gat cca aac ctg ttg  gtg aag cag cag act  cca cca tct cag      4536
Leu  Asp Pro Asn Leu Leu  Val Lys Gln Gln Thr  Pro Pro Ser Gln
1460                 1465                 1470

cag  cag cca ctc cat cag  cca gcc atg aag tct  ttc ctt gac aat      4581
Gln  Gln Pro Leu His Gln  Pro Ala Met Lys Ser  Phe Leu Asp Asn
1475                 1480                 1485

gtc  atg ccc cac act aca  cct gag ctg caa aaa  ggg cca tca cca      4626
Val  Met Pro His Thr Thr  Pro Glu Leu Gln Lys  Gly Pro Ser Pro
1490                 1495                 1500

ata  aat gct ttc agc aac  ttc cct ata ggc ttg  aac tca aac ttg      4671
Ile  Asn Ala Phe Ser Asn  Phe Pro Ile Gly Leu  Asn Ser Asn Leu
1505                 1510                 1515

aat  gta aat atg gat atg  aac agt att aaa gag  cca cag tca aga      4716
Asn  Val Asn Met Asp Met  Asn Ser Ile Lys Glu  Pro Gln Ser Arg
1520                 1525                 1530

cta  agg aag tgg acg aca  gtg gac agc att tct  gtg aac aca tct      4761
Leu  Arg Lys Trp Thr Thr  Val Asp Ser Ile Ser  Val Asn Thr Ser
1535                 1540                 1545

ttg  gat caa aac tcc agc  aaa cat ggt gct att  tca agt ggt ttc      4806
Leu  Asp Gln Asn Ser Ser  Lys His Gly Ala Ile  Ser Ser Gly Phe
1550                 1555                 1560

agg  ctg gaa gag tct cca  ttt gtt ccc tat gac  ttt atg aac agc      4851
Arg  Leu Glu Glu Ser Pro  Phe Val Pro Tyr Asp  Phe Met Asn Ser
1565                 1570                 1575

agt  act tca cca gcc agt  cct cca ggt tca ata  gga gat ggc tgg      4896
Ser  Thr Ser Pro Ala Ser  Pro Pro Gly Ser Ile  Gly Asp Gly Trp
1580                 1585                 1590

cca  cgt gcc aaa tcg cct  aac ggc tct agc agt  gtt aat tgg cca      4941
Pro  Arg Ala Lys Ser Pro  Asn Gly Ser Ser Ser  Val Asn Trp Pro
1595                 1600                 1605

cca  gaa ttt cgt cct ggt  gag cca tgg aaa ggt  tat cca aac att      4986
Pro  Glu Phe Arg Pro Gly  Glu Pro Trp Lys Gly  Tyr Pro Asn Ile
1610                 1615                 1620

gac  cct gaa act gac cct  tac gtc act cct ggc  agt gtc ata aac      5031
Asp  Pro Glu Thr Asp Pro  Tyr Val Thr Pro Gly  Ser Val Ile Asn
1625                 1630                 1635

aat  ctt tca att aat act  gtg cgg gaa gtt gac  cac ctc agg gac      5076
Asn  Leu Ser Ile Asn Thr  Val Arg Glu Val Asp  His Leu Arg Asp
1640                 1645                 1650

agg  aac agt ggg tca tcc  tca tcc ttg aac acc  acg ctg cct tca      5121
Arg  Asn Ser Gly Ser Ser  Ser Ser Leu Asn Thr  Thr Leu Pro Ser
1655                 1660                 1665

act  agt gcc tgg tca tcc  att cgt gcc tcc aac  tac aac gtt ccc      5166
Thr  Ser Ala Trp Ser Ser  Ile Arg Ala Ser Asn  Tyr Asn Val Pro
1670                 1675                 1680

ctc  agc agt aca gca caa  agc act tca gcc aga  aat agt gat tcc      5211
Leu  Ser Ser Thr Ala Gln  Ser Thr Ser Ala Arg  Asn Ser Asp Ser
1685                 1690                 1695

aaa  ttg aca tgg tct cct  ggt tca gtt aca aac  acc tct ctg gct      5256
Lys  Leu Thr Trp Ser Pro  Gly Ser Val Thr Asn  Thr Ser Leu Ala
1700                 1705                 1710
```

```
cat  gag ctg tgg aag gtc  cct ttg cca cct aaa  aac atc act gct      5301
His  Glu Leu Trp Lys Val  Pro Leu Pro Pro Lys  Asn Ile Thr Ala
1715                 1720                 1725

ccg  tcc cgc cca cct ccg  gga ctg act ggt cag  aag cca ccc ttg      5346
Pro  Ser Arg Pro Pro Pro  Gly Leu Thr Gly Gln  Lys Pro Pro Leu
1730                 1735                 1740

tct  acg tgg gat aat tct  ccc ctt cgt ata ggt  gga gga tgg gga      5391
Ser  Thr Trp Asp Asn Ser  Pro Leu Arg Ile Gly  Gly Gly Trp Gly
1745                 1750                 1755

aat  tct gac gcc aga tat  acc cca ggt tcc agc  tgg ggt gag agc      5436
Asn  Ser Asp Ala Arg Tyr  Thr Pro Gly Ser Ser  Trp Gly Glu Ser
1760                 1765                 1770

agc  tca ggg aga ata aca  aat tgg ctt gtt cta  aaa aac ctt aca      5481
Ser  Ser Gly Arg Ile Thr  Asn Trp Leu Val Leu  Lys Asn Leu Thr
1775                 1780                 1785

cct  cag atc gat ggc tca  act ctg cgc act ctg  tgc atg cag cac      5526
Pro  Gln Ile Asp Gly Ser  Thr Leu Arg Thr Leu  Cys Met Gln His
1790                 1795                 1800

ggc  ccg ctg atc aca ttc  cac ctg aac ctc cct  cac gga aat gct      5571
Gly  Pro Leu Ile Thr Phe  His Leu Asn Leu Pro  His Gly Asn Ala
1805                 1810                 1815

ctg  gtc cgc tac agt tca  aaa gaa gag gta gtg  aag gca caa aag      5616
Leu  Val Arg Tyr Ser Ser  Lys Glu Glu Val Val  Lys Ala Gln Lys
1820                 1825                 1830

tct  ctg cac atg tgt gta  ctg ggg aac act act  att ctt gct gag      5661
Ser  Leu His Met Cys Val  Leu Gly Asn Thr Thr  Ile Leu Ala Glu
1835                 1840                 1845

ttt  gcc agt gaa gag gag  atc agt cgt ttc ttt  gca caa agc cag      5706
Phe  Ala Ser Glu Glu Glu  Ile Ser Arg Phe Phe  Ala Gln Ser Gln
1850                 1855                 1860

tct  ctg acc cct tct ccc  ggc tgg cag tct ctc  ggg tcc agc cag      5751
Ser  Leu Thr Pro Ser Pro  Gly Trp Gln Ser Leu  Gly Ser Ser Gln
1865                 1870                 1875

agc  cgg ctg ggc tcc ctc  gac tgt tcc cac tca  ttc tcc agc cgg      5796
Ser  Arg Leu Gly Ser Leu  Asp Cys Ser His Ser  Phe Ser Ser Arg
1880                 1885                 1890

acc  gat ctc aat cac tgg  aat ggt gct ggg ctg  tcg gga act aac      5841
Thr  Asp Leu Asn His Trp  Asn Gly Ala Gly Leu  Ser Gly Thr Asn
1895                 1900                 1905

tgt  gga gac ctt cac ggc  act tca ctc tgg ggg  acc ccg cat tat      5886
Cys  Gly Asp Leu His Gly  Thr Ser Leu Trp Gly  Thr Pro His Tyr
1910                 1915                 1920

tcc  acaagcctgt ggggtccccc aagcagcagc gacccccgag gaattagcag        5939
Ser
1925

cccatctccc attaacgctt ttctttctgt tgaccacctg ggtgggggtg gagagtccat   5999

gtaacagtgt agatgcagac tcaccgaccg ggacctcaga cgcgagggaa aggagcacta   6059

agtggggctc gccgcctgca gccaggggcc gcctgtggga acagctattc tctgcacatt   6119

ttccactttg ttttccccaa aacatatcag tttgaatact tgaatcatgc aggccaatat   6179

tataatgtga aaaggtatct actctattta cactcccaaa tagcgccata catgctaaac   6239

cgtagagaat gagctcgctt gtgtctattc atcatgttta gcctttggat tctttttttt   6299

tttttccttc tattcctccc caaccccccc ccccgcccct ttttttctct cttgcaaaac   6359

catttttttgg gctgataacg tatgagcttt tccctttgca ctgaatgatg ttctctccgt  6419

ctcatcggca gtatgggggg cagctgtccc agtgtcaatg tttactcaag ggtgttctta   6479
```

```
ggaggcgtgc gctctctact atgccttgat gttgcctacc ttattgtggt atcgtggagt   6539

ttaaaagatc aagttaggat gctgacttag gattattaat gaaagtgttg caccagtttt   6599

ttcatgttgt aaaactaaag aatttcgctc tgcagtttga aaaactgtgg ccacagctgt   6659

gacttgcagc ccacctgcca cccaggacgg gccctgcact ttgaataggc tttccatttt   6719

gttttggagg ttctcacttt gaaccttctt gtttacagat ttttttgttt gtttttttgag   6779

aaaaaaaaat gtttactctt ccatcattta aaaaaaatgt aaaagacaaa aaaaaaatgg   6839

aggatgattt aaaagatgct ttctatctct gggaaaaagg agcagcattt ggccatgttc   6899

ttttgttttt ctattcctgt cccaaatcaa agagcatggt tctcaggaaa accagttccc   6959

cagtttaaaa aaaaaaaaaa aaattccttg tagtttctta gaggaaaaaa agaaaaaccc   7019

caacttttag cactgatact acatattgct ctgttaaaga attttctctg ccaaaaaaaa   7079

agaaaaaaca aaaaaacgct taaagctgga gtttgacatt ctgctttcag atgctgtctt   7139

tttattagtg agtgatgatg gtttgctaat aatcaatagg taataatttt ttgtaatccc   7199

atcaagtggc tccatatgtt tctgctctct cgtgactgtg ttaatgttta actgttgtac   7259

cttaaagccg aaatcagtaa ctatgcatac tgtaaccaag gtattgggct tacagagttg   7319

tttgttgtat aaagaaaatt ttaaatgttg ttgcaaacta acgagttaca ccattttaaa   7379

ctttctttcc tcccccctt ttttgcccac aaatggtatt ataatgcttg cttagtcaaa   7439

gaagagagac taaacaaggg taaaaatttt aacagtacag aatttgccat catatcattg   7499

ccttgattct aactgtttgt gtcctaagat gcaaaagaag tcagtggctt ttaactgttt   7559

acaaatagaa tgtgattgta aaatgtacag tttggttgtg tttgaattat gaaatttctt   7619

cagatataat aaaccatgac tttttggctg ctcaacatta attgtctcct ttttgtgaat   7679

ttatttgtag gctctttttt ataatgaaag tttcaaagtt gctatgtatg agggttctca   7739

tagagcaacc gattaaaaat ctaagcaaat atttgaacat tttatctgaa ctcatcacaa   7799

tttcaccctg aaataatgtg agaacaatgg gaaactgtag cttgctcctt cccaccctct   7859

ctgagcatct ttgggatctt gttgctcaaa actcttctgt gacttcatct tccccaccat   7919

ttgtgcccat ctcaagcctc agcaagaaac catgtggaac atgaagctta atgacttgac   7979

agtgtactag tgttaaactc tcatacctct gttacaaagc gagaaacgcc acacccggac   8039

tggccttttc ttccccccttc acggccctcg cttctccctg caggagctcg gggcgaaac   8099

ctgtgtatgg atttcagtgt atgacttcag atcatgctcc aacttgccag gtgtgagcta   8159

atgttgtcgg acaccttact ataagcaaat gttattcagt gcgttcaatg tatattgact   8219

tccatactgg tttttccaaa aaccaaaggt agctttgaaa aaccatgtct ggaaatgttt   8279

ggagcgttaa gctgattgac cttctgacct tggggctttg agtagtatat aattcataac   8339

tgcgttaatt gtattgttaa agtgtttggg agttttttgc gcttgttatg tggaaataaa   8399

gtgtttgatt taaaattttt taaaaaaaaa aaaaaaaaa                          8438
```

<210> SEQ ID NO 16
<211> LENGTH: 1925
<212> TYPE: PRT
<213> ORGANISM: Homo sapiens

<400> SEQUENCE: 16

```
Met Arg Glu Leu Glu Ala Lys Ala Thr Lys Asp Val Glu Arg Asn Leu
1               5                   10                  15

Ser Arg Asp Leu Val Gln Glu Glu Glu Gln Leu Met Glu Glu Lys Lys
            20                  25                  30
```

```
Lys Lys Lys Asp Asp Lys Lys Lys Lys Glu Ala Ala Gln Lys Lys Ala
        35                  40                  45

Thr Glu Gln Lys Ile Lys Val Pro Glu Gln Ile Lys Pro Ser Val Ser
    50                  55                  60

Gln Pro Gln Pro Ala Asn Ser Asn Asn Gly Thr Ser Thr Ala Thr Ser
65                  70                  75                  80

Thr Asn Asn Asn Ala Lys Arg Ala Thr Ala Asn Asn Gln Gln Pro Gln
                85                  90                  95

Gln Gln Gln Gln Gln Gln Gln Pro Gln Gln Gln Gln Pro Gln Gln Gln
            100                 105                 110

Pro Gln Pro Gln Pro Gln Gln Gln Gln Pro Gln Gln Gln Pro Gln Ala
        115                 120                 125

Leu Pro Arg Tyr Pro Arg Glu Val Pro Pro Arg Phe Arg His Gln Glu
    130                 135                 140

His Lys Gln Leu Leu Lys Arg Gly Gln His Phe Pro Val Ile Ala Ala
145                 150                 155                 160

Asn Leu Gly Ser Ala Val Lys Val Leu Asn Ser Gln Ser Glu Ser Ser
                165                 170                 175

Ala Leu Thr Asn Gln Gln Pro Gln Asn Asn Gly Glu Val Gln Asn Ser
            180                 185                 190

Lys Asn Gln Ser Asp Ile Asn His Ser Thr Ser Gly Ser His Tyr Glu
        195                 200                 205

Asn Ser Gln Arg Gly Pro Val Ser Ser Thr Ser Asp Ser Ser Thr Asn
    210                 215                 220

Cys Lys Asn Ala Val Val Ser Asp Leu Ser Glu Lys Glu Ala Trp Pro
225                 230                 235                 240

Ser Ala Pro Gly Ser Asp Pro Glu Leu Ala Ser Glu Cys Met Asp Ala
                245                 250                 255

Asp Ser Ala Ser Ser Ser Glu Ser Glu Arg Asn Ile Thr Ile Met Ala
            260                 265                 270

Ser Gly Asn Thr Gly Gly Glu Lys Asp Gly Leu Arg Asn Ser Thr Gly
        275                 280                 285

Leu Gly Ser Gln Asn Lys Phe Val Val Gly Ser Ser Ser Asn Asn Val
    290                 295                 300

Gly His Gly Ser Ser Thr Gly Pro Trp Gly Phe Ser His Gly Ala Ile
305                 310                 315                 320

Ile Ser Thr Cys Gln Val Ser Val Asp Ala Pro Glu Ser Lys Ser Glu
                325                 330                 335

Ser Ser Asn Asn Arg Met Asn Ala Trp Gly Thr Val Ser Ser Ser Ser
            340                 345                 350

Asn Gly Gly Leu Asn Pro Ser Thr Leu Asn Ser Ala Ser Asn His Gly
        355                 360                 365

Ala Trp Pro Val Leu Glu Asn Asn Gly Leu Ala Leu Lys Gly Pro Val
    370                 375                 380

Gly Ser Gly Ser Ser Gly Ile Asn Ile Gln Cys Ser Thr Ile Gly Gln
385                 390                 395                 400

Met Pro Asn Asn Gln Ser Ile Asn Ser Lys Val Ser Gly Gly Ser Thr
                405                 410                 415

His Gly Thr Trp Gly Ser Leu Gln Glu Thr Cys Glu Ser Glu Val Ser
            420                 425                 430

Gly Thr Gln Lys Val Ser Phe Ser Gly Gln Pro Gln Asn Ile Thr Thr
        435                 440                 445
```

```
Glu Met Thr Gly Pro Asn Asn Thr Thr Asn Phe Met Thr Ser Ser Leu
    450                 455                 460

Pro Asn Ser Gly Ser Val Gln Asn Asn Glu Leu Pro Ser Ser Asn Thr
465                 470                 475                 480

Gly Ala Trp Arg Val Ser Thr Met Asn His Pro Gln Met Gln Ala Pro
                485                 490                 495

Ser Gly Met Asn Gly Thr Ser Leu Ser His Leu Ser Asn Gly Glu Ser
            500                 505                 510

Lys Ser Gly Gly Ser Tyr Gly Thr Thr Trp Gly Ala Tyr Gly Ser Asn
        515                 520                 525

Tyr Ser Gly Asp Lys Cys Ser Gly Pro Asn Gly Gln Ala Asn Gly Asp
    530                 535                 540

Thr Val Asn Ala Thr Leu Met Gln Pro Gly Val Asn Gly Pro Met Gly
545                 550                 555                 560

Thr Asn Phe Gln Val Asn Thr Asn Lys Gly Gly Gly Val Trp Glu Ser
                565                 570                 575

Gly Ala Ala Asn Ser Gln Ser Thr Ser Trp Gly Ser Gly Asn Gly Ala
            580                 585                 590

Asn Ser Gly Gly Ser Arg Arg Gly Trp Gly Thr Pro Ala Gln Asn Thr
        595                 600                 605

Gly Thr Asn Leu Pro Ser Val Glu Trp Asn Lys Leu Pro Ser Asn Gln
    610                 615                 620

His Ser Asn Asp Ser Ala Asn Gly Asn Gly Lys Thr Phe Thr Asn Gly
625                 630                 635                 640

Trp Lys Ser Thr Glu Glu Glu Asp Gln Gly Ser Ala Thr Ser Gln Thr
                645                 650                 655

Asn Glu Gln Ser Ser Val Trp Ala Lys Thr Gly Gly Thr Val Glu Ser
            660                 665                 670

Asp Gly Ser Thr Glu Ser Thr Gly Arg Leu Glu Glu Lys Gly Thr Gly
        675                 680                 685

Glu Ser Gln Ser Arg Asp Arg Arg Lys Ile Asp Gln His Thr Leu Leu
    690                 695                 700

Gln Ser Ile Val Asn Arg Thr Asp Leu Asp Pro Arg Val Leu Ser Asn
705                 710                 715                 720

Ser Gly Trp Gly Gln Thr Pro Ile Lys Gln Asn Thr Ala Trp Asp Thr
                725                 730                 735

Glu Thr Ser Pro Arg Gly Glu Arg Lys Thr Asp Asn Gly Thr Glu Ala
            740                 745                 750

Trp Gly Ser Ser Ala Thr Gln Thr Phe Asn Ser Gly Ala Cys Ile Asp
        755                 760                 765

Lys Thr Ser Pro Asn Gly Asn Asp Thr Ser Ser Val Ser Gly Trp Gly
    770                 775                 780

Asp Pro Lys Pro Ala Leu Arg Trp Gly Asp Ser Lys Gly Ser Asn Cys
785                 790                 795                 800

Gln Gly Gly Trp Glu Asp Asp Ser Ala Ala Thr Gly Met Val Lys Ser
                805                 810                 815

Asn Gln Trp Gly Asn Cys Lys Glu Glu Lys Ala Ala Trp Asn Asp Ser
            820                 825                 830

Gln Lys Asn Lys Gln Gly Trp Gly Asp Gly Gln Lys Ser Ser Gln Gly
        835                 840                 845

Trp Ser Val Ser Ala Ser Asp Asn Trp Gly Glu Thr Ser Arg Asn Asn
    850                 855                 860

His Trp Gly Glu Ala Asn Lys Lys Ser Ser Ser Gly Gly Ser Asp Ser
```

```
865                 870                 875                 880

Asp Arg Ser Val Ser Gly Trp Asn Glu Leu Gly Lys Thr Ser Ser Phe
                885                 890                 895

Thr Trp Gly Asn Asn Ile Asn Pro Asn Asn Ser Ser Gly Trp Asp Glu
            900                 905                 910

Ser Ser Lys Pro Thr Pro Ser Gln Gly Trp Gly Asp Pro Pro Lys Ser
        915                 920                 925

Asn Gln Ser Leu Gly Trp Gly Asp Ser Ser Lys Pro Val Ser Ser Pro
    930                 935                 940

Asp Trp Asn Lys Gln Gln Asp Ile Val Gly Ser Trp Gly Ile Pro Pro
945                 950                 955                 960

Ala Thr Gly Lys Pro Pro Gly Thr Gly Trp Leu Gly Gly Pro Ile Pro
                965                 970                 975

Ala Pro Ala Lys Glu Glu Glu Pro Thr Gly Trp Glu Glu Pro Ser Pro
            980                 985                 990

Glu Ser Ile Arg Arg Lys Met Glu  Ile Asp Asp Gly Thr  Ser Ala Trp
        995                 1000                1005

Gly Asp  Pro Ser Lys Tyr Asn  Tyr Lys Asn Val Asn  Met Trp Asn
    1010                1015                1020

Lys Asn  Val Pro Asn Gly Asn  Ser Arg Ser Asp Gln  Gln Ala Gln
    1025                1030                1035

Val His  Gln Leu Leu Thr Pro  Ala Ser Ala Ile Ser  Asn Lys Glu
    1040                1045                1050

Ala Ser  Ser Gly Ser Gly Trp  Gly Glu Pro Trp Gly  Glu Pro Ser
    1055                1060                1065

Thr Pro  Ala Thr Thr Val Asp  Asn Gly Thr Ser Ala  Trp Gly Lys
    1070                1075                1080

Pro Ile  Asp Ser Gly Pro Ser  Trp Gly Glu Pro Ile  Ala Ala Ala
    1085                1090                1095

Ser Ser  Thr Ser Thr Trp Gly  Ser Ser Ser Val Gly  Pro Gln Ala
    1100                1105                1110

Leu Ser  Lys Ser Gly Pro Lys  Ser Met Gln Asp Gly  Trp Cys Gly
    1115                1120                1125

Asp Asp  Met Pro Leu Pro Gly  Asn Arg Pro Thr Gly  Trp Glu Glu
    1130                1135                1140

Glu Glu  Asp Val Glu Ile Gly  Met Trp Asn Ser Asn  Ser Ser Gln
    1145                1150                1155

Glu Leu  Asn Ser Ser Leu Asn  Trp Pro Pro Tyr Thr  Lys Lys Met
    1160                1165                1170

Ser Ser  Lys Gly Leu Ser Gly  Lys Lys Arg Arg Arg  Glu Arg Gly
    1175                1180                1185

Met Met  Lys Gly Gly Asn Lys  Gln Glu Glu Ala Trp  Ile Asn Pro
    1190                1195                1200

Phe Val  Lys Gln Phe Ser Asn  Ile Ser Phe Ser Arg  Asp Ser Pro
    1205                1210                1215

Glu Glu  Asn Val Gln Ser Asn  Lys Met Asp Leu Ser  Gly Gly Met
    1220                1225                1230

Leu Gln  Asp Lys Arg Met Glu  Ile Asp Lys His Ser  Leu Asn Ile
    1235                1240                1245

Gly Asp  Tyr Asn Arg Thr Val  Gly Lys Gly Pro Gly  Ser Arg Pro
    1250                1255                1260

Gln Ile  Ser Lys Glu Ser Ser  Met Glu Arg Asn Pro  Tyr Phe Asp
    1265                1270                1275
```

```
Lys Asp  Gly Ile Val Ala Asp  Glu Ser Gln Asn Met  Gln Phe Met
    1280                 1285                 1290

Ser Ser  Gln Ser Met Lys Leu  Pro Pro Ser Asn Ser  Ala Leu Pro
    1295                 1300                 1305

Asn Gln  Ala Leu Gly Ser Ile  Ala Gly Leu Gly Met  Gln Asn Leu
    1310                 1315                 1320

Asn Ser  Val Arg Gln Asn Gly  Asn Pro Ser Met Phe  Gly Val Gly
    1325                 1330                 1335

Asn Thr  Ala Ala Gln Pro Arg  Gly Met Gln Gln Pro  Pro Ala Gln
    1340                 1345                 1350

Pro Leu  Ser Ser Ser Gln Pro  Asn Leu Arg Ala Gln  Val Pro Pro
    1355                 1360                 1365

Pro Leu  Leu Ser Pro Gln Val  Pro Val Ser Leu Leu  Lys Tyr Ala
    1370                 1375                 1380

Pro Asn  Asn Gly Gly Leu Asn  Pro Leu Phe Gly Pro  Gln Gln Val
    1385                 1390                 1395

Ala Met  Leu Asn Gln Leu Ser  Gln Leu Asn Gln Leu  Ser Gln Ile
    1400                 1405                 1410

Ser Gln  Leu Gln Arg Leu Leu  Ala Gln Gln Gln Arg  Ala Gln Ser
    1415                 1420                 1425

Gln Arg  Ser Val Pro Ser Gly  Asn Arg Pro Gln Gln  Asp Gln Gln
    1430                 1435                 1440

Gly Arg  Pro Leu Ser Val Gln  Gln Gln Met Met Gln  Gln Ser Arg
    1445                 1450                 1455

Gln Leu  Asp Pro Asn Leu Leu  Val Lys Gln Gln Thr  Pro Pro Ser
    1460                 1465                 1470

Gln Gln  Gln Pro Leu His Gln  Pro Ala Met Lys Ser  Phe Leu Asp
    1475                 1480                 1485

Asn Val  Met Pro His Thr Thr  Pro Glu Leu Gln Lys  Gly Pro Ser
    1490                 1495                 1500

Pro Ile  Asn Ala Phe Ser Asn  Phe Pro Ile Gly Leu  Asn Ser Asn
    1505                 1510                 1515

Leu Asn  Val Asn Met Asp Met  Asn Ser Ile Lys Glu  Pro Gln Ser
    1520                 1525                 1530

Arg Leu  Arg Lys Trp Thr Thr  Val Asp Ser Ile Ser  Val Asn Thr
    1535                 1540                 1545

Ser Leu  Asp Gln Asn Ser Ser  Lys His Gly Ala Ile  Ser Ser Gly
    1550                 1555                 1560

Phe Arg  Leu Glu Glu Ser Pro  Phe Val Pro Tyr Asp  Phe Met Asn
    1565                 1570                 1575

Ser Ser  Thr Ser Pro Ala Ser  Pro Pro Gly Ser Ile  Gly Asp Gly
    1580                 1585                 1590

Trp Pro  Arg Ala Lys Ser Pro  Asn Gly Ser Ser Ser  Val Asn Trp
    1595                 1600                 1605

Pro Pro  Glu Phe Arg Pro Gly  Glu Pro Trp Lys Gly  Tyr Pro Asn
    1610                 1615                 1620

Ile Asp  Pro Glu Thr Asp Pro  Tyr Val Thr Pro Gly  Ser Val Ile
    1625                 1630                 1635

Asn Asn  Leu Ser Ile Asn Thr  Val Arg Glu Val Asp  His Leu Arg
    1640                 1645                 1650

Asp Arg  Asn Ser Gly Ser Ser  Ser Ser Leu Asn Thr  Thr Leu Pro
    1655                 1660                 1665
```

```
Ser Thr  Ser Ala Trp Ser Ser  Ile Arg Ala Ser Asn  Tyr Asn Val
    1670                 1675                 1680

Pro Leu  Ser Ser Thr Ala Gln  Ser Thr Ser Ala Arg  Asn Ser Asp
    1685                 1690                 1695

Ser Lys  Leu Thr Trp Ser Pro  Gly Ser Val Thr Asn  Thr Ser Leu
    1700                 1705                 1710

Ala His  Glu Leu Trp Lys Val  Pro Leu Pro Pro Lys  Asn Ile Thr
    1715                 1720                 1725

Ala Pro  Ser Arg Pro Pro Pro  Gly Leu Thr Gly Gln  Lys Pro Pro
    1730                 1735                 1740

Leu Ser  Thr Trp Asp Asn Ser  Pro Leu Arg Ile Gly  Gly Gly Trp
    1745                 1750                 1755

Gly Asn  Ser Asp Ala Arg Tyr  Thr Pro Gly Ser Ser  Trp Gly Glu
    1760                 1765                 1770

Ser Ser  Ser Gly Arg Ile Thr  Asn Trp Leu Val Leu  Lys Asn Leu
    1775                 1780                 1785

Thr Pro  Gln Ile Asp Gly Ser  Thr Leu Arg Thr Leu  Cys Met Gln
    1790                 1795                 1800

His Gly  Pro Leu Ile Thr Phe  His Leu Asn Leu Pro  His Gly Asn
    1805                 1810                 1815

Ala Leu  Val Arg Tyr Ser Ser  Lys Glu Glu Val Val  Lys Ala Gln
    1820                 1825                 1830

Lys Ser  Leu His Met Cys Val  Leu Gly Asn Thr Thr  Ile Leu Ala
    1835                 1840                 1845

Glu Phe  Ala Ser Glu Glu Glu  Ile Ser Arg Phe Phe  Ala Gln Ser
    1850                 1855                 1860

Gln Ser  Leu Thr Pro Ser Pro  Gly Trp Gln Ser Leu  Gly Ser Ser
    1865                 1870                 1875

Gln Ser  Arg Leu Gly Ser Leu  Asp Cys Ser His Ser  Phe Ser Ser
    1880                 1885                 1890

Arg Thr  Asp Leu Asn His Trp  Asn Gly Ala Gly Leu  Ser Gly Thr
    1895                 1900                 1905

Asn Cys  Gly Asp Leu His Gly  Thr Ser Leu Trp Gly  Thr Pro His
    1910                 1915                 1920

Tyr Ser
    1925


<210> SEQ ID NO 17
<211> LENGTH: 10092
<212> TYPE: DNA
<213> ORGANISM: Homo sapiens
<220> FEATURE:
<221> NAME/KEY: CDS
<222> LOCATION: (68)..(5188)

<400> SEQUENCE: 17

cggcggagcc ccggcggggc gtttggtttc ggtttggccc tgactgggat tagtgttgac      60

gatcgaa atg gga gtc ccc aag ttt tac aga tgg atc tca gag cgg tat      109
        Met Gly Val Pro Lys Phe Tyr Arg Trp Ile Ser Glu Arg Tyr
        1               5                   10

ccc tgt ctc agc gaa gtg gtg aaa gag cat cag att cct gaa ttt gac      157
Pro Cys Leu Ser Glu Val Val Lys Glu His Gln Ile Pro Glu Phe Asp
15                  20                  25                  30

aac ttg tac ctg gat atg aat gga att ata cat cag tgc tcc cat cct      205
Asn Leu Tyr Leu Asp Met Asn Gly Ile Ile His Gln Cys Ser His Pro
                35                  40                  45
```

-continued

```
aat gat gat gat gtt cac ttt aga att tca gat gat aaa atc ttt act      253
Asn Asp Asp Asp Val His Phe Arg Ile Ser Asp Asp Lys Ile Phe Thr
            50                  55                  60

gat att ttt cac tac ctg gag gtg ttg ttt cgc att att aaa ccc agg      301
Asp Ile Phe His Tyr Leu Glu Val Leu Phe Arg Ile Ile Lys Pro Arg
        65                  70                  75

aaa gtg ttc ttt atg gct gta gat ggt gtg gct cct cga gca aaa atg      349
Lys Val Phe Phe Met Ala Val Asp Gly Val Ala Pro Arg Ala Lys Met
    80                  85                  90

aac cag cag cgt ggg agg cgt ttt agg tca gca aag gag gca gaa gac      397
Asn Gln Gln Arg Gly Arg Arg Phe Arg Ser Ala Lys Glu Ala Glu Asp
95                  100                 105                 110

aaa att aaa aag gca ata gag aag gga gaa act ctt cct aca gag gcc      445
Lys Ile Lys Lys Ala Ile Glu Lys Gly Glu Thr Leu Pro Thr Glu Ala
                115                 120                 125

aga ttt gat tcc aac tgt atc aca cca gga act gaa ttt atg gcc agg      493
Arg Phe Asp Ser Asn Cys Ile Thr Pro Gly Thr Glu Phe Met Ala Arg
            130                 135                 140

tta cat gaa cat ctg aag tat ttt gta aat atg aaa att tcc aca gac      541
Leu His Glu His Leu Lys Tyr Phe Val Asn Met Lys Ile Ser Thr Asp
        145                 150                 155

aag tca tgg caa gga gtt acc atc tac ttc tca ggc cat gag act cct      589
Lys Ser Trp Gln Gly Val Thr Ile Tyr Phe Ser Gly His Glu Thr Pro
    160                 165                 170

gga gaa gga gag cat aaa atc atg gaa ttt atc aga tcc gag aaa gca      637
Gly Glu Gly Glu His Lys Ile Met Glu Phe Ile Arg Ser Glu Lys Ala
175                 180                 185                 190

aag cca gat cat gat cca aac acc aga cac tgt ctt tat ggt tta gat      685
Lys Pro Asp His Asp Pro Asn Thr Arg His Cys Leu Tyr Gly Leu Asp
                195                 200                 205

gct gac ttg att atg ctt gga tta aca agt cat gag gca cat ttt tct      733
Ala Asp Leu Ile Met Leu Gly Leu Thr Ser His Glu Ala His Phe Ser
            210                 215                 220

ctc tta aga gaa gaa gtt cga ttt ggt ggc aaa aaa aca caa cgg gta      781
Leu Leu Arg Glu Glu Val Arg Phe Gly Gly Lys Lys Thr Gln Arg Val
        225                 230                 235

tgt gct cca gaa gaa act aca ttt cac ctt cta cac ttg tct tta atg      829
Cys Ala Pro Glu Glu Thr Thr Phe His Leu Leu His Leu Ser Leu Met
    240                 245                 250

aga gag tat att gac tat gag ttt tca gta tta aaa gaa aag atc aca      877
Arg Glu Tyr Ile Asp Tyr Glu Phe Ser Val Leu Lys Glu Lys Ile Thr
255                 260                 265                 270

ttt aaa tat gat att gaa agg ata ata gat gat tgg att ttg atg ggg      925
Phe Lys Tyr Asp Ile Glu Arg Ile Ile Asp Asp Trp Ile Leu Met Gly
                275                 280                 285

ttt ctt gtt ggt aat gat ttt atc cct cat cta cct cat tta cat att      973
Phe Leu Val Gly Asn Asp Phe Ile Pro His Leu Pro His Leu His Ile
            290                 295                 300

aat cat gat gca ctg cct ctt ctt tat gga aca tat gtt acc atc ctg     1021
Asn His Asp Ala Leu Pro Leu Leu Tyr Gly Thr Tyr Val Thr Ile Leu
        305                 310                 315

cca gaa ctt ggg ggt tat att aat gaa agt ggg cac ctc aac tta cct     1069
Pro Glu Leu Gly Gly Tyr Ile Asn Glu Ser Gly His Leu Asn Leu Pro
    320                 325                 330

cga ttt gag aaa tac ctt gtg aaa cta tca gat ttt gat cgg gag cac     1117
Arg Phe Glu Lys Tyr Leu Val Lys Leu Ser Asp Phe Asp Arg Glu His
335                 340                 345                 350

ttc agt gaa gtt ttt gtg gac cta aaa tgg ttt gaa agc aaa gtt ggt     1165
Phe Ser Glu Val Phe Val Asp Leu Lys Trp Phe Glu Ser Lys Val Gly
                355                 360                 365
```

```
aac aag tac ctc aat gaa gca gca ggt gtc gca gca gaa gaa gcc agg      1213
Asn Lys Tyr Leu Asn Glu Ala Ala Gly Val Ala Ala Glu Glu Ala Arg
            370                 375                 380

aac tac aag gaa aag aaa aag tta aag ggc cag gaa aat tct ctg tgt      1261
Asn Tyr Lys Glu Lys Lys Lys Leu Lys Gly Gln Glu Asn Ser Leu Cys
        385                 390                 395

tgg act gct tta gac aaa aat gaa ggc gaa atg ata act tct aag gat      1309
Trp Thr Ala Leu Asp Lys Asn Glu Gly Glu Met Ile Thr Ser Lys Asp
    400                 405                 410

aat tta gaa gat gag act gaa gat gat gac cta ttt gaa act gag ttt      1357
Asn Leu Glu Asp Glu Thr Glu Asp Asp Asp Leu Phe Glu Thr Glu Phe
415                 420                 425                 430

aga caa tat aaa aga aca tat tac atg acg aag atg ggg gtt gac gta      1405
Arg Gln Tyr Lys Arg Thr Tyr Tyr Met Thr Lys Met Gly Val Asp Val
                435                 440                 445

gta tct gat gac ttt ctg gct gat caa gct gca tgt tat gtt cag gca      1453
Val Ser Asp Asp Phe Leu Ala Asp Gln Ala Ala Cys Tyr Val Gln Ala
            450                 455                 460

ata cag tgg att ttg cac tat tac tat cat gga gtt cag tcc tgg agc      1501
Ile Gln Trp Ile Leu His Tyr Tyr Tyr His Gly Val Gln Ser Trp Ser
        465                 470                 475

tgg tat tat cct tat cat tat gca cct ttc ctg tct gat ata cac aac      1549
Trp Tyr Tyr Pro Tyr His Tyr Ala Pro Phe Leu Ser Asp Ile His Asn
    480                 485                 490

atc agt aca ctc aaa atc cat ttt gaa cta gga aaa cct ttt aag cca      1597
Ile Ser Thr Leu Lys Ile His Phe Glu Leu Gly Lys Pro Phe Lys Pro
495                 500                 505                 510

ttt gaa cag ctt ctt gct gta ctt cca gca gcc agc aaa aat tta ctt      1645
Phe Glu Gln Leu Leu Ala Val Leu Pro Ala Ala Ser Lys Asn Leu Leu
                515                 520                 525

cct gca tgc tac cag cat ttg atg acc aat gaa gac tca cca att ata      1693
Pro Ala Cys Tyr Gln His Leu Met Thr Asn Glu Asp Ser Pro Ile Ile
            530                 535                 540

gaa tat tac cca cct gat ttt aaa act gac cta aat ggg aaa caa cag      1741
Glu Tyr Tyr Pro Pro Asp Phe Lys Thr Asp Leu Asn Gly Lys Gln Gln
        545                 550                 555

gaa tgg gaa gct gtg gtg tta atc cct ttt att gat gag aag cga tta      1789
Glu Trp Glu Ala Val Val Leu Ile Pro Phe Ile Asp Glu Lys Arg Leu
    560                 565                 570

ttg gaa gcc atg gag aca tgt aac cac tcc ctc aaa aag gaa gag agg      1837
Leu Glu Ala Met Glu Thr Cys Asn His Ser Leu Lys Lys Glu Glu Arg
575                 580                 585                 590

aaa aga aac caa cat agt gag tgc cta atg tgc tgg tat gat aga gac      1885
Lys Arg Asn Gln His Ser Glu Cys Leu Met Cys Trp Tyr Asp Arg Asp
                595                 600                 605

aca gag ttt atc tat cct tct cca tgg cca gaa aag ttc cct gcc ata      1933
Thr Glu Phe Ile Tyr Pro Ser Pro Trp Pro Glu Lys Phe Pro Ala Ile
            610                 615                 620

gaa cga tgt tgt aca agg tat aaa ata ata tcc tta gat gct tgg cgt      1981
Glu Arg Cys Cys Thr Arg Tyr Lys Ile Ile Ser Leu Asp Ala Trp Arg
        625                 630                 635

gta gac ata aac aaa aac aaa ata acc aga att gac cag aaa gca tta      2029
Val Asp Ile Asn Lys Asn Lys Ile Thr Arg Ile Asp Gln Lys Ala Leu
    640                 645                 650

tat ttc tgt gga ttt cct act ctg aaa cac atc aga cac aaa ttt ttt      2077
Tyr Phe Cys Gly Phe Pro Thr Leu Lys His Ile Arg His Lys Phe Phe
655                 660                 665                 670

ttg aag aaa agt ggt gtt caa gta ttc cag caa agc agt cgt gga gaa      2125
Leu Lys Lys Ser Gly Val Gln Val Phe Gln Gln Ser Ser Arg Gly Glu
```

```
                675                 680                 685

aac atg atg ttg gaa atc tta gtg gat gca gaa tca gat gaa ctt acc      2173
Asn Met Met Leu Glu Ile Leu Val Asp Ala Glu Ser Asp Glu Leu Thr
            690                 695                 700

gta gaa aat gta gct tca tca gtg ctt gga aaa tct gtc ttt gtt aat      2221
Val Glu Asn Val Ala Ser Ser Val Leu Gly Lys Ser Val Phe Val Asn
        705                 710                 715

tgg cct cac ctt gag gaa gct aga gtc gtg gct gta tca gat gga gaa      2269
Trp Pro His Leu Glu Glu Ala Arg Val Val Ala Val Ser Asp Gly Glu
    720                 725                 730

act aag ttt tac ttg gaa gaa cct cca gga aca cag aag ctt tat tca      2317
Thr Lys Phe Tyr Leu Glu Glu Pro Pro Gly Thr Gln Lys Leu Tyr Ser
735                 740                 745                 750

gga aga act gcc cca cca tct aaa gtg gtt cat ctt gga gat aaa gaa      2365
Gly Arg Thr Ala Pro Pro Ser Lys Val Val His Leu Gly Asp Lys Glu
                755                 760                 765

caa tct aac tgg gca aaa gaa gta caa gga att tca gaa cac tac ctg      2413
Gln Ser Asn Trp Ala Lys Glu Val Gln Gly Ile Ser Glu His Tyr Leu
            770                 775                 780

aga aga aaa gga ata ata ata aat gaa aca tct gca gtt gtg tat gct      2461
Arg Arg Lys Gly Ile Ile Ile Asn Glu Thr Ser Ala Val Val Tyr Ala
        785                 790                 795

cag tta ctc aca ggt cgt aaa tat caa ata aat caa aat ggt gaa gtt      2509
Gln Leu Leu Thr Gly Arg Lys Tyr Gln Ile Asn Gln Asn Gly Glu Val
    800                 805                 810

cgt cta gag aaa cag tgg tca aaa caa gtt gtt cct ttt gtt tat caa      2557
Arg Leu Glu Lys Gln Trp Ser Lys Gln Val Val Pro Phe Val Tyr Gln
815                 820                 825                 830

act att gtc aag gac atc cga gct ttc gac tcc cgt ttc tcc aat atc      2605
Thr Ile Val Lys Asp Ile Arg Ala Phe Asp Ser Arg Phe Ser Asn Ile
                835                 840                 845

aaa aca ttg gat gat ttg ttt cct ctg aga agt atg gtc ttt atg ctg      2653
Lys Thr Leu Asp Asp Leu Phe Pro Leu Arg Ser Met Val Phe Met Leu
            850                 855                 860

gga act ccc tat tat ggc tgc act gga gaa gtt cag gat tca ggt gat      2701
Gly Thr Pro Tyr Tyr Gly Cys Thr Gly Glu Val Gln Asp Ser Gly Asp
        865                 870                 875

gtg att aca gaa ggt agg att cgt gtg att ttc agc att cca tgt gaa      2749
Val Ile Thr Glu Gly Arg Ile Arg Val Ile Phe Ser Ile Pro Cys Glu
    880                 885                 890

ccc aat ctt gat gct tta ata cag aac cag cat aaa tat tct ata aag      2797
Pro Asn Leu Asp Ala Leu Ile Gln Asn Gln His Lys Tyr Ser Ile Lys
895                 900                 905                 910

tac aac cca gga tat gtg ttg gcc agt cgc ctt gga gtg agt gga tac      2845
Tyr Asn Pro Gly Tyr Val Leu Ala Ser Arg Leu Gly Val Ser Gly Tyr
                915                 920                 925

ctt gtt tca agg ttt aca gga agt att ttt att gga aga gga tct agg      2893
Leu Val Ser Arg Phe Thr Gly Ser Ile Phe Ile Gly Arg Gly Ser Arg
            930                 935                 940

aga aac cct cat gga gac cat aaa gca aat gtg ggt tta aat ctc aaa      2941
Arg Asn Pro His Gly Asp His Lys Ala Asn Val Gly Leu Asn Leu Lys
        945                 950                 955

ttc aac aag aaa aat gag gag gta cct gga tat act aag aaa gtt gga      2989
Phe Asn Lys Lys Asn Glu Glu Val Pro Gly Tyr Thr Lys Lys Val Gly
    960                 965                 970

agt gaa tgg atg tat tca tct gca gca gaa caa ctt ctg gca gag tac      3037
Ser Glu Trp Met Tyr Ser Ser Ala Ala Glu Gln Leu Leu Ala Glu Tyr
975                 980                 985                 990

tta gag aga gct cca gaa cta ttt agt tat  ata gcc aaa aat agc  caa    3085
```

```
Leu Glu Arg Ala Pro Glu Leu Phe Ser Tyr  Ile Ala Lys Asn Ser  Gln
                995                 1000                 1005

gag gat gtg ttc  tat gaa gat gac att  tgg cct gga gaa aat  gag      3130
Glu Asp Val Phe  Tyr Glu Asp Asp Ile  Trp Pro Gly Glu Asn  Glu
            1010                 1015                 1020

aat ggt gct gaa  aaa gtt caa gaa att  att act tgg cta aaa  gga      3175
Asn Gly Ala Glu  Lys Val Gln Glu Ile  Ile Thr Trp Leu Lys  Gly
            1025                 1030                 1035

cat cct gtc agt  act tta tct cgt tct  tct tgt gat tta caa  att      3220
His Pro Val Ser  Thr Leu Ser Arg Ser  Ser Cys Asp Leu Gln  Ile
            1040                 1045                 1050

ctg gat gca gct  att gtt gag aaa att  gag gaa gaa gtc gaa  aag      3265
Leu Asp Ala Ala  Ile Val Glu Lys Ile  Glu Glu Glu Val Glu  Lys
            1055                 1060                 1065

tgc aag caa aga  aag aat aat aag aag  gtg cga gta aca gtg  aaa      3310
Cys Lys Gln Arg  Lys Asn Asn Lys Lys  Val Arg Val Thr Val  Lys
            1070                 1075                 1080

ccc cat ttg cta  tac aga cct tta gaa  cag caa cat gga gtc  att      3355
Pro His Leu Leu  Tyr Arg Pro Leu Glu  Gln Gln His Gly Val  Ile
            1085                 1090                 1095

cct gat cgg gat  gca gaa ttt tgt ctt  ttt gac cgt gtt gta  aat      3400
Pro Asp Arg Asp  Ala Glu Phe Cys Leu  Phe Asp Arg Val Val  Asn
            1100                 1105                 1110

gtg aga gaa aac  ttc tca gtt cca gtt  ggc ctt cga ggc acc  atc      3445
Val Arg Glu Asn  Phe Ser Val Pro Val  Gly Leu Arg Gly Thr  Ile
            1115                 1120                 1125

ata gga ata aaa  gga gct aat aga gaa  gcc gat gta cta ttt  gaa      3490
Ile Gly Ile Lys  Gly Ala Asn Arg Glu  Ala Asp Val Leu Phe  Glu
            1130                 1135                 1140

gta tta ttt gat  gaa gaa ttt cct gga  ggg tta aca ata aga  tgc      3535
Val Leu Phe Asp  Glu Glu Phe Pro Gly  Gly Leu Thr Ile Arg  Cys
            1145                 1150                 1155

tca cct ggt aga  ggt tat cga ctg cca  aca agt gcc ttg gtg  aac      3580
Ser Pro Gly Arg  Gly Tyr Arg Leu Pro  Thr Ser Ala Leu Val  Asn
            1160                 1165                 1170

ctt tct cat ggg  agt cgc tct gaa act  gga aat cag aag ttg  aca      3625
Leu Ser His Gly  Ser Arg Ser Glu Thr  Gly Asn Gln Lys Leu  Thr
            1175                 1180                 1185

gcc atc gta aaa  cca caa cca gct gta  cat caa cat agc tca  agt      3670
Ala Ile Val Lys  Pro Gln Pro Ala Val  His Gln His Ser Ser  Ser
            1190                 1195                 1200

tca tca gtt tcc  tct ggg cat ttg gga  gcc ctc aac cat tcc  cct      3715
Ser Ser Val Ser  Ser Gly His Leu Gly  Ala Leu Asn His Ser  Pro
            1205                 1210                 1215

caa tca ctt ttt  gtt cct act caa gta  cct act aaa gat gat  gat      3760
Gln Ser Leu Phe  Val Pro Thr Gln Val  Pro Thr Lys Asp Asp  Asp
            1220                 1225                 1230

gaa ttc tgc aac  att tgg cag tcc tta  cag gga tct gga aag  atg      3805
Glu Phe Cys Asn  Ile Trp Gln Ser Leu  Gln Gly Ser Gly Lys  Met
            1235                 1240                 1245

caa tac ttt cag  cca act ata caa gag  aag ggt gca gtt cta  cct      3850
Gln Tyr Phe Gln  Pro Thr Ile Gln Glu  Lys Gly Ala Val Leu  Pro
            1250                 1255                 1260

caa gaa ata agc  caa gta aat caa cat  cat aaa tct ggc ttt  aat      3895
Gln Glu Ile Ser  Gln Val Asn Gln His  His Lys Ser Gly Phe  Asn
            1265                 1270                 1275

gac aac agt gtt  aaa tat cag caa aga  aaa cat gac cct cac  aga      3940
Asp Asn Ser Val  Lys Tyr Gln Gln Arg  Lys His Asp Pro His  Arg
            1280                 1285                 1290
```

```
aaa ttt aaa gaa  gag tgt aag agt cct  aaa gct gag tgt tgg  tcc      3985
Lys Phe Lys Glu  Glu Cys Lys Ser Pro  Lys Ala Glu Cys Trp  Ser
            1295                 1300                 1305

caa aaa atg tcc  aat aag cag cct aac  tct gga att gag aac  ttt      4030
Gln Lys Met Ser  Asn Lys Gln Pro Asn  Ser Gly Ile Glu Asn  Phe
            1310                 1315                 1320

tta gca tct ttg  aat atc tcc aaa gaa  aat gaa gta cag tca  tct      4075
Leu Ala Ser Leu  Asn Ile Ser Lys Glu  Asn Glu Val Gln Ser  Ser
            1325                 1330                 1335

cat cat ggg gag  cct cca agt gaa gag  cat ttg tca cca cag  tca      4120
His His Gly Glu  Pro Pro Ser Glu Glu  His Leu Ser Pro Gln  Ser
            1340                 1345                 1350

ttt gcc atg gga  aca cgg atg ctt aaa  gaa att cta aaa att  gat      4165
Phe Ala Met Gly  Thr Arg Met Leu Lys  Glu Ile Leu Lys Ile  Asp
            1355                 1360                 1365

ggc tct aac act  gtg gac cat aag aat  gaa atc aaa cag att  gct      4210
Gly Ser Asn Thr  Val Asp His Lys Asn  Glu Ile Lys Gln Ile  Ala
            1370                 1375                 1380

aat gaa atc cct  gtt tcc tct aac aga  aga gat gaa tat gga  tta      4255
Asn Glu Ile Pro  Val Ser Ser Asn Arg  Arg Asp Glu Tyr Gly  Leu
            1385                 1390                 1395

ccc tct cag cct  aaa caa aat aag aaa  tta gca tct tat atg  aac      4300
Pro Ser Gln Pro  Lys Gln Asn Lys Lys  Leu Ala Ser Tyr Met  Asn
            1400                 1405                 1410

aag cct cac agt  gct aat gag tac cat  aat gtt cag tct atg  gac      4345
Lys Pro His Ser  Ala Asn Glu Tyr His  Asn Val Gln Ser Met  Asp
            1415                 1420                 1425

aat atg tgt tgg  cct gcc ccc agc cag  atc cct cct gta tcc  aca      4390
Asn Met Cys Trp  Pro Ala Pro Ser Gln  Ile Pro Pro Val Ser  Thr
            1430                 1435                 1440

cca gta act gaa  ctt tct cga att tgt  tcc ctt gtt gga atg  cca      4435
Pro Val Thr Glu  Leu Ser Arg Ile Cys  Ser Leu Val Gly Met  Pro
            1445                 1450                 1455

caa cct gat ttc  tcc ttt ctt agg atg  cca cag aca atg acc  gtt      4480
Gln Pro Asp Phe  Ser Phe Leu Arg Met  Pro Gln Thr Met Thr  Val
            1460                 1465                 1470

tgc caa gta aaa  tta tct aat ggc tta  ctg gta cat ggg cca  cag      4525
Cys Gln Val Lys  Leu Ser Asn Gly Leu  Leu Val His Gly Pro  Gln
            1475                 1480                 1485

tgc cac tct gaa  aat gaa gcc aaa gag  aaa gct gca ctt ttt  gct      4570
Cys His Ser Glu  Asn Glu Ala Lys Glu  Lys Ala Ala Leu Phe  Ala
            1490                 1495                 1500

tta caa cag ttg  ggc tcc tta ggc atg  aat ttc cct ttg cct  tca      4615
Leu Gln Gln Leu  Gly Ser Leu Gly Met  Asn Phe Pro Leu Pro  Ser
            1505                 1510                 1515

caa gta ttt gca  aat tat cct tca gct  gta cca cct gga acc  att      4660
Gln Val Phe Ala  Asn Tyr Pro Ser Ala  Val Pro Pro Gly Thr  Ile
            1520                 1525                 1530

cct cca gcc ttt  ccc cca cct act ggc  tgg gat cac tat gga  agc      4705
Pro Pro Ala Phe  Pro Pro Pro Thr Gly  Trp Asp His Tyr Gly  Ser
            1535                 1540                 1545

aac tat gca ttg  ggg gca gct aat ata  atg cct tcg tcg tct  cat      4750
Asn Tyr Ala Leu  Gly Ala Ala Asn Ile  Met Pro Ser Ser Ser  His
            1550                 1555                 1560

ctc ttt ggc tca  atg cca tgg gga cca  tcg gtg cca gtt cct  ggg      4795
Leu Phe Gly Ser  Met Pro Trp Gly Pro  Ser Val Pro Val Pro  Gly
            1565                 1570                 1575

aag ccc ttc cat  cat act tta tat tct  ggg acc atg ccc atg  gct      4840
Lys Pro Phe His  His Thr Leu Tyr Ser  Gly Thr Met Pro Met  Ala
            1580                 1585                 1590
```

-continued

```
ggg gga ata cca  ggg ggt gtg cac aat  cag ttt ata cct ctg  cag      4885
Gly Gly Ile Pro  Gly Gly Val His Asn  Gln Phe Ile Pro Leu  Gln
            1595                 1600                 1605

gtt act aaa aaa  agg gtt gca aac aaa  aag aac ttt gag aat  aag      4930
Val Thr Lys Lys  Arg Val Ala Asn Lys  Lys Asn Phe Glu Asn  Lys
            1610                 1615                 1620

gaa gcc cag agt  tct caa gcc act cca  gtt cag act agc cag  cca      4975
Glu Ala Gln Ser  Ser Gln Ala Thr Pro  Val Gln Thr Ser Gln  Pro
            1625                 1630                 1635

gat tct tcc aac  att gtc aaa gta agt  cca cgg gag agc tca  tca      5020
Asp Ser Ser Asn  Ile Val Lys Val Ser  Pro Arg Glu Ser Ser  Ser
            1640                 1645                 1650

gct tct ttg aag  tcc tct ccg att gct  caa cct gca tct tct  ttt      5065
Ala Ser Leu Lys  Ser Ser Pro Ile Ala  Gln Pro Ala Ser Ser  Phe
            1655                 1660                 1665

caa gtt gaa act  gcc tct caa ggc cat  agt ata tct cac cat  aag      5110
Gln Val Glu Thr  Ala Ser Gln Gly His  Ser Ile Ser His His  Lys
            1670                 1675                 1680

tca aca cca atc  tct tct tca aga aga  aaa tca aga aaa ctg  gct      5155
Ser Thr Pro Ile  Ser Ser Ser Arg Arg  Lys Ser Arg Lys Leu  Ala
            1685                 1690                 1695

gtt aat ttt ggt  gtt tct aaa cct tct  gag taa atttggctct            5198
Val Asn Phe Gly  Val Ser Lys Pro Ser  Glu
            1700                 1705

tagaattaag ttaatttctt ctctttccat ctacctttt ataaatacat atctatgtct   5258

cataaaaatt agaatgtact attttaaaat aatatgtgta aattgaaatt tttttcattt   5318

ttaagttatc aggcactttt catgctgttt aaaagactgt gtatcaaatt gtgcacttta   5378

agtatgtgca gtttgttgta tgtcaattat acctcaataa atctgtaata aaaaactaaa   5438

ttaaaccttg cattaaaata atatcacagt atcagtggac taaacattaa aatgtaccac   5498

tctaatcatt ggcctcatga ttgaagcatc ctgaactatg aattagacat cagttagcaa   5558

taataagcat tttttacact atcattgagg aataattaca tggagcatga aatttgggcc   5618

tccagtataa cttactgaat gtggatttta tttctctttt taatgatgta agaaaattgt   5678

caggagaatg gctcttattt atgtgtgttt taacttatgc tttgttgcct ctgagggtct   5738

ttagacctgc tgtgaaagga tcacatttgt tgtggtgctg ccagttttgc tttattctaa   5798

attttgtacc aaagcaactt tagaataatc agaatatttc atctaactgc ttagaactat   5858

aaatagcatt ctaaatttga gtaaatacaa ttttttaggt tactcaagaa ccagcattag   5918

taatttctag taaaattgtt tcaaaatcta cagggtacaa tgattacaaa ttaatcttct   5978

aacaaaataa aatatgaaat attagtcatg ttaattaata aactgtatta ttttgtatag   6038

ctttttattt gcttacctga cattttatga gagcttcata gttggtcggt atgtagtgct   6098

tcttgggact gaagaaattc taattgttgt ttaagttcca aggtgtgcta caatatagga   6158

ggcacagtca tcagtttgtg acatacatta tttactgcct atttcattct gattctatat   6218

ttttagcttt atgctgaact gttcaatgat gctgggattc tctctttgca tgtcatatgt   6278

gaatgtgtgg ttcaagctgt aactgttgaa attattttag aatttatgac gatttctcag   6338

cagggcctat gtttatatat atatatatat ttattcttta gtttttgtga tatgcttata   6398

tttttaagga agtaagttat agcatacttt tttaaaagta ggaaccacaa tctttatatg   6458

gagcagcttg ttatatctga ttttcatgta actcattgga aactctgcca tgactcttaa   6518

agtagtctta cttgtttttt aaaatgctgg tattaaacta aatggactcc tttcactaac   6578
```

```
tgctgatttc agagtttaaa tgttagcagg atatttgtgt attagcagtg ccttcagtat   6638
aagagagaaa tattcattat ctgtcattta tcatagtcgt ataagtttcc atgattttat   6698
tttctgttat tttcataagt tcagatgttt atcagttccc aacattgttt ctttatctgt   6758
agtgggatct tgagtaatga ggctcaagta aatcctcaat gtgtataatt attgcctcat   6818
aaactctctc tttgttttta aaggaaacat ctattatggt aatacaaaga aaagttaaat   6878
tgtgacagta atgttatatt aacctcttcc tactttaaag tgtgaaatgt ttcacctcag   6938
ctgtacaaac tccagcattg agaatttgcc tcactcatta ctcctgtgtg acagttatat   6998
aaatagcatg cagctcacat ctgttttaga gcatagaaga agcggcacct gccatcttct   7058
gaaaactcca aagggaaatt tcagtagaca tagtgcacta aacccataag gatacttgac   7118
caatatttga gcacagcaag ctgacagttc tatacagata ggcagtgaaa gagttttatt   7178
ttccagccag gcgcagtggc tcaaatccca gcacttcggg aggctaaggc aggcggatca   7238
cttgaggtcc ggagttccag acaagcctgg ccaacatgat gaagccctgt ctctactaaa   7298
aatacaaaaa ttagccgggc gtgatggcac atgcctttag tcccagctac tcgggaggct   7358
gaggcatgag aatcatttga acccgcgagg cagagtctgc agtgagccga gattgcacca   7418
ctgcactcca gcctggagag cagagcaaga ctctgtctca aaaaaaagaa aaaagtttta   7478
ttatccttac ttttttttta acattattat tctaaaggtc aaaactgaga agagattaag   7538
ataggagaga gctccataat ggctggatag tggtcaggca ttctctattc ttttccccct   7598
gtagacccat tctaaatgtg ggcctgaggt caatgggaga tgtgccctcc ctatggagga   7658
tgtaagaagc agaggccatt tctgccccat gttgaggaaa caatctgttg atagacctgg   7718
aatttagagt atatctgaaa agcagttgga cttcaagaaa tttaaaattc tctctttgag   7778
atggggtgga ctaagaccac ccccaaagtt taaaaatatg ctcattcaac ttgaatcttc   7838
tgaggacttt ttgtgaaaat ggtggactgt ttagggcata ggacagattc cccaaattgc   7898
tttatgcttc cacataacta gagcacttca atctatttaa gcctttgtct cctaactgaa   7958
acattatttc taaatatttc tattcaataa gtttttttctt ttttgagcaa cttaagtgaa   8018
ttttgaagat tgctccttcc agtctcgttc cttttcacat tttcctgcat tacctaataa   8078
ttacctcagc gttagaattt gaatgtatta attgatttaa acatcatgta gactaaagtc   8138
ttaaacatct aagactcagt tgtagttgca gaaaaaaatt aaagtcacct ctactgaacc   8198
ttggtttcaa tttaagattt ttcttgcttt tcaaaggggt aactaataaa gattgaaggg   8258
tttttttccc gattggtgga ggaatgaaga actattgatg caagtttttt tattgtttct   8318
ttctatgatc aggtacctgc tttcatttta gactgctact tccaaactaa gctagattct   8378
tggttttaat gagaggaggc agagagaggg aggcagatgg aagaagaaaa acagttaaat   8438
aagacatacc cagtcactgc atttttggac tataccgtat ctttctagca caaggaaata   8498
gataaactgt aaggtctttt ttactcactt tttatttatg tgttctattt gtgttagtca   8558
taactgttta tagtggttgt ctaattttta cttttattat atgagataga gctgtgcaga   8618
tcttcactca agttagttct gtcacgcttc ttcccattat ttagagcaca gttttttaaa   8678
gcaactgtac aatttctcag ccttatgagc ttgctgtatt tcttggtatc atgttgcttc   8738
caaattttgt ttttactgta gaagacaatt aatttattgt agagaagtgg ctgtgaaagt   8798
cgttctctgt ctttaaaaat caattgcaga agttcatttg tcatttttct agagataaat   8858
tatagtactc aaactggcag tgctcagtat atacattttg taagctttgt cagtgaaacc   8918
atcagttttg caggagcttc ctttcctagt caagataaag cttaaaattc cagaaattaa   8978
```

```
tgtcgttcgg actgacttta ttcatatttc catcaaactt ctccaataca gtaagagata   9038

gtgttgaacc agcatcaagt ctccagaaac atggcagagc agacaggccg ttaagtttca   9098

cagacatcat agatcctttt cttaaagaag aaaaacatgt ataaaatagt tttagtagtc   9158

caaaatgtca actatctgta gctgcttttg tgtgtgtgtc agtgaacaaa taataatgcc   9218

ttgctcaatc aatgcattca gccatctcaa gtgcaatttg tgaaggagac tatggtttcc   9278

aaaagataca tttttttaca aagttaaacc tgtaaaaagt cttttttttt ttccctccag   9338

ccgtacacca actgcacttg gttgtttcag cagttggtat actattaaat tgtccaggcc   9398

aaataggttt ctgtagctgt tttagtaatt tgaagccaaa ttctcatgct gtttctcatt   9458

aaaaagaatg agaatttggt ccatagttag ctttaagttc tctcttcctt tctttccctt   9518

acagttaagg gtttggtggg ggatggggag gttgttttcg ttttttggat ttttttgtct   9578

tttggcttta agtatcatat tttcttttgc ctgtatccaa ctgcttcttt gagtattttc   9638

atctagttta atgtgagtaa tagatgctgt gctgtcattg aagtgttcaa cattttgttc   9698

atttaaacaa aagtgtaatt catacatata tagatacata tcttaattga tttctcaact   9758

attttataag taactggaat ttttcattag atcttataca gagaagtatt ttattaaaaa   9818

ttcaaaaggg aagactttta tgtgctcatt ttgtaatttt tgattttaaa tatctttaca   9878

ttgtctgcca attaaagtgt tttaaacttg cattggaatg gactccgaat gtatttttgt   9938

ggtgttacgt tatccgtaga tttctagcat gaagttagcc tcacgatgct gtgcaaagga   9998

ttttaaaata tgagagtcac tgaaagagtt taaacatctg ttcatgttaa atgctctatg  10058

gattttaatt aaagacttga gaatgatttt ataa                              10092
```

<210> SEQ ID NO 18
<211> LENGTH: 1706
<212> TYPE: PRT
<213> ORGANISM: Homo sapiens

<400> SEQUENCE: 18

```
Met Gly Val Pro Lys Phe Tyr Arg Trp Ile Ser Glu Arg Tyr Pro Cys
1               5                   10                  15

Leu Ser Glu Val Val Lys Glu His Gln Ile Pro Glu Phe Asp Asn Leu
            20                  25                  30

Tyr Leu Asp Met Asn Gly Ile Ile His Gln Cys Ser His Pro Asn Asp
        35                  40                  45

Asp Asp Val His Phe Arg Ile Ser Asp Asp Lys Ile Phe Thr Asp Ile
    50                  55                  60

Phe His Tyr Leu Glu Val Leu Phe Arg Ile Ile Lys Pro Arg Lys Val
65                  70                  75                  80

Phe Phe Met Ala Val Asp Gly Val Ala Pro Arg Ala Lys Met Asn Gln
                85                  90                  95

Gln Arg Gly Arg Arg Phe Arg Ser Ala Lys Glu Ala Glu Asp Lys Ile
            100                 105                 110

Lys Lys Ala Ile Glu Lys Gly Glu Thr Leu Pro Thr Glu Ala Arg Phe
        115                 120                 125

Asp Ser Asn Cys Ile Thr Pro Gly Thr Glu Phe Met Ala Arg Leu His
    130                 135                 140

Glu His Leu Lys Tyr Phe Val Asn Met Lys Ile Ser Thr Asp Lys Ser
145                 150                 155                 160

Trp Gln Gly Val Thr Ile Tyr Phe Ser Gly His Glu Thr Pro Gly Glu
                165                 170                 175
```

```
Gly Glu His Lys Ile Met Glu Phe Ile Arg Ser Glu Lys Ala Lys Pro
            180                 185                 190

Asp His Asp Pro Asn Thr Arg His Cys Leu Tyr Gly Leu Asp Ala Asp
        195                 200                 205

Leu Ile Met Leu Gly Leu Thr Ser His Glu Ala His Phe Ser Leu Leu
    210                 215                 220

Arg Glu Glu Val Arg Phe Gly Gly Lys Lys Thr Gln Arg Val Cys Ala
225                 230                 235                 240

Pro Glu Glu Thr Thr Phe His Leu Leu His Leu Ser Leu Met Arg Glu
                245                 250                 255

Tyr Ile Asp Tyr Glu Phe Ser Val Leu Lys Glu Lys Ile Thr Phe Lys
            260                 265                 270

Tyr Asp Ile Glu Arg Ile Ile Asp Asp Trp Ile Leu Met Gly Phe Leu
        275                 280                 285

Val Gly Asn Asp Phe Ile Pro His Leu Pro His Leu His Ile Asn His
    290                 295                 300

Asp Ala Leu Pro Leu Leu Tyr Gly Thr Tyr Val Thr Ile Leu Pro Glu
305                 310                 315                 320

Leu Gly Gly Tyr Ile Asn Glu Ser Gly His Leu Asn Leu Pro Arg Phe
                325                 330                 335

Glu Lys Tyr Leu Val Lys Leu Ser Asp Phe Asp Arg Glu His Phe Ser
            340                 345                 350

Glu Val Phe Val Asp Leu Lys Trp Phe Glu Ser Lys Val Gly Asn Lys
        355                 360                 365

Tyr Leu Asn Glu Ala Ala Gly Val Ala Ala Glu Glu Ala Arg Asn Tyr
    370                 375                 380

Lys Glu Lys Lys Lys Leu Lys Gly Gln Glu Asn Ser Leu Cys Trp Thr
385                 390                 395                 400

Ala Leu Asp Lys Asn Glu Gly Glu Met Ile Thr Ser Lys Asp Asn Leu
                405                 410                 415

Glu Asp Glu Thr Glu Asp Asp Asp Leu Phe Glu Thr Glu Phe Arg Gln
            420                 425                 430

Tyr Lys Arg Thr Tyr Tyr Met Thr Lys Met Gly Val Asp Val Val Ser
        435                 440                 445

Asp Asp Phe Leu Ala Asp Gln Ala Ala Cys Tyr Val Gln Ala Ile Gln
    450                 455                 460

Trp Ile Leu His Tyr Tyr Tyr His Gly Val Gln Ser Trp Ser Trp Tyr
465                 470                 475                 480

Tyr Pro Tyr His Tyr Ala Pro Phe Leu Ser Asp Ile His Asn Ile Ser
                485                 490                 495

Thr Leu Lys Ile His Phe Glu Leu Gly Lys Pro Phe Lys Pro Phe Glu
            500                 505                 510

Gln Leu Leu Ala Val Leu Pro Ala Ala Ser Lys Asn Leu Leu Pro Ala
        515                 520                 525

Cys Tyr Gln His Leu Met Thr Asn Glu Asp Ser Pro Ile Ile Glu Tyr
    530                 535                 540

Tyr Pro Pro Asp Phe Lys Thr Asp Leu Asn Gly Lys Gln Gln Glu Trp
545                 550                 555                 560

Glu Ala Val Val Leu Ile Pro Phe Ile Asp Glu Lys Arg Leu Leu Glu
                565                 570                 575

Ala Met Glu Thr Cys Asn His Ser Leu Lys Lys Glu Glu Arg Lys Arg
            580                 585                 590
```

```
Asn Gln His Ser Glu Cys Leu Met Cys Trp Tyr Asp Arg Asp Thr Glu
        595                 600                 605

Phe Ile Tyr Pro Ser Pro Trp Pro Glu Lys Phe Pro Ala Ile Glu Arg
    610                 615                 620

Cys Cys Thr Arg Tyr Lys Ile Ile Ser Leu Asp Ala Trp Arg Val Asp
625                 630                 635                 640

Ile Asn Lys Asn Lys Ile Thr Arg Ile Asp Gln Lys Ala Leu Tyr Phe
                645                 650                 655

Cys Gly Phe Pro Thr Leu Lys His Ile Arg His Lys Phe Phe Leu Lys
            660                 665                 670

Lys Ser Gly Val Gln Val Phe Gln Gln Ser Ser Arg Gly Glu Asn Met
        675                 680                 685

Met Leu Glu Ile Leu Val Asp Ala Glu Ser Asp Glu Leu Thr Val Glu
    690                 695                 700

Asn Val Ala Ser Ser Val Leu Gly Lys Ser Val Phe Val Asn Trp Pro
705                 710                 715                 720

His Leu Glu Glu Ala Arg Val Val Ala Val Ser Asp Gly Glu Thr Lys
                725                 730                 735

Phe Tyr Leu Glu Glu Pro Pro Gly Thr Gln Lys Leu Tyr Ser Gly Arg
            740                 745                 750

Thr Ala Pro Pro Ser Lys Val Val His Leu Gly Asp Lys Glu Gln Ser
        755                 760                 765

Asn Trp Ala Lys Glu Val Gln Gly Ile Ser Glu His Tyr Leu Arg Arg
    770                 775                 780

Lys Gly Ile Ile Ile Asn Glu Thr Ser Ala Val Val Tyr Ala Gln Leu
785                 790                 795                 800

Leu Thr Gly Arg Lys Tyr Gln Ile Asn Gln Asn Gly Glu Val Arg Leu
                805                 810                 815

Glu Lys Gln Trp Ser Lys Gln Val Val Pro Phe Val Tyr Gln Thr Ile
            820                 825                 830

Val Lys Asp Ile Arg Ala Phe Asp Ser Arg Phe Ser Asn Ile Lys Thr
        835                 840                 845

Leu Asp Asp Leu Phe Pro Leu Arg Ser Met Val Phe Met Leu Gly Thr
    850                 855                 860

Pro Tyr Tyr Gly Cys Thr Gly Glu Val Gln Asp Ser Gly Asp Val Ile
865                 870                 875                 880

Thr Glu Gly Arg Ile Arg Val Ile Phe Ser Ile Pro Cys Glu Pro Asn
                885                 890                 895

Leu Asp Ala Leu Ile Gln Asn Gln His Lys Tyr Ser Ile Lys Tyr Asn
            900                 905                 910

Pro Gly Tyr Val Leu Ala Ser Arg Leu Gly Val Ser Gly Tyr Leu Val
        915                 920                 925

Ser Arg Phe Thr Gly Ser Ile Phe Ile Gly Arg Gly Ser Arg Arg Asn
    930                 935                 940

Pro His Gly Asp His Lys Ala Asn Val Gly Leu Asn Leu Lys Phe Asn
945                 950                 955                 960

Lys Lys Asn Glu Glu Val Pro Gly Tyr Thr Lys Lys Val Gly Ser Glu
                965                 970                 975

Trp Met Tyr Ser Ser Ala Ala Glu Gln Leu Leu Ala Glu Tyr Leu Glu
            980                 985                 990

Arg Ala Pro Glu Leu Phe Ser Tyr  Ile Ala Lys Asn Ser  Gln Glu Asp
        995                 1000                1005

Val Phe  Tyr Glu Asp Asp Ile  Trp Pro Gly Glu Asn  Glu Asn Gly
```

```
    1010                1015                1020

Ala Glu  Lys Val Gln Glu Ile  Ile Thr Trp Leu Lys  Gly His Pro
    1025                1030                1035

Val Ser  Thr Leu Ser Arg Ser  Ser Cys Asp Leu Gln  Ile Leu Asp
    1040                1045                1050

Ala Ala  Ile Val Glu Lys Ile  Glu Glu Glu Val Glu  Lys Cys Lys
    1055                1060                1065

Gln Arg  Lys Asn Asn Lys Lys  Val Arg Val Thr Val  Lys Pro His
    1070                1075                1080

Leu Leu  Tyr Arg Pro Leu Glu  Gln Gln His Gly Val  Ile Pro Asp
    1085                1090                1095

Arg Asp  Ala Glu Phe Cys Leu  Phe Asp Arg Val Val  Asn Val Arg
    1100                1105                1110

Glu Asn  Phe Ser Val Pro Val  Gly Leu Arg Gly Thr  Ile Ile Gly
    1115                1120                1125

Ile Lys  Gly Ala Asn Arg Glu  Ala Asp Val Leu Phe  Glu Val Leu
    1130                1135                1140

Phe Asp  Glu Glu Phe Pro Gly  Gly Leu Thr Ile Arg  Cys Ser Pro
    1145                1150                1155

Gly Arg  Gly Tyr Arg Leu Pro  Thr Ser Ala Leu Val  Asn Leu Ser
    1160                1165                1170

His Gly  Ser Arg Ser Glu Thr  Gly Asn Gln Lys Leu  Thr Ala Ile
    1175                1180                1185

Val Lys  Pro Gln Pro Ala Val  His Gln His Ser Ser  Ser Ser Ser
    1190                1195                1200

Val Ser  Ser Gly His Leu Gly  Ala Leu Asn His Ser  Pro Gln Ser
    1205                1210                1215

Leu Phe  Val Pro Thr Gln Val  Pro Thr Lys Asp Asp  Asp Glu Phe
    1220                1225                1230

Cys Asn  Ile Trp Gln Ser Leu  Gln Gly Ser Gly Lys  Met Gln Tyr
    1235                1240                1245

Phe Gln  Pro Thr Ile Gln Glu  Lys Gly Ala Val Leu  Pro Gln Glu
    1250                1255                1260

Ile Ser  Gln Val Asn Gln His  His Lys Ser Gly Phe  Asn Asp Asn
    1265                1270                1275

Ser Val  Lys Tyr Gln Gln Arg  Lys His Asp Pro His  Arg Lys Phe
    1280                1285                1290

Lys Glu  Glu Cys Lys Ser Pro  Lys Ala Glu Cys Trp  Ser Gln Lys
    1295                1300                1305

Met Ser  Asn Lys Gln Pro Asn  Ser Gly Ile Glu Asn  Phe Leu Ala
    1310                1315                1320

Ser Leu  Asn Ile Ser Lys Glu  Asn Glu Val Gln Ser  Ser His His
    1325                1330                1335

Gly Glu  Pro Pro Ser Glu Glu  His Leu Ser Pro Gln  Ser Phe Ala
    1340                1345                1350

Met Gly  Thr Arg Met Leu Lys  Glu Ile Leu Lys Ile  Asp Gly Ser
    1355                1360                1365

Asn Thr  Val Asp His Lys Asn  Glu Ile Lys Gln Ile  Ala Asn Glu
    1370                1375                1380

Ile Pro  Val Ser Ser Asn Arg  Arg Asp Glu Tyr Gly  Leu Pro Ser
    1385                1390                1395

Gln Pro  Lys Gln Asn Lys Lys  Leu Ala Ser Tyr Met  Asn Lys Pro
    1400                1405                1410
```

```
His Ser Ala Asn Glu Tyr His Asn Val Gln Ser Met Asp Asn Met
    1415                1420                1425

Cys Trp Pro Ala Pro Ser Gln Ile Pro Pro Val Ser Thr Pro Val
    1430                1435                1440

Thr Glu Leu Ser Arg Ile Cys Ser Leu Val Gly Met Pro Gln Pro
    1445                1450                1455

Asp Phe Ser Phe Leu Arg Met Pro Gln Thr Met Thr Val Cys Gln
    1460                1465                1470

Val Lys Leu Ser Asn Gly Leu Leu Val His Gly Pro Gln Cys His
    1475                1480                1485

Ser Glu Asn Glu Ala Lys Glu Lys Ala Ala Leu Phe Ala Leu Gln
    1490                1495                1500

Gln Leu Gly Ser Leu Gly Met Asn Phe Pro Leu Pro Ser Gln Val
    1505                1510                1515

Phe Ala Asn Tyr Pro Ser Ala Val Pro Pro Gly Thr Ile Pro Pro
    1520                1525                1530

Ala Phe Pro Pro Pro Thr Gly Trp Asp His Tyr Gly Ser Asn Tyr
    1535                1540                1545

Ala Leu Gly Ala Ala Asn Ile Met Pro Ser Ser Ser His Leu Phe
    1550                1555                1560

Gly Ser Met Pro Trp Gly Pro Ser Val Pro Val Pro Gly Lys Pro
    1565                1570                1575

Phe His His Thr Leu Tyr Ser Gly Thr Met Pro Met Ala Gly Gly
    1580                1585                1590

Ile Pro Gly Gly Val His Asn Gln Phe Ile Pro Leu Gln Val Thr
    1595                1600                1605

Lys Lys Arg Val Ala Asn Lys Lys Asn Phe Glu Asn Lys Glu Ala
    1610                1615                1620

Gln Ser Ser Gln Ala Thr Pro Val Gln Thr Ser Gln Pro Asp Ser
    1625                1630                1635

Ser Asn Ile Val Lys Val Ser Pro Arg Glu Ser Ser Ser Ala Ser
    1640                1645                1650

Leu Lys Ser Ser Pro Ile Ala Gln Pro Ala Ser Ser Phe Gln Val
    1655                1660                1665

Glu Thr Ala Ser Gln Gly His Ser Ile Ser His His Lys Ser Thr
    1670                1675                1680

Pro Ile Ser Ser Ser Arg Arg Lys Ser Arg Lys Leu Ala Val Asn
    1685                1690                1695

Phe Gly Val Ser Lys Pro Ser Glu
    1700                1705


<210> SEQ ID NO 19
<211> LENGTH: 19
<212> TYPE: RNA
<213> ORGANISM: artificial
<220> FEATURE:
<223> OTHER INFORMATION: siRNA

<400> SEQUENCE: 19

cgaguaggcu ucgugacuu                                               19


<210> SEQ ID NO 20
<211> LENGTH: 19
<212> TYPE: RNA
<213> ORGANISM: artificial
<220> FEATURE:
```

```
<223> OTHER INFORMATION: siRNA

<400> SEQUENCE: 20

caucggacaa gagugugau                                        19


<210> SEQ ID NO 21
<211> LENGTH: 19
<212> TYPE: RNA
<213> ORGANISM: artificial
<220> FEATURE:
<223> OTHER INFORMATION: siRNA

<400> SEQUENCE: 21

ugcuugaagc agcucugga                                        19


<210> SEQ ID NO 22
<211> LENGTH: 21
<212> TYPE: RNA
<213> ORGANISM: artificial
<220> FEATURE:
<223> OTHER INFORMATION: siRNA

<400> SEQUENCE: 22

gcagaaaccc uaugagauuu u                                     21


<210> SEQ ID NO 23
<211> LENGTH: 22
<212> TYPE: RNA
<213> ORGANISM: artificial
<220> FEATURE:
<223> OTHER INFORMATION: siRNA

<400> SEQUENCE: 23

gugacauccu gccaccucac uu                                    22


<210> SEQ ID NO 24
<211> LENGTH: 19
<212> TYPE: RNA
<213> ORGANISM: artificial
<220> FEATURE:
<223> OTHER INFORMATION: siRNA

<400> SEQUENCE: 24

uagcggacca gacauuucu                                        19


<210> SEQ ID NO 25
<211> LENGTH: 19
<212> TYPE: RNA
<213> ORGANISM: artificial
<220> FEATURE:
<223> OTHER INFORMATION: siRNA

<400> SEQUENCE: 25

agaugaacuu accguagaa                                        19


<210> SEQ ID NO 26
<211> LENGTH: 1144
<212> TYPE: DNA
<213> ORGANISM: Homo sapiens

<400> SEQUENCE: 26

aacggtgcgc tggagcgagt gagcagcgat acctagggcg gaagtgctct cggcggaagt     60

gatcgctgtg tgaatcgtgg gtgggatggc cgcgggccgc ctctttctaa gtcggcttcg    120

agcacccttc agttccatgg ccaagagccc actcgagggc gtttcctcct ccagaggcct    180
```

```
gcacgcgggg cgcgggcccc gaaggctctc catcgaaggc aacattgctg tgggaaagtc    240

cacgtttgtg aagttactca cgaaaactta cccagaatgg cacgtagcta cagaacctgt    300

agcaacatgg cagaatatcc aggctgctgg cacccaaaaa gcctgcactg cccaaagtct    360

tggaaacttg ctggatatga tgtaccggga gccagcacga tggtcctaca cattccagac    420

attttccttt ttgagccgcc tgaaagtaca gctggagccc ttccctgaga aactcttaca    480

ggccaggaag ccagtacaga tctttgagag gtctgtgtac agtgacaggt atatctttgc    540

aaagaatctt tttgaaaatg gttccctcag tgacatcgag tggcatatct atcaggactg    600

gcattctttt ctcctgtggg agtttgccag ccggatcaca ttacatggct tcatctacct    660

ccaggcttct ccccaggttt gtttgaagag actgtaccag agggccaggg aggaggagaa    720

aggaattgag ctggcctatc tagagcagct gcatggccaa cacgaagcct ggcttattca    780

caagacaacg aagctccact ttgaggctct gatgaacatt ccagtgctgg tgttggatgt    840

caatgatgat tttctgagg aagtaaccaa acaagaagac ctcatgagag aggtaaacac     900

ctttgtaaag aatctgtaac caataccatg aagttcaggc tgtgatctgg gctccctgac    960

tttctgaagc tagaaaaatg ttgtgtctcc caaccacctt tccatcccca gcccctctca   1020

tccctggagc actctgccgc tcaagagctg gtttgttaat tattgttaga ctttgccatt   1080

gttttctttt gtacctgaag cattttgaaa ataaagttta cttaagttat gcttgttttt   1140

ctaa                                                                1144
```

<210> SEQ ID NO 27
<211> LENGTH: 996
<212> TYPE: DNA
<213> ORGANISM: Homo sapiens

<400> SEQUENCE: 27

```
atgtggctgt gggaggacca gggcggcctc ctgggccctt tctccttcct gctgctagtg     60

ctgctgctgg tgacgcggag cccggtcaat gcctgcctcc tcaccggcag cctcttcgtt    120

ctactgcgcg tcttcagctt tgagccggtg ccctcctgca gggccctgca ggtgctcaag    180

ccccgggacc gcatttctgc catcgcccac cgtggcggca gccacgacgc gcccgagaac    240

acgctggcgg ccattcggca ggcagctaag aatggagcaa caggcgtgga gttggacatt    300

gagtttactt ctgacgggat tcctgtctta atgcacgata acacagtaga taggacgact    360

gatgggactg ggcgattgtg tgatttgaca tttgaacaaa ttaggaagct gaatcctgca    420

gcaaaccaca gactcaggaa tgatttccct gatgaaaaga tccctaccct aagggaagct    480

gttgcagagt gcctaaacca taacctcaca atcttctttg atgtcaaagg ccatgcacac    540

aaggctactg aggctctaaa gaaaatgtat atggaatttc ctcaactgta taataatagt    600

gtggtctgtt ctttcttgcc agaagttatc tacaagatga gacaaacaga tcgggatgta    660

ataacagcat taactcacag accttggagc ctaagccata caggagatgg gaaaccacgc    720

tatgatactt tctggaaaca ttttatattt gttatgatgg acattttgct cgattggagc    780

atgcataata tcttgtggta cctgtgtgga atttcagctt tcctcatgca aaaggatttt    840

gtatccccgg cctacttgaa gaagtggtca gctaaaggaa tccaggttgt tggttggact    900

gttaatacct ttgatgaaaa gagttactac gaatcccatc ttggttccag ctatatcact    960

gacagcatgg tagaagactg cgaacctcac ttctag                              996
```

<210> SEQ ID NO 28

<211> LENGTH: 1664
<212> TYPE: DNA
<213> ORGANISM: Homo sapiens

<400> SEQUENCE: 28
gcatttggtg ccgtggaagg gaaaaagggg gactgcagta tgcgtcacac ccggaagcgg 60
cgagccggaa gtggggttag ccaggttatc cccaggggtg gagaagcgga ggcccaggag 120
gagggggaat aaagaaggtg gaggatcctg gctaccactc tgaatccgat accgcttctc 180
ttagacctca gcgacagaaa aagggaaggg tgtctcatcc cccttcctcc tctcctccct 240
gtcctgagcc ttagccatgg ccgaggcagg ggctgggctg agcgagaccg tcactgagac 300
aacggttacc gtgacaaccg agcccgagaa ccggagcctt accatcaaac ttcggaaacg 360
gaagccagag aaaaaggtag aatggacaag tgacactgtg gacaatgaac acatgggccg 420
ccgctcatcc aaatgctgct gtatttatga gaaacctcgg gcctttggcg agagctccac 480
ggaaagtgat gaggaggaag aagagggctg tggtcataca cactgtgtac gtggccaccg 540
caaaggacgg cgtcgtgcaa ccctaggacc gacccccacc acccctcccc agcctcctga 600
cccttcccag ccccctccag ggccaatgca gcactaaatc cctctctcct ccagcattcc 660
tgtgtctgtc tggccctaaa tgtatccatg tggctacttc tccagccccc tccttccctc 720
tcttctgcct gatagaggga agaggaagag gaggacgaac agagatcctg aaattctgac 780
ttgctgctat tccagaaccc agcctcctgg gtttccccag tcctcatttt tcctcccaat 840
acccaccctt ctctctcgag ggatctaggc accttggtcc cagtgtcttc cttttgttct 900
cactgccaaa ctgcctgtcc tgggatctag ttatcttggc cctgcactct caacatgagt 960
agcgaacact taaattgggt tttcaacagt cccagctttc actgccaggg tcccagtcag 1020
attccaggaa tttgcgccct aactttgctt gctaatcctg gtttagagct atcccactaa 1080
aatatttaat cctaattctt agtccttgcc tgtgagatat gaggtcttac aggagacctc 1140
agagctccca gcccttctcc tcctgctaac ccttctcaca ccctcaagag gagttagaaa 1200
agaggtcctt gtcattctca cctcttatgg aaaatggaat aagaaataat catatccttt 1260
cttcccaccc ttctcctgtt atttaggatt tctgacaaag ctggcttgag attggtcact 1320
tagagccgac tgtctcctct gccttttgtt tttcagcttc agagacagat ccaatatagt 1380
cccagggacc tgggtctctg ggagaggaag gaagagggag ggagcaaaga gattggggta 1440
tgtcccctgt agtacactct tacctcttac ttcctagact ttgatttctc cggcagccca 1500
gatgttcagt tctcttggcc cctctctacc ccttactggg atccggtttt cattttccgg 1560
tccttttgcc atacacagtt acagagatca gtcaaatcca taccaccact gagatctcat 1620
ttattgccac agatgcacaa aataaataac ccaaaatcac aaaa 1664

<210> SEQ ID NO 29
<211> LENGTH: 3372
<212> TYPE: DNA
<213> ORGANISM: Homo sapiens

<400> SEQUENCE: 29
gggagcagtg cccgagcgcg gtttctctta aggttctgca gggcaaggct gtctgggaca 60
ggcttggcca tggatccgct ctcagagctg caggatgatc tgaccttgga tgacaccagc 120
gaggctctga accagctgaa gctggcctcc atcgatgaga agaactggcc ctcggatgaa 180
atgcctgact tccccaagtc agatgactcc aaaagcagct ccccggaact tgtcacacac 240
ctgaagtggg atgacccata ctatgacatc gcccggcacc agatcgtgga ggtggcagga 300

```
gatgacaagt atgggcggaa gatcattgtg tttagtgcct gtcgaatgcc ccccagccac    360
cagctcgacc acagcaagct cctggggtac ctgaagcaca ccctggacca gtacgtggag    420
agtgactaca cacttctgta tctgcaccac ggcctgacca gcgacaacaa gccctccctc    480
agctggctcc gtgatgccta ccgggagttt gaccgcaagt acaagaagaa catcaaggcc    540
ttgtacatcg tgcatccaac catgttcatc aaaactctgc tcatcctctt caagcccctc    600
atcagcttca agttcgggca gaagatcttc tatgtgaatt acctgagcga gctgagcgag    660
cacgtgaagc tggagcagct ggggatccct cgccaagtgc tcaaatatga cgacttcctg    720
aaatccacac agaagagccc cgcgacagcc cccaagccca tgcccccacg gcccccccctg    780
cccaaccagc agtttggagt ctcgctgcag cacctccagg agaagaatcc agagcaggag    840
cccattccca ttgtactcag ggagactgtt gcctacttac aggcccacgc tctcaccacc    900
gagggcatct tccggaggtc ggccaacacc caagtggtcc gggaagtgca gcagaagtac    960
aacatggggc tgcctgtgga tttcgaccag tacaatgagc tgcacctgcc agcagtcatc   1020
ctcaagacct tcctccggga gcttcctgag cccctgctca cctttgacct ctacccccat   1080
gtggtgggct tcctcaacat tgatgaaagc cagagggtgc cagcgacact gcaggtcctc   1140
cagacgctgc ccgaggagaa ctaccaggtg cttcgtttcc tgactgcttt cctggtgcag   1200
atttctgcac acagtgacca gaacaagatg accaacacta acctggctgt tgttttcggc   1260
cctaacctgc tgtgggccaa ggatgcggcc atcaccctca aggccattaa tcccatcaac   1320
accttcacca agttccttct ggatcaccaa ggggagctgt tcccaagccc ggaccccagc   1380
gggctctgaa cctggcccct gccccaccag ccccttctct ggtagcccgg gtttggactc   1440
ttcctcctgg catcaggggc catgaagccc cctggagaga gatgttggag ccacccatca   1500
ggcatgctct cccccacctc tgtccagccc gcctcacggc cctggcggcc tcgctgttac   1560
cagaagacgt tttctctgc cttacacttc tcactgcctc tctggacacc gggcttttgc   1620
tgggctctcc agagctgggc ttggctcttc cagctggaga aggactgagc cccagtaacc   1680
cctttcctgc tttttcctgc ctctgtttcc ctagcaagtg tggatgaatc aaatgactgc   1740
cggctgggct ggtagcaggg gccagtcctc ccctcttgat tgctgggaat gagcagctga   1800
gctctttggt gtggacaccg ccccaagctg aggtgcctcc ctatctggta ggctgccctg   1860
ctttgcagaa gccccactgc atgaaggcct gagtgcaagc acccttgctc ctgtactgcc   1920
cccagcagcg cagtctgggg tatttcccct gctgaggagt gacagggctg gagactgtgt   1980
ctgctttctg cctcctcttc cacacatcct gggtcagcct ttcccaagtg atactgcccc   2040
tggggtgtcc taacccettg gttgtgcagg gactggtagc ttggatgaca tggctcagag   2100
tcccagcatc cacttgaaac ctccctctcc acctccccgc ccccgagagc tacagcgtgt   2160
gatggaatca gtgaccggcc aggttagcct ctcccctctt ggcctccttt cccacacggg   2220
cagatcatca gccttcatgt tcttgtggac ctgtctgtta cggagtcaca ctggcccctg   2280
ccccagccag aggtgactca gtgcctcagg atcttatggc tccttcctcc agctggggga   2340
ctcttaaagg ggctggggta gagactaaga gtgcccgtag gaggggcaga gattgtgctg   2400
ataggtcagt ccagataggt gggttctagc aatttcccca ggggattaag gggctctagg   2460
gccacctttt ttttttttt tctgagatgg agtctcgctc tgtcaccagg ctggagtgca   2520
gtggcgcgat ctcggcacac ctccgccttc tgggttcaag caattctcct gcctcagcct   2580
cctgagtagc tgggactata ggtgcatgcc accatgccca gctaattttt gtatttttag   2640
```

```
tagagacggg gtttcaccat gttggccagg atggtctcga tctcctgacc tcatgatcca   2700

cccacctcgg cctcccaaag tgctgggatt ccaggcgtga gccactgcgc ccggccagcc   2760

ctgttgtctt tcaaagaacc tcggccccag tgatggctga tctcactccc actgtctcgt   2820

agaattacac tccttcctgg ggatccctct tcctgcagcc ttgtccttgg ggagtacagg   2880

gaagtacctg cagtgaccct gcccccatga ccttggccag gcaggatgat tccagagccc   2940

gtactgtggg gatcctcact gaccagccca gccccatccg caagccaggc tgggcctggg   3000

cataacttcg ctgggctctc ccaagaccat cagcagtgca tccagccccc tggggcctgg   3060

gctgctgctg gttcttcatc agtcccttgg tctctagcct cggccagggc tgctctgctc   3120

tccgccctcc tttgtgtatc aagtgtcgct cacagcccca ttcactgggg agcctttcgg   3180

atctatttgg tctttctcat gtcccccact ggtctgtacc ccagggagcg ggtgcttgta   3240

ctgtgtgaat ccagtgttca cattcacact taatgacttc cttggcacca atcatgtatt   3300

tcaccgtttg cactttttgt atttcaataa aaatgttgat gcaaaaaaaa aaaaaaaaaa   3360

aaaaaaaaaa aa                                                       3372
```

```
<210> SEQ ID NO 30
<211> LENGTH: 2500
<212> TYPE: DNA
<213> ORGANISM: Homo sapiens

<400> SEQUENCE: 30

gtcctgagta ttgctcttca cgcttcagtc ggacaggcct gtattccatg ggaaagtcca     60

ttggccattt ttaactgggg ctatttcttt tctcttatgg actatatcag gccacagtgg    120

tctccaaggg catgatactc aaaggttgtc tcctgtatcc tttgtgctct cccaggaata    180

agcaaagatg tgccaggctg tggaaaatag cctatggagg attactaaag atagtgactg    240

gctccctctt aacattttat gtggttctct gtcttgatgg cgggatggtg ctcatgagga    300

agcaagtgcc atcaaggttc atgtacccca aagagtggca gcacctcacc atgttcatcc    360

tcctcactct taatggctgt gtggacttca tgagcaagaa tgtgctgcct cagaggtgtg    420

tgggcctaga aaaaggtacc ctggtcctga tcatctacga gctcctgctg ctgatggtgt    480

cacatgttaa agattcagaa ggggtggagc tgcacgttta ttctctgctc atcttggtgg    540

tgttcctgct gttgctggtg ttgactgcag agctgtgggc tcccaacatg tgtcatctcc    600

agctgatgga gacctttctg attctgatga tgggctcctg gctgatgcag gcaggcttta    660

ttctatacag acccgtctct ggctacccat ggcaggacga tgacatcagt gacatcatgt    720

ttgtcaccac cttcttctgc tggcatgtga tgatcaatgc ctcattcctg ttgggaatct    780

atggcttctc ttccttttgg tatcattgtt tcagacccag cttgaagctg actgggccca    840

aagaagctcc atattatgca agcactccag gacccctcta caagttgcta caggaagtgg    900

agcagtcaga gaaagaggac caggctctcc tccttccaaa gagctccccc tgagacaggg    960

cctacagtgg ctggcacatc gtccacctca tcttcctcct gttggctcct cagccacgag   1020

catggtaccc tccttggtaa aggtaatggc cttgaaggct agcagttggt cccgtctgct   1080

ggttcatttt cttttcttct cttttctttt tttttttttt tgagacagag tctcgctctg   1140

ttgcccagcc tggagtgcaa tggcacaatc tcagctcagt gcaacctccg cctcccgagt   1200

tcaagcgatt ctcctgcctc agcctcccga gtagctgcaa ttacaggagc ctgccaccat   1260

gcccgtgctg gtgcattttc tgtccctgag cctctaatta ctgagaagat aaggggagag   1320

ggattgagaa agagacgctg atgggatttg cgggagggag ggaaaaggac gaggagaaca   1380
```

```
cttcttctta gtgtgcaaga aaagccactg gggaagaga atgcaacaaa aggaagagct   1440

gtgaagggag gagaacagag tctagcagtt atgctgtcat tagcgtcatc aggcacaagg   1500

gattgccttt tacctgaggg aataaagact tctcacaact caaaactgga cccattcaaa   1560

tctcatcttg ataaagaaaa gtgggtactt tacgtgctca ccaaagtggt gccaccatgt   1620

ggaaatagca tgatagaatt tataattaat tcatacaggc tgaaattatg ctcgctttgc   1680

ctccttctct ctccgcagct ttcaagaatt ggcttcattt caaactttac atataaagtg   1740

agacttttta aatacttaat aacatttcaa atttccataa tttaaatttg tatagaattc   1800

aactgctata gcatttttat agcattcaaa tgcttggtac ttccctgact tctcatttta   1860

ttactcttat tctagcccaa actttccttt tcaccatgac cacccttgca catgcaattt   1920

agcagatacc attcttgggt ctttgcaaat ttcttttcct tgcaaatcac agccagtcat   1980

cctacagtca catatttacc atgttattcg attcccagaa taaacctaca tccaccccca   2040

caccgcacca agtatcccca aggtggcctt ctccagaact cttactgatt cccttgtttt   2100

ggaactcttg ggcacttaca ttaaatctgc tttgttagtt tgctcataca ggtgacccac   2160

tttcttttat actgctgctg aaatcatttt ctttcagaag gttcttcctc acccactaaa   2220

gtacaggctc ctaaagggaa aagactttgc cttatccaag ttaccaaatt tcctatgtat   2280

actccagcta tggatcatgg ttatgtttaa taaagccttc tttgcttcca gagtcttccc   2340

taatcctgtt tcttctaaat gtattgctgg acaggttgga ggttttgtga atctctctgg   2400

gtgacaacaa cagtcctgaa cactgagtca ctgccttagt aatgcaccca ctctcttcct   2460

tgttttgggg tataataaaa tccagtaact tgtttctgaa                         2500
```

<210> SEQ ID NO 31
<211> LENGTH: 1660
<212> TYPE: DNA
<213> ORGANISM: Homo sapiens

<400> SEQUENCE: 31

```
acagtccctc cgggtggcgg ggcgccccga gcgtggcagc gcgctaggcg gcagcagcgg     60

gcgcggagcg gggcgcggcc gccgcgcgtt ccctcttggc ggggttggcc ggccggggcg    120

gggcgcggcg ctccggctcg aggcattcgg agctgcggga gccgggctgg caggagcagg    180

atggcggcgg cggcggctgc aggcgaggcg cgccgggtgc tggtgtacgg cggcaggggc    240

gctctgggtt ctcgatgcgt gcaggctttt cgggcccgca actggtgggt tgccagcgtt    300

gatgtggtgg agaatgaaga ggccagcgct agcatcattg ttaaaatgac agactcgttc    360

actgagcagg ctgaccaggt gactgctgag gttggaaagc tcttgggtga agagaaggtg    420

gatgcaattc tttgcgttgc tggaggatgg gccgggggca atgccaaatc caagtctctc    480

tttaagaact gtgacctgat gtggaagcag agcatatgga catcgaccat ctccagccat    540

ctggctacca agcatctcaa ggaaggaggc ctcctgacct tggctggcgc aaaggctgcc    600

ctggatggga ctcctggtat gatcgggtac ggcatggcca agggtgctgt tcaccagctc    660

tgccagagcc tggctgggaa gaacagcggc atgccgcccg gggcagccgc catcgctgtg    720

ctcccggtta ccctggatac cccgatgaac aggaaatcaa tgcctgaggc tgacttcagc    780

tcctggacac ccttagaatt cctagttgaa actttccatg actggatcac agggaaaaac    840

cgaccgagct caggaagcct aatccaggtg gtaaccacag aaggaaggac ggaactcacc    900

ccagcatatt tttaggcctc atctcagtgc ctatgagggg cctgccagaa aagtcactaa    960
```

cctgtctcag tgtggccttg tccagccttg tgttttctgt aacccctgtt tgtggtacga 1020
gataatgagt cctatttttc tctcacataa tatgcatttg ctctcctagg acagtgtaat 1080
acatttatgt gaagtaaaga catgcgagac tggtggcctg caaatagcat ccgttgatct 1140
gtgttaactg catagggagg gctctgcata gcacctgcta tagcggtgtc atgttggatc 1200
gcttttgtga ctgttcatct gtccttgaca gtggctgtca tcttgactac tttgttgatt 1260
tgttggtatt ggggacattt taaaggctga gttatttttg aatgtcatgt ttatgtcata 1320
gacgtagttt tcgcatcctt gaattaaact gccttaactc cttttgtggt ataagcaaaa 1380
ctacatggac tctgtcctgg tatccttttc ctgtgtggtt gccccgtgtc ctctggccta 1440
gggttaagtg tgcaagataa ctactcgtga gtattcagaa tgttgttcct aataaatgca 1500
cttgttgtct gtcttcttta atcaaatcac atcttatata cagcagtcag agatgagtat 1560
actagaatca tggattgctg gaggtctttt aatctgatgt tctcagaagg gggtggattt 1620
aaatcctgaa ataaatattt caacacaaga acaaaaaaaa 1660

<210> SEQ ID NO 32
<211> LENGTH: 6469
<212> TYPE: DNA
<213> ORGANISM: Homo sapiens

<400> SEQUENCE: 32
ggcgcttcct gttccggcgc caggaggagc cgcgcgctgc tggtgctgtt gccgccgctg 60
ctctagctgc cgtcagtcag gctgcgcccg cgtcttcagg gcccagtccc tcggacccat 120
cgccgcttct agaccctact gcggtctcgg atattgccgg gaaaatgtct gatgaatttt 180
cgttggcaga tgcactacct gaacactccc ctgccaaaac ctctgctgtg agcaatacaa 240
aacctggcca acctcctcaa ggctggccag gctccaaccc ttggaataat ccgagtgctc 300
catcttcagt gccatctgga ctcccaccaa gtgcaacacc ctccactgtg ccttttggac 360
cagcaccaac aggaatgtat ccctccgtgc ctcccaccgg accacctcca ggacccccag 420
caccctttcc tccttccgga ccatcatgtc ccccacctgg tggtccttat ccagccccaa 480
ctgtgccggg ccctggcccc acagggccat atcctacacc aaatatgccc tttccagagc 540
tacccagacc atatggtgca cccacagatc cagctgcagc tggtccttta ggtccatggg 600
gatccatgtc ttctggacct tgggcgccag gaatgggagg gcagtatcct accoctaata 660 tgccatatcc atctccaggc ccatatcccg ctcctcctcc tccccaagcc cctggggcag 720
caccacctgt tccatggggc accgttccac caggagcctg ggaccacca gcaccatatc 780 ctgcccctac aggatcgtat cccacaccag gactctatcc tactcccagt aatcctttcc 840
aagtgccttc aggaccttct ggtgctccac caatgcctgg tggcccccat tcttaccatt 900
aagttaacaa tggacgaaga gatgacgctt tgctttttga agtacatgta tatgcacatg 960
aatgcatata taaaaattgc tggtttcact attagagggc attcatgaaa gaacaactct 1020
tgcacctctc agagaagata actgcctctt gtacttggat gcgtagtaca tcatatgtat 1080
acaatcagat aaaagcatag aagtaaatca ttcggatgtg atttttattt ggttttcatg 1140
gaaagttaaa gtgataaagt atattgaata gttctttgac agaatttgtt taaactatga 1200
aactacacac ttaaaaatct aagatgtgga ttattgttag aatctgcaac ttcattggca 1260
aattatttca agtatttttc tataatcact ttccccttct aaataaataa acttcgagaa 1320
taacccatca taatccaaac aaatgatgcc tcaacatttt gagctgctct gtcggacaaa 1380
taaacctggt cctcttgagg ttatattttg gatatacatt tttaaactgt cagtaattat 1440

```
tgtcagatgt ggagttcaat agccagccag tgttcatttt tatccttgag cttttagtaa   1500
aaacttcctg gttttatttt tagtcattgg gtcatacagc actaaagtct gctatttatg   1560
gaaactaact tttttgtttt taatccaggc caacatgtat gtaaattaaa tttttagata   1620
attgattatc tctttgtact acttgagatt tgattatgag atgtgcatat tgctttggga   1680
agagctcgag gaaggaaata attctctcct ttgttttgaa cctcaaacta gataaaccct   1740
aggaattgct taactgcaac aagtaatttt cattcccaca aaaacctgag gcagctcttt   1800
tgcccagagc gttccctgta gccaccccca ccccacttgc ccttggttct ttagaaggag   1860
cacacacatc ccttgattcc tccctgatgt ggtaaactgg cacactccag ggtctaaaa    1920
cataaaacag ttgtgtttag ggaaccttaa gtcatgcaga catgactgtt ctctttgtac   1980
aagtgtgaat caaaatatgt atctcttttt cagagtctgg ttaagctatg tcattgtcta   2040
ctgcatagtt tcctgagtct gtttgtaaag tgcttatggc taacagttca gttctgtatt   2100
tgttgacagg taaataagtg gagttgagtg ccatctttga aaaaattacc ctctagctct   2160
aacactgaaa ataataataa attgtagatc tctgcaacta agtttaaagc agtgtgactg   2220
tgttgcttaa atatcaagta ttgtttataa ccaccaaaaa aaaaaagccc tggtagtttt   2280
ttggcacctt atgtttaaat cagattctta gatttggagt agacctgacc ttgttattta   2340
ttagataaca ttttgaatgt atccattgga tttctaaaat gtattgtgaa tttctcagac   2400
aaacaggatt tatgctggag ctctgttttg cttagaaata aaatatttag tagtttattt   2460
ctgctctaat taaaatgtca agaatgccaa atgctgccag ttttttggtt tgatagctac   2520
ctccttctaa gaaagcaaaa tggttacctt tgagaggaac attcagtgtt taatcatccc   2580
ttatgttaac tagatgatag attcaagctt ttagaaatga gaaagtagaa actaatttgt   2640
taagatattt tcagactgcg gaatgttgtt agctttttct ttcacttctc ttcaaggaca   2700
ggtgttagct gtctacaata ctgttgaact ctgttgtcaa agtagccccc ttagtctaca   2760
aggcaggtag ccttggcttg aattatcaat atcaaaatgt cagttaacca tggagggata   2820
aagtaatgtg aaaagtgaga tggctgcaaa gatagctctc cttacagtta ttttggctgt   2880
cctacattgg gataagctga caaattagca gtatttagtt taacactgga gcaaatataa   2940
tttgagtagg aagaagagat agcaggtttg ggaatctata attatgaagt ccattgattt   3000
tgggagaaaa tctgttgcta aaggatttga agggccatga acacaatttg ggattattac   3060
tccctataag tataataatt ttgctagtga cccatactgt ccagtgtgcc ctaaatcata   3120
ctgctattgt actccctttg ttttcaagga ctttgcaact ggtatttggg ggagattttt   3180
ttttttttt gagacggagt ctcgctctgt cgcccatgct ggagtgcagt ggtgctatct    3240
tggttcactg caagctccat ctcccaggtt cacaccattc tcctgcctca gcctcccaag   3300
cagctgggac tacaggtgcc cgccaccatg cccggctaat tttttttttt tttttttttt   3360
agtagagatg gggtttcact gtgttagcca ggatggtctc gatctcctga cctcgtgatc   3420
tgcccgcctt ggcttcccaa agtgctggga ttacaggcgt gagccaccac gtccggccga   3480
tttttttttt ttttttaat gtaagaatgg agataaaagg gataatataa tttgctttta    3540
tattgttatt tttgtaaagc atcttttctt caattcttgt tggcattctg ggccaaaata   3600
tttcaggttg gttcggtgtg gagttaagaa aagcaggcgt tttagtggag aaatggggaa   3660
cagcatcaag aaaggctttt ttcctttttt cttttttttt tggagacaga gtcttgccct   3720
gtcacccagg ctggagtgca atggcgtgat cttggctcgc tgcaacctct gcctccaggt   3780
```

```
tcaaacgatt cttctgcctc agcctcccaa gtagctggga ttacaggtgc ccgccaccac   3840
acccattttt gtatttttag tagagacggg ggtttcacca tgttggccag ggtggtctga   3900
aactcctgac ctcgtgatcc gcctgcctca gcctcccaaa gtgctgagat tacaggcgtg   3960
agccaccatg cgtgaccttt ttttcttttt aaaagggaac aatgttgctt tcaaaacaag   4020
acatgctagg ctgaaactga tttatggaaa agactgcttg ttagcaagta tatttggtct   4080
tgagggggat acagattata gaatatgctg acatttgggc ttcagaggaa gaattttcaa   4140
atctaatgga aatagttgag gtgttcagga atgctgtttc ttggagttgg aagcttaggt   4200
tttgaaatgt tgaaaccaaa aagacaaaaa ttaaaacata gaccttaggt cgtcattcac   4260
acccggttct caagaatcaa gtggagcact tcaaagacct tggcttgtct gtcccatcct   4320
gccactttct catcttttca tgcttttgaa gacaccattt acagctctga ctcagcccta   4380
ttttgtgtaa agtaatatat tgattattca gaaatagaca atacattttt taattaccca   4440
aggactgact gttttgtgca ttttactgtt ggttgtcttc agtagagaat agtaataggg   4500
cagagaaaag tatatatttt gcctcagtca gtcccaccac cacaatggac tattgggata   4560
ttttctaaaa aaccaatcaa tttgcccatg attacctcac aaataattag tgctacctgg   4620
ggtactctca aatatacagc ttttgaaact gtagatgaaa aaagctctac tcagagtttt   4680
tgtcaagact gtgcctgggt tgaatatcag tcaattgcct acacttctaa acaataagtg   4740
ccaatgtctc aattttctca ccctgaatga tagaagctag ctttatcaaa tgccaaggtt   4800
agaaagcctg gaaataaaac ttaagcacag acattcaagt ttttgaaaag cataagccta   4860
aattcagata aatcacactg atatattgta ctatgcatag aaagttgtag gtggcgttca   4920
gggaagactt tgattttaat aaagcaatat ttagtattga agacaaacac tttttatttt   4980
cagatttctg ccaagtaaaa cagaaattgc caataaaata atcagtattt tgtaaatggc   5040
aggcaagctt ctggctgtcg aaaacatctg agtcatttat tcagtagaca atatgtcctt   5100
gatccaggtt ctttgccagc tataagggaa tccctgtcct tgagaggctc atagtctata   5160
agtaacatta cagaatttgt tagcataccc attcattatt agttttacct aaacgtgtta   5220
ggatcactac tggtggaaat tgtaaccagc ctttgggcat cttaaagggt gacatgtggc   5280
atgccttttt tttttttaa gaatttaatg tttttcaaga ttgtagtgtt gatcagcgca   5340
acaattcaag tgtgcaaagt aacaggatag tttgcctctt cactttaccc ctggataaag   5400
gcactttcac tgcctgtcac tgatcagcag atactgactt gttgccatta agtgaacttg   5460
acttcttatg tgtgctctat gagtttgttg taattttctt cttgaaattg tgatttttca   5520
ctgacagtaa tgacaaattt aatgtatgta attgtctatg cattttaagt taaactgcct   5580
aaaatgtgat ttgagacata tacatatgtt tgtattataa attgtaagca atcagtttga   5640
gatactaggt tttatcacct gctgctgtat ttgtaaacaa agacaaatgt tgctttaaga   5700
agtaattata attaggaata ggctatggat gtgatacttg gtattttta agataaactt   5760
gtttgctttt gtgtattata cctggaaact tttttaaaa aatgtatttt catggtttca   5820
cagattttc atgttatttt attctttagg cccaattctg ggcttctctg agcaagtcca   5880
gagcctaatt aactgtaaat ttgttgtcaa aaaggaagaa aaaagggcct gagatacctc   5940
tttgcatgtg acctgcattc actaaggata tctggaaacc acccttcctc cgcaaaccct   6000
ctcagcaaca tggtgtccat tgtggtgatt ttctcttctt ttaaggctag gctactcttg   6060
gtaaccagat tatccgtata tatgataata tgaagtcagg gaactttctc tgtctgtccc   6120
tactcccctc actcccccac tttctgttat gaaagatagt tctactttta tcattaactg   6180
```

```
ctacgcattt agtgagggtc acattattaa acttggagtt taccattttc ccacaggaga   6240

tttcgctggc attccttgga actcccaatt tcagtagggc aatgaatgaa tgaatacttt   6300

gcagtgctac ttttggaagg aatttctgct ttttgcctta tgattggaca aaatgcagct   6360

gtaaaatttt aaattgtttt tgatatgtta ttcaatatcc catgaaagta ttcacctaaa   6420

gtggagttat gaaatggatg gtgaaataat aagaccattc tggagcagg               6469
```

<210> SEQ ID NO 33
<211> LENGTH: 1972
<212> TYPE: DNA
<213> ORGANISM: Homo sapiens

<400> SEQUENCE: 33

```
ggaacccaca ggcgcgcgcg ccgctgcttc tggccgggcg cgggtcgtgg tgcaccacgg     60

gagcgccgca ccggccggca tggaggagcg cggcgattcc gagccgaccc ccggctgcag    120

cggcctgggt ccgggcggtg ttcgcggctt tggcgacggc ggtggagctc cttcgtgggc    180

ccctgaggac gcctggatgg gcactcaccc taagtatcta gaaatgatgg aattagatat    240

aggagatgcc acccaagttt atgtagcgtt cttggtttac ctggacctca tggaaagcaa    300

aagctggcat gaagtaaact gtgtaggatt accagaactc cagctcatct gccttgttgg    360

tactgagata gaaggggagg ggttacagac tgtggtgcct acccccatca ctgcttccct    420

cagccataac aggataaggg agatcttgaa ggcatctcga aagttgcaag gtgatccaga    480

tttgccgatg tcttttactt tggccatagt ggagtctgat tctacaatag tctattataa    540

acttactgat ggatttatgc tgccagaccc tcagaatatt tctcttagaa gatgacatcc    600

atgtttcctg atgcttgttt tattcataca agattggatt tgagacccat cagactgctt    660

catcttttat ctcagaaata gggttgacgt acatagtgag ggttgacttc cccattccat    720

aaggttttca ttctgaagag taaaacttcc ccaggtagaa gactttctcc ttcttaaaaa    780

atatagggtg atttctttaa aactttgtta tctagagaca gtttaattac agttatatac    840

aggtttatgc ctaggatgta ttcagatggg tgggacctgt gtgctgcttt tgtcatccca    900

cactcaaagt tgtctctttg tttcttgctg ccactgccag ctcattgttg agactgccat    960

ttctttctct tactcagctc tccccagtgc cttttggcca ctgcagctac cgtagaatgg   1020

cattttatat gtaccttgtc acccacttct gtttactttt tcctctccag taaaaagtaa   1080

aagatttctt tcaattggtc ttcccattgc agttactgtt atttctcttt tttggttaac   1140

tttaaatcaa aactcaaaat atgttcatcc agagtgtgtc ttaagtaact tacgtgtctt   1200

aagtaacagg gaccagagac atgttaccta caagagttct gggctatcct tttcattctt   1260

atcacatatc atagcttgaa tattacaaca gtgtgggaga gaatcaaccg taaaaatgtc   1320

ttcattaatt agacccagtt attccacttt tgttaatgtc tctcaaattg tacaaagtat   1380

aaaaaattat atgcacaaag atgttccaag tgacattact tttagtagcc caaattataa   1440

accactttaa agtttggggt aaagattggc aaactttttc tataaagggc cagaaagtaa   1500

ctattttagg tttttaaacc tactgtctct gtcataactt gtcaacactg ctgtatgaag   1560

cacaaaagca gccatagaca atacataaac aatacgggcg tggctttgtt ccagtaaaac   1620

tttgtttaca aatgtggtgc catagtttgt catccctggg tctaggaaat agtcaataaa   1680

cagatatata caaatgatac ataatgtact tattaaaaat tagtaatgaa tattattaaa   1740

aacatgaaaa tattacctta agtaaaaatt gcaagacgga aaagtgtata agtgggtgta   1800
```

```
atcatggctg aaataacaga ccaagcatat gataaaaaga taacaaagta aatcaaatta   1860

ctaactggtt atagtgggat aggaggcaga aaatggatga ctttgtcttt tctcaatgtt   1920

tttatttgta ttttataata aaaatgtttt aaaattaaaa aaaaaaaaaa aa           1972


<210> SEQ ID NO 34
<211> LENGTH: 1853
<212> TYPE: DNA
<213> ORGANISM: Homo sapiens

<400> SEQUENCE: 34

ggcgcggcgc ggcgcagtcg gctcgagtac tccccgtaac gaggaggtgt tctcggccgt     60

cccacccttc actgccgtct ccgggctgcg ccgccggagc cgggacgcgc ctccgcagcc    120

ctcgccgcct ccatccccgc ggccgcagct cctctcgccg tccgcgcgca caccatgacg    180

aagaacgaga agaagtccct caaccagagc ctggccgagt ggaagctctt catctacaac    240

ccgaccaccg gagaattcct ggggcgcacc gccaagagct ggggtttgat cttgctcttc    300

tacctagttt tttatgggtt cctggctgca ctcttctcat tcacgatgtg ggttatgctt    360

cagactctca acgatgaggt tccaaaatac cgtgaccaga ttcctagccc aggactcatg    420

gtttttccaa aaccagtgac cgcattggaa tatacattca gtaggtctga tccaacttcg    480

tatgcagggt acattgaaga ccttaagaag tttctaaaac catatacttt agaagaacag    540

aagaacctca cagtctgtcc tgatggagca ctttttgaac agaagggtcc agtttatgtt    600

gcatgtcagt ttcctatttc attacttcaa gcatgcagtg gtatgaatga tcctgatttt    660

ggctattctc aaggaaaccc ttgtattctt gtgaaaatga acagaataat tggattaaag    720

cctgaaggag tgccaaggat agattgtgtt tcaaagaatg aagatatacc aaatgtagca    780

gtttatcctc ataatggaat gatagactta aaatatttcc catattatgg gaaaaaactg    840

catgttgggt atctacagcc attggttgct gttcaggtca gctttgctcc taacaacact    900

gggaaagaag taacagttga gtgcaagatt gatggatcag ccaacctaaa aagtcaggat    960

gatcgtgaca agtttttggg acgagttatg ttcaaaatca cagcacgtgc atagtatgag   1020

taggatatct ccacagagta aatgttgtgt tgtctgtctt cattttgtaa cagctggacc   1080

ttccattcta gaattatgag accaccttgg agaaaggtgt gtggtacatg acattgggtt   1140

acatcataac gtgcttccag atcatagtgt tcagtgtcct ctgaagtaac tgcctgttgc   1200

ctctgctgcc ctttgaacca gtgtacagtc gccagatagg gaccggtgaa cacctgattc   1260

caaacatgta ggatgggggt cttgtcctct ttttatgtgg tttaattgcc aagtgtctaa   1320

agcttaatat gccgtgctat gtaaatattt tatggatata acaactgtca tattttgatg   1380

tcaacagagt tttagggata aaatggtacc cggccaacat caagtgactt tatagctgca   1440

agaaatgtgg tatgtggaga agttctgtat gtgaggaagg aaaaaaagaa aataaaagtg   1500

tgtttgaaaa atattatctt gggttctttg taaaatttat tttttacatg ctgaattagc   1560

ctcgatcttt ttgattaaga gcacaaactt ttttttgtaa aacatgtaaa aaaaaaaact   1620

gggattaatt tttagtgttg gaactgcctc ttattttagg ctgtagataa aatagcattt   1680

ttaggttagc cagtgtgact atgcacctaa ttttttatga gattaaattc ataagactta   1740

atttgtacaa tagtttgtga aatatcttgt tactgctttt atttagcaga ctgtggactg   1800

taataaagta tataaattgt gaaatataaa aacttggaac ttattcaaag ctt           1853


<210> SEQ ID NO 35
<211> LENGTH: 1736
```

<212> TYPE: DNA
<213> ORGANISM: Homo sapiens

<400> SEQUENCE: 35
gataagaccg gccccttccg gttacgaaac cttagcaaga tggcggctcc ctgggcgtcc 60
ctgcgcctgg tcgcccccat gtggaatggg cgtatcaggg gcatccatcg cctgggtgcg 120
gcagtggccc cagagggcaa tcagaagaag aaaaggacaa tactccagtt cctgaccaac 180
tatttctacg atgtggaggc tctgagggat tacttgctcc aaagggagat gtacaaggtg 240
catgagaaaa atcgatctta cacctggctg gagaagcaac atggtccata cggcgcaggt 300
gcctttttca tcctgaagca gggaggcgca gtcaagtttc gagacaagga gtggatcagg 360
ccagataagt atggccattt ctctcaggag ttctggaatt tctgtgaagt gcctgtcgaa 420
gctgtggatg ccggtgactg tgacatcaac tacgagggcc tggataacct cctccgcctg 480
aaggagctcc agtccttgtc gctgcagcgc tgctgccacg tggacgactg gtgtctcagc 540
cgcctctacc cactggccga ctcgttgcag gagctctcgc tggccggttg cccccgcatc 600
tccgaacggg gcctcgcctg cctccaccac ctccagaacc tccgcaggct ggacatctcg 660
gacctccctg ccgtgtccaa ccctggcctc actcagatat tggtggagga gatgctgccc 720
aattgcgagg ttgtgggagt cgactgggct gagggcctga agtcagggcc ggaggagcag 780
cctcgggaca cagccagccc tgtccctgcc tagcctttag ccctgtcccc actcacgtgg 840
cttctcagcg ggctgcatgg aatgtctggt agctcaccac acttctggct tccatttgtc 900
ttcactcaac gtcagggtgg gggagtggtg ctggccaatc acaggagaga gcgtgagttc 960
ccagtattta ttcctggctg cccttggcta aaggtcacag ctcctgtcac cctgtcaggc 1020
agccctttcc atgcccctgt tcaggcctgg ggaggtaaag gctcaggctg ttagtagccg 1080
cagagagcca cactcacctt gtcaggagac tcttctcaaa ctgtccttat gtgagtgcac 1140
tgccatttct tgcagggacc ctgactgaca caggggctac tactgacact ttacagggat 1200
ggttctcccc cgtgcagggc cgctgtgccc actgcaggac atgcagcatc cttcgcccca 1260
ctccactcac taaaggccag cgcaccccag gccccatagt attgctggtt atggatttat 1320
tgactttatg ttccaaattc agctttttca gttggctgtt ttttgaaagg ggataagctt 1380
tgtcagtaga gggcaccaaa caggcattat aggaggaaag gcgcctcctt cgtggttctt 1440
gttggttgtg cttctgcctc tggacgccgc agtgcatgtg gcttccccag cacccagctc 1500
ctgaagcacc aggcggtcag cagctgccct tggcaccctc cagccctcag aagttgcgta 1560
ggagacacag cgcctccact gaggcacctc tctgggaata acgttcccca gcaccccaaa 1620
tggatttcca gtcaattcag aagcatttta ccagtgaagc cctcattatt ccagttcact 1680
gttaaagcca gtaattctct atattaaact ttccctgttc aagttaaaaa aaaaaa 1736

<210> SEQ ID NO 36
<211> LENGTH: 3470
<212> TYPE: DNA
<213> ORGANISM: Homo sapiens

<400> SEQUENCE: 36
ggagtgtagg ccagggggtt ggcggtgccg tgtcatggag gctcagtctc tgagcagcca 60
ttgaagggga aggaactgcg ggtgtgtgtg tgtatgtgtg tgtgtatgtg tgtgcgcgcg 120
tgcgtgcgtg tgtgtgcgcg cgctagtgtg tggacaagga ggtgggggca gctgagttag 180
agtcccaact cttggactcc atttgctatt ctcttctttc tcccccacac ctatctggtg 240

```
gtggtagtgg gcgtttatat ttgcgttcct tttcattcat ttctaaatct cttaaaaatt    300
ttgggttggg ggtattgggg aaggcaggaa agggaaaagg agagtagtag ctgaagagca    360
agaggaggac atggagatga agaagaagat taacctggag ttaaggaaca gatccccgga    420
ggaggtgaca gagttagtcc ttgataattg cctgtgtgtc aatggggaaa ttgaaggcct    480
gaatgatact ttcaaagaac tagaatttct gagtatggct aatgtggaac taagttcgct    540
ggcccggctt cccagcttaa ataaacttcg aaaattggag cttagtgata atataatttc    600
tggaggcttg gaagtcctgg cagagaaatg tccaaatctt acctacctca atctgagtgg    660
aaacaaaata aaagatctca gtacagtaga agctctgcaa aatcttaaaa atttgaaaag    720
tcttgacctg tttaactgtg agatcacaaa cctggaagat tatagagaaa gtatttttga    780
actactgcag caaatcacat acttagatgg atttgatcag gaggataatg aagcgccgga    840
ctctgaagag gaggatgatg aggatggcga tgaagatgat gaagaggaag aggaaaatga    900
agctggtcca ccggaaggat atgaggaaga ggaggaggaa gaggaagagg aggatgagga    960
tgaggatgaa gatgaagatg aagcaggttc agagttggga gagggagaag aggaagtggg   1020
cctctcatac ttaatgaaag aagaaattca ggatgaagaa gatgatgatg actatgttga   1080
agaaggggaa gaagaggaag aagaggaaga aggaggtctt cgaggggaga agaggaaacg   1140
agatgctgaa gacgatggag aggaagaaga tgactagatc attctaagac cagattctct   1200
aatgtttctg ggtgtgcaat agagtgatca catctttgtt tcttcatgta cgatagctat   1260
ccctacagaa gataatgtgt aactttttat aggaaaagtg tggttttact atttttgcct   1320
tatcattcca aataagaact agtctgttaa tgatcatatt gtatgtagag aaaaattttc   1380
attgactccc attgtggaat tccctagcaa tttatttaga cttaattttt taaattcaag   1440
cttactgtat tagtcatttt tagcccataa ttaaaacatg atcactttta cacaggtgta   1500
gtatggtgca tttcattcct tatttataaa ttaactgaaa ttacagtttg ctataatata   1560
aaatgacaat agtctcttga gtggtaagtt ggttattttt ttagaggtga tccaggaatc   1620
tttagtttga aggcagttac cttttttttt tttttttttt tttgactaag agtgtttggt   1680
tgctttttttg tcacaagtaa cttggaaaat agaagcagaa tagtaaaggt tctattcagc   1740
aacatagttc atggattttg tggaggttct attcagtaat atggttcatg gatttagtgg   1800
tgactgataa gattttattt ttgaaggaaa aattgcttat actaagtcca gagacatgca   1860
ggtgagccct tttgtcaggc tgcaaatcat gacatgccga tggttgttta ttttgttttt   1920
aggtgtgcat tctttttctt cttagcaatt cctttatgat caccttccct tcttgtttca   1980
ctccctcccg ctctctcaaa aggaacttgg gaaacttgtg aaacccagga aaacctttag   2040
tcttatacct caactacctt tcagtcctgt ctgggtttta aataagtgaa gtagaagaaa   2100
ttgagtattt tctgacataa gaatatatta tcaatacagt tttatgcagt aagctctcct   2160
taccataaat gtttcttggt tgacaacatc taagacaata ttagtgggat gaagaaagaa   2220
aagcaggggt gcttttggaa gcagtgttag tgttcctcaa aagtcggaac aattgcctgt   2280
tgatatatta ataagacatt aaagtcaaat tttaatgttg gcctctcaaa tgatttggat   2340
accactctgc aaagtatttc taacctttaa ttcccagttt taaaacagat ataataatag   2400
catttaattg gaatatacta ggcagctgga aaagtatttg aaactaaatt gacattaaaa   2460
ttaagatttg ttttcaagtg gatgtccatt aaaagtagaa aaatatttgg gataagtgag   2520
tgtgtgtttc cttacatggc tactaaataa aatataatga gtatacaagt atatctcctc   2580
ttttgctatg gaggctccat gttcaaggca atggcttttt aaatcttggc tatctaaaat   2640
```

```
tttttccctt tgttttgaat atttgtaagt ttttaagaag ttagtgtcag caaattaatt   2700

gaagttatgc ttctatactg ggacatattt aaatactgag tatagtactg ctgctactgc   2760

ttctacaatg taaaatgtat gacttggtgt tttaaagtaa aaattatgat gttacttgtg   2820

gagaaactaa aaatgttgta caactgaccg aaagaaaacc cttggggata agtttagtga   2880

ggggattgga atccccaaaa agataacatt tttcttctgc ttttaaaaac tgaaattccc   2940

tgttctagtt cctaacaatt ctcattacat actatgccag attacaaaat acttattttt   3000

aaaatgaaat ctatatattg actttcttat caatcatctt actgtgcaat caaaattaga   3060

gtactttggt ttgaaaacaa cacttagagc ctccagataa cttttaagac ttatttagct   3120

ttgtgggtgg tattttcatg caaataagta agggtgggtt ttatattttg tagaagtttt   3180

cggtcctatt ttaatgctct ttgtatggca gtatgtatat attgtgttaa gttcctcaag   3240

aatctcctta aaaactttga agttaatact tttgtgcaac tgtgttttga ataaagccat   3300

gacagtgtta aaaacaaaca aaaaaatttg cagtactcct gattattctt ttattgtttt   3360

tgactgttcc ctgttttttt ctgtgactgc tgtaacttaa agtttttgaa actgaattgc   3420

ttcaaataaa ttgaagattt gttataatga ttaaaaaaaa aaaaaaaaaa              3470
```

<210> SEQ ID NO 37
<211> LENGTH: 1360
<212> TYPE: DNA
<213> ORGANISM: Homo sapiens

<400> SEQUENCE: 37

```
gcccttgcct tgagtcagtg cgctgctctc cagcccgctt gaacgctccc cgcagccacc     60

gccacccatt ggaatggcca acaggggacc tgcatatggc ctgagccggg aggtgcagca    120

gaagattgag aaacaatatg atgcagatct ggagcagatc ctgatccagt ggatcaccac    180

ccagtgccga aaggatgtgg gccggcccca gcctggacgc gagaacttcc agaactggct    240

caaggatggc acggtgctat gtgagctcat taatgcactg taccccgagg ggcaggcccc    300

agtaaagaag atccaggcct ccaccatggc cttcaagcag atggagcaga tctctcagtt    360

cctgcaagca gctgagcgct atggcattaa caccactgac atcttccaaa ctgtggacct    420

ctgggaagga aagaacatgg cctgtgtgca gcggacgctg atgaatctgg gtgggctggc    480

agtagcccga gatgatgggc tcttctctgg ggatcccaac tggttcccta agaaatccaa    540

ggagaatcct cggaacttct cagataacca gctgcaagag ggcaagaacg tgatcgggtt    600

acagatgggc accaaccgcg gggcgtctca ggcaggcatg actggctacg ggatgccacg    660

ccagatcctc tgatcccacc ccaggccttg cccctgccct cccacgaatg gttaatatat    720

atgtagatat atattttagc agtgacattc ccagagagcc ccagagctct caagctcctt    780

tctgtcaggg tgggggggttc agcctgtcct gtcacctctg aggtgcctgc tggcatcctc    840

tcccccatgc ttactaatac attcccttcc ccatagccat caaaactgga ccaactggcc    900

tcttcctttc ccctgggacc aaaatttagg ggcctcagtc cctcaccgcc atgccctggc    960

ctattctgtc tctccttctt ccccctggcc tgttctgtct ctgagctctg tgtcctccgt   1020

tcattccatg gctgggagtc actgatgctg cctctgcctt ctgatgctgg actggccttg   1080

cttctacaag tatgcttctc ccacagctgt ggctgcagga acttaattta tagggaggag   1140

cctgtggcag ctgctgcccc agccacagct gcactgactg tgctcaccac acatctgggg   1200

cagccttccc tggcaggggc cctcgtggct tctcattttc cattcccttc actgtggcta   1260
```

aggggtgggg tgaggggatg gagagggagg gctgcctacc atggtctggg gcttgaggaa 1320
gatgagtttg ttgatttaaa taaagaattt gtcatttttg 1360

<210> SEQ ID NO 38
<211> LENGTH: 3556
<212> TYPE: DNA
<213> ORGANISM: Homo sapiens

<400> SEQUENCE: 38
tcgcggcttc cggtgctagg tggagggaag gaaggaggga gccggggagt gggccagggc 60
agcagccggg ctgaagtcgg cttggggagc cagagggagc ggagcggaac ctgcggggca 120
gaggcggcgg ccgcagcggc gcagctgata gcaggaacag gatcaagtct tccataccag 180
ggaccaggcc aaaaccagac tgccactgcc cctacttggg ccccactgtc cccagaaagc 240
agctgctgtg atcatgggca atatctttgg aaaccttctc aagagcctga ttgggaagaa 300
ggagatgcgc atcctgatgg tgggcctgga tgccgcagga aagaccacca tcctatacaa 360
gctgaaactg gggggagatcg tcaccaccat ccctaccatt gggttcaatg tggagacagt 420
ggagtataag aacatcagct ttacagtgtg ggatgtgggt ggccaggaca agattcgacc 480
cctctggaga cactacttcc agaacaccca agggttgata tttgtggtcg acagcaatga 540
tcgggagcga gtaaatgagg cccgggaaga gctgatgaga atgctggcgg aggacgagct 600
ccgggatgct gtactccttg tctttgcaaa caaacaggat ctgcctaatg ctatgaacgc 660
tgctgagatc acagacaagc tgggcctgca ttcccttcgt caccgtaact ggtacattca 720
ggccacctgt gccaccagcg gggacgggct gtacgaaggc ctggactggc tggccaatca 780
gctcaaaaac aagaagtgaa agccagacag ccctaacaaa gcaccccacc cacccctgac 840
atacctactg tcaccctgcc ccagtcctac cccttcctct ccatgcaagt gtggccaggg 900
ccctgggtat catgtccaca tgcccagcaa gagccttgcc tcccctgcct cccctccttt 960
ttcctgtcca cctatatgac caatccctaa ttgctgtcct gatgatgagt cattccaatt 1020
tactggattt aaaacaaaaa gttgttacgg tttcatgggg tggcccctct ctctctcacc 1080
ctctgggttt cgggaggtcg agtggggtat tctctttgtt tggcagtggt tgctgtcctc 1140
ttggcatctg agtcctttcc ctgtccccac aagcccttct actccctgtt tgcctttcct 1200
ttgccaccct ctccctgttt tacatggaaa ttgcacgggc ctctctgtgt ttgcgtgcat 1260
gtgtgcgcct gtatatacat gtatagagag atatatttgt gggggccggg gggagcgggg 1320
agggggtgga gtgaagctca gggcttgcag ccaggacact gcccactgga gcctgtcatc 1380
tgccccttcc gtgttggtga gattaaggga agaaggtggg agggcattag tcaagccgga 1440
ctgccccagt ctttgactgg ttaccctcct ctctgcaggt aggtttttct ggatgatagg 1500
acagatgatg gattcttcac caccattttc cttgtactct tctctccacc cttcttaggg 1560
ctggaggatg gcatttatct ctagatgact gttcccaagg agatgccact ctgctctgcc 1620
ttactgttgg gaaggagaga ggaacccact cactcttatc agcttagagt gttcaactga 1680
tccttcccca ccatcttcag atctgttcct ctggagcttg actggggggt ggggatggca 1740
agtccatggt gtgtgttagg gacccagggc attgggggaa gggaggcgaa ggcctgaggt 1800
tttccatctt cattctcttt tgttattagg agaaggtgag gcatgggcca atcccattcc 1860
tgccttccag tgccccacca cccttctgat cttaggggtt ggatgggtca tctgtccttg 1920
gtcagaattt tctcacccta gtactcctac tggcctgacc agggctgact gggtattcta 1980
atgaggagct gggaagtggg gtgacatagc tgaccttagt atcaaccccc ctcttctcca 2040

```
actcttgttt tctagtccag gatatgctaa aggacgaaga ttttctattg tttccaggcc   2100
ctcagaccat ccttgctgtc ccttcaccct ccatgcccct gccatcctca ctcacttctc   2160
ataaatggat ctgggggtta gagtggagga aataaaatcc tgaagtggtt gtcagtgctt   2220
gtgggatgca gtggtcttca ggattctccc cgcattatta tgtagttgtt cagaagctgt   2280
tgctactgcg tctctctgtc tgcagggggc acttgttcct gaggtcctcg cctgggtcct   2340
gacttctgta gtttctgtga agacgtggct gtcctgtggg ctcctgtgtg tgctggctgc   2400
gccctgagct ccgagacagc tgcccataac ctgctaaggt cagggcccag ggccccccac   2460
agcatggctg agggacccct tcccagtagg gctgtcccaa gccccactcc atggggccag   2520
gtttcctggc cacttttgtt gatagcagat ggatcaatat tagtaacccc atccaagatt   2580
gaactgtgaa agagaggttc caggggtatc tccctcagtg ccagttactt agtgatgtgt   2640
tacccaggat gcagcaggtg tgtgcaggta tcttgctctc taggcctgtg tgtgtgtgtg   2700
agtgtgtgtg tatatgggtg tgggtgtgtt tgtgtgtggt ggttgtgggg ggggtgttgg   2760
aggttctatt tcatttaaaa atgtattcat ttccctggcc ccacagatgc ttccctccat   2820
actttttatt tgctctgttt cctcagattt attttgtctt gccccattgc ctctccttcc   2880
ttgaactctt tccttttcaa tctcaactca ttcactgctg ttgctcattt gccctttttcc   2940
atgtattttt tcctacttag gattttccac tctatctttg tggttcatga ggactttgcc   3000
tcttctcctg cctcattccc tgactttctc tagttagatg tcagtcctaa ataggttttc   3060
ctcacttcag gcctcacccc tcaccttgtt tttttggggg ctccagggac caatctgggg   3120
ctggaaatgt taggaggttg ccttggtgct gccccagatc tgtccagcag ggggcagtaa   3180
gtgatcttgg tagtatccct ggctgctaag cccttggcag gggtggtcct ttctacattc   3240
ccattcactt aacagctctt ttgggattgg gtgtttcatt ccatttctgc ccactccctc   3300
tcctctcctc tctggtaggt ttaattttat gctttccctg attccagctt tctgcttcct   3360
gaggactccc gctcccccca ccccaaagtt tgtctgtggt gttatagtgg taactgcagt   3420
tcctcctctg gaatgtagac tgtatatgtt taataactca ccttctctat ccttgctcaa   3480
aatgtgggat aacgcgatga ctgtgaccct ggttggaaat taaacttgtt ttatgcaaaa   3540
aaaaaaaaaa aaaaaa                                                   3556
```

<210> SEQ ID NO 39
<211> LENGTH: 1220
<212> TYPE: DNA
<213> ORGANISM: Homo sapiens

<400> SEQUENCE: 39

```
cccccactgg ctgctctgaa aagccatctt tgcattgttc ctcatccgcc tccttgctcg     60
ccgcagccgc ctccgccgcg cgcctcctcc gccgccgcgg actccggcag ctttatcgcc    120
agagtccctg aactctcgct ttctttttaa tcccctgcat cggatcaccg gcgtgcccca    180
ccatgtcaga cgcagccgta gacaccagct ccgaaatcac caccaaggac ttaaaggaga    240
agaaggaagt tgtggaagag gcagaaaatg gaagagacgc ccctgctaac gggaatgcta    300
atgaggaaaa tggggagcag gaggctgaca atgaggtaga cgaagaagag gaagaaggtg    360
gggaggaaga ggaggaggaa gaagaaggtg atggtgagga agaggatgga gatgaagatg    420
aggaagctga gtcagctacg ggcaagcggg cagctgaaga tgatgaggat gacgatgtcg    480
ataccaagaa gcagaagacc gacgaggatg actagacagc aaaaaaggaa aagttaaact    540
```

```
aaaaaaaaaa aggccgccgt gacctattca ccctccactt cccgtctcag aatctaaacg    600

tggtcacctt cgagtagaga ggcccgcccg cccaccgtgg gcagtgccac ccgcagatga    660

cacgcgctct ccaccaccca acccaaacca tgagaatttg caacagggga ggaaaaaaga    720

accaaaactt ccaaggccct gcttttttc ttaaaagtac tttaaaaagg aaatttgttt    780

gtatttttta tttacatttt atatttttgt acatattgtt agggtcagcc atttttaatg    840

atctcggatg accaaaccag ccttcggagc gttctctgtc ctacttctga ctttacttgt    900

ggtgtgacca tgttcattat aatctcaaag gagaaaaaaa accttgtaaa aaaagcaaaa    960

atgacaacag aaaaacaatc ttattccgag cattccagta actttttgt gtatgtactt   1020

agctgtacta taagtagttg gtttgtatga gatggttaaa aaggccaaag ataaaaggtt   1080

tcttttttt tcctttttg tctatgaagt tgctgtttat ttttttggc ctgtttgatg   1140

tatgtgtgaa acaatgttgt ccaacaataa acaggaattt tattttgctg agttgttcta   1200

acaaaaaaa aaaaaaaaaa                                                1220
```

<210> SEQ ID NO 40
<211> LENGTH: 1045
<212> TYPE: DNA
<213> ORGANISM: Homo sapiens

<400> SEQUENCE: 40

```
actatccggc gccgagccgg aggggggaaa cggcgcccgc cgcccgcccg gagcccgcga     60

gcaaccccag tccccccac ccgcgcgtgg cggcgccggc tccctagcca ccgcggcccc    120

accctcttcc ggcctcagct gtccgggctg ctttcgcctc cgcctgtgga tgctgcgcct    180

ctccgaacgc aacatgaagg tgctccttgc cgccgccctc atcgcggggt ccgtcttctt    240

cctgctgctg ccgggacctt ctgcggccga tgagaagaag aaggggccca aagtcaccgt    300

caaggtgtat tttgacctac gaattggaga tgaagatgta ggccgggtga tctttggtct    360

cttcggaaag actgttccaa aaacagtgga taattttgtg gccttagcta caggagagaa    420

aggatttggc tacaaaaaca gcaaattcca tcgtgtaatc aaggacttca tgatccaggg    480

cggagacttc accaggggag atggcacagg aggaaagagc atctacggtg agcgcttccc    540

cgatgagaac ttcaaactga agcactacgg gcctggctgg gtgagcatgg ccaacgcagg    600

caaagacacc aacggctccc agttcttcat cacgacagtc aagacagcct ggctagatgg    660

caagcatgtg gtgtttggca aagttctaga gggcatggag gtggtgcgga aggtggagag    720

caccaagaca gacagccggg ataaaccct gaaggatgtg atcatcgcag actgcggcaa    780

gatcgaggtg gagaagccct ttgccatcgc caaggagtag ggcacaggga catctttctt    840

tgagtgaccg tctgtgcagg ccctgtagtc cgccacaggg ctctgagctg cactggcccc    900

ggtgctggca tctggtggag cggacccact cccctcacat tccacaggcc catggactca    960

cttttgtaac aaactcctac caacactgac caataaaaa aaatgtgggt tttttttt   1020

ttaatataaa aaaaaaaaaa aaaaa                                         1045
```

<210> SEQ ID NO 41
<211> LENGTH: 2161
<212> TYPE: DNA
<213> ORGANISM: Homo sapiens

<400> SEQUENCE: 41

```
ggaggagctg ttttgcggcg ggcggagctg caggctgggc agggcttagc ctgtgcgctt     60

ctgctggcct ccttttcgcc ctcccacccg cactgcagtc tccagcctga gccatgggcc    120
```

```
gccgagccct cctgctcctg cttctgtctt ttctggcgcc ctgggccacc atagccctcc    180
ggccggcctt aagggccctc ggcagcctac acttgccaac caaccccaca tccctcccgg    240
ctgtagccaa gaactattcg gttctctact tccaacagaa ggttgatcat tttggattta    300
atactgtgaa aacttttaat cagcggtacc tagtagctga taaatactgg aagaaaaatg    360
gtggatcaat acttttctac actggtaatg aaggggacat tatctggttt tgtaataaca    420
cggggttcat gtgggatgtg gctgaggaac tgaaagctat gttggtgttt gctgaacatc    480
gatactatgg agagtctctc ccctttggtg acaactcatt caaggattcc agacacttga    540
atttcctgac atcagaacaa gctctggctg attttgcaga gttaatcaaa cacttgaaaa    600
gaacaatccc aggagctgaa aatcaacctg tcattgccat aggaggctcc tatggtggca    660
tgcttgccgc ctggtttagg atgaaatatc ctcatatggt agttggagct cttgcagctt    720
ctgcccctat ctggcagttt gaggatttag taccttgtgg tgtatttatg aagatcgtaa    780
ctacagattt taggaaaagc ggtccacatt gttcagagag catccacagg tcctgggatg    840
ccattaatcg actctcaaat actggcagtg gtttgcagtg gcttactgga gcccttcact    900
tatgcagccc attaacttct caggacatcc aacatttgaa agactggatc tctgaaacct    960
gggtgaatct ggcaatggtg gactatcctt atgcctctaa ctttttacag cctttgcctg   1020
cttggcctat caaggtagtg tgccagtatt tgaaaaatcc caatgtatct gattcactgc   1080
tgctgcagaa tatttttcaa gctctgaatg tatattacaa ttattcgggc caggtgaaat   1140
gcctgaatat ttcagagaca gcaactagca gtctgggaac actgggttgg agctatcagg   1200
cctgcacaga agtagtcatg ccctttttgta ctaatggtgt cgatgacatg tttgaacctc   1260
actcatggaa cttaaaggaa ctttctgatg actgttttca acagtggggt gtgagaccaa   1320
ggccctcctg gatcactact atgtatggag gcaaaaacat tagttcacac acaaacattg   1380
ttttcagcaa tggtgaacta gacccctggt caggaggtgg agtaactaag gatatcacag   1440
acactctggt tgcagtcacc atctcagagg gggcccacca cttagatctc cgcaccaaga   1500
atgccttgga tcctatgtct gtgctgttag cccgctcctt ggaagttaga catatgaaga   1560
attggatcag agatttctat gacagtgcgg gaaagcagca ctgagaaact tttgattgtt   1620
ttcaatttct tcttttatgt tcacaccacc acattcccat tcactttgat tttctacatg   1680
taattacctt cttttgttta tcattagatt tgatggggcc aaagttgaga tagaatagag   1740
ggtgatgacg gtaagagcaa gtgtcccatg aatgtgattt cctgggttct cactgtcttt   1800
gcaccacgtc taggaagaat cttcttgata gctctcccac accatcagtg gccctcataa   1860
ctggagtaga gttcctggtt gcttttcata agagggagag ttactttctt tgtatctctg   1920
caagcagaga tttctctttg gttttgaggt tgaagtgtct ttggcccatt tgtaagtccc   1980
catccctacc ctacacaaag taaaagcaga agatagataa aaaatgatgt aattgcagct   2040
ggtaggatgt ctggtgccaa tccaggaagt gagagccatt tcttttgtac cggatttaat   2100
gactttgaac tgtgctgtaa ataaataata cagctggacc ttaaaaaaaa aaaaaaaaaa   2160
a                                                                   2161
```

<210> SEQ ID NO 42
<211> LENGTH: 6104
<212> TYPE: DNA
<213> ORGANISM: Homo sapiens

<400> SEQUENCE: 42

```
agaagcgccc ggagcccgcg gggcgacgtc acccccggct ccgcccccgt ccctccccga     60

gcaaagtaac tcttgactaa caggagcagc ctccgccgag catggagagc tgccgccgcg    120

gccggccggc gacgctggcg acgctttcgc ccctgaggta gtttggcgac cgcgaagaag    180

gaaaaagggc gggcgggcgg ctgtcctctc accgtcctca ccccgcgagg cccggcccgc    240

tcctccgtcg tggatttcgc ggcgatcccc ccggcagctc tttgcaaagc tgcttgaaac    300

ttctcccaaa ctcggcatgg atacgactgc ggcggcggcg ctgcctgctt ttgtggcgct    360

cttgctcctc tctccttggc ctctcctggg atcggcccaa ggccagttct ccgcaggtgg    420

ctgtactttt gatgatggtc caggggcctg tgattaccac caggatctgt atgatgactt    480

tgaatgggtg catgttagtg ctcaagagcc tcattatcta ccacccgaga tgccccaagg    540

ttcctatatg atagtggact cttcagatca cgaccctgga gaaaaagcca gacttcagct    600

gcctacaatg aaggagaacg acactcactg cattgatttc agttacctat tatatagcca    660

gaaaggactg aatcctggca ctttgaacat attagttagg gtgaataaag gacctcttgc    720

caatccaatt tggaatgtga ctggattcac gggtagagat tggcttcggg ctgagctagc    780

agtgagcacc ttttggccca atgaatatca ggtaatattt gaagctgaag tctcaggagg    840

gagaagtggt tatattgcca ttgatgacat ccaagtactg agttatcctt gtgataaatc    900

tcctcatttc ctccgtctag gggatgtaga ggtgaatgca gggcaaaacg ctacatttca    960

gtgcattgcc acagggagag atgctgtgca taacaagtta tggctccaga gacgaaatgg   1020

agaagatata ccagtagccc agactaagaa catcaatcat agaaggtttg ccgcttcctt   1080

cagattgcaa gaagtgacaa aaactgacca ggatttgtat cgctgtgtaa ctcagtcaga   1140

acgaggttcc ggtgtgtcca attttgctca acttattgtg agagaaccgc caagacccat   1200

tgctcctcct cagcttcttg gtgttgggcc tacatatttg ctgatccaac taaatgccaa   1260

ctcgatcatt ggcgatggtc ctatcatcct gaaagaagta gagtaccgaa tgacatcagg   1320

atcctggaca gaaacccatg cagtcaatgc tccaacttac aaattatggc atttagatcc   1380

agataccgaa tatgagatcc gagttctact tacaagacct ggtgaaggtg gaacggggct   1440

cccaggacct ccactaatca ccagaacaaa atgtgcagaa cctatgagaa ccccaaagac   1500

attaaagatt gctgaaatac aggcaagacg gattgctgtg gactgggaat ccttgggtta   1560

caacattacg cgttgccaca cttttaatgt cactatctgc taccattact tccgtggtca   1620

caacgagagc aaggcagact gtttggacat ggaccccaaa gcccctcagc atgttgtgaa   1680

ccatctgcca ccttatacaa atgtcagcct caagatgatc ctaaccaatc cagagggaag   1740

gaaggagagt gaagagacaa ttattcaaac tgatgaagat gtgcctggtc ccgtaccagt   1800

aaaatctctt caaggaacat cctttgaaaa taagatcttc ttgaactgga aagaaccttt   1860

ggatccaaat ggaatcatca ctcaatatga gatcagctat agcagtataa gatcatttga   1920

tcctgcagtt ccagtggctg gacctcccca gactgtatca aatttatgga acagtacaca   1980

ccatgtcttt atgcatctcc accctggaac cacgtaccag tttttcataa gagccagcac   2040

ggtcaaaggc tttggtccag ccacagccat caatgtcacc accaatatct cagctccaac   2100

tttacctgac tatgaaggag ttgatgcctc tctcaatgaa actgccacca caataactgt   2160

attgttgaga ccagcacaag ccaaaggtgc tcctatcagt gcttatcaga ttgttgtgga   2220

agaactgcac ccacaccgaa ccaagagaga agccggagcc atggaatgct accaggttcc   2280

tgtcacatac caaaatgcca tgagtggggg tgcaccgtat tactttgctg cagaactccc   2340

cccgggaaac ctacctgagc ctgccccgtt cactgtgggt gacaatcgga cctaccaagg   2400
```

```
cttttggaac cctcctttgg ctccgcgcaa aggatacaac atctatttcc aggcgatgag   2460
cagtgtggag aaggaaacta aaacccagtg cgtacgcatt gctacaaaag cagcagcaac   2520
agaagaacca gaagtgatcc cagatcccgc caagcagaca gacagagtgg tgaaaatagc   2580
aggaattagt gctggaattt tggtgttcat cctccttctc ctagttgtca tattaattgt   2640
aaaaaagagc aaacttgcta aaaaacgcaa agatgccatg ggaataccc ggcaggagat   2700
gactcacatg gtgaatgcaa tggatcgaag ttatgctgat cagagcactc tgcatgcaga   2760
agatcctctt tccatcacct tcatggacca acataacttt agtccaagat atgagaacca   2820
cagtgctaca gcagagtcca gtcgccttct agacgtacct cgctacctct gtgaggggac   2880
ggaatcccct taccagacag gacagctgca tccagccatc agggtagctg atttactgca   2940
gcacattaat ctcatgaaga catcagacag ctatgggttc aaagaggaat atgagagctt   3000
ttttgaagga cagtcagcat cttgggatgt agctaaaaaa gatcaaaata gagcaaaaaa   3060
ccgatatgga aacattatag catatgatca ctccagagtg attttgcaac ccgtagagga   3120
tgatccttcc tcagattata ttaatgccaa ctatattgat ggctaccaga gaccaagtca   3180
ttacattgca acccaaggtc ccgttcatga aacagtgtat gatttctgga ggatgatttg   3240
gcaagaacaa tctgcttgca ttgtgatggt tacaaattta gttgaggttg gccgggttaa   3300
atgctataaa tattggcctg atgatactga agtttatggt gacttcaaag taacgtgtgt   3360
agaaatggaa ccacttgctg aatatgtagt taggacattc accctggaaa ggagggggta   3420
caatgaaatc cgtgaagtta aacagttcca tttcacgggc tggcctgacc atggagtgcc   3480
ctaccatgct acagggctgc tttcctttat ccggcgagtc aagttatcaa accctcccag   3540
tgctggcccc atcgttgtac attgcagtgc tggtgctgga cgaactggct gctacattgt   3600
gattgacatc atgctagaca tggctgaaag agagggtgtt gttgatattt acaattgtgt   3660
caaagcctta agatctcggc gtattaatat ggtccagaca gaggaacagt acattttttat   3720
tcatgatgcc attttagaag cctgcttatg tggagaaact gccatacctg tctgtgaatt   3780
taaagctgca tattttgata tgattagaat agactcccag actaactctt cacatctcaa   3840
ggatgaattt cagactctga attcagtcac ccctcgacta caagctgaag actgcagtat   3900
agcgtgcctg ccaaggaacc atgacaagaa ccgtttcatg gacatgctgc cacctgacag   3960
atgtctgcct tttttaatta caattgatgg ggagagcagt aactacatca atgctgctct   4020
tatggacagc tacaggcaac cagctgcttt catcgtcaca caataccctc tgccaaacac   4080
tgtaaaagac ttctggagat tagtgtatga ttatggctgt acctccattg tgatgttaaa   4140
cgaagtcgac ttgtcccagg gctgccctca gtactggcca gaggaaggga tgctacgata   4200
tggccccatc caagtggaat gtatgtcttg ttcaatggac tgtgatgtga tcaaccggat   4260
ttttaggata tgcaatctaa caagaccaca ggaaggttat ctgatggtgc aacagtttca   4320
gtacctagga tgggcttctc atcgagaagt gcctggatcc aaaaggtcat tcttgaaact   4380
gatacttcag gtggaaaagt ggcaggagga atgcgaggaa ggggaaggcc ggacgattat   4440
ccactgccta aatggtggcg ggcgaagtgg catgttctgt gctataggca tcgttgttga   4500
aatggtgaaa cggcaaaatg ttgtcgatgt tttccatgca gtaaagacac tgaggaacag   4560
caagccaaac atggtggaag ccccggagca ataccgtttc tgctatgatg tagctttgga   4620
gtacctggaa tcatcttagt tgggtgagac tctttaaagt gcatccatga agaaacctgt   4680
ccatctattg agccagcagc tgttgtacct gttacacttg tgcagaaaga ttttaatgtg   4740
```

```
gggggtggga gacttttaca tttgagaggt aaaagtattt tttttatgaa gttgtgtatc   4800
ttaataaaaa ggactgaatt agtttttatt actatattaa agcatcaaca tttcatgcca   4860
cataaattat atttaataag aaccagattg aaatgagaac gtattggtgt ttgtacagtg   4920
aacatgccac ctttttttctc atggtttcag tagagcagct accacatgtt gcatgagttc  4980
atactttcta cgtggcattt ttctcccttt ctaaaatgaa agctgatgaa tcttaaaagg   5040
aagaagaaaa gaaaagctgt gcaaattcat agtaaagttc gtttttttata tgtttccagt  5100
gtagcagatc tctatataaa tatataaata tatataactg gcttattttc ttttaatgtg   5160
caatgatggc tggatcattt aaagttcttt ttagaaaata acataagcca aagactcaag   5220
tgtaaatatg tctatatgga gaaagcacat tatatttatt ggttacttac attccttttt   5280
tgatggctaa aatactacca ccacacaatc atcttttttt tcctgaagaa agctttttct   5340
ttagctaaaa tcaattgtaa acgatttttg tagattattt tttgtatgtt ttagtgtaag   5400
tagaagataa actttttatt cataaaccag gaagcaatgt tctttatagt gattctcttg   5460
tgtacatgct tgtgaattaa atttgtgtaa aatcccttgg caattgggtc ttttaatata   5520
ggaccaaatt aaaacatttt gctgaatatg tatagttttt cacaatttca ttaggtaaat   5580
aatggtttgg tgatcataca tgagaaatgt acacattaaa aggccttgct gacaacttgc   5640
acaatgttga acatagcctt taagcatcat ttaaatttta aaggaatgga gtttttcagc   5700
ctgtggccca gcactggtca agaaaacaag atggcaacat atatgctttc agggtcaaat   5760
ttgagcaaac tgtaaactgt cagggtgata aaatgtttct cttgatgttt acatgcacaa   5820
gctttgcgtt ctgactataa aaagtgtgaa caaatcaatg ccagattcct gttttgcgca   5880
ttgtcatggg attcttaagt gaacctttct aaatgtggtc ttgttcacat gctccacgta   5940
gctgtaactt cacatcatca gcttgcagtt tgtaattgac taaagcattc cagtgtcctc   6000
tttctagatt gccagctcat gacatggtgc ttataaagat ttaattaaag taagaatgaa   6060
ataaagtttt tataattata acagttaaaa aaaaaaaaaa aaaa                     6104
```

<210> SEQ ID NO 43
<211> LENGTH: 5841
<212> TYPE: DNA
<213> ORGANISM: Homo sapiens

<400> SEQUENCE: 43

```
ctccgcaccc ccccctgccc ccccaccgtt cgccgctgca ggcggtcggc cgccgcgatg     60
aaggcgagct cgggggatca ggggagcccc ccgtgcttcc tgcgcttccc gcggcctgtg    120
cgggtggtaa gtggcgccga ggccgagctc aagtgcgtgg tcctggggga gccgccgcct    180
gtagtggtgt gggagaaggg cggcagcag ctggcggcct cggaacgcct gagcttcccg     240
gcggacggcg cggagcacgg cctgctgctg accgccgcac tgcccaccga cgcgggggtc    300
tacgtgtgcc gcgcccgcaa cgcggccggc gaggcctacg cggcggccgc cgtcaccgtg    360
ctggagccgc cggcctccga ccccgagctg cagcccgccg agcgcccgct gccatcgccg    420
gggtccgggg agggcgcccc ggtcttcctc acggggcctc gatcccagtg ggtgctgcgg    480
ggggcggagg tggtgctgac gtgccgggcg gggggcctcc ccgagcccac actgtactgg    540
gagaaggacg ggatggccct ggacgaagtg tgggacagca gccacttcgc gctccagccg    600
ggccgcgccg aggacggccc cggcgcgagc ctggcactgc gcatcctggc ggctcggctg    660
ccggattccg gcgtctacgt gtgccacgcc cgcaacgcgc acggccacgc gcaggcgggg    720
gcgctgctcc aggtgcacca gcccccccgag agcccgcccg cggaccccga cgaggccccc   780
```

```
gcgccggtgg tggagccgct caagtgcgcg cctaagacct tctgggtgaa cgagggcaag    840
cacgccaagt tccgctgcta cgtgatgggc aagcccgagc ccgagatcga atggcactgg    900
gagggccgcc cgctgctccc ggaccgccgc cgcctcatgt accgcgaccg cgacggcggc    960
ttcgtgctca aggtgcttta ctgccaggcc aaggatcgtg ggctctacgt ctgcgccgcg   1020
cgcaactcgg cgggccagac gctcagtgcc gtgcagctgc acgtgaaaga gccccgcctc   1080
cggttcacac ggcccctgca ggacgtggag ggccgtgagc acgggattgc cgtgctggaa   1140
tgtaaagtac ccaactcccg catccccacg gcctggttcc gtgaggacca gcggctgctg   1200
ccctgccgca agtacgagca gatcgaagag ggcactgtcc ggcgcctcat catccacagg   1260
ctgaaggcag acgatgatgg tatctacctg tgcgagatgc ggggccgggt gcgcaccgtg   1320
gccaacgtca cagtcaaagg gcccatcctg aagcgcctgc cccggaagct cgacgtcctg   1380
gaaggagaga atgctgtgct gctagtggaa actctagagg ccggggtcga gggacgctgg   1440
agccgtgatg gggaggagct gccggtcatc tgccagagca gctcaggcca catgcatgcc   1500
ctggtccttc caggggtcac ccgagaggat gctggcgagg tcacctttag cctgggcaac   1560
tcccgtacca ctacgcttct cagagtaaaa tgtgtcaagc acagtccccc aggacccccc   1620
atattggcag agatgttcaa gggccacaag aacacggtcc tgttgacctg gaagcctccc   1680
gagccagctc ccgagacccc attcatctac cggctggagc ggcaggaagt gggctctgaa   1740
gactggattc agtgcttcag catcgagaaa gccggagccg tggaggtgcc gggcgactgt   1800
gtgccctccg agggtgacta ccgcttccgc atctgcacag tcagcggaca tggccgtagt   1860
ccccacgtgg tgttccacgg ttctgctcac cttgtgccca cagctcgcct ggtggcaggt   1920
ctggaggatg tgcaggtata cgacggggaa gatgccgtct tctccctcga tctctccacc   1980
atcatccagg gtacctggtt ccttaatggg gaagagctca agagtaacga gccggagggc   2040
caggtggaac ctggggccct gcggtaccgt atagagcaga agggtctgca gcacagactc   2100
atcctgcatg ccgtcaagca ccaggacagc ggtgccctgg tcggcttcag ctgccccggc   2160
gtgcaggact cagctgccct cacaatccaa gagagcccgg tgcacatcct gagcccccag   2220
gacagggtgt cgttgacctt cacaacctca gagcgggtgg tgctgacttg tgagctctca   2280
agggtggact tcccggcaac ctggtacaag gatgggcaga aggtggagga gagcgagttg   2340
ctggtggtga agatggatgg gcgcaaacac cgtctgatcc tgcctgaggc caaagtccag   2400
gacagtggcg agtttgagtg caggacagaa ggggtctcgg ccttcttcgg cgtcactgtc   2460
caagatcctc ccgtgcacat cgtggacccc cgagaacatg tgttcgtgca tgccataact   2520
tccgagtgtg tcatgctggc ctgtgaggtg gaccgagagg acgcccctgt gcgttggtac   2580
aaggacgggc aggaggtgga ggagagtgac ttcgtggtgc tggagaatga ggggccccat   2640
cgccgcctgg tgctgcccgc cacccagccc tcagacgggg gcgagtttca gtgcgtcgct   2700
ggagatgagt gtgcctactt cactgtcacc atcacagacg tctcctcgtg gatcgtgtat   2760
cccagcggca aggtgtatgt ggcagccgtg cgcctggagc gtgtggtgct gacctgtgag   2820
ctatgccggc cctgggcaga ggtgcgctgg accaaggatg gagaggaggt ggtggagagc   2880
cccgcgctgc tcctgcagaa ggaagacact gtccgccgcc tggtgctgcc cgctgtccag   2940
ctcgaggact ccggcgagta cttgtgtgaa attgacgatg agtcggcctc cttcactgtc   3000
accgtcacag aacccccagt gcggatcata taccctcgcg atgaggtgac cttgatcgcc   3060
gtgaccttgg agtgtgtggt gctgatgtgt gaactgtctc gggaggatgc ccctgtgcgc   3120
```

```
tggtacaagg atgggctgga agtggaggag agcgaggccc tggtgctgga gagggatggg   3180
ccacgctgcc gcctggtgct acctgctgct cagcccgagg acgggggcga gtttgtatgt   3240
gatgctggag atgactcggc cttcttcact gtcactgtca cagccccacc agagaggatt   3300
gtgcacccgg cagcccgctc cctggatctg cattttgggg ctccagggcg cgtggagctg   3360
cgctgtgagg tggccccagc tgggtctcag gtgcgctggt acaaggacgg gctggaagtg   3420
gaggcatcag atgccctgca gctgggtgcc gaggggccca cccgcaccct gaccctgccc   3480
cacgcccagc ctgaggacgc cggggagtat gtgtgtgaga cccggcatga ggccatcacc   3540
ttcaatgtca tcctggctga gcctccagtg cagttccttg ctctagagac aactccaagc   3600
ccgctctgtg tggcccctgg ggagccagtg gtgctgagct gtgaactgtc ccgggctggc   3660
gcccccgtgg tctggagcca caatgggagg cccgtgcagg agggcgaggg cctagagctc   3720
catgccgagg gcccccgccg agtcctctgc atccaggctg caggcccagc ccatgcaggg   3780
ctctacacct gccagtctgg agcagccccc ggagccccaa gcctcagctt caccgtccag   3840
gtggctgagc cccctgtgcg ggtggtagct cccgaggcag cccagacgag ggttcggagc   3900
accccaggcg gggacctaga gctggtggtg cacctctccg ggccaggggg ccctgtacgc   3960
tggtacaagg acggggagcg actggcaagc caggggcggg tgcagctgga gcaggccggg   4020
gccaggcagg tgctgcgggt gcagggggca cggagcgggg acgctgggga gtacctgtgc   4080
gatgcgcccc aggacagccg catcttcctt gtcagcgtgg aagagccact gctggtgaag   4140
ctggtctcgg agctgacacc actcactgtc cacgagggcg atgatgccac gttccggtgt   4200
gaagtctccc caccagatgc cgatgtcacc tggctgcgca atggggccgt cgtcactcca   4260
gggccccagg tggagatggc ccagaatggt tcaagccgca tcttaacctt gcgaggctgc   4320
caactggggg atgcagggac cgtgactttg cgggcaggga gcacggccac aagtgcccgg   4380
ctccatgttc gagagacaga gctgctgttc ctacggcggt tgcaggatgt gcgggcagag   4440
gaaggccagg atgtgtgtct cgaagtggag acaggccgag tgggtgcagc gggggccgtg   4500
cgctgggtgc gaggtgggca gcccctgccc cacgactctc gcctgtccat ggcccaggat   4560
gggcacatcc accgcctctt catccatggt gtcatactgg ccgaccaggg cacctacggc   4620
tgcgagagcc accacgatcg caccctggcc aggctcagcg tgaggccgag gcagctgagg   4680
gtgctgcggc ctctggagga cgtgaccatc agtgaggggg gcagtgccac cttccagctg   4740
gagctgtccc aggaaggtgt gaccggggag tgggcccggg gtggagtaca gctgtatcca   4800
ggacccaagt gtcacatcca ctcggacggc caccgtcacc gactggtact caatggcctg   4860
ggcctggccg actcaggctg tgtctccttc acagcggatt ccctgcgctg cgcagccaga   4920
ctcattgtga gagaggtccc agtgaccatc gtgcgggggc cacacgacct agaggtgacc   4980
gagggcgaca cagctacgtt cgagtgcgag ctttcccaag ctttggctga tgttacctgg   5040
gagaaggacg ggaacgcgct tacgcctagc ccgcggctcc ggctccaggc cctcggcacg   5100
cgccgccttc tccagctgcg acgctgcggc ccctcggacg ccgggaccta cagctgcgcg   5160
gtggggacgg cccgcgccgg accggtccgc ctgaccgtgc gcgagcgtac tgtggcggta   5220
ctctccgagc tgcggtcggt gagcgcccgc gaaggcgacg gcgctacgtt cgagtgcacc   5280
gtgtcggagg tcgagaccac ggggcgctgg gagctcggag gccgcccgct gagacccgga   5340
gcccgcgtcc gcatccgaca ggaagggaag aaacacattc tggtgcttag cgagctgcgc   5400
gccgaggacg ccggtgaagt ccgcttccag gcggggcccg cccagtccct ggctctactg   5460
gaagtggagg cattgcctct ccagatgtgc cgccaccccc ctcgcgagaa gaccgttctg   5520
```

```
gtgggccgcc gggcggtgct ggaggtgact gtgtcccgct cggggggcca cgtgtgctgg   5580

ctgcgggagg gggccgagct gtgcccggga gataagtatg agatgcgcag ccacggcccc   5640

acccacagcc tggtcatcca tgacgttcga cctgaggacc aaggcactta ctgctgccag   5700

gccggccagg acagcaccca cacacggctg ctggtagagg gcaactagga gaacctaacc   5760

aggccaggcg ggtgcccttg gacagcttgg aaggcgtttg cccttaccct gggcaggggt   5820

agagagacaa ggaacaataa a                                             5841
```

<210> SEQ ID NO 44
<211> LENGTH: 4540
<212> TYPE: DNA
<213> ORGANISM: Homo sapiens

<400> SEQUENCE: 44

```
aggagacgcg tagccgccgt cgccgccgcc gggggatgtg gccggcgcct gcctctagcc     60

gcgccgcctc ttgagtacca gccgccgctg cagccgccgc cgccgcctag ccgtgcggtg    120

ccaggccgcg ccctccccgg gcgcccgccg gctcgcatgc cgaggggctc cggggcgtag    180

ctgcgcgccc ggcgccgcct ccgggctcct tcggccccgc catgggctgc tgcagctccg    240

cctcctccgc cgcgcagagc tccaaacgag aatggaagcc gctggaggac cgtagctgca    300

cagacatacc atggctgctg ctcttcatcc tcttctgcat tgggatggga tttatttgtg    360

gcttttcaat agcaacaggt gcagcagcaa gactagtgtc aggatacgac agctatggaa    420

atatctgtgg gcagaaaaat acaaagttgg aagcaatacc aaacagtggc atggaccaca    480

cccagcggaa gtatgtattc tttttggatc catgcaacct ggacttgata aaccggaaga    540

ttaagtctgt agcactgtgt gtagcagcgt gtccaaggca agaactgaaa actctgagtg    600

atgttcagaa gtttgcagag ataaatggtt cagccctatg tagctacaac ctaaagcctt    660

ctgaatacac tacatctcca aaatcttctg ttctctgccc caaactacca gttccagcga    720

gtgcacctat tccattcttc catcgctgtg ctcctgtgaa catttcctgc tatgccaagt    780

ttgcagaggc cctgatcacc tttgtcagtg acaatagtgt cttacacagg ctgattagtg    840

gagtaatgac cagcaaagaa attatattgg gactttgctt gttatcacta gttctatcca    900

tgattttgat ggtgataatc aggtatatat caagagtact tgtgtggatc ttaacgattc    960

tggtcatact cggttcactt ggaggcacag gtgtactatg gtggctgtat gcaaagcaaa   1020

gaaggtctcc caaagaaact gttactcctg agcagcttca gatagctgaa gacaatcttc   1080

gggccctcct catttatgcc atttcagcta cagtgttcac agtgatctta ttcctgataa   1140

tgttggttat gcgcaaacgt gttgctctta ccatcgcctt gttccacgta gctggcaagg   1200

tcttcattca cttgccactg ctagtcttcc aacccttctg gactttcttt gctcttgtct   1260

tgttttgggt gtactggatc atgacacttc tttttcttgg cactaccggc agtcctgttc   1320

agaatgagca aggctttgtg gagttcaaaa tttctgggcc tctgcagtac atgtggtggt   1380

accatgtggt gggcctgatt tggatcagtg aatttattct agcatgtcag cagatgacag   1440

tggcaggagc tgtggtaaca tactatttta ctagggataa aaggaatttg ccatttacac   1500

ctattttggc atcagtaaat cgccttattc gttaccacct aggtacggtg gcaaaaggat   1560

ctttcattat cacattagtc aaaattccgc gaatgatcct tatgtatatt cacagtcagc   1620

tcaaaggaaa ggaaaatgct tgtgcacgat gtgtgctgaa atcttgcatt tgttgccttt   1680

ggtgtcttga aaagtgccta aattatttaa atcagaatgc atacacagcc acagctatca   1740
```

```
acagcaccaa cttctgcacc tcagcaaagg atgcctttgt cattctggtg gagaatgctt   1800
tgcgagtggc taccatcaac acagtaggag attttatgtt attccttggc aaggtgctga   1860
tagtctgcag cacaggttta gctgggatta tgctgctcaa ctaccagcag gactacacag   1920
tatgggtgct gcctctgatc atcgtctgcc tctttgcttt cctagtcgct cattgcttcc   1980
tgtctattta tgaaatggta gtggatgtat tattcttgtg ttttgccatt gatacaaaat   2040
acaatgatgg gagccctggc agagaattct atatggataa agtgctgatg gagtttgtgg   2100
aaaacagtag gaaagcaatg aaagaagctg gtaagggagg cgtcgctgat tccagagagc   2160
taaagccgat ggcttcggga gcaagttctg cttgaaccta gccgacggtt atggaaaccc   2220
attgacattc caaaacaata tatacacata actatgtatt tgtgtgtgtg ggtgtgtgta   2280
tatatgtata tgtatgtgtg tatatatgta tatgtatata cacacacaca cataaatcag   2340
ccaaaatcag agaaaaggaa cagggattta ataccttttt tatgcttatt tttgtcaaac   2400
atgtactcct ttcatacggg tggcttttac aaggcaactt ccgtcattta atgttttcaa   2460
ctgtaattgt cttaatggaa atgttaaaat tcatatctga ttaacatttt taataactta   2520
gaggagattt taactttatt taaaaatagg taaaattatt gtacctaatt atgtctaaag   2580
tttattcagg ggtaatttcc ctgatgtctg tataaaatca agatcttatt ttactgatgc   2640
ataagtccta gtgggtcaag actaggcata tgctttcaga taaataagga attactccaa   2700
tcagttttcc ccaatcaaag aagccatgtc attttacttt tagaaacata caattgggcc   2760
caatatggga attttcataa tagttcatac atttgtcagc caacattaaa aggtaaccaa   2820
ctcctcaggt atttgtagtt taccctaacg cttctttaaa agaaagtagg taaaaaaaga   2880
aaagggtaga taatctttcg tatgcaaact tttcccttat attttgtctt tctttccttt   2940
ttgactttag tagcatcctc cacacatttg tgtgcctgat ttgaaaggaa gctggggcac   3000
ccagcgagtt tagcctttaa gtttctgtgt attgatttgc agattaagta atgctgggag   3060
gaataaagaa gggacagaaa catggaacat aaagcattga aaattccggt gcttgggctt   3120
cggcttcaga gtaacgtcag tggcttaggg ttaaacggcc attttattca aatgcttgct   3180
atacaatctg aaaacacact ggcaggtgct cctctccttg gcaattcatt gagtatccag   3240
agttctacga tgtttaactg aagaattggc taatgttttg atcctccagt gtgactgttg   3300
tttttgtttg ggggtgggtt tggggttttt tgctttttta ttcctgaagc ttaccagata   3360
tgaatggcta atactccatt gttctgcttg ttgtaatggt gaatgcttta agaaaaaaaa   3420
gtgtaatttg ctaagaataa ttcatgatct gtttatgcga taactccttt ttgttacaat   3480
tttttaaaa aaagctattt ttgttaatgt aaagtaaata tttcagagca aattttttaa   3540
acttattgca ctaaatacag gctctgtaca aaaaaaaaaa aaaaaaaaaa gcctcagcat   3600
tttatcattc catggaagga gaatcttttg aaagaaagca ttgcctccta ccagaactag   3660
acagtgaatt agatcggtat tatggaaatg catacaagta atgtcactag ggcttaataa   3720
gcagccgttt gctaatgtgc ttcctttcaa agggttggac ctttaaattg ctgcaaaagg   3780
taaattgtat tttttttaa gtattggtgt tctttactct agctaggcta aaatttgcta   3840
aatgccttgg tttcttttaa aagttcatgt aatatttctg atttttcaga atatttgcaa   3900
taagagtctg gattttaaaa aacacatgca tacacacaat taagagctca tgtcttagca   3960
agatctggga aaccaacatt gcgagagtag ctattttgaa agaataattc tccagaagtt   4020
aacatctaat atctagtatc accaaacagt atcgctgttc tcttttattc atttgaaatg   4080
aatataatta tataactaac aattgtccaa atagatgaga gagcaaatca tgtgagaaaa   4140
```

ttcagaatac catctgtttc atagccgcac agattttgga ctttcacaaa cattgggaac 4200
taaatttaga attggcaaaa gtctagaaga tgggtatcaa aacagaagac attccaggag 4260
ctagcaattt taagaggtgt ccctccaaag tgacctgatg gaagtcctga acttggaaat 4320
taggttctac tcacttggac atccctgcat catggactgt tgctgctccc tgttccatat 4380
gctcgcaatc tcagctattt ggaagctacc aggaatgctt tctaattatc atttgcaact 4440
agaactgtaa tcagaaagaa attttgtatt tttgtataac ttgattgtgt gccattttat 4500
ataacaggtc ctgttttaca aataaatttt gttttactaa 4540

<210> SEQ ID NO 45
<211> LENGTH: 660
<212> TYPE: DNA
<213> ORGANISM: Homo sapiens

<400> SEQUENCE: 45
actataaaga cagtaaaaag atcagtggtt atctttgcag atgccaccat cactgtgagc 60
cctgtactat cagccatggt caactccgtc gtctttttttg acatcaccgt cgacggcaag 120
cccttgggcc gcatctccat caaactgttt gcagacaaga ttctaaagac agcggaaaac 180
tttcgtgctc tgagcactgg agagaaagga tttcgttata agggttcctg ctttcacaga 240
attattccag ggtttatgtg tcagggtggt gacttcacac gccataatgg cactggtgac 300
aagtccatct atggggagaa atttgatgat gagaacctca tccgaaagca tacaggttct 360
ggcatcttgt ccatggcaaa tgctggaccc aacacaaatg gttcccagtt tttcatctgt 420
gctgccaaga ctgagtggtt ggatggcaag catgtggcct ttggcaaggt gaaagaacgt 480
gtgaatattg tggaagccat ggagcacttt gggtacagga atagcaagac cagcaagaag 540
atcaccattg ctgactgtgg acaattctaa tgagtttgac ttgtgtttta ttttcaccac 600
cagacccatt ccttctgtag ctcaggagag caccccctcca ccacatttgc ttgcaatatc 660

<210> SEQ ID NO 46
<211> LENGTH: 3181
<212> TYPE: DNA
<213> ORGANISM: Homo sapiens

<400> SEQUENCE: 46
aaacgcgcac gcgcaaatct agggcgacgc ttgacagagc ttgggagggt gcgcctgctt 60
tcgccctcct tctccagcgg gaggggcgcg cacttccgcg gggcggagtc cgtctagtgc 120
tgacgttggc agccgaaccc aaagtagatc gaggcggcgg gctgcacatt cccgttgttg 180
cgttgcgttt ccttcctctt tcactccgcg ctcacggcgg cggccaaagc ggcggcgacg 240
gcggcgcgag aacgacccgg cggccagttc tcttcctcct gcgcacctgc cccgctcggt 300
cagtcagtcg gcggccggcg cccggcttgt gctcagacct cgcgcttgcg gcgcccaggc 360
ccagcggccg tagctagcgt ctggcctgag aacctcggcg ctccggcggc gcgggcacca 420
cgagccgagc ctcgcagcgg ctccagagga ggcaggcgag tgagcgagtc cgaggggtgg 480
ccggggcagg tggtggcgcc gcgaagatgg tcgccaagca aaggatccgt atggccaacg 540
agaagcacag caagaacatc acccagcgcg gcaacgtcgc caagacctcg agaaatgccc 600
ccgaagagaa ggcgtctgta ggaccctggt tattggctct cttcattttt gttgtctgtg 660
gttctgcaat tttccagatt attcaaagta tcaggatggg catgtgaagt gactgacctt 720
aagatgtttc cattctcctg tgaattttaa cttgaactca ttcctgatgt ttgataccct 780

-continued ggttgaaaac aattcagtaa agcatcctgc ctcagaatga ctttcctatc atgcttcatg 840
tgtcattcca aggtttcttc atgagtcatt ccaagttttc tagtccatac cacagtgcct 900
tgcaaaaaac accacatgaa taaagcaata aaatttgatt gttaagatac agtagtggac 960
cctacttatt cagtcaatta agagtaagtt tttttatgtg gttattaaaa cagtatgaac 1020
aattagtcta actctgcata gacagggtct agattttgtt aacccaaatg tataactgca 1080
gttagcttaa attacaattt gaagtcttgt ggtttttata tagctaggca ctttattact 1140
cttttgaact gaaagcacac tcccttatag gttcatgtaa ctgtcctgta ataaggtgct 1200
tataaatgga acaactacac agcctagttt tgccacaacc tttagcatct aaaaagtttt 1260
aaaagcttct aaatgtctaa tataaaggga gatgcttata gccacaacat ctattttacc 1320
aatattgttt ccattacact accttggatt ttgcatgagt gagtatagta acccaagatg 1380
ccataaaaaa aaaacttgat cgttttctga cttaatcagt tactgtggtt tcactaaaag 1440
ctaccgtggt ggagtgaagt cagtcaggga aggtttgttt atgttacatt tatttcacca 1500
gaactatttt aatatatcaa aggggtttac tatgccaaac aaaattctag ggaaaaatac 1560
tgctaaaaat ggatgcctca tcagaacatg ctgttgagtc caatgtgcca taagacattt 1620
tagcatgtta aatagcactt ttaatagcaa aaaaaggcac atcaactgcg aagttatcct 1680
tagtttgcaa atgctttttc tagattaatg atttttcaat cattagggta ctagacacat 1740
cagcctaaag tggcatctgg aattgaatgg atttactgat aatgatcagt ctttagtctt 1800
ccctttgtta tatgacttta taggttatga ttgatcaaat ttacgtttta ctaatggtaa 1860
gggtgagggt catagggcag gttttgggtt ttctagtact gttgaaaact gcaagtattg 1920
gctatttgta tacttagcca taacttggtg aaaaaaaacc tgagcagtgt ctatgtatta 1980
atgcgttgga aagaaagctg cttgtgtttg ctttgttaat tgcctcagga tatttctttt 2040
aaaataagct gttttaagag gaacagaagg gaaatctgct acctagtcta tacacagcgt 2100
gaacctcaca gggggcttct gataccctca aacatggaga acagtaaggg agcagagtgg 2160
ttaaggactt tcaggaactt aactattctg gaataaggaa tgaatcaact gaccttgggc 2220
cagcaggttt ttaactaaat tgttacttgc ctttctcacc cagttaatca gtctctgtac 2280
ttgtttccct ttttgaaaca agtgtcttgg ttaactaatt ctgttttatg gttgtgctaa 2340
attcatagca ggtgccttat tctttgcttt tagtcaaacc attccatatc agaattttcc 2400
ttggtttact atagatattt ggctttaagt tgttgtttgt gttttttaat gtacaatgtt 2460
ctgataaatt tgactgttaa attgctatag ctagcaatca ttttacatat gtaaaattgc 2520
attccctttg tatttcatgt gtaattcacc aattaagtgc agtttatatt caggttggat 2580
tatgcatgtt taggtaaacg aaagctgtgt cttacttgat ttattcttta aaaataaagt 2640
tccctgaata tttgatgctt ttcttctaaa cggaaatgat tttacagtta tctgagtgta 2700
ccttttatag ttagtagaaa atgattttaa agaatgttta gtattgtact taaatggtat 2760
gcagaggcac agatgtaagg tttataactg gaaataggtg gtaagaaaaa tatatagaaa 2820
gcacaatgat ttgaatattt ttccacttag gatttcctaa tctccttgtc atccaattca 2880
agctcaagat gaagcacaat tctttgatct ccctttgcca gttgaatttt atagatcatc 2940
taatgttgag cacagtatga gaataaatat tggggttgtc aacattactc agttactctt 3000
tgtggtttaa ctctaacatt tcaacaagtt gtcaattaat tgtatctgtt gggttgtata 3060
taatgttgct caaaataatt aagtggactt ccaaaaataa gatttccatt gtaacaggat 3120
gcattgtgat gggctttgac ttacattaaa gaaatgtgga tagtcaactg caaaaaaaaa 3180
a 3181

<210> SEQ ID NO 47
<211> LENGTH: 988
<212> TYPE: DNA
<213> ORGANISM: Homo sapiens

<400> SEQUENCE: 47
cgtttctctc cctgctttcc tctgccgcat ggtcctgggc cgttggcgtc ggaagcctga 60
agcatgggcg ctgagtggga gctgggggcc gaggctggcg gttcgctgct gctgtgcgcc 120
gcgctgctgg cggcgggctg cgccctgggc ctgcgcctgg gccgcgggca gggggcggcg 180
gaccgcgggg cgctcatctg gctctgctac gacgcgctgg tgcacttcgc gctggaaggc 240
ccttttgtct acttgtcttt agtaggaaac gttgcaaatt ccgatggctt gattgcttct 300
ttatggaaag aatatggcaa agctgatgca agatgggttt attttgatcc aaccattgtg 360
tctgtggaaa ttctgaccgt cgccctggat gggtctctgg cattgttcct catttatgcc 420
atagtcaaag aaaaatatta ccggcatttc ctgcagatca ccctgtgcgt gtgcgagctg 480
tatggctgct ggatgacctt cctcccagag tggctcacca gaagccccaa cctcaacacc 540
agcaactggc tgtactgttg gctttacctg ttttttttta acggtgtgtg ggttctgatc 600
ccaggactgc tactgtggca gtcatggcta gaactcaaga aaatgcatca gaaagaaacc 660
agttcagtga agaagtttca gtgaactttc aaaaccataa acaccattat ctaacttcat 720
gaaccagaat gaatcaaatc tttttgtttg gccaaaatgt aatacattcc agtctacact 780
ttgtttttgt attgttgctc ctgaacaacc tgtttcaaat tggttttaag gcgaccagtt 840
ttcgttgtat tgttgttcaa ttaaatggtg atatagggaa aagagaacaa atttgaattt 900
gtaataataa aatgtttaat tatacatttt atggctggca ttaattgttc cacattagta 960
aaaccaatta tcttagaaaa aaaaaaaa 988

<210> SEQ ID NO 48
<211> LENGTH: 3284
<212> TYPE: DNA
<213> ORGANISM: Homo sapiens

<400> SEQUENCE: 48
gagcggtgcc gcaccggccg cgggcgcagg gagtattatg ggctgtgggt gccgctgagc 60
aagatggagc tgtctgcagt gggcgagcgg gtcttcgcgg ccgaatccat catcaaacgg 120
cggatccgaa agggacgcat cgagtacctg gtgaaatgga aggggtgggc gatcaagtac 180
agcacttggg agcccgagga gaacatcctg gactcgcggc tcattgcagc cttcgaacaa 240
aaggagaggg agcgtgagct gtatgggccc aagaagaggg gacccaaacc caaaactttc 300
ctcctgaagg cgcgggccca ggccgaggcc ctccgcatca gtgatgtgca tttctctgtc 360
aagccgagcg ccagtgcctc ctcgcccaag ctgcactcca gcgcagccgt gcaccggctc 420
aagaaggaca tccgccgctg ccaccgtatg tcccgccgtc ccctgccccg cccggacccg 480
caggggggca gccccggact gcgcccgccc atttcgccct tctcggagac ggtgcgcatc 540
atcaaccgca aggtgaagcc gcgggagccc aagcggaacc gcatcatcct gaacctgaag 600
gtgatcgaca agggcgctgg cggcgggggc gccgggcagg gggccggggc gctggcccgc 660
cccaaagtcc cctcgcggaa ccgcgttata ggcaagagca agaagttcag cgagagcgtc 720
ctgcgtacac agatccgcca catgaagttc ggcgcctttg cgctgtacaa gcctccgccc 780

```
gccccccctgg tagccccgtc ccccggcaag gctgaggcct cagccccggg ccctgggcta    840

cttctggccg cccccgccgc cccctacgac gcccgcagct ctggctcctc cggctgcccc    900

tcgcctacac cacagtcctc tgaccccgac gacacgcccc ccaagctcct ccccgagacc    960

gtgagcccat ccgcccccag ctggcgcgag ccggaggtgc tcgacctgtc cctccctccc   1020

gagtcggcag ccaccagcaa gcgggcaccg cctgaggtca cagctgctgc cggcccggca   1080

cctcccacgg cccctgagcc cgccggtgcc tcctccgagc ccgaggctgg ggactggcgc   1140

cccgagatgt caccctgctc caatgtggtc gtcaccgatg tcaccagcaa cctcctgacg   1200

gtcacaatca aggaattctg caaccctgag gatttcgaga aggtggctgc tggggtagca   1260

ggcgccgctg gggcggtggc cagcattggg gcgagcaagt gagggggctc caccaaggag   1320

gggggcttgg gggggccctc ctgcccgaag tcatactctt gctcccaccc cacccttgcc   1380

cccagccctc tctccctgtg ctttgcttgt ctcaaatggc tcggtgttga cccagggatg   1440

gggctgggta gttggggtcc cagaaagccg ggggtagggg ccaccctgga atggggcagg   1500

ggaagggcac accccctgcc catgcatggt agcccactgg gtggtttctg gaaagcccta   1560

gaaactaggg ttcctctgcc ccttccacat cccacctgtc tctctagctt gcttcctgct   1620

ctcctgtgcg gcgtctgatt tctcggtgct aacctggcag ctgtggggcc cttaggagcc   1680

ccccaccgag ggtggacaca gtccctttcc ttcctgcaga tgcctaggca ggaggagggc   1740

ttcctgcctg tttggcaaag tcccaggcag aggccaagga tgaggcctga ctcggctcct   1800

ccctccacat cagccagggc atcagaagtt gggccagggc ggggtcttcc ctgctcgatt   1860

ttggacgagg cctaagtaga cccccctatgc cctgccccag ccctggctct ttcctaaccc   1920

cctcaacggt gggaggaact ggcagagggt gcgcctggcc acagcctccc cgcatctaaa   1980

ggccccttca gttcttgacc aaaggtgcta cgagaacctg ccgtggaaac ttccagttgt   2040

gcgtctgccc cactcgctgt gtttgtccgt gggttcatac atgcattggg tgctaggccc   2100

caggctgccg ggtggcaccc tttacagttc ctttgaacag gggcattgaa ggcctggact   2160

gcctctcgcc tcagtaggcc tggggaccag gcttgggtct ggaggtttgc tgtggaagtc   2220

accaggcctc ccctcctggc ccaggtgtgc tgggggcacc gtgccccca cccccctgcc   2280

ctcctcaggg tggtcagccc aacctgtcgg accttcactt cacatcatgg tggggaccga   2340

gatagagagg gagaccccat tccaagctcc ctcttcctcc cggtgtttgg ggaggatgct   2400

gaagaatcca ttcccgaggg cctcccggct tgtcccagcc cctcttttgc ttctgaccac   2460

ggaggctttc tcacagccca gcctgcctga agcaaaggag gctcccgtgt cctgggcagc   2520

ttctgtttcc ctctgctgcc tgggagctga ggcacccgtg ccagtggcag aggccacagc   2580

cccagcctta ggccaggccc tgggagggca ggcaggcaaa ggggagacca gagggtctgt   2640

gttctccagg agaatgaggg tgttggtccc agaattggga ccggggcccc gctggccagc   2700

cctgggccac ttcccgggtc tccattgtgc gtgggtggcg tgttccaggc gtggctggag   2760

ctggcttcct ggctgtgctg ccatgggccc ctccctcaga agcacgttgg caggaggccg   2820

atcagaaccc tagcgccttt ggtcctaaga atgggaggct gccttccttc ccaatctccc   2880

tgccagggcc cacagcgtgg ccctagccct cccctccccg ggatgtagaa cggggaccct   2940

cgcagggttg gggcgggggc tgatactcct cggcccctcc ctaccctgcc ctgtgtgttg   3000

gctttgtggc cgtccaagtg ccaattggct tttcgcccaa ataagggctg gtatttctcc   3060

tctgtccttg gaggtgattt ccccctgacc ccctccccca ggtgagtgac cacctgggtg   3120

ccagttacag gtgtttccag agaccataga aatgtgtttt cctgagagtt cgtgtcattc   3180
```

gtgacttttt tgtaaagaag ttgtgttttc agaggtgatt ttatgacagg aaagtgaaag 3240
aattagtttt gcaaaaaaac aaaaacaaaa aaaaaaaaaa aaaa 3284

<210> SEQ ID NO 49
<211> LENGTH: 1437
<212> TYPE: DNA
<213> ORGANISM: Homo sapiens

<400> SEQUENCE: 49
ccgggacaaa atgtcagcga ggcgcctgga gggggatcta ccatctcgga ctcccgaccc 60
gccgccggct ccggccgcgt ttcccgggta aagggcactg ctgatggttc ttcagaactc 120
aggaatcgtg ttgcatgcat tgtttctacc cacctgagat ggttggaaac cctgaggcaa 180
tgacagggac cccagaatcc ttgggaaatt acccactgtc taatttaaag cgtgcgggcg 240
ccgcagaatg aggagtggcg agccggcctg caccatggac caggcccgcg ggctggacga 300
cgcggcggcg cggggcggtc agtgtccggg actggggccg gcgccgacgc cgacgcctcc 360
cggccgcctg gggcgccat actccgaggc ctggggctac ttccacctgg cgccggggcg 420
ccccgggcat ccgtcgggcc actgggccac ctgccgtctg tgcggggagc aggtgggccg 480
cggcccgggc ttccacgcgg ggacctcggc gttgtggagg cacctgagga gcgcgcaccg 540
gcgggagctg gagagcagcg gcgccgggag ctccccacct gccgcgccct gcccgccgcc 600
gcccggcccc gctgcggccc ccgagggcga ctgggcgcgc ctgctggaac agatgggcgc 660
gctggccgtg cgcggcagcc ggcgggagcg ggagctggag cggcgcgagc tggccgtgga 720
gcagggcgag cgcgccctgg agcggaggcg gagggcgctg caggaggaag agcgcgccgc 780
ggcccaggcg cgccgggaac tgcaggccga gcgggaggcg ctgcaggcgc ggctgcggga 840
tgtgagccgc cgtgagggcg ccctgggctg ggcccccgct gcgccgccgc cgctcaagga 900
cgaccccgag ggtgacaggg acggctgcgt catcacaaag gtcctcctgt aggggtgtgg 960
ccacttcccc accccaggac agcgcttctc cgtccaatgc caatgccttc agaccccgct 1020
gggaccgaag ccgtaaccga agccaggccc gcagccgcta ctcactcgga agctccagct 1080
aactgtagga tcttccacac cctaaggctt cagcttgaga agcacttcga agccagagca 1140
gaaccaaaac tcacttccat ggggtcaccg ggggtgcctg ggcggccttt cgtgggcatg 1200
cacgcaagga attggggtgg cacacgggac acccgagagc tccaggagcc ccgtgaaccc 1260
agaccaccca gtgccatggc cacttagggc tgggaacccg aacctggtga ctttgaaagg 1320
atagagcttc attccatacc aaagacttat cacaccatgt gcctatacac ccagcagccc 1380
aaggtggagg gtgcgtggaa atgagaaagc tttttacccc aaaaaaaaaa aaaaaaa 1437

<210> SEQ ID NO 50
<211> LENGTH: 1514
<212> TYPE: DNA
<213> ORGANISM: Homo sapiens

<400> SEQUENCE: 50
gccagagcct agaccagtga gccaactgtg cgaaccagac ccggcagcct tgctcagttc 60
agcatagcgg agcggatccg atcggatcgg agcggatcgg agcacaccgg agcaggctca 120
tcgagaaggc gtctgcgaga ccatggagaa cggatacacc tatgaagatt ataagaacac 180
tgcagaatgg cttctgtctc acactaagca ccgacctcaa gttgcaataa tctgtggttc 240
tggattagga ggtctgactg ataaattaac tcaggcccag atctttgact acggtgaaat 300

```
ccccaacttt ccccgaagta cagtgccagg tcatgctggc cgactggtgt ttgggttcct    360

gaatggcagg gcctgtgtga tgatgcaggg caggttccac atgtatgaag ggtacccact    420

ctggaaggtg acattcccag tgagggtttt ccaccttctg ggtgtggaca ccctggtagt    480

caccaatgca gcaggagggc tgaaccccaa gtttgaggtt ggagatatca tgctgatccg    540

tgaccatatc aacctacctg gtttcagtgg tcagaaccct ctcagagggc ccaatgatga    600

aaggtttgga gatcgtttcc ctgccatgtc tgatgcctac gaccggacta tgaggcagag    660

ggctctcagt acctggaaac aaatggggga gcaacgtgag ctacaggaag gcacctatgt    720

gatggtggca ggccccagct ttgagactgt ggcagaatgt cgtgtgctgc agaagctggg    780

agcagacgct gttggcatga gtacagtacc agaagttatc gttgcacggc actgtggact    840

tcgagtcttt ggcttctcac tcatcactaa caaggtcatc atggattatg aaagcctgga    900

gaaggccaac catgaagaag tcttagcagc tggcaaacaa gctgcacaga aattggaaca    960

gtttgtctcc attcttatgg ccagcattcc actccctgac aaagccagtt gacctgcctt   1020

ggagtcgtct ggcatctccc acacaagacc caagtagctg ctaccttctt tggccccttg   1080

ctggagtcat gtgcctctgt ccttaggttg tagcagaaag gaaaagattc ctgtccttca   1140

cctttcccac tttcttctac cagacccttc tggtgccaga tcctcttctc aaagctggga   1200

ttacaggtgt gagcatagtg agaccttggc gctacaaaat aaagctgttc tcattcctgt   1260

tctttcttac acaagagctg gagcccgtgc cctaccacac atctgtggag atgcccagga   1320

tttgactcgg gccttagaac tttgcatagc agctgctact agctctttga gataatacat   1380

tccgaggggc tcagttctgc cttatctaaa tcaccagaga ccaaacaagg actaatccaa   1440

tacctcttgg attttattta atgtcataat gttgtcagaa taaagagaaa gatgaaataa   1500

aaaaaaaaaa aaaa                                                     1514
```

<210> SEQ ID NO 51
<211> LENGTH: 1159
<212> TYPE: DNA
<213> ORGANISM: Homo sapiens

<400> SEQUENCE: 51

```
gctgggagta gagggcagag ctcccacccc gccccgcccc caggggggcgc cccgggcccg     60

gcgcgagagg aggcagaggg ggcgtcaggc cgcgggagag gaggccatgg gcgcgcgcgg    120

ggcgctgctg ctggcgctgc tgctggctcg ggctggactc aggaagccgg agtcgcagga    180

ggcggcgccg ttatcaggac catgcggccg acgggtcatc acgtcgcgca tcgtgggtgg    240

agaggacgcc gaactcgggc gttggccgtg gcaggggagc ctgcgcctgt gggattccca    300

cgtatgcgga gtgagcctgc tcagccaccg ctgggcactc acggcggcgc actgctttga    360

aactgacctt agtgatccct ccgggtggat ggtccagttt ggccagctga cttccatgcc    420

atccttctgg agcctgcagg cctactacac ccgttacttc gtatcgaata tctatctgag    480

ccctcgctac ctggggaatt caccctatga cattgccttg gtgaagctgt ctgcacctgt    540

cacctacact aaacacatcc agcccatctg tctccaggcc tccacatttg agtttgagaa    600

ccggacagac tgctgggtga ctggctgggg gtacatcaaa gaggatgagg cactgccatc    660

tccccacacc ctccaggaag ttcaggtcgc catcataaac aactctatgt gcaaccacct    720

cttcctcaag tacagtttcc gcaaggacat ctttggagac atggtttgtg ctggcaatgc    780

ccaaggcggg aaggatgcct gcttcggtga ctcaggtgga cccttggcct gtaacaagaa    840

tggactgtgg tatcagattg gagtcgtgag ctggggagtg ggctgtggtc ggcccaatcg    900
```

gcccggtgtc tacaccaata tcagccacca ctttgagtgg atccagaagc tgatggccca 960
gagtggcatg tcccagccag acccctcctg gccgctactc tttttccctc ttctctgggc 1020
tctcccactc ctggggccgg tctgagccta cctgagccca tgcagcctgg ggccactgcc 1080
aagtcaggcc ctggttctct tctgtcttgt ttggtaataa acacattcca gttgatgcct 1140
tgcagggcat tcttcaaaa 1159

<210> SEQ ID NO 52
<211> LENGTH: 2276
<212> TYPE: DNA
<213> ORGANISM: Homo sapiens

<400> SEQUENCE: 52
gaacgtggta taaaaggggc gggaggccag gctcgtgccg ttttgcagac gccaccgccg 60
aggaaaaccg tgtactatta gccatggtca accccaccgt gttcttcgac attgccgtcg 120
acggcgagcc cttgggccgc gtctcctttg agctgtttgc agacaaggtc ccaaagacag 180
cagaaaattt tcgtgctctg agcactggag agaaaggatt tggttataag ggttcctgct 240
ttcacagaat tattccaggg tttatgtgtc agggtggtga cttcacacgc cataatggca 300
ctggtggcaa gtccatctat ggggagaaat ttgaagatga gaacttcatc ctaaagcata 360
cgggtcctgg catcttgtcc atggcaaatg ctggacccaa cacaaatggt tcccagtttt 420
tcatctgcac tgccaagact gagtggttgg atggcaagca tgtggtgttt ggcaaagtga 480
aagaaggcat gaatattgtg gaggccatgg agcgctttgg gtccaggaat ggcaagacca 540
gcaagaagat caccattgct gactgtggac aactcgaata agtttgactt gtgttttatc 600
ttaaccacca gatcattcct tctgtagctc aggagagcac ccctccaccc catttgctcg 660
cagtatccta gaatctttgt gctctcgctg cagttccctt tgggttccat gttttccttg 720
ttccctccca tgcctagctg gattgcagag ttaagtttat gattatgaaa taaaaactaa 780
ataacaattg tcctcgtttg agttaagagt gttgatgtag gctttatttt aagcagtaat 840
gggttacttc tgaaacatca cttgtttgct taattctaca cagtacttag atttttttta 900
ctttccagtc ccaggaagtg tcaatgtttg ttgagtggaa tattgaaaat gtaggcagca 960
actgggcatg gtggctcact gtctgtaatg tattacctga ggcagaagac cacctgaggg 1020
taggagtcaa gatcagcctg ggcaacatag tgagacgctg tctctacaaa aaataattag 1080
cctggcctgg tggtgcatgc ctagtcctag ctgatctgga ggctgacgtg ggaggattgc 1140
ttgagcctag agtgagctat tatcatgcca ctgtacagcc tgggtgttca cagatcttgt 1200
gtctcaaagg taggcagagg caggaaaagc aaggagccag aattaagagg ttgggtcagt 1260
ctgcagtgag ttcatgcatt tagaggtgtt cttcaagatg actaatgtca aaaattgaga 1320
catctgttgc ggtttttttt tttttttttt cccctggaat gcagtggcgt gatctcagct 1380
cactgcagcc tccgcctcct gggttcaagt gattctagtg cctcagcctc ctgagtagct 1440
gggataatgg gcgtgtgcca ccatgcccag ctaatttttg tatttttagt atagatgggg 1500
tttcatcatt ttgaccaggc tggtctcaaa ctcttgacct cagctgatgc gcctgccttg 1560
gcctcccaaa ctgctgagat tacagatgtg agccaccgca ccctacctca ttttctgtaa 1620
caaagctaag cttgaacact gttgatgttc ttgagggaag catattgggc tttaggctgt 1680
aggtcaagtt tatacatctt aattatggtg gaattcctat gtagagtcta aaaagccagg 1740
tacttggtgc tacagtcagt ctccctgcag agggttaagg cgcagactac ctgcagtgag 1800

```
gaggtactgc ttgtagcata tagagcctct ccctagcttt ggttatggag gctttgaggt   1860
tttgcaaacc tgaccaattt aagccataag atctggtcaa agggataccc ttcccactaa   1920
ggacttggtt tctcaggaaa ttatatgtac agtgcttgct ggcagttaga tgtcaggaca   1980
atctaagctg agaaaacccc ttctctgccc accttaacag acctctaggg ttcttaaccc   2040
agcaatcaag tttgcctatc ctagaggtgg cggatttgat catttggtgt gttgggcaat   2100
ttttgtttta ctgtctggtt ccttctgcgt gaattaccac caccaccact tgtgcatctc   2160
agtcttgtgt gttgtctggt tacgtattcc ctgggtgata ccattcaatg tcttaatgta   2220
cttgtggctc agacctgagt gcaaggtgga aataaacatc aaacatcttt tcatta       2276
```

<210> SEQ ID NO 53
<211> LENGTH: 2026
<212> TYPE: DNA
<213> ORGANISM: Homo sapiens

<400> SEQUENCE: 53

```
caatcccccc tcccccccca atctgtcttt ctagcatgtt gcccttttc aaccacattt      60
gtgtttcagg tgtagagagg agagagagtg aacagggagc ggggcttttg tctgttggtc    120
tccctggact gaagagaggg agaatagaag cccaagacta agattctcaa aatggtttat    180
tacccagaac tctttgtctg ggtcagtcaa gaaccatttc caaacaagga catggaggga    240
aggcttccta agggaagact tcctgtccca aaggaagtga accgcaagaa gaacgatgag    300
acaaacgctg cctccctgac tccactgggc agcagtgaac tccgctcccc aagaatcagt    360
tacctccact ttttttaatc gtaacacctc catttgtatt acatatggtg tatgggtatt    420
gatgaggtca tggtatcata tatgggattt ttttctgtgt aaatcatcaa gtataagaag    480
aaactatggg actctgagcc ttgctttaga gaatttacag tggacaaata ggtgtcatca    540
aaccagtttt taatcattct gactcaagtg aaaacgctca gaatttcaca ctgtgaatcc    600
acgtttacaa cccttacagg tgggccttca ggcctggttc gctacaacaa tgtcttccac    660
aactcaaact cccaccgcgc tcacacaacc ggtccactcc tgccttttca ctcacacagc    720
tcccgactgc ttcttgcaga ggctgagagt cccccccccca cctttttttt catttagatg    780
taacaaacct agtagtttat gttcatcaat tgtctgtata tctctatatt ttatccatgt    840
actcttttga tgtatagaag tagtttgaaa ctcattgttt ccttgtggta agtgaccgag    900
atgctgccac aggacctgag acactgatga atggtgctat tttggacttt caacatgctc    960
cttggcgagg tagctctgat ggagttattt tttatttcca tgttctaaga aggtgttggt   1020
actctgtttc cctgaatgtt gttctctaga ctggattgac ttgttttcct tgtgtcttca   1080
gtgtggcttt cttcctcagt gttgtaggtt gagcgaatgc taccagagtg tgagagacca   1140
ttgtctcgtt ggctggcgct cacggacatg cagtcacggt agcgggagca atcacaaaac   1200
tgtaatttac ttaccaaatc tcttcctttc cgtagcctcg cctgcctgac ttagagaaag   1260
aaaagcaata attttacagg cattttgagg tgtctctttg ggttctttct gtttgaaagg   1320
atatttgtcg aaaaaaagag caaaaccgtt ttaaataaac tccccctgga aaaaaaccca   1380
aaacactggc atctgagtgg gaatatgaaa atgacacctt ttccaaatat taaattggaa   1440
aacaaggtct acaaaatcat gatacttttt taaaaggcag agcattcttt tttcggcaat   1500
tttgataagc aaggtgtaga tttacatttt tgtccttgct cccaacgaaa tggataaaca   1560
aaaataaatt accatctact catggaatgt tgttgtgtta gccagtctga aagcccacct   1620
taatttttat ataactgtct ttagctcttc ttttgacagg gcaggccttg ttctgaactg   1680
```

```
tttcgcttct gactgttaaa caccgatgac gcatgcactg cacttcttcg ttttcttctt   1740

gctcccccat tggcctgagt ttcttgtgca ttactcctct ccctccttcg ttagaatagg   1800

tatatcagct gtgtaaatag agcaagaaaa cagtattctg catctgtggc atttatgtag   1860

agttgcagtt gtgtactgct gaaaatgcag gcttttgtaa cagtgtgatc tttactgatg   1920

cactcatgac aagtacccaa tgtattttag ctattttagt agtatttgtt caataaatac   1980

gcaagctgta aggtaaaaaa aaaaaaaaaa aaaaaaaaaa aaaaaa                  2026


<210> SEQ ID NO 54
<211> LENGTH: 5273
<212> TYPE: DNA
<213> ORGANISM: Homo sapiens

<400> SEQUENCE: 54

aaggactaga gagcgagccg caaggaagtc ggtgcagtcg agaccccccct ccccatccca     60

gcgcatcgcg tctccgccga gcttgagggc acgccgggga cccctcccca gagccggccg    120

gaccccaggt gccgaggcct tggggagcgc ggggcgtccc gggtcgcggt gccctcggga    180

cgagacagcc cctggcagtg ccaccaccgc agccgccggg cgatctccaa gcggcgatct    240

ctaagcgctg ctctctgctc ggccgcgggc caggagggga gggtccggcc ttgccccgca    300

ggcgtccatt ggcggcttcc cccggcctcc gcgccatgcc gcgggccgtg tgaaaggcgg    360

cagcaccgga acccgcaggt gtccgcgggc gcgccaagcc cttttgggta gggggcgcct    420

tactcgctat gctgcaaggg ccccgggcct tggcttcggc cgctgggcag accccgaagg    480

tggtgcccgc gatgagcccc acagagctgt ggccatccgg cctcagcagc cccccagctct    540

gcccagctac tgctacctac tacacaccgc tgtacccgca gacggcgcct cccgcagcgg    600

cgccaggcac ctgcctcgac gccactcccc acggacccga gggccaagtt gtgcgatgcc    660

tgccggcagg ccggctgccg gccaaaagga agctggatct ggaggggatt gggaggcccg    720

tcgtccctga gttcccaacc cccaagggga agtgcatcag agtggatggc ctccccagcc    780

ccaaaacccc caaatccccc ggggagaaga ctcggtatga cacttcgctg gggctgctca    840

ccaagaagtt catttacctc ctgagcgagt cagaggatgg ggtcctggac ctgaactggg    900

ccgctgaggt gctggacgtg cagaagcggc gcatctatga catcaccaac gtgctggaag    960

gcatccagct catccgcaag aaggccaaga acaacatcca gtgggtaggc aggggaatgt   1020

ttgaagaccc caccagacct gggaagcagc aacagctggg gcaggagctg aaggagctga   1080

tgaacacgga gcaggccttg gaccagctca tccagagctg ctctctgagc ttcaagcacc   1140

tgactgagga caaggccaac aagaggctgg cctatgtgac ttaccaggat atccgtgctg   1200

ttggcaactt taaggagcag acagtgattg ccgtcaaggc cctctccgcag acgagactgg   1260

aagtgcccga caggactgag gacaacctgc agatatatct caagagcacc caagggccca   1320

tcgaagtcta cctgtgccca gaggaggtgc aggagccgga cagtccttcc gaggagcctc   1380

tcccctctac ctccaccctc tgccccagcc ctgactctgc ccagcccagc agcagcaccg   1440

accctagcat catggagccc acagcatcct cagtgccagc accagcgcca accccccagc   1500

aggccccacc gcctccatcc ctggtcccct tggaggctac tgacagcctg ctggagctgc   1560

cgcaccccact cctgcagcag actgaggacc agttcctgtc cccgaccctg gcgtgcagct   1620

cccctctgat cagcttctcc ccatccttgg accaggacga ctacctgtgg ggcttggagg   1680

cgggtgaggg catcagcgat ctcttcgact cctacgacct tggggacctg ttgattaatt   1740
```

```
gagtggccct gcctgccccc agcagcctgc ccccgactct acctcctcac agacaggctg   1800
acagcccctc tgcctgcaca gggacattgg acactaggtg ctgccctcag ggcatggggt   1860
ctcctcgcct ttcctgcccc agccggcaga agctgtgtgg ggagatatga atggtacggg   1920
tgaggagtgg ataaggggtg gtcctcacct tcctaatgga agctgggcct agggaggccc   1980
atccagtctt ctgacttctg acctctcaca agaaggctgc aggtgaggtg gccaagtcca   2040
gggaaaggcc ctgctacctc cttttgaggg gtaattagga ccctcgacgt accaagaagc   2100
acataatgcc tttgtattta tttcaggttg agttgtttgt ttgtcctccc tgagttttag   2160
cagggaggtt gttctagttt ttagtgagac ctctgcagac aggcccatca ctgtccatgt   2220
tccagggcag gtctgggttt ccaagggagg ggcccaggct acatccttgg tttccccact   2280
gtggtggggg ctgggactct gaggggctgt ccagtctgct agaatgctaa ttgcacttag   2340
gcctcatggt tctagtaaac ggcagctgtg ggccctttg  cctcttcccc tgttcttggc   2400
ctcacatctc cagctgagct gccggtcttg gcttcctggt cgcctctgtc ccagagatgg   2460
tcccagggag ccatcctagg gcaggtagca ctgaggctcc tgtggaaaca ggagccacct   2520
gctcaggaga cccctttcct gaggaagtcc ttacctctcc ccttgagatg taaaaatggt   2580
ccagcagaga caagctcccg tggaaaacag acaggagcat gggggcagct gtcatggctg   2640
tggcgggcac ttttcctcag agtttctgcc ttgcgctggt ccaggagcca ttttgcacca   2700
aggacttggt aggcagaggc agccccactg taaagaaggg tcagattaaa acaaaaaact   2760
gccaaaagca tcccctctgc cccccatgtg gcactggcat cattctctgc ttccctggga   2820
ggaatttttt caccatgtta ttgaagggga tggttcatta aggactccac ccctcagagc   2880
tcactcagac cccaaggaca gaggtgactg gggcttggtg acttgttcac tccttttttc   2940
ccaggtatac tgaaggggtg acagagagag gtcttcatgg cagaccaggc cttcacagct   3000
aatggggaga ggaactcatg ttacctctgc aggcctgggg tcctgagggg gtcttttggc   3060
ttcagcctgt tcccccagag gcttgatcat cccacattgt cccttcagct cagctgctct   3120
tctcccccac ccaccctggg atgtgggtgc tctgggctga accaaggcta tgacttctgg   3180
agagaggctc aggggttggt ctgagaggcc tgccatccac ccctcaggga gctaggtttt   3240
ctcagaggct cagctggaca gcacttttta gaaaagtttg tagcattaag ctggtttaaa   3300
atatgaagtt ggttttgttg gatggctcct gagctgactg actgatgtct gaagtttgag   3360
acgagggatt atttcagggt ggggcccaat gtgatctaat gcccagctgg ggacaattgt   3420
gcctcatcat ttgctcaaat tcctgggccc ccaagttagc cccctcccag gagtggtcag   3480
cgggtcacag ctgcccccac tctataagca gggctaattg tgtacccttt gcagaaatgc   3540
ttttggtctc ctacccaaat actcacaagg gtcttatcag acgcccgtct taaagtccag   3600
catgctcagg gaccctgtgt aggatctcgt ttgtggtgag tgggctgctc tgaggtctcc   3660
actgggctgc catttagcca tgtgccatct ctgaagtcag aggtgtttga ctcccattcc   3720
ttgggctctg gagctttccc caagaattac atcagagaaa aggaagaagg ggcctgcagg   3780
acccattggg aatgagttta atactgaagt ctggaatgta agctcatgcc ctagaggcct   3840
ctccatatgg ctggtcaggg gagctgcctt caggcttgtg ccccgtgtgc tcagcagctg   3900
cctctgtccc cctctactgt ccctttcaca ccttgcctgg ccaaggggct agacctccca   3960
ggctaagcct cagattcagt gcaggacaca agctcatgcc cccgtcttgc cagtgacact   4020
tgaagcctcc cgacttccac agagtgcttc aggacacatt ttgagtggta ttttcttttc   4080
tttttttctt cttttttttt ttttttgaga tggagtctcg ctctgttgcc caggctggag   4140
```

```
tgcagtggcc tgatctcggc tcactgcaac ctctgcctcc caggttcaag cgattcttct   4200
gcctcagcct ccagagtagc tgggactata gacatgcacc accacgcccg gctaattttg   4260
tatttttggt cgagacgggg ttttgccatg ttagtcaggc tggtcttgaa ctcctgacct   4320
caagtgatcc accacctcgg cctcccaaag tgttgagatg acaggcacga gccaccaggc   4380
ccagcctgag tggtattttc tttagggacc aggtagactt taaaacgagg gtaagagaaa   4440
agccagtgtc tttctgaggt aaataatttc tgccaggaaa cttcccagcc ccaccagcag   4500
ccccccctaaa aaaatcactc gtgtccccag ggacttctaa agcttggggc tccaggaaat   4560
catccagtag agttggagat tcagagattt cttgaagcca gggacatgct cctaactcct   4620
ttcccattaa aggtgttaga atagaccaga gggtgtccct tttccacagt aatgggatcg   4680
gctggtgtgc cttcagggag gaagagggag gtggtcaagc ttgaaaaact ggctttagga   4740
tggttctgac tttgttctcc ctccccaagt gttctcaacc tccattctgc agtgttcaga   4800
gttttaggga aagggtttgg gtgccccagc atccaggtgt tgtgtggctt agcgcatgtg   4860
aagtgaaaac cttctggggt tgtttggaag cagctttctg gttcttgtga ttgtatcctg   4920
aggtcccaga accctattct cccacgagga tcctcagtga ccatggtggc cacacgcctg   4980
gccagcctgc tggctcctgg gtgagctgaa gaaccttgcc tgtggcactt ttcgagggtg   5040
agctggaacc gagagaacat ggtccccgtg ctgggactca tgcgggtcat ttcctgccgg   5100
cctggtttcg cctggtcgtg tctttatgag caccatgtaa gcctccttgt attgagataa   5160
ttgggcatta aacattaaac tgcagctctg ggaaaaaaaa aaaaaaaaaa aaaaaaaaaa   5220
aaaaaaaaaa aaaaaaaaaa aaaaaaaaaa aaaaaaaaaa aaaaaaaaaa aaa          5273
```

<210> SEQ ID NO 55
<211> LENGTH: 3060
<212> TYPE: DNA
<213> ORGANISM: Homo sapiens

<400> SEQUENCE: 55

```
gcggtcaaat tataatacat aaaagttgtc agggcggaga gcaagacatt actcttctcg     60
gattgccggt tcgctcgcga gacttgagcg ttgctaggag attcggcagg cgggcggagc    120
cagactcggc ggggcgggga ggggtggggc taggctcggc gaggcgagga agggtgggtg    180
gagccaggct tggcgggctg tgcgtgctcg cggtgggcgg tggcggcggc tgcctcgcga    240
aggttcgaga tccgtcgcgt gcgggaggcg ggccgcgatc ttgcgcaggg tcggtgtggg    300
cgcaggctgc agcgccgcga ctcgtgcggg taggcgtctg cgctcggttt gagggctcgg    360
cgcggggttt cctgttcctc cttctgcgcg gctgcagctc gggacttcgg cctgacccag    420
cccccatggc ttcagaagag ctacagaaag atctagaaga ggtaaaggtg ttgctggaaa    480
aggctactag gaaaagagta cgtgatgccc ttacagctga aaaatccaag attgagacag    540
aaatcaagaa caagatgcaa cagaaatcac agaagaaagc agaacttctt gataatgaaa    600
aaccagctgc tgtggttgct cccattacaa cgggctatac ggtgaaaatc agtaattatg    660
gatgggatca gtcagataag tttgtgaaaa tctacattac cttaactgga gttcatcaag    720
ttcccactga gaatgtgcag gtgcatttca cagagaggtc atttgatctt ttggtaaaga    780
atctaaatgg gaagagttac tccatgattg tgaacaatct cttgaaaccc atctctgtgg    840
aaggcagttc aaaaaaagtc aagactgata cagttcttat attgtgtaga aagaaagtgg    900
aaaacacaag gtgggattac ctgacccagg ttgaaaagga gtgcaaagaa aaagagaagc    960
```

```
cctcctatga cactgaaaca gatcctagtg agggattgat gaatgttcta aagaaaattt   1020
atgaagatgg agacgatgat atgaagcgaa ccattaataa agcctgggtg gaatcaagag   1080
agaagcaagc caaaggagac acggaatttt gagactttaa agtcgttttg ggaactgtga   1140
tgtgatgtgg aaatactgat gtttccagta agggaatatt ggtgagctgc atatataaat   1200
ttgacagata gctatttaca tagccttcta agtaaaggca atgaattctc catttcctac   1260
tggaggattt atttaaataa aatatgctta ttaaacactc ctgcaaagat ggttttatta   1320
gtaccctggt cattttgttc aaggaagggt tatattgcat tctcacgtga aatataaaaa   1380
gcaagtcttg cccaataaaa acgctacatt gtgtgtattt tttgttcagc taagaattgg   1440
aaaagtattt gcttgccttt taagttactg acatcagctt ccaccagtgt aaaaattgag   1500
taaaacctga agttttgcat aaaatgcaaa tcggtgcctg tgcttgaagg ttgctgtaga   1560
gcatctgacc ccttattacc accttaagca atgtatatgc catgcattac catgcactaa   1620
ttcaatcaca ggtgtttcta tctagattta aatatatttg tcaatgaatg tggaatagaa   1680
aatctaaaca tgacaataat agacatatct ttgtatggta ccagttagtt ttgccgtgga   1740
tcagatggtt tataaaagta ataaccataa agcaaaaaat aatttgaaag cccgtctatt   1800
cctatgctca ataaagttaa gtttttcttc attagaacag ttttatgatt tatttgtcta   1860
ggagtatgtc agaaaaatca ggcttttagt aggaattact cctattcccc ctgaagtcag   1920
gaccagtgcc tgtgatctcc attactttat tttcctggag gtattagcca acacagttag   1980
atcagagaaa gcaattgaag ccaggcatga aggctggcgc ccgtaatccc agctactaag   2040
gctggaggat cacttcagcc caggagttta aggctgcagt gagctatgat gatgccactg   2100
tactgcagct tgggtaacag attgagaacc tgtctcatta aaaaaaaaaa aaaaaaaaaa   2160
gccgttagac acacaggaaa aatccagaag ggtaaactaa actaaagcta caattaatat   2220
gggaatttgg aagaagtggt aggatttaaa atacagaaac agtttatgta taggatagct   2280
ataagtaaat actgaaacac attatgcctc tgtaattggg gttgacacat gaacagaata   2340
gcagacacaa tgcatatgaa agttacagaa tatggtaaaa gtggggtaaa gatgggtttt   2400
taatgatact aagataactg aaaataggca tatagatata ttccaagccg cctgacgatc   2460
taattgtaaa aagtaaagca tacaaatact agaagaaaat ggaggaaaac gacattatat   2520
gtgacttaaa acctagaaga aataaataaa actattgatc aattttaact acataaaaat   2580
gtttatagga caagaaaaac cccaccataa cccaaggcaa acaatgtatt gacaggattc   2640
caataattaa gaatacttca tacaaaaaga aatgtaaatg acctttaaca tgtaaagatg   2700
ctcaccttgt tcagaagaga ataaaccagt gtttttacct ttcacttgaa aaagaagtat   2760
aaaaacaact gtattgagtt gaggctgtgg agaaataagg acacatatat gggaatggaa   2820
tgcaaaagtt aaactttggt taacaagaat atttgggcag gtgcagtggc tcacacctgt   2880
aatcccaaca ccttgggagg ccaaggtggg cggatcactt gaggtcagga gttcaagacc   2940
atctggccaa catggtgaaa ccctgtctct actgaaaata aaaaaaacta gctgggcatg   3000
gtggcagatg cctgtaactc cagctactcg ggagactgaa ggacaagaat cacttgaacc   3060
```

```
<210> SEQ ID NO 56
<211> LENGTH: 2618
<212> TYPE: DNA
<213> ORGANISM: Homo sapiens

<400> SEQUENCE: 56

attggacggc tgagtctggc tacgcgggcc tccgcgggag cgcgaccggg ccaatcaaga     60
```

```
gcttggcgta ttttacaaac tgagaaagta gctccagcag cacccgagag ggtcaggaga    120
aaagcggagg aagctgggta ggccctgagg ggcctcggta agccatcatg accacccggc    180
aagccacgaa ggatcccctc ctccggggtg tatctcctac ccctagcaag attccggtac    240
gctctcagaa acgcacgcct ttccccactg ttacatcgtg cgccgtggac caggagaacc    300
aagatccaag gagatgggtg cagaaaccac cgctcaatat tcaacgcccc ctcgttgatt    360
cagcaggccc caggccgaaa gccaggcacc aggcagagac atcacaaaga ttggtgggga    420
tcagtcagcc tcggaacccc ttggaagagc tcaggcctag ccctaggggt caaaatgtgg    480
ggcctgggcc ccctgcccag acagaggctc cagggaccat agagtttgtg gctgaccctg    540
cagccctggc caccatcctg tcaggtgagg gtgtgaagag ctgtcacctg gggcgccagc    600
ctagtctggc taaaagagta ctggttcgag gaagtcaggg aggcaccacc cagagggtcc    660
agggtgttcg ggcctctgca tatttggccc ccagaacccc cacccaccga ctggaccctg    720
ccagggcttc ctgcttctct aggctggagg gaccaggacc tcgaggccgg acattgtgcc    780
cccagaggct acaggctctg atttcacctt caggaccttc ctttcaccct tccactcgcc    840
ccagtttcca ggagctaaga agggagacag ctggcagcag ccggacttca gtgagccagg    900
cctcaggatt gctcctggag accccagtcc agcctgcttt ctctcttcct aaaggagaac    960
gcgaggttgt cactcactca gatgaaggag gtgtggcctc tcttggtctg gcccagcgag   1020
taccattaag agaaaaccga gaaatgtcac ataccaggga cagccatgac tcccacctga   1080
tgccctcccc tgcccctgtg gcccagccct tgcctggcca tgtggtgcca tgtccatcac   1140
cctttggacg ggctcagcgt gtaccctccc caggccctcc aactctgacc tcatattcag   1200
tgttgcggcg tctcaccgtt caacctaaaa cccggttcac acccatgcca tcaaccccca   1260
gagttcagca ggcccagtgg ctgcgtggtg tctcccctca gtcctgctct gaagatcctg   1320
ccctgccctg ggagcaggtt gccgtccggt tgtttgacca ggagagttgt ataaggtcac   1380
tggagggttc tgggaaacca ccggtggcca ctccttctgg accccactct aacagaaccc   1440
ccagcctcca ggaggtgaag attcaacgca tcggtatcct gcaacagctg ttgagacagg   1500
aagtagaggg gctggtaggg ggccagtgtg tccctcttaa tggaggctct tctctggata   1560
tggttgaact tcagcccctg ctgactgaga tttctagaac tctgaatgcc acagagcata   1620
actctgggac ttcccacctt cctggactgt taaaacactc agggctgcca aagccctgtc   1680
ttccagagga gtgcggggaa ccacagccct gccctccggc agagcctggg cccccagagg   1740
ccttctgtag gagtgagcct gagataccag agccctccct ccaggaacag cttgaagtac   1800
cagagcccta ccctccagca gaacccaggc ccctagagtc ctgctgtagg agtgagcctg   1860
agataccgga gtcctctcgc caggaacagc ttgaggtacc tgagccctgc cctccagcag   1920
aacccaggcc cctagagtcc tactgtagga ttgagcctga gataccggag tcctctcgcc   1980
aggaacagct tgaggtacct gagccctgcc ctccagcaga acccgggccc cttcagccca   2040
gcacccaggg gcagtctgga cccccagggc cctgccctag ggtagagctg gggcatcag    2100
agccctgcac cctggaacat agaagtctag agtccagtct accaccctgc tgcagtcagt   2160
gggctccagc aaccaccagc ctgatcttct cttcccaaca cccgctttgt gccagccccc   2220
ctatctgctc actccagtct ttgagacccc cagcaggcca ggcaggcctc agcaatctgg   2280
cccctcgaac cctagccctg agggagcgcc tcaaatcgtg tttaaccgcc atccactgct   2340
tccacgaggc tcgtctggac gatgagtgtg ccttttacac cagccgagcc cctccctcag   2400
```

```
gccccacccg ggtctgcacc aaccctgtgg ctacattact cgaatggcag gatgccctgt   2460

gtttcattcc agttggttct gctgcccccc agggctctcc atgatgagac aaccactcct   2520

gccctgccgt acttcttcct tttagccctt atttattgtc ggtctgccca tgggactggg   2580

agccgcccac ttttgtcctc aataaagttt ctaaagta                           2618
```

<210> SEQ ID NO 57
<211> LENGTH: 1444
<212> TYPE: DNA
<213> ORGANISM: Homo sapiens

<400> SEQUENCE: 57

```
ggagaagggg tggggcaggg tatcgctgac tcagcagctt ccaggttgct ctgatgatat     60

attaaggctc ctgaatccta agagaatgtt ggtgaagatc ttaacaccac gccttgagca    120

agtcgcaaga gcgggaggac acagaccagg aaccgagaag ggacaagcac atggaagcca    180

gcccagcatc cgggcccaga cacttgatgg atccacacat attcacttcc aactttaaca    240

atggcattgg aaggcataag acctacctgt gctacgaagt ggagcgcctg gacaatggca    300

cctcggtcaa gatggaccag cacaggggct ttctacacaa ccaggctaag aatcttctct    360

gtggctttta cggccgccat gcggagctgc gcttcttgga cctggttcct tctttgcagt    420

tggacccggc ccagatctac agggtcactt ggttcatctc ctggagcccc tgcttctcct    480

ggggctgtgc cggggaagtg cgtgcgttcc ttcaggagaa cacacacgtg agactgcgta    540

tcttcgctgc ccgcatctat gattacgacc ccctatataa ggaggcactg caaatgctgc    600

gggatgctgg ggcccaagtc tccatcatga cctacgatga atttaagcac tgctgggaca    660

cctttgtgga ccaccaggga tgtcccttcc agccctggga tggactagat gagcacagcc    720

aagccctgag tgggaggctg cgggccattc tccagaatca gggaaactga aggatgggcc    780

tcagtctcta aggaaggcag agacctgggt tgagcagcag aataaaagat cttcttccaa    840

gaaatgcaaa cagaccgttc accaccatct ccagctgctc acagacgcca gcaaagcagt    900

atgctcccga tcaagtagat tttaaaaaa tcagagtggg ccgggcgcgg tggctcacgc     960

ctgtaatccc agcactttgg aggccaaggc gggtggatca cgaggtcagg agatcgagac   1020

catcctggct aacacggtga aaccctgtct ctactaaaaa tacaaaaaat tagccaggcg   1080

tggtggcggg cgcctgtagt cccagctact ctggaggctg aggcaggaga gtagcgtgaa   1140

cccgggaggc agagcttgcg gtgagccgag attgcgctac tgcactccag cctgggcgac   1200

agtaccagac tccatctcaa aaaaaaaaaa accagactga attaatttta actgaaaatt   1260

tctcttatgt tccaagtaca caatagtaag attatgctca atattctcag aataattttc   1320

aatgtattaa tgaaatgaaa tgataatttg gcttcatatc tagactaaca caaaattaag   1380

aatcttccat aattgctttt gctcagtaac tgtgtcatga attgcaagag tttccacaaa   1440

cact                                                                1444
```

<210> SEQ ID NO 58
<211> LENGTH: 857
<212> TYPE: DNA
<213> ORGANISM: Homo sapiens

<400> SEQUENCE: 58

```
caagcctgga agaactcgtc atgctctttg tagcgtggtg cttctgttgc tcacaggaca     60

acttgccttt gatgattttc aagagagttg tgctatgatg tggcaaaagt atgcaggaag    120

caggcggtca atgcctctgg gagcaaggat ccttttccac ggtgtgttct atgccggggg    180
```

```
ctttgccatt gtgtattacc tcattcaaaa gtttcattcc agggctttat attacaagtt    240

ggcagtggag cagctgcaga gccatcccga ggcacaggaa gctctgggcc ctcctctcaa    300

catccattat ctcaagctca tcgacaggga aaacttcgtg gacattgttg atgccaagtt    360

gaagattcct gtctctggat ccaaatcaga gggccttctc tacgtccact catccagagg    420

tggccccttt cagaggtggc accttgacga ggtcttttta gagctcaagg atggtcagca    480

gattcctgtg ttcaagctca gtggggaaaa cggtgatgaa gtgaaaaagg agtagagacg    540

acccagaaga cccagcttgc ttctagtcca tccttccctc atctctacca tatggccact    600

ggggtggtgg cccatctcag tgacagacac tcctgcaacc cagttttcca gccaccagtg    660

ggatgatggt atgtgccagc acatggtaat tttggtgtaa ttctaacttg ggcacaacaa    720

atgctatttg tcatttttaa actgaatccg aaagaaactc ctattataaa tttaagataa    780

tgtaatgtat ttgaaagtgc tttgtataaa aaagcacatg ataaaaggaa tcagaattaa    840

taaaatgttt gttgatc                                                   857
```

```
<210> SEQ ID NO 59
<211> LENGTH: 1647
<212> TYPE: DNA
<213> ORGANISM: Homo sapiens

<400> SEQUENCE: 59

gcgcgcgggt ttcgttgacc cgcggcgttc acgggaattg ttcgctttag tgccggcgcc     60

atggggtcgg agctgatcgg gcgcctagcc ccgcgcctgg gcctcgccga gcccgacatg    120

ctgaggaaag cagaggagta cttgcgcctg tcccgggtga agtgtgtcgg cctctccgca    180

cgcaccacgg agaccagcag tgcagtcatg tgcctggacc ttgcagcttc ctggatgaag    240

tgccccttgg acagggctta tttaattaaa ctttctggtt tgaacaagga gacatatcag    300

agctgtctta aatcttttga gtgtttactg ggcctgaatt caaatattgg aataagagac    360

ctagctgtac agtttagctg tatagaagca gtgaacatgg cttcaaagat actaaaaagc    420

tatgagtcca gtcttcccca gacacagcaa gtggatcttg acttatccag gccacttttc    480

acttctgctg cactgctttc agcatgcaag attctaaagc tgaaagtgga taaaaacaaa    540

atggtagcca catccggtgt aaaaaaagct atatttgatc gactgtgtaa acaactagag    600

aagattggac agcaggtcga cagagaacct ggagatgtag ctactccacc acggaagaga    660

aagaagatag tggttgaagc ccccagcaaag gaaatggaga aggtagagga gatgccacat    720

aaaccacaga aagatgaaga tctgacacag gattatgaag aatggaaaag aaaaattttg    780

gaaaatgctg ccagtgctca aaaggctaca gcagagtgat ttcagcttcc aaactggtat    840

acattccaaa ctgatagtac attgccatct ccaggaagac ttgacggctt tgggattttg    900

tttaaacttt tataataagg atcctaagac tgttgccttt aaatagcaaa gcagcctacc    960

tggaggctaa gtctgggcag tgggctggcc cctggtgtga gcattagacc agccacagtg   1020

cctgattggt atagccttat gtgctttcct acaaaatgga attggaggcc gggcgcagtg   1080

gctcacgcct gtaatcccag cactttggga ggccaaggtg ggtggatcac ctgaggtcag   1140

gagctcgaga ccagcctggc caacatggtg aaaccccatc tctactaaaa atacaaaaat   1200

tagccaggtg tgatggtgca tgcctgtaat cccagctcct cagtaggctg agacaggagc   1260

atcacttgaa cgtgggaggc agaggttgca gtgagccgag attgcaccac cgcactccag   1320

cctgggtgac agagcgagac ttatctcata aataaataga tagatactcc agcctgggtg   1380
```

acagagcgag acttatagat agatagatag atagatggat agatagatag atagatagat 1440
agatagataa acggaattgg agccattttg ctttaagtga atggcagtcc cttgtcttat 1500
tcagaatata aaattcagtc tgaatggcat cttacagatt ttacttcaat ttttgtgtac 1560
ggtatttttt atttgactaa atcaatatat tgtacagcct aagttaataa atgttattta 1620
tatatgcaaa aaaaaaaaaa aaaaaaa 1647

<210> SEQ ID NO 60
<211> LENGTH: 2288
<212> TYPE: DNA
<213> ORGANISM: Homo sapiens

<400> SEQUENCE: 60
ggggctgcag ctccgtcagc ccggcagagc caccctgagc tcggtgagag caaagccaga 60
gcccccagtc ctttgctcgc cggcttgcta tctctctcga tcactccctc ccttcctccc 120
tcccttcctc ccggcggccg cggcggcgct ggggaagcgg tgaagaggag tggcccggcc 180
ctggaagaat gcggctctga caaggggaca gaacccagcg cagtctcccc acggtttaag 240
cagcactagt gaagcccagg caacccaacc gtgcctgtct cggaccccgc acccaaacca 300
ctggaggtcc tgatcgatct gcccaccgga gcctccgggc ttcgacatgc tggaggagcc 360
ccggccgcgg cctccgccct cgggcctcgc gggtctcctg ttcctggcgt tgtgcagtcg 420
ggctctaagc aatgagattc tgggcctgaa gttgcctggc gagccgccgc tgacggccaa 480
caccgtgtgc ttgacgctgt ccggcctgag caagcggcag ctaggcctgt gcctgcgcaa 540
ccccgacgtg acggcgtccg cgcttcaggg tctgcacatc gcggtccacg agtgtcagca 600
ccagctgcgc gaccagcgct ggaactgctc cgcgcttgag ggcggcggcc gcctgccgca 660
ccacagcgcc atcctcaagc gcggtttccg agaaagtgct tttccttct ccatgctggc 720 tgctggggtc atgcacgcag tagccacggc ctgcagcctg ggcaagctgg tgagctgtgg 780
ctgtggctgg aagggcagtg gtgagcagga tcggctgagg gccaaactgc tgcagctgca 840
ggcactgtcc cgaggcaaga gtttccccca ctctctgccc agccctggcc ctggctcaag 900
ccccagccct ggcccccagg acacatggga atggggtggc tgtaaccatg acatggactt 960
tggagagaag ttctctcggg atttcttgga ttccagggaa gctccccggg acatccaggc 1020
acgaatgcga atccacaaca acagggtggg gcgccaggtg gtaactgaaa acctgaagcg 1080
gaaatgcaag tgtcatggca catcaggcag ctgccagttc aagacatgct ggagggcggc 1140
cccagagttc cgggcagtgg gggcggcgtt gagggagcgg ctgggccggg ccatcttcat 1200
tgatacccac aaccgcaatt ctggagcctt ccagccccgt ctgcgtcccc gtcgcctctc 1260
aggagagctg gtctactttg agaagtctcc tgacttctgt gagcgagacc ccactatggg 1320
ctccccaggg acaaggggcc gggcctgcaa caagaccagc cgcctgttgg atggctgtgg 1380
cagcctgtgc tgtggccgtg ggcacaacgt gctccggcag acacgagttg agcgctgcca 1440
ttgccgcttc cactggtgct gctatgtgct gtgtgatgag tgcaaggtta cagagtgggt 1500
gaatgtgtgt aagtgagggt cagccttacc ttggggctgg ggaagaggac tgtgtgagag 1560
gggcgccttt tcagcccttt gctctgattt ccttccaagg tcactcttgg tccctggaag 1620
cttaaagtat ctacctggaa acagctttag ggtggtgggg ggtcaggtgg actctgggat 1680
gtgtagcctt ctccccaaca attggagggt cttgagggga agctgccacc cctcttctgc 1740
tccttagaca cctgaatgga ctaagatgaa atgcactgta ttgctcctcc cacttctcaa 1800
ctccagagcc cctttaaccc tgattcatac tccttttggc tggggagtcc ctatagtttc 1860

```
accactcctc tcccttgagg gataacccca ggcactgttt ggagccataa gatctgtatc   1920

tagaaagaga tcacccactc ctatgtacta tccccaaact cctttactgc agcctgggct   1980

ccctcttgtg ggataatggg agacagtggt agagaggttt ttcttgggaa agagacagag   2040

tgctgagggg cactctcccc tgaatcctca gagagttgtc tgtccaggcc cttagggaag   2100

ttgtctcctt ccattcagat gttaatgggg accctccaaa ggaaggggtt ttcccatgac   2160

tcttggagcc tctttttcct tcttcagcag gaagggtggg aagggataat ttatcatact   2220

gagacttgtt cttggttcct gtttgaaact aaaataaatt aagttactgg aaaaaaaaaa   2280

aaaaaaaa                                                            2288
```

<210> SEQ ID NO 61
<211> LENGTH: 15123
<212> TYPE: DNA
<213> ORGANISM: Homo sapiens

<400> SEQUENCE: 61

```
tagtaagcaa aattttgtta tcaaggcaaa cagaaaagag aagtgcattt agagtcagaa     60

aggcctcgat tcaaattctt gtccccttct tcccacccct gctagtcata caaccacaag    120

aaaattgcta gcctgcatct taggctcctc attagtgaaa tggatgatca agtctatctt    180

gcaggagggt gtgagtgcat caagttaaat taaatatata cacagtgtct gtcattcagt    240

tggcatcgac attacctatt atactattta ttattattac ctgtatttcc atggatttta    300

ggttttgcta tggttttcat gctctcagtg taccctcctt cttctttcta acattccatc    360

caaacagtcc tgctagatgc tgttctcttg gcatggctag ccagctttcc caaagcctcc    420

ataggccact aagcttctgt ccacacggct ggctggtccg tcagtttaag tcacccaatt    480

caactgacat catgacagct tgcaaattcc aaaatcactg ttggtaattt agatgtggta    540

gtgtttatgc ctggcctatg aattatacca ccacgtcttt atttatatgc aacttgcatc    600

atgctgtgtt gaaagcagct tcccagtcca gcacttgaaa atacttctca gataggtttt    660

catagcaatt aaaaaataaa cacaaaaccc gggaaagcta tgtctgtgta cccaaaagat    720

acctaagaac acagtagcat agagagcagg ctgagttgtc tcactcaagg atgtgagttc    780

agattcattg atctccctga ctgaaaacta tcacccattg attgaggcac tgtatatctt    840

atctcagaat gaaatgaatt cttaagtctc atgaattcta catgaatgaa tgaaagtgtt    900

tctgcaactt tcacttctct tgcagcccac caaaaacaat ggcattttct aataggaaaa    960

acacattgaa cgctgtatat gtgcgtatgt atatgtgtgt gtagtacata catatacttt   1020

attttgagac aggttctcac tctgttgcac agggtggagt gcagtggtgt gcacagccta   1080

ctgcagcctc aatttcccag gctcaagcaa tccccctgcc ttagtctccc aagtagctgg   1140

gaccacaggt gtgcaccatc acgcctggct ttttttggtt tcatatatat atgttgccta   1200

agctggtctc aaactcctga tctcaagcaa tcctcctgct ttggcctccc aaagtgctgg   1260

gactacagaa cacctacact tttatacatt ctatatgcat caaacaaaca tatgtctgtg   1320

acaagagagc agcctatcac agcccagaga cttcagaatg gggacaggtt ggaaggagga   1380

gctacctatc cctgagatga tgaagaggac cagtgcccat tccaggagac atcaccgcag   1440

ccctgaggaa tcggctatgg gcaccagcag ggcacagtgc cacacctcgc caatgccttg   1500

tcctcctttt ccatagtgag tcagtcagca agcgtcgcat tgccctggga tcggcactgc   1560

acgtagaagt gagttccaca ctctcttcct cccataggga gatcactttt ctcattctaa   1620
```

```
gggttccagg cacactcaca atggtggcat ttgctgagca gtggcttgaa taaagggctc   1680
tcagaaagca agatgtaact cagagcatag gcttgtcctc cagggcaccc agccccagga   1740
atgctcttgg ggaatgacct gcagcctccc agtgaaagag agaataaaag aaagccccag   1800
caggcgagct gggcagtaga gagtcctgta attccacctt ggcaagcacc atttgcaaga   1860
acgaactggg ataaggtaaa caaaatattg cctaaaagag gcttgtccaa agaagtcaga   1920
atacgctctt catttacctc taaattatgt ttcttaaata ccaagtaacc tgcagtaccc   1980
cctgccgcca ccaaaaaaaa agagagaaat acttttttttt ctcctatcca ctgcagaatc   2040
aattttacag tggttctgca gttaatcctt tcagtacacc ataaatctaa atactcaaaa   2100
aaacctgtgc cttttcaatt gctactaaat cacgagaaga ctgatttaca tagtctcctt   2160
ttatctccct tggcgggtaa gtactcagct ctgctcgtta ctaatattga aacaacagcc   2220
cttgaattga gtgatttccc tagaaaggtt aaggtgaccg aatctgaaca ctccctccat   2280
gtcttggaca cgaagttttt tgctgcgtag acagttttat cccctcacc ccaaggtcaa   2340
ttgcacgaat tcttttggaa aacaggacct atggcatttc ccagacaaat caccgtgaac   2400
cctgtactgt gcattgctgt cctaaaatta acacataaat ctattgccgc caaagattct   2460
gtcatttgtg ttacataatt gcctttcatt tgaactcatt aatcaaattg gggtttttaa   2520
gcaacaccta attaattctt taactggctc atattatacc tttaatgact tccaccaggg   2580
taaaaaccac tgatcactga gttctatttt gaaactacgg acgtcgagtt tcctctttca   2640
cccagaattt tcagatcttg tttaaaaagt tgggtgtggt ttcatggggg gagggggaag   2700
agcgagagga gaccagaggg acgggggcgg ggactctgca agaaaaacct tcccggtgca   2760
atcgtgatct gggaggccca cgtatggcgc ctctccaaag gctgcagaag tttcttgcta   2820
acaaaaagtc cgcacattcg agcaaagaca ggctttagcg agttattaaa aacttagggg   2880
cgctcttgtc ccccacaggg cccgaccgca cacagcaagg cgatggccca gctgtaagtt   2940
ggtagcactg agaactagca gcgcgcgcgg agcccgctga gacttgaatc aatctggtct   3000
aacggtttcc cctaaaccgc taggagccct caatcggcgg gacagcaggg cgcggtgagt   3060
caccgccggt gactaagcga ccccacccct ctccctcggg ctttcctctg ccaccgccgt   3120
ctcgcaactc ccgccgtccg aagctggact gagcccgtta ggtccctcga cagaacctcc   3180
cctcccccca acatctctcc gccaaggcaa gtcgatggac agaggcgcgg gccggagcag   3240
ccccccttc caagcgggcg gcgcgcgagg ctgcggcgag gcctgagccc tgcgttcctg   3300
cgctgtgcgc gcccccaccc cgcgttccaa tctcaggcgc tctttgtttc tttctccgcg   3360
acttcagatc tgagggattc cttactcttt cctcttcccg ctcctttgcc cgcgggtctc   3420
cccgcctgac cgcagccccg agaccgccgc gcacctcctc ccacgcccct ttggcgtggt   3480
gccaccggac ccctctggtt cagtcccagg cggacccccc cctcaccgcg cgaccccgcc   3540
tttttcagca ccccagggtg agcccagctc agactatcat ccggaaagcc cccaaaagtc   3600
ccagcccagc gctgaagtaa cgggaccatg cccagtccca ggccccggag caggaaggct   3660
cgagggcgcc cccaccccac ccgcccaccc tccccgcttc tcgctaggtc cctattggct   3720
ggcgcgctcc gcggctggga tggcagtggg aggggaccct ctttcctaac ggggttataa   3780
aaacagcgcc ctcggcgggg tccagtcctc tgccactctc gctccgaggt ccccgcgcca   3840
gagacgcagc cgcgctccca ccacccacac ccaccgcgcc ctcgttcgcc tcttctccgg   3900
gagccagtcc gcgccaccgc cgccgcccag gccatcgcca ccctccgcag ccatgtccac   3960
caggtccgtg tcctcgtcct cctaccgcag gatgttcggc ggcccgggca ccgcgagccg   4020
```

```
gccgagctcc agccggagct acgtgactac gtccacccgc acctacagcc tgggcagcgc    4080
gctgcgcccc agcaccagcc gcagcctcta cgcctcgtcc ccgggcggcg tgtatgccac    4140
gcgctcctct gccgtgcgcc tgcggagcag cgtgcccggg gtgcggctcc tgcaggactc    4200
ggtggacttc tcgctggccg acgccatcaa caccgagttc aagaacaccc gcaccaacga    4260
gaaggtggag ctgcaggagc tgaatgaccg cttcgccaac tacatcgaca aggtgcgctt    4320
cctggagcag cagaataaga tcctgctggc cgagctcgag cagctcaagg gccaaggcaa    4380
gtcgcgcctg gggagacctct acgaggagga gatgcgggag ctgcgccggc aggtggacca    4440
gctaaccaac gacaaagccc gcgtcgaggt ggagcgcgac aacctggccg aggacatcat    4500
gcgcctccgg gagaagtaag gctgcgccca tgcaagtagc tgggcctcgg gagggggctg    4560
gagggagagg ggaacgcccc cccggccccc gcgagagctg ccacgccctt ggggatgtgg    4620
ccgggggggag gcctgccagg gagacagcgg agagcggggc tgtggctgtg gtggcgcagc    4680
cccgcccaga acccagacct tgcagttcgc atttcctcct ctgtccccac acattgccca    4740
aggacgctcc gtttcaagtt acagatttct taaaactacc actttgtgtg cagttgaagg    4800
cccttgggca caatgagagc cagtcctcca aactttcaga aagtttcctg ccccttctgg    4860
caggctgcca atcaccgggc gggagaagga aggaggggaa ggcggtggag ggagcgagac    4920
aaagggatgg tccctcgggg gcggggatgg cggggctgtc ctgtaggtct gtgcggccac    4980
cgtgattgcc cctctgcgcg gtgcccgaag tcccgctgaa acctgccgag ggcagcaggt    5040
ctgaaagctg caggcgctag ttgcgcggag gtggcgcagc tgctctggag gcgcagagcg    5100
aatacgtggt gtttgggtgt ggccgccccg cccctggcgg tttcctcgtt cccctttggt    5160
taatgcgcaa ctgtttcaga ttgcaggagg agatgcttca gagagaggaa gccgaaaaca    5220
ccctgcaatc tttcagacag gtttgtagac tctcttccca ctcgcagccg cctgacccca    5280
cccaacacaa cccacgagca attctaaaag ttgcttaact cacgtctaaa aagtgcaaaa    5340
cttcagggct gcgcgtaaag ccctctagtg gcgggaagac cacaggttgg agcttctcat    5400
gattagaaaa atattaataa aacccccttga gcgatttttt tttttttttt gagacggagt    5460
cttactctgt cgcccaggct ggagtgcagt ggcgagatct tggctcactg catcctccgc    5520
ctcccgggtt caagcgatcc ttgaatgatt tctaagcagt tccttgggac ataaagaaaa    5580
atcttttaac tttttacttt gtttcccaaa tgttgcacag ttttgcaaca cattgacctt    5640
ctggtttcga acggttacaa ttttagattg tggtttgcca aagtcaagtt gcttaatttt    5700
tacaaggcca caaaaagcgc aattatgccc tgcagtttaa aatggaaaac gtgttggaag    5760
ataagaaaac ttagtttcca actggaatgg agccagcaag tttcttttct tctttgcaaa    5820
ttctattgtg tcattaaagt tcgatggaag tatcactatg cacaactatt ttgtgatcta    5880
ataagggtga aaaggagcca tctgtcccct tggctaaggg gtattaatgg tttctatggg    5940
cttcactatg gaatgtagat acagacattc tggcaaatgt ggtggctctg gacagaaata    6000
ataggagtct ttgtattccc agggaagctt tgcaacaggc tacattctta ctgaatatgt    6060
aatgatgtaa gcacggttct aattggacac aagtatttgc taacatccgt tatctaatat    6120
ctggcccaga cttgagaagt aggtaatgta aaaagttttt aaagctacaa gcatacctca    6180
cattttaaaa gtcctttctt gattgggttc ttgtgttctt tagcactctt gccataaaaa    6240
ataataacag taataaaccc aaggctgaaa aactgaattt taactaaagg gtttttgtgc    6300
gtgttttttt ttttttcac caaaattaga tggacttaca gaatttttaa cttaaaattg    6360
```

-continued

```
gaatccaaaa gccagaagat ccccattata gtttatagtt gtattccctg gaatatttac   6420
tgggattaac tgcaaagcac tctcagatga atagtgtagt ataacatttt gaaactgaaa   6480
tacatttacc aaattaattt aaccacagca atgtgtgtgg ttcattttag tccttgagca   6540
tttttgatta tcatacctgt catgttttct gcagtgtagt gagttaacat aaaacaacat   6600
caatacaaaa gatcctctgt ttcgagatta agcaaaattc ctcattctct tcaatgtgat   6660
agaataccac attgatcttt ctttggaggt tagtaaaata tcttttatgt atttttcagg   6720
gcttaacaag taaaaatcaa tgttttcatc aagtctgatc tttttgtcac ccactcttca   6780
ttcatttttc cactaaggtg atagaaaagt ctcaacagtt taagaccgta aggctatgaa   6840
ctccaaatat aattgctgac aagataagca atcctcacgc atccttttga gaggaaataa   6900
aatcttagtt gcaagattac atattctgat ttggaatgct gagcttttta aatggaaata   6960
tagaaggacg gctgaatcag caaaaatcct ttatgtagtt tcattctttg caagcttgac   7020
cagtcattct gaaacaggct aactgaactg atacagtggc aagtgaaaaa gacatgcctt   7080
tacaggatga gtcaaaggag ttttagaaga aaaatccacc agagaaagcc aagcaaatac   7140
agttcagagt tacatttctt ttccattttt tcctgaactg aatctttggc atgcatatcc   7200
tgaattgggt tattgaatat aaatctagcc ttgtacaatg gatgccagat gactacatat   7260
ttgctttgga gcctaaggat aagtttcaaa agatttgagt ggagaagaaa agctaaaact   7320
cttgaagcac aagtttctgt tctccatgta ctcaagtgta catgaagttg tgaaaatttg   7380
tccacctcta tcatcatgtt attccatgaa attacaaaac aaatcttaaa aatgttgtgg   7440
catagatttt ctagatttaa aaagtaatta aattaaatga attactttat tttttgagac   7500
agagtgtcac tctgttgccc aggctggagt gcagtggcac tatgttggct cactgcaacc   7560
tctgcctcct gggttgaaga aattctcctg cctcaacctc ccaagtagct gggactacag   7620
gcatgtgcca ccacacccag ctaatttttg tatttttggt agagacgggg tttcgccatg   7680
ttggctaggc tggtctcgaa ctcctgacct caagtgatcc acccgtctca gcctcccaaa   7740
gtgctgggat tacaggcata agccaccatg accagcctta aaaagtaatt ttaaaatatc   7800
actggtaaaa tgtggattca gtcatgattg agtgcagttt accatgtgtg tggacattta   7860
tttattttaa aattgtctga tcaccacctt gagtaaaaca caagcagtca caattaaaat   7920
atattagtga gcaggagaaa gcacagcata ttatagcact gaatgattta taaacctatt   7980
ccagggtcat aaaatgtgtc aacggctttt ctatagtaag gagactaggt tcagatggtt   8040
aatctaagac aaataaatga gataagccat acacttttac atcctccatg tcctgtcttt   8100
tctctgttca aaataggatg ttgacaatgc gtctctggca cgtcttgacc ttgaacgcaa   8160
agtggaatct ttgcaagaag agattgcctt tttgaagaaa ctccacgaag aggttagtgg   8220
agtgactttc ggggaatgaa tgagggtaag gcagccccca cggttggcag agctgaccgt   8280
ctgtctgttc tttttgcagg aaatccagga gctgcaggct cagattcagg aacagcatgt   8340
ccaaatcgat gtggatgttt ccaagcctga cctcacggct gccctgcgtg acgtacgtca   8400
gcaatatgaa agtgtggctg ccaagaacct gcaggaggca gaagaatggt acaaatccaa   8460
ggtaggaaac aaatcagtgc ggcttcaacc aaagaaaagc attgtgttct caaaacccca   8520
tacctgtgtg tgattcctaa atatcctcta gctccaatgc aaagctggct ttgacttctt   8580
gctcatattg tgtttgccac cacagcctcc ccaccactca catcacctcc tttatttatt   8640
tatttatttt cttatttatt tatgagacag agtcttgctc tactgcccag gctggagtgc   8700
agtggcaaca tcttggcaca ctgcaacctc cgcctcccag gttcaagtga ttctcctgcc   8760
```

```
tcagccccct aagagctgga accacaggca agcaccacca tgcccggcta atttttgtat   8820
```

ttttagtaga gatggggttt caccatgttg accaggcttc tctcaaactc ctgacctcag 8880
gtgatccacc ctcctcagcc tcccaaaatg ttgggattac aggcatgcgc caccacgcct 8940
ggccacatca cctccttcag aatagcagac tctcttcccc ctaaccttgc ctccaagtaa 9000
accccaatgc catacctttg acctccactg tgttgaaatg agcactgtag agtgaactct 9060
gaaaatacta atgtcagtac tccactgctc tttccctggc tttcaaaaca gaaatttaaa 9120
cctatactgg aagacattca gtgagaaata tgattttttt tttctaagag agtcaaaaga 9180
cttgaatgtg agcaatctac atttctgttt tcttcccaac agtttgctga cctctctgag 9240
gctgccaacc ggaacaatga cgccctgcgc caggcaaagc aggagtccac tgagtaccgg 9300
agacaggtgc agtccctcac ctgtgaagtg gatgccctta aggaaccgt gagtaccaac 9360 cctgcagtaa aagagggaaa ataatgaccc attctgctga ctaggctcat gatgatacct 9420
gaacaaaatg ttgagtgagt aaaaatgtat atcataatgc aaagaaaatg agttatcaag 9480
acagactcaa aagggacttc atggaactct tgaaggtttt agcttgccta tatcattgct 9540
tctaatatga aggacttggt actcgcattc tccacctaaa attagagtgg tcgccatttg 9600
ccgctaatgg aaattattgc agaaggtctg taaatggttc tgggaacagc tgggtttttc 9660
tgagaaataa caccagacat ctttctcacc ccctgcagaa tgagtccctg gaacgccaga 9720
tgcgtgaaat ggaagagaac tttgccgttg aagctgctaa ctaccaagac actattggcc 9780
gcctgcagga tgagattcag aatatgaagg aggaaatggc tcgtcacctt cgtgaatacc 9840
aagacctgct caatgttaag atggcccttg acattgagat tgccacctac aggaagctgc 9900
tggaaggcga ggagagcagg tagggaactc agacttggat gcgtgaacta atggtgacca 9960
tttgttaggc cctgtgccac tggctctaa gcagtgtcac atttaatctt tagaaagttt 10020
ctttgaggta actgctttcc actttttgta gaggaggaat ttgaattgag agagagtaag 10080
tgacttgctg aaaaagggtt aatcaacagc agagctggga tttgaaccca taactctgtc 10140
aaagcctcca ctcctaactc ctgttcatgc tcctgtggag aaaatgcttg tagtaacata 10200
ttttaaatgt actaacaaga ccagtcatgg gaaaatgttt ctgagacaaa tctctagttt 10260
atgatttaaa acagtacgtt ttcttacgtg acgaaaacaa aaagtgtgtt aatttgttcc 10320
cagtggttga agttatttgc caacaatttt actgtttctc ttcatctgtt tataggattt 10380
ctctgcctct tccaaacttt tcctccctga acctgagggg taagcatttt atttcccttt 10440
aggaaaaacg tcagctgctt gtaaccactg tgtttatgtc aaagcattca tttttttag 10500 gatatctgaa aaaatgccat ataagagaaa actctataaa acatctataa ttttcgaacc 10560
caagtacact cttgcattct atgctttaag ttaaatgcaa actccttttt ccttcttcct 10620
gctgcaagta ctatctcatc ctgatgctca agagtgtcag ggcctgggtt tccaaacaga 10680
gactacccta aaattatttg gcgagtagta ctttacacaa ttgcctctcc cccacaaatc 10740
ataattgttt cagtaaaatg gttacttggt ttttccaaga aaaaactcgt ttttactcat 10800
ttttggcctg tttgtttatt tagaaactaa tctggattca ctccctctgg ttgataccca 10860
ctcaaaaagg acacttctga ttaagacggt tgaaactaga gatggacagg ttggtatctt 10920
ttaaggaaaa aatagggtaa tctcagacag gagttgatat attttaaaat cagtgaatct 10980
gaatctcaga tacagctggc taatttgaga ggttcaggtt tcattcatgc ctactaaaaa 11040
aagaataggc ttcttcttcc agcagtacac acagccaact aattatttgg ctcctggatg 11100

```
tgaagttgag atagcagtct tcctgtgctc cagaattagt gatttgcttt ggtgcttaat  11160
ttgaagtggg agtaagcttc cttaaaccac ttcctaaagc agctacatga aacagcttca  11220
ctagactacc tcaatatgag gaatgttttg atcctggaca tatggtgtct tcctacctcc  11280
atactttata gattcctaaa cccatctata taatacaagc atgtgccata cgatcattta  11340
gtttcttatt acctccctat gccaggaaag aaatagttgc aatttattgt agtcatcatg  11400
aaatcttccc ttgcacataa atttaaaatg tacctgctgc acattttaat atgtcttaat  11460
tgcttttaaa cttggctgta ttgtgtacaa ctattatacc atcttttata aacacagttt  11520
tttaagaaat ttctttttgt aagttacaac attccactgg atccttatat tgcctgtagt  11580
ggaagagggt cttgtgtgtc tgccccttct agttttcact catgcagaag caacataacc  11640
ttctgatttg cacaataaat tacatatatt tagcaggatt tttatttgcc gtgatatata  11700
ggataattta gtctttggca tgtggcatta tatttatttt ggtttttttt tttaaacagg  11760
ttatcaacga aacttctcag catcacgatg accttgaata aaaattgcac acactcagtg  11820
cagcaatata ttaccagcaa gaataaaaaa gaaatccata tcttaaagaa acagctttca  11880
agtgcctttc tgcagttttt caggagcgca agatagattt ggaataggaa taagctctag  11940
ttcttaacaa ccgacactcc tacaagattt agaaaaaagt ttacaacata atctagttta  12000
cagaaaaatc ttgtgctaga atacttttta aaaggtattt tgaataccat taaaactgct  12060
ttttttttc cagcaagtat ccaaccaact tggttctgct tcaataaatc tttggaaaaa  12120
ctcttttgtt gtgttattta ttggataata tctaaacaat tctctacttg gtcctattag  12180
ttaatttgtc attacaatca tgtaagttga taaattcagg ttatttatgc ttgagatgta  12240
gttcttaatt ttgtcatttt tgatagacct cacttctttt tattattact taaaaacatt  12300
tacaaatagg tggtgtcgaa taaaataact tgtaccaaaa tgaagatagg tctctctaaa  12360
atgagctcag gtctgtgatt ttaatcataa caaacagact tcctaaaatt aaaaaataaa  12420
aacttttttt agtacatata gcatatgagt aacacaaatt ccactttggg agttaaagca  12480
taggaagttg ccaagatata ggggcttatc ttccgctagc aagatgcaga gaaatggaaa  12540
aagttcacca agtttttctt ttatttaaga caggatctca ctttgtcact caagctggag  12600
taaagtgact caatcatagt tcactgcagc caacaactcc taggctcagg caatcctccc  12660
acctcagcct cctcagtagc taggagtact caaaacaaat aaacgaatgt ctaactttag  12720
cctaaaatgt gagttgtctt cccaaaacta gccacacacc tggctaattt ttttaatttt  12780
ttgtagagat ggggtctgga agtgttgtcc agcctagtct ggaactcttg tgctcaagtg  12840
atcctccctc ggcctcctaa aaagctggga ttacaggcat gagccaccac actcagccta  12900
gttcaccaag atttaatata tgaaaccgtt ctgctttatt gtgtgtgtgt gtgatagcta  12960
tatctatatc catctatcta tagatacaga tatttgtaaa gacctttgtg tttggagaat  13020
ggcattaggc acaaaataaa acctcctacc ttttcttcca gggagatgag attattacat  13080
gtgaatcgca tggtgctaac tgtaggtgta ataaggtttc aaagtctgga gcaataaaaa  13140
tgaagtgggg cagtcatgga aagctcccta gaaagcactc agtgtgagca tagaacttac  13200
ataaatagac gagagaaggt attgccaaga ggcaatagtg tagtaatggt caataatgtg  13260
tgttctggag tgaaaacttc gagtacattc tcggacatct ctaagtttca aattatggaa  13320
atattattat cttctctcct ccgagaatga tgtggtagac attgtcataa tttttctgtg  13380
tttgcatctg cctctctctg gagttaacta gtgagatggt tctcacaaag ccctgcccat  13440
ttgcaggaat gttcactgtg attttcatca ttttggttac cgtgggtact gcatgaataa  13500
```

```
agaaaggatt ggggctggat gcagtggctc atgcctgtaa tatcagcact ttgggaggct  13560
gaggcgggtg gatcacttga agtcaggagt tccggactag cctggccaac acggcgaaat  13620
cctgtctcca caaaaaatac aaaaattagc cagccgtggt ggtggatgcc tataacccca  13680
gctactctgg aggcagaggc agtagaattg cttcagcttg gaaggtagag gtttcagtga  13740
gccaagactg taccactaaa ctccagcctg agtgacagag cgagatcctg tcttagaaat  13800
aaagaaaaaa aggattggct gctgaagtaa ctcctagcca ttctaaaggt aaattctaaa  13860
tgtaaaagta aactttacat tctagtttac ttgggacatt cttggtttat gactgttgtg  13920
taagcataat tattaataat aacagtttgg acaatagatt gtatgtggtc aggtcatgct  13980
acccttagaa taatcttaca gaaaatgtgt ctgtcccctc agcccccata ttcaaacaac  14040
tgacatggac aatggcataa ttaattttat tagtgtaaac atccaggtct ttgggccctt  14100
atgaaacctt ttctatttga tttttcgttt tgctttctgt tctttagcca ttctcaccac  14160
tgttccccgc agcctcctaa ccctaggatc cctgtctcct cttccacttg tatcccacct  14220
ttggcttata agggtcatcc agggaagacc ccagccccat attggctttc ttcacacacc  14280
agactcatta ttattttttt aaaaattgaa aaacaagcca cagttttctt tcaggggaaa  14340
agaaccagga cagcaagttc tgctcatacc tattgagatt agtagactcc cactcttaaa  14400
aatcctttac agatggaggc caggcatggt gaccaaggtg ggtggatccc ctgaggtcag  14460
gagtccaaga ccagcctggc caataaggcg aaaccccgtc tctactaaag acacaaaaac  14520
tagccagggg tggtggtgca cacctgtaat ctcaactact cgggaggctg aggcacgaga  14580
attgcttgaa cccaggagat ggaggttgca gtgagccgag attgtgccac tgcactccag  14640
cctgggcaac agagtgagac tctgtctcag aaaaagaaaa aatatccttt acagatggaa  14700
acaacagaca ctgggcactt caaaaaggag gaggttggga ggagggcaag ggttgaaaaa  14760
ccacctgttg agtacttggg tgatgggttc aatagaagcc caagctctag cattacgcaa  14820
tatatctatg taacaaacct gcacatatac cccctgaatc tcaattaaaa aaaaaaatat  14880
cttacagctc tttctaaagt cacatcccag aaatggaaaa gaggagtggg cctcccttat  14940
ctgtgactgt cagaaattag accataatga aaagcttcac aggtgcccca tctccgaaga  15000
attcaaattt atttcagtct tcttctattt tatctttaat tatactgtta gtgtttttcc  15060
ttatcttcca ctttgaaaaa tttataaaaa gaaattatgt tctcaccacc tatggtgaaa  15120
gag                                                                15123
```

<210> SEQ ID NO 62
<211> LENGTH: 3053
<212> TYPE: DNA
<213> ORGANISM: Homo sapiens

<400> SEQUENCE: 62

```
gagcgcggct ggagtttgct gctgccgctg tgcagtttgt tcaggggctt gtggtggtga     60
gtccgagagg ctgcgtgtga gagacgtgag aaggatcctg cactgaggag gtggaaagaa    120
gaggattgct cgaggaggcc tggggtctgt gaggcagcgg agctgggtga aggctgcggg    180
ttccggcgag gcctgagctg tgctgtcgtc atgcctcaaa cccgatccca ggcacaggct    240
acaatcagtt ttccaaaaag gaagctgtct cgggcattga acaaagctaa aaactccagt    300
gatgccaaac tagaaccaac aaatgtccaa accgtaacct gttctcctcg tgtaaaagcc    360
ctgcctctca gccccaggaa acgtctgggc gatgacaacc tatgcaacac tccccattta    420
```

```
cctccttgtt ctccaccaaa gcaaggcaag aaagagaatg gtccccctca ctcacataca    480
cttaagggac gaagattggt atttgacaat cagctgacaa ttaagtctcc tagcaaaaga    540
gaactagcca aagttcacca aaacaaaata ctttcttcag ttagaaaaag tcaagagatc    600
acaacaaatt ctgagcagag atgtccactg aagaaagaat ctgcatgtgt gagactattc    660
aagcaagaag gcacttgcta ccagcaagca aagctggtcc tgaacacagc tgtcccagat    720
cggctgcctg ccagggaaag ggagatggat gtcatcagga atttcttgag ggaacacatc    780
tgtgggaaaa aagctggaag cctttacctt tctggtgctc ctggaactgg aaaaactgcc    840
tgcttaagcc ggattctgca agacctcaag aaggaactga aaggctttaa aactatcatg    900
ctgaattgca tgtccttgag gactgcccag gctgtattcc cagctattgc tcaggagatt    960
tgtcaggaag aggtatccag gccagctggg aaggacatga tgaggaaatt ggaaaaacat   1020
atgactgcag agaagggccc catgattgtg ttggtattgg acgagatgga tcaactggac   1080
agcaaaggcc aggatgtatt gtacacgcta tttgaatggc catggctaag caattctcac   1140
ttggtgctga ttggtattgc taataccctg gatctcacag atagaattct acctaggctt   1200
caagctagag aaaaatgtaa gccacagctg ttgaacttcc caccttatac cagaaatcag   1260
atagtcacta ttttgcaaga tcgacttaat caggtatcta gagatcaggt tctggacaat   1320
gctgcagttc aattctgtgc ccgcaaagtc tctgctgttt caggagatgt tcgcaaagca   1380
ctggatgttt gcaggagagc tattgaaatt gtagagtcag atgtcaaaag ccagactatt   1440
ctcaaaccac tgtctgaatg taaatcacct tctgagcctc tgattcccaa gagggttggt   1500
cttattcaca tatcccaagt catctcagaa gttgatggta acaggatgac cttgagccaa   1560
gaaggagcac aagattcctt ccctcttcag cagaagatct tggtttgctc tttgatgctc   1620
ttgatcaggc agttgaaaat caaagaggtc actctgggga agttatatga agcctacagt   1680
aaagtctgtc gcaaacagca ggtggcggct gtggaccagt cagagtgttt gtcactttca   1740
gggctcttgg aagccagggg cattttagga ttaaagagaa acaaggaaac ccgtttgaca   1800
aaggtgtttt tcaagattga agagaaagaa atagaacatg ctctgaaaga taaagcttta   1860
attggaaata tcttagctac tggattgcct taaattcttc tcttacaccc cacccgaaag   1920
tattcagctg gcatttagag agctacagtc ttcattttag tgctttacac attcgggcct   1980
gaaaacaaat atgacctttt ttacttgaag ccaatgaatt ttaatctata gattctttaa   2040
tattagcaca gaataatatc tttgggtctt actattttta cccataaaag tgaccaggta   2100
gacccttttt aattacattc actacttcta ccacttgtgt atctctagcc aatgtgcttg   2160
caagtgtaca gatctgtgta gaggaatgtg tgtatattta cctcttcgtt tgctcaaaca   2220
tgagtgggta tttttttgtt tgtttttttt gttgttgttg tttttgaggc gcgtctcacc   2280
ctgttgccca ggctggagtg caatggcgcg ttctctgctc actacagcac ccgcttccca   2340
ggttgaagtg attctcttgc ctcagcctcc cgagtagctg ggattacagg tgcccaccac   2400
cgcgcccagc taatttttta atttttagta gagacagggt tttaccatgt tggccaggct   2460
ggtcttgaac tcctgaccct caagtgatct gcccaccttg gcctccctaa gtgctgggat   2520
tataggcgtg agccaccatg ctcagccatt aaggtatttt gttaagaact ttaagtttag   2580
ggtaagaaga atgaaaatga tccagaaaaa tgcaagcaag tccacatgga gatttggagg   2640
acactggtta aagaatttat ttctttgtat agtatactat gttcatggtg cagatactac   2700
aacattgtgg cattttagac tcgttgagtt tcttgggcac tcccaagggc gttggggtca   2760
taaggagact ataactctac agattgtgaa tatatttatt ttcaagttgc attctttgtc   2820
```

```
tttttaagca atcagatttc aagagagctc aagctttcag aagtcaatgt gaaaattcct   2880

tcctaggctg tcccacagtc tttgctgccc ttagatgaag ccacttgttt caagatgact   2940

actttggggt tgggttttca tctaaacaca tttttccagt cttattagat aaattagtcc   3000

atatggttgg ttaatcaaga gccttctggg tttggtttgg tggcattaaa tgg          3053


<210> SEQ ID NO 63
<211> LENGTH: 1937
<212> TYPE: DNA
<213> ORGANISM: Homo sapiens

<400> SEQUENCE: 63

gtacctcacg gaagccggct ttggccctgc ggctgctacc gtcgccgcgg agaaattgtt     60

ggatctggca gtctaggaat gaatctcctc tcagccttta agctcacctg gtcagaatcc    120

ttggatgagc ctgtgggacc gttcctccta gcccggtggt ttggaaccag tggctttggg    180

actgtaagag gatggacaaa gattctcagg ggctgctaga ttcatccctg atggcatcag    240

gcactgccag ccgctcagag gatgaggagt cactggcagg gcagaagcga gcctcctccc    300

aggccttggg caccatccct aaacggagaa gctcctccag gttcatcaag aggaagaagt    360

tcgatgatga gctggtggag agcagcctgg caaaatcttc tacccgggca aaggggggcca    420

gtggggtgga accagggcgc tgttcgggga gtgaaccctc ctccagtgag aagaagaagg    480

tatccaaagc cccagcact cctgtgccac ccagcccagc cccagcccct ggactcacca     540

agcgtgtgaa gaagagtaaa cagccacttc aggtgaccaa ggatctgggc cgctggaagc    600

ctgcagatga cctcctgctc ataaatgctg tgttgcagac caacgacctg acctccgtcc    660

acctgggcgt gaaattcagc tgccgcttca cccttcggga ggtccaggag cgttggtacg    720

ccctgctcta cgatcctgtc atctccaagt tggcctgtca ggccatgagg cagctgcacc    780

cagaggctat tgcagccatc cagagcaagg ccctgtttag caaggctgag gagcagctgc    840

tgagcaaagt gggatcgacc agccagccca ccttggagac cttccaggac ctgctgcaca    900

gacaccctga tgccttctac ctggcccgta ccgcgaaggc cctgcaggcc cactggcagc    960

tcatgaagca gtattacctg ctggaggacc agacagtgca gccgctgccc aaaggggacc   1020

aagtgctgaa cttctctgat gcagaggacc tgattgatga cagtaagctc aaggacatgc   1080

gagatgaggt cctggaacat gagctgatgg tggctgaccg gcgccagaag cgagagattc   1140

ggcagctgga acaggaactg cataagtggc aggtgctagt ggacagcatc acaggcatga   1200

gctctccgga cttcgacaac cagacactgg cagtgctgcg ggccgcatg gtgcggtacc    1260

tgatgcgctc gcgtgagatc accctgggca gagcaaccaa ggataaccag attgatgtgg   1320

acctgtctct ggagggtccg gcctggaaga tatcccggaa acaaggtgtc atcaagctga   1380

agaacaacgg tgatttcttc attgccaatg agggtcgacg gcccatctac atcgatggac   1440

ggccggtgct ctgtggctcc aaatggcgcc tcagcaacaa ctctgtggtg gagatcgcca   1500

gcctgcgatt cgtcttcctt atcaaccagg acctcattgc cctcatcagg gctgaggctg   1560

ccaagatcac accacagtga ggagtggtgg caggactcgt gggccctctc cggcctgttt   1620

cccctgccac tccagccccc ttgagctggg aactcaggct cctggaaaaa cctgggcagt   1680

gggaggctca gctgcgggcc attgatttga gcctttgagg gaggataggg ctggcctttg   1740

tgaagccagc agaggctgag aacctcaggc ttccctagat ccagagcccc tccccatctt   1800

cctctctcta aaaacaaccc taccccccat tgccaccttc actcctgtgt ctccagctga   1860
```

ttagcctcag actcttcttt tattgttttt cttttgtaaa taaaaagcac caggttccaa 1920
aaaaaaaaaa aaaaaaa 1937

<210> SEQ ID NO 64
<211> LENGTH: 1583
<212> TYPE: DNA
<213> ORGANISM: Homo sapiens

<400> SEQUENCE: 64
gatagttttt tttttttttt ttttgaccaa tgaaagcgca gatttattga ggggaaagta 60
cactccacag aagtggaatg taggtgtggg agcaggcgac caagcggctc aagaaccccg 120
attacaatgt tttttagggt tttattaggt tggtgcaaaa gtaattgcgg tttttgccat 180
gaataagcta gaattttata ataccccaag agttctttaa aggcctccaa tcctatgaag 240
gactggtgca caaccaatca gaggctgaag tggagacttc tgtcttgtta ccacaggagt 300
gaggacgtgg cctgtgtgct gcctcatctt gcctagaact agctgcacct gctgttcttt 360
tgcttatgcc ttcattcttg gttaccctaa ttccctattc tcctgcctca ctctgaggca 420
ttagagttgg tttttcagtc tgccagggac aaaagagaac taatccagat aggaccatgc 480
caaggaagat agaggagagg ctaaagaaag agtacaaagg tcaatcagtc gttcccatgg 540
aaaaacaact ctcctgctta tatagtcaat tattgtgtcc aattcattca gcaaaacatt 600
tattcatgta atatccctta cttggtattc taacttatat tttcaactca ttttaggaac 660
ttgaagtcag tctcaggtaa agaacaatga aagagaaatc tcagcttggt attggtaatg 720
gtggtgataa tctccacctg gagacactag gcgtatgtta aattatcgag cttgttatct 780
ttcctgggaa gtgattatca tttgtttctc ttgtgacagc ggggagtgtt ctgcatgagg 840
aactaatatg ataccagaaa aacaggtgaa atgccagtta cagaaactta ttaccaacga 900
ctatctaata actgcgatga cagaaatagg tcaattgaac catgagtgga tggtgaaaaa 960
aatttacact tcacagaagt tttctttct tttttttttt ttttttttt gagacaaagt 1020 ctcgttctgt cccagactgg agcactattc acaatagcca aaatatggaa tcaacctaga 1080
tgtccaacaa cagataaatg gataaagaaa atgtggttta tacacacaaa ggaatactat 1140
tcaaagacca gaatgaaatc ctatcacctg aggcaacatg gatggaaatg gaggacatta 1200
tttaagtgaa ataagccagg aacataaaca tgcacattcc cactcatatg tggaagcttt 1260
aaaaaaaaaa aaaaaagctg ggtgcggtgg ctcacgcctg caatcccagc accctgggag 1320
gctgaggcgg gtggatcacc tgaggtcggg agttcaagac cagcccgacc aacatggaga 1380
aaccctgtct ccaccaaaaa cacaaaatta gccggggtgg tggtgcatgc ctgtaatccc 1440
agctactcag gaggccgagg caggagaacc gcttgaaccc aggaggcaga ggctgcggtg 1500
agccaagatc atgccactgc actccagcct gggcaaaaag agcgaaactc catctcaaaa 1560
aaaaaaaaaa aaaaaaaaaa aaa 1583

<210> SEQ ID NO 65
<211> LENGTH: 2483
<212> TYPE: DNA
<213> ORGANISM: Homo sapiens

<400> SEQUENCE: 65
actccccgcg cgcatccgtg cgccgcccga ggctgtctaa ggagtcggcg gccattttgt 60
tcttctcgtg gttccagtgg ggagagaagg aggaagtagg gagcggggtg gcaggggggg 120
gacccgccgc ggctgctgcc accgccgcca ccaccgcctc tgctcgtggc gtgggaaagg 180

```
aggtgtgagt cccgggcgcg agccggcggc ggcgccgctg cgggagggtc ggcggtggga    240
aggcgatggc ggatttagat aaactcaaca tcgacagcat tatccaacgg ctgctggaag    300
tgagagggtc caagcctggt aagaatgtcc agcttcagga gaatgaaatc agaggactgt    360
gcttaaagtc tcgtgaaatc tttctcagtc agcctatcct actagaactt gaagcaccac    420
tcaaaatatg tggtgacatc catggacaat actatgattt gctgcgactt tttgagtacg    480
gtggtttccc accagaaagc aactacctgt ttcttgggga ctatgtggac aggggaaagc    540
agtcattgga gacgatctgc ctcttactgg cctacaaaat aaaatatcct gagaattttt    600
ttcttctcag agggaaccat gaatgtgcca gcatcaacag aatttatgga ttttatgatg    660
aatgtaaaag aagatacaac attaaactat ggaaaacttt cacagactgt tttaactgtt    720
taccgatagc agccatcgtg gatgagaaga tattctgctg tcatggaggt ttatcaccag    780
atcttcaatc tatggagcag attcggcgaa ttatgcgacc aactgatgta ccagatcaag    840
gtcttctttg tgatcttttg tggtctgacc ccgataaaga tgtcttaggc tggggtgaaa    900
atgacagagg agtgtccttc acatttggtg cagaagtggt tgcaaaattt ctccataagc    960
atgatttgga tcttatatgt agagcccatc aggtggttga agatggatat gaattttttg   1020
caaagaggca gttggtcact ctgttttctg cgcccaatta ttgcggagag tttgacaatg   1080
caggtgccat gatgagtgtg gatgaaacac taatgtgttc ttttcagatt ttaaagcctg   1140
cagagaaaaa gaagccaaat gccacgagac ctgtaacgcc tccaaggggt atgatcacaa   1200
agcaagcaaa gaaatagatg tcgttttgac actgcctagt cgggacttgt aacatagagt   1260
atataacctt catttttaag actgtaatgt gtactggtca gcttgctcag atagatctgt   1320
gtttgtgggg gcccttcctt ccatttttga tttagtgaat ggcatttgct ggttataaca   1380
gcaaatgaaa gactcttcac tccaaaaaga aaagtgtttt gttttttaat tctctgttcc   1440
ttttgcaaac aattttaatg atggtgttaa agctgtacac cccaggacag tttatcctgt   1500
ctgaggagta agtgtacaat tgatcttttt taattcagta caacccataa tcatgtaaat   1560
gctcattttc tttaggacat aaagagagcc ctagggtgct ctgaatctgt acatgttctt   1620
gtcataaaat gcatactgtt gatacaaacc actgtgaaca tttttattt gagaattttg    1680
tttcaaaggg attgcttttt cctctcattg tcttgttatg tacaaactag tttttatagc   1740
tatcaacatt aggagtaact ttcaaccttg ccagcatcac tggtatgatg tatatttaat   1800
taaagcacac ttttccccga ccgtatactt aaaatgacaa agccattctt ttaaatattt   1860
gtgactcttt cctaaagcca aagtttctgt tgaattatgt tttgacacac ccctaagtac   1920
aaggtggtat ggttgtatac acatgctgcc ttcttgggga ttcaaaaaca ggtttttgat   1980
tttgaatagc aattagtgat atagtgctgt ttaagctact aacgataaaa ggtaataaca   2040
ttttatacaa tttccatata gtctattcat taagtaatct ttttacagtt gcatcaggcc   2100
tgaacccgtc cattcagaaa gcttcaaatt atagaaacaa tactgttcta tacgagtgac   2160
cgattatgct ttctttggcc tacattcttt attctgcggt gaagttgagg cttataagtt   2220
aaaacaaagg aactaactta ctgtccacca gtttatacag aactcacagt acctatgact   2280
tttttaaact aagatctgtt aaaaaagaaa tctgtttcaa cagatgaccg tgtacaatac   2340
cgtgtggtga aaatgaattc agacttatta aatgatgaac ttgttaaatc ttctcagtgt   2400
ctatttatca gcacaataca cacaggagaa ctgttgatgg catattgaat agattttcct   2460
gaataaattg ctctggaaac cac                                           2483
```

<210> SEQ ID NO 66
<211> LENGTH: 1780
<212> TYPE: DNA
<213> ORGANISM: Homo sapiens

<400> SEQUENCE: 66
gaaacccagc tgcagaggct gcagccccgg tccccagcgg ctaaaggacc cccgagctcg 60
gggaggggga ggccgctccg gcccagcgct ctgcgccctc cggctccccc tccccctcct 120
tccctgctcc ttcgctctgc aggtctcgga ggaccccatc ctagccctac ctgtctcggc 180
ccgcaacctc cccgaagccg tcggtgccac tcccagccca tgtgggcccc cgcgggctgc 240
ccacgcctgt cccccagctc cccgttccgc tgggctttac cctcgccagg ggtggctttc 300
tgagccgccc gctccgtgcc cctctctgca gcctctcctg ccactcgggg cccccgttcc 360
ccctcccggc ggcgggggc tgcccccggg gggctggcgg agctgggccg cgggggcccc 420
ggggccggcg gtgccggggt catcgggatg atgcggacgc agtgtctgct ggggctgcgc 480
acgttcgtgg ccttcgccgc caagctctgg agcttcttca tttaccttct gcggaggcag 540
atccgcacgg taattcagta ccaaactgtt cgatatgata tcctcccctt atctcctgtg 600
tcccggaatc ggctagccca ggtgaagagg aagatcctgg tgctggatct ggatgagaca 660
cttattcact cccaccatga tggggtcctg aggcccacag tccggcctgg tacgcctcct 720
gacttcatcc tcaaggtggt aatagacaaa catcctgtcc ggtttttgt acataagagg 780
ccccatgtgg atttcttcct ggaagtggtg agccagtggt acgagctggt ggtgtttaca 840
gcaagcatgg agatctatgg ctctgctgtg gcagataaac tggacaatag cagaagcatt 900
cttaagagga gatattacag acagcactgc actttggagt tggcagcta catcaaggac 960
ctctctgtgg tccacagtga cctctccagc attgtgatcc tggataactc cccaggggct 1020
tacaggagcc atccagacaa tgccatcccc atcaaatcct ggttcagtga ccccagcgac 1080
acagcccttc tcaacctgct cccaatgctg gatgccctca ggttcaccgc tgatgttcgt 1140
tccgtgctga gccgaaacct tcaccaacat cggctctggt gacagctgct ccccctccac 1200
ctgagttggg gtggggggga aagggagggc gagcccttgg gatgccgtct gatgccctgt 1260
ccaatgtgag gactgcctgg gcagggtctg cccctcccac ccctctctgc cctgggagcc 1320
ctacactcca cttggagtct ggatggacac atgggccagg ggctctgaag cagcctcact 1380
cttaacttcg tgttcacact ccatggaaac cccagactgg gacacaggcg gaagcctagg 1440
agagccgaat cagtgtttgt gaagaggcag gactggccag agtgacagac atacggtgat 1500
ccaggaggct caaagagaag ccaagtcagc tttgttgtga tttgattttt tttaaaaaac 1560
tcttgtacaa aactgatcta attcttcact cctgctccaa gggctgggct gtgggtggga 1620
tactgggatt ttgggccact ggattttccc taaatttgtc ccccctttac tctccctcta 1680
tttttctctc cttagactcc ctcagacctg taaccagctt tgtgtctttt ttcctttttct 1740
ctcttttaaa ccatgcatta taactttgaa accaaagcgg 1780

<210> SEQ ID NO 67
<211> LENGTH: 1746
<212> TYPE: DNA
<213> ORGANISM: Homo sapiens

<400> SEQUENCE: 67
ggaggccggc tatttgaagg cggcgcgcgg actaggtgcg cacttcagtt ctcggagaga 60
agaggcggga gtggacctgg tcagccctac cccactgacc ccaccggacc caggcgcggc 120

```
ctccgccaca gccacagccc ctgcccctgc tgcggcgcgg cgaggcgagg cgatggccaa    180

ggtgtcggtg ctgaacgtgg cggtcctgga gaacccgagc cctttccaca gccccttccg    240

gttcgagatc agcttcgagt gcagtgaagc cctggcggac gacctggagt ggaagatcat    300

ttatgttggc tcggctgaga gtgaggaatt tgatcagatc ctagactcgg tgctggtggg    360

ccctgtgcca gcagggagac acatgtttgt ctttcaggcc gacgccccca acccatccct    420

catcccagag actgatgccg tgggtgtgac tgtggtcctc atcacctgca cctaccatgg    480

acaggagttc atccgagtgg gctactacgt caacaacgag tacctcaacc ctgagctgcg    540

tgagaacccg cccatgaagc cagatttctc ccagctccag cggaacatct tggcctcgaa    600

cccccgggtg acccgcttcc atatcaactg ggacaacaac atggacaggc tggaggccat    660

agagacccag gacccctccc tgggctgcgg cctcccactc aactgcactc ctatcaaggg    720

cttggggctc cctggctgca tccctggcct cctccctgag aactccatgg actgcatcta    780

actgcaggaa cccagagtgt cccagcacgc cgggaggggc aaccaggcct cccagcgagt    840

cctgcagggc ccatctagag gactttgggg gccatcagct gcaatccagg tctgtcaaac    900

tcagccccta ggaaagaaca ggccttgggt ctcccctagt cctggccaga aggatgatct    960

cgcttttcct ctacaggcct ataagaagca ggtacttcag ttctaaattc tgacttgtgt   1020

tcttttcgtc ttcataaatt ctaactaagg ccactgtgcc actgtgcacc cttgagtacc   1080

attgatccaa agctttccca cagacctccc tggcccacct agaggctttc ttggtcagtg   1140

cctgtcaagg ctccagtcct gctgagccaa aggctttgtc attcctttct cttcctgtac   1200

atctgagcag acccactcca gctttctggt gtcacaggcg ggaatgttag ttagtaggta   1260

gacttagatc ccatttctgt cctgctccca ggaagattct taggtcctct tcaatccagc   1320

agcccctccc agaggtgtga tcagcaggat gctgaggaac catgttgcct ttcctgtcaa   1380

tcacagccac cttcctgtta tctcctaaat ggatctggct tttcctggag gctgccatgg   1440

ttggaagatg gtatcagagg gcctgcctgg gcagtctgtc tccgggccag ggtcagggac   1500

cctctgcctc tggcagcctt aacctgtcct ctgctaggac cagggtgatt tcaagccagg   1560

gaagcaactg ggaccctgaa aactgtccct ccccagcccg ctccccctct ctgtgccctg   1620

gtccccttgc tgccatgtgg atgctgttgt gattgctgtt tgtatattat caaaatgttt   1680

ttatattaaa aatgtttggt ctgaaaatta aaagcacttc atttagaatg aaaaaaaaaa   1740

aaaaaa                                                              1746
```

<210> SEQ ID NO 68
<211> LENGTH: 945
<212> TYPE: DNA
<213> ORGANISM: Homo sapiens

<400> SEQUENCE: 68

```
ctgggtgtac agcgtcctcg aaaccacgag caagtgagca gatcctccga ggcaccaggg     60

actccagccc atgccatggc ggattctgag cgcctctcgg ctcctggctg ctgggccgcc    120

tgcaccaact tctcgcgcac tcgaaaggga atcctcctgt ttgctgagat tatattatgc    180

ctggtgatcc tgatctgctt cagtgcctcc acaccaggct actcctccct gtcggtgatt    240

gagatgatcc ttgctgctat tttctttgtt gtctacatgt gtgacctgca caccaagata    300

ccattcatca actggccctg gagtgatttc ttccgaaccc tcatagcggc aatcctctac    360

ctgatcacct ccattgttgt ccttgttgag agaggaaacc actccaaaat cgtcgcaggg    420
```

```
gtactgggcc taatcgctac gtgcctcttt ggctatgacg cctatgtcac cttccccgtt    480

cggcagccaa gacatacagc agcccccact gaccccgcag atggcccggt gtaggcgaac    540

ttccctcatt tctctctgca atctgcaaat aactcctcca ttgaaataac tcctccccac    600

cccaacaaca acattcccag cagaccaact cccacccccct ctttgaggta aaagtgcctt   660

tattgggaga cttttgtctt ccagcctgcc aatcaaccct cctgggtgtg gccaccatat    720

gtgtgtgcct aggtcctcct tctgcacgat ccaataggag acaccagttc tgactgaacc    780

atgcccccac ctaagtcaca aaatgaggga agtggggagt tagatttcag agtccaggcc    840

ctaggttggg acccactcca aataatctcc tcggtgtggg tggtggttct atagagggat    900

aaatgaataa taaacattgt taaaatataa aaaaaaaaaa aaaaa                    945
```

<210> SEQ ID NO 69
<211> LENGTH: 2208
<212> TYPE: DNA
<213> ORGANISM: Homo sapiens

<400> SEQUENCE: 69

```
ggggcctgcc acgaggccgc agtataaccg cgtggcccgc gcgcgcgctt ccctcccggc     60

gcagtcaccg gcgcggtcta tggctgcgac ttctctaatg tctgctttgg ctgcccggct    120

gctgcagccc gcgcacagct gctcccttcg ccttcgccct ttccacctcg cggcagttcg    180

aaatgaagct gttgtcattt ctggaaggaa actggcccag cagatcaagc aggaagtgcg    240

gcaggaggta gaagagtggg tggcctcagg caacaaacgg ccacacctga gtgtgatcct    300

ggttggcgag aatcctgcaa gtcactccta tgtcctcaac aaaaccaggg cagctgcagt    360

tgtgggaatc aacagtgaga caattatgaa accagcttca atttcagagg aagaattgtt    420

gaatttaatc aataaactga ataatgatga taatgtagat ggcctccttg ttcagttgcc    480

tcttccagag catattgatg agagaaggat ctgcaatgct gtttctccag acaaggatgt    540

tgatggcttt catgtaatta atgtaggacg aatgtgtttg gatcagtatt ccatgttacc    600

ggctactcca tggggtgtgt gggaaataat caagcgaact ggcattccaa ccctagggaa    660

gaatgtggtt gtggctggaa ggtcaaaaaa cgttggaatg cccattgcaa tgttactgca    720

cacagatggg gcgcatgaac gtcccggagg tgatgccact gttacaatat ctcatcgata    780

tactcccaaa gagcagttga agaaacatac aattcttgca gatattgtaa tatctgctgc    840

aggtattcca aatctgatca cagcagatat gatcaaggaa ggagcagcag tcattgatgt    900

gggaataaat agagttcacg atcctgtaac tgccaaaccc aagttggttg gagatgtgga    960

ttttgaagga gtcagacaaa aagctgggta tatcactcca gttcctggag gtgttggccc   1020

catgacagtg gcaatgctaa tgaagaatac cattattgct gcaaaaaagg tgctgaggct   1080

tgaagagcga gaagtgctga agtctaaaga gcttggggta gccactaatt aactactgtg   1140

tcttctgtgt cacaaacagc actccaggcc agctcaagaa gcaaagcagg ccaatagaaa   1200

tgcaatattt ttaatttatt ctactgaaat ggtttaaaat gatgccttgt atttattgaa   1260

agcttaaatg ggtgggtgtt tctgcacata cctctgcagt acctcaccag ggagcattcc   1320

agtatcatgc agggtcctgt gatctagcca ggagcagcca ttaacctagt gattaatatg   1380

ggagacatta ccatatggag gatggatgct tcactttgtc aagcacctca gttacacatt   1440

cgccttttct aggattgcat ttcccaagtg ctattgcaat aacagttgat actcatttta   1500

ggtaccaaac cttttgagtt caactgatca aaccaaagga aaagtgttgc tagagaaaat   1560

tagggaaaag gtgaaaaaga aaaaatggta gtaattgagc agaaaaaaat taatttatat   1620
```

```
atgtattgat tggcaaccag atttatctaa gtagaactga attggctagg aaaaaagaaa   1680
aactgcatgt taatcatttt cctaagctgt ccttttgagg cttagtcagt ttattgggaa   1740
aatgtttagg attattcctt gctattagta ctcattttat gtatgttacc cttcagtaag   1800
ttctccccat tttagttttc taggactgaa aggattcttt tctacattat acatgtgtgt   1860
tgtcatattt ggcttttgct atatacttta acttcattgt taaatttttg tattgtatag   1920
tttctttggt gtatcttaaa acctattttt gaaaaacaaa cttggcttga taatcatttg   1980
ggcagcttgg gtaagtacgc aacttacttt tccaccaaag aactgtcagc agctgcctgc   2040
ttttctgtga tgtatgtatc ctgttgactt ttccagaaat tttttaagag tttgagttac   2100
tattgaattt aatcagactt tctgattaaa gggttttctt tctttttttaa taaaacacat   2160
ctgtctggta tggtatgaat ttctgaaaaa aaaaaaaaaa aaaaaaaa               2208
```

<210> SEQ ID NO 70
<211> LENGTH: 2873
<212> TYPE: DNA
<213> ORGANISM: Homo sapiens

<400> SEQUENCE: 70

```
attttcagat gagcctcgga gctgcctgta gttgcccagc tagtatttaa ggactgcaga     60
ggttgcgctc ttgattgcgg ggctagaagt gtgttctaca gggaagcggg gaacttcgtt    120
ccagcagcgc cgaaacccgc acggccccta ggctgtccct ccgcgcccgg gtgacttcct    180
ttcagatccc cagcgaagct cccagcggag ccctcccacc cctcgcccgc ttgctcccgt    240
ctgcgggtct ggagtagcgc tcgcgattgg ccccgatcac cgccgcggtc ctgccccctc    300
gttgcagaga ttccgattgg gtgaggctca cgaagctctg cccccacggt ggccggagca    360
gccggaagct agcatggcgg ccgccggggc tgcggctaca cacctagagg tggcccgggg    420
caagcgcgcc gccctcttct tcgctgcggt ggccatcgtg ctggggctac cgctctggtg    480
gaagaccacg gagacctacc gggcctcgtt gccttactcc cagatcagtg gcctgaatgc    540
ccttcagctc cgcctcatgg tgcctgtcac tgtcgtgttt acgcgggagt cagtgcccct    600
ggacgaccag gagaagctgc ccttcaccgt tgtgcatgaa agagagattc ctctgaaata    660
caaaatgaaa atcaaatgcc gtttccagaa ggcctatcgg agggctttgg accatgagga    720
ggaggccctg tcatcgggca gtgtgcaaga ggcagaagcc atgttagatg agcctcagga    780
acaagcggag ggctccctga ctgtgtacgt gatatctgaa cactcctcac ttcttcccca    840
ggacatgatg agctacattg ggcccaagag gacagcagtg gtgcggggga taatgcaccg    900
ggaggccttt aacatcattg gccgccgcat agtccaggtg gcccaggcca tgtctttgac    960
tgaggatgtg cttgctgctg ctctggctga ccaccttcca gaggacaagt ggagcgctga   1020
gaagaggcgg cctctcaagt ccagcttggg ctatgagatc accttcagtt tactcaaccc   1080
agaccccaag tcccatgatg tctactggga cattgagggg gctgtccggc gctatgtgca   1140
acctttcctg aatgccctcg gtgccgctgg caacttctct gtggactctc agattcttta   1200
ctatgcaatg ttgggggtga atccccgctt tgactcagct tcctccagct actatttgga   1260
catgcacagc ctcccccatg tcatcaaccc agtggagtcc cggctgggat ccagtgctgc   1320
ctccttgtac cctgtgctca actttctact ctacgtgcct gagcttgcac actcaccgct   1380
gtacattcag gacaaggatg gcgctccagt ggccaccaat gccttccata gtccccgctg   1440
ggtggcatt atggtatata atgttgactc caaaacctat aatgcctcag tgctgccagt   1500
```

```
gagagtcgag gtggacatgg tgcgagtgat ggaggtgttc ctggcacagt tgcggttgct   1560

ctttgggatt gctcagcccc agctgcctcc aaaatgcctg ctttcagggc ctacgagtga   1620

agggctaatg acctgggagc tagaccggct gctctgggct cggtcagtgg agaacctggc   1680

cacagccacc accaccctta cctccctggc gcagcttctg ggcaagatca gcaacattgt   1740

cattaaggac gacgtggcat ctgaggtgta caaggctgta gctgccgtcc agaagtcggc   1800

agaagagttg gcgtctgggc acctggcatc tgcctttgtc gccagccagg aagctgtgac   1860

atcctctgag cttgccttct ttgacccgtc actcctccac ctcctttatt tccctgatga   1920

ccagaagttt gccatctaca tcccactctt cctgcctatg gctgtgccca tcctcctgtc   1980

cctggtcaag atcttcctgg agacccgcaa gtcctggaga aagcctgaga agacagactg   2040

agcagggcag cacctccata ggaagccttc ctttctggcc aaggtgggcg gtgttagatt   2100

gtgaggcacg tacatggggc ctgccggaat gacttaaata tttgtctcca gtctccactg   2160

ttggctctcc agcaaccaaa gtacaacact ccaagatggg ttcatctttt cttcctttcc   2220

cattcacctg gctcaatcct cctccaccac caggggcctc aaaaggcaca tcatccgggt   2280

ctccttatct tgtttgataa ggctgctgcc tgtctccctc tgtggcaagg actgtttgtt   2340

cttttgcccc atttctcaac atagcacact tgtgcactga gaggagggag cattatggga   2400

aagtccctgc cttccacacc tctctctagt ccctgtggga cagccctagc ccctgctgtc   2460

atgaaggggc caggcattgg tcacctgtgg gaccttctcc ctcactcccc tccctcctag   2520

ttggctttgt ctgtcaggtg cagtctggcg ggagtccagg aggcagcagc tcaggacatg   2580

gtgctgtgtg tgtgtgtgtg tgtgtgtgtg tgtgtgtgtg tcagaggttc cagaaagttc   2640

cagatttgga atcaaacagt cctgaattca aatccttgtt tttgcactta ttgtctggag   2700

agctttggat aaggtattga atctctctga gcctcagttt ttcatttgtt caaatggcac   2760

tgatgatgtc tcccttacaa gatggttgtg aggagtaaat gtgatcagca tgtaaagtgt   2820

ctggcgtgta gtaggctctt aataaacact ggctgaatat gaattggaat gat          2873
```

<210> SEQ ID NO 71
<211> LENGTH: 2896
<212> TYPE: DNA
<213> ORGANISM: Homo sapiens

<400> SEQUENCE: 71

```
acgcttgcgc gcgggattta aactgcggcg gtttacgcgg cgttaagact tcgtagggtt     60

agcgaaattg aggtttcttg gtattgcgcg tttctcttcc ttgctgactc tccgaatggc    120

catggactcg tcgcttcagg cccgcctgtt tcccggtctc gctatcaaga tccaacgcag    180

taatggttta attcacagtg ccaatgtaag gactgtgaac ttggagaaat cctgtgtttc    240

agtggaatgg gcagaaggag gtgccacaaa gggcaaagag attgattttg atgatgtggc    300

tgcaataaac ccagaactct tacagcttct tcccttacat ccgaaggaca atctgccctt    360

gcaggaaaat gtaacaatcc agaaacaaaa acggagatcc gtcaactcca aaattcctgc    420

tccaaaagaa agtcttcgaa gccgctccac tcgcatgtcc actgtctcag agcttcgcat    480

cacggctcag gagaatgaca tggaggtgga gctgcctgca gctgcaaact cccgcaagca    540

gttttcagtt cctcctgccc ccactaggcc ttcctgccct gcagtggctg aaataccatt    600

gaggatggtc agcgaggaga tggaagagca agtccattcc atccgaggca gctcttctgc    660

aaaccctgtg aactcagttc ggaggaaatc atgtcttgtg aaggaagtgg aaaaaatgaa    720

gaacaagcga gaagagaaga aggcccagaa ctctgaaatg agaatgaaga gagctcagga    780
```

```
gtatgacagt agttttccaa actgggaatt tgcccgaatg attaaagaat ttcgggctac    840
tttggaatgt catccactta ctatgactga tcctatcgaa gagcacagaa tatgtgtctg    900
tgttaggaaa cgcccactga ataagcaaga attggccaag aaagaaattg atgtgatttc    960
cattcctagc aagtgtctcc tcttggtaca tgaacccaag ttgaaagtgg acttaacaaa   1020
gtatctggag aaccaagcat tctgctttga ctttgcattt gatgaaacag cttcgaatga   1080
agttgtctac aggttcacag caaggccact ggtacagaca atctttgaag gtggaaaagc   1140
aacttgtttt gcatatggcc agacaggaag tggcaagaca catactatgg gcggagacct   1200
ctctgggaaa gcccagaatg catccaaagg gatctatgcc atggcctccc gggacgtctt   1260
cctcctgaag aatcaaccct gctaccggaa gttgggcctg gaagtctatg tgacattctt   1320
cgagatctac aatgggaagc tgtttgacct gctcaacaag aaggccaagc tgcgcgtgct   1380
ggaggacggc aagcaacagg tgcaagtggt ggggctgcag gagcatctgg ttaactctgc   1440
tgatgatgtc atcaagatga tcgacatggg cagcgcctgc agaacctctg ggcagacatt   1500
tgccaactcc aattcctccc gctcccacgc gtgcttccaa attattcttc gagctaaagg   1560
gagaatgcat ggcaagttct ctttggtaga tctggcaggg aatgagcgag gcgcggacac   1620
ttccagtgct gaccggcaga cccgcatgga gggcgcagaa atcaacaaga gtctcttagc   1680
cctgaaggag tgcatcaggg ccctgggaca gaacaaggct cacaccccgt tccgtgagag   1740
caagctgaca caggtgctga gggactcctt cattgggggag aactctagga cttgcatgat   1800
tgccacgatc tcaccaggca taagctcctg tgaatatact ttaaacaccc tgagatatgc   1860
agacagggtc aaggagctga gcccccacag tgggcccagt ggagagcagt tgattcaaat   1920
ggaaacagaa gagatggaag cctgctctaa cggggcgctg attccaggca atttatccaa   1980
ggaagaggag gaactgtctt cccagatgtc cagctttaac gaagccatga ctcagatcag   2040
ggagctggag gagaaggcta tggaagagct caaggagatc atacagcaag gaccagactg   2100
gcttgagctc tctgagatga ccgagcagcc agactatgac ctggagacct ttgtgaacaa   2160
agcggaatct gctctggccc agcaagccaa gcatttctca gccctgcgag atgtcatcaa   2220
ggccttgcgc ctggccatgc agctggaaga gcaggctagc agacaaataa gcagcaagaa   2280
acggccccag tgacgactgc aaataaaaat ctgtttggtt tgacacccag cctcttccct   2340
ggccctcccc agagaacttt gggtacctgg tgggtctagg cagggtctga gctgggacag   2400
gttctggtaa atgccaagta tgggggcatc tgggcccagg gcagctgggg agggggtcag   2460
agtgacatgg gacactcctt ttctgttcct cagttgtcgc cctcacgaga ggaaggagct   2520
cttagttacc cttttgtgtt gcccttcttt ccatcaaggg gaatgttctc agcatagagc   2580
tttctccgca gcatcctgcc tgcgtggact ggctgctaat ggagagctcc ctggggttgt   2640
cctggctctg gggagagaga cggagccttt agtacagcta tctgctggct ctaaaccttc   2700
tacgcctttg ggccgagcac tgaatgtctt gtactttaaa aaaatgtttc tgagacctct   2760
ttctacttta ctgtctccct agagatccta gaggatccct actgttttct gttttatgtg   2820
tttatacatt gtatgtaaca ataaagagaa aaaataaatc agctgtttaa gtgtgtggaa   2880
aaaaaaaaaa aaaaaa                                                   2896
```

<210> SEQ ID NO 72
<211> LENGTH: 1433
<212> TYPE: DNA
<213> ORGANISM: Homo sapiens

<400> SEQUENCE: 72

```
acccctccat ttctcgccat ggcccctgca ctgctcctga tccctgctgc cctcgcctct     60
ttcatcctgg cctttggcac cggagtggag ttcgtgcgct ttacctccct tcggccactt    120
cttggaggga tcccggagtc tggtggtccg gatgcccgcc agggatggct ggctgccctg    180
caggaccgca gcatccttgc ccccctggca tgggatctgg ggctcctgct tctatttgtt    240
gggcagcaca gcctcatggc agctgaaaga gtgaaggcat ggacatcccg gtactttggg    300
gtccttcaga ggtcactgta tgtggcctgc actgccctgg ccttgcagct ggtgatgcgg    360
tactgggagc ccatacccaa aggccctgtg ttgtgggagg ctcgggctga gccatgggcc    420
acctgggtgc cgctcctctg ctttgtgctc catgtcatct cctggctcct catctttagc    480
atccttctcg tctttgacta tgctgagctc atgggcctca aacaggtata ctaccatgtg    540
ctggggctgg gcgagcctct ggccctgaag tctccccggg ctctcagact cttctcccac    600
ctgcgccacc cagtgtgtgt ggagctgctg acagtgctgt gggtggtgcc taccctgggc    660
acggaccgtc tcctccttgc tttcctcctt accctctacc tgggcctggc tcacgggctt    720
gatcagcaag acctccgcta cctccgggcc cagctacaaa gaaaactcca cctgctctct    780
cggccccagg atggggaggc agagtgagga gctcactctg gttacaagcc ctgttcttcc    840
tctcccactg aattctaaat ccttaacatc caggccctgg ctgcttcatg ccagaggccc    900
aaatccatgg actgaaggag atgccccttc tactacttga gactttattc tctgggtcca    960
gctccatacc ctaaattctg agtttcagcc actgaactcc aaggtccact tctcaccagc   1020
aaggaagagt ggggtatgga agtcatctgt cccttcactg tttagagcat gacactctcc   1080
ccctcaacag cctcctgaga aggaaaggat ctgccctgac cactcccctg gcactgttac   1140
ttgcctctgc gcctcagggg tccccttctg caccgctggc ttccactcca agaaggtgga   1200
ccagggtctg caagttcaac ggtcatagct gtccctccag gccccaacct tgcctcacca   1260
ctcccggccc tagtctctgc acctccttag gccctgcctc tgggctcaga ccccaaccta   1320
gtcaagggga ttctcctgct cttaactcga tgacttgggg ctccctgctc tcccgaggaa   1380
gatgctctgc aggaaaataa aagtcagcct ttttctacaa aaaaaaaaaa aaa          1433
```

<210> SEQ ID NO 73
<211> LENGTH: 6628
<212> TYPE: DNA
<213> ORGANISM: Homo sapiens

<400> SEQUENCE: 73

```
ctcctcggtg caacctatat aaggctcaca gtctgcgctc ctggtacacg cgcttcaact     60
tcggttggtg tgtgtcgaag aaacctgact gcgccctgag gagaacagcg gagaaggtcc    120
accgagcctg gcgaaaggtc cgctgagcgg gctgtcgtcc ggagccactc cgggctgcgg    180
agcacccagt ggagaccgcg cctggctcag gtgtgggacc ccatccttcc tgtcttcgca    240
gaggagtcct cgcgtgaaat aagcgggttt tgaaaacaaa aaaaagaagg agtggaagag    300
ggggccagga tccaggcctc catccccaca gaagtgaagc tacagctggg aggtctcctc    360
ccaccccaac cgtcaccctg ggtcccgact gcccacctcc tcctcctccc cctcccccca    420
acaacaacaa caacaacaac tccaagcaca ccggccataa gagtgcgtgt gtccccaaca    480
tgaccgaacg aagaagggac gagctctctg aagagatcaa caacttaaga gagaaggtca    540
tgaagcagtc ggaggagaac aacaacctgc agagccaggt gcagaagctc acagaggaga    600
acaccaccct tcgagagcaa gtggaaccca cccctgagga tgaggatgat gacatcgagc    660
```

```
tccgcggtgc tgcagcagct gctgccccac cccctccaat agaggaagag tgcccagaag    720
acctcccaga gaagttcgat ggcaacccag acatgctggc tcctttcatg gcccagtgcc    780
agatcttcat ggaaaagagc accagggatt tctcagttga tcgtgtccgt gtctgcttcg    840
tgacaagcat gatgaccggc cgtgctgccc gttgggcctc agcaaagctg gagcgctccc    900
actacctgat gcacaactac ccagctttca tgatggaaat gaagcatgtc tttgaagacc    960
ctcagaggcg agaggttgcc aaacgcaaga tcagacgcct gcgccaaggc atggggtctg   1020
tcatcgacta ctccaatgct ttccagatga ttgcccagga cctggattgg aacgagcctg   1080
cgctgattga ccagtaccac gagggcctca gcgaccacat tcaggaggag ctctcccacc   1140
tcgaggtcgc caagtcgctg tctgctctga ttgggcagtg cattcacatt gagagaaggc   1200
tggccagggc tgctgcagct cgcaagccac gctcgccacc ccgggcgctg gtgttgcctc   1260
acattgcaag ccaccaccag gtagatccaa ccgagccggt gggaggtgcc cgcatgcgcc   1320
tgacgcagga agaaaaagaa agacgcagaa agctgaacct gtgcctctac tgtggaacag   1380
gaggtcacta cgctgacaat tgtcctgcca aggcctcaaa gtcttcgccg gcgggaaact   1440
ccccggcccc gctgtagagg gaccttcagc gaccgggcca gaaataataa ggtccccaca   1500
agatgatgcc tcatctccac acttgcaagt gatgctccag attcatcttc cgggcagaca   1560
caccctgttc gtccgagcca tgatcgattc tggtgcttct ggcaacttca ttgatcacga   1620
atatgttgct caaaatggaa ttcctctaag aatcaaggac tggccaatac ttgtggaagc   1680
aattgatggg cgccccatag catcgggccc agttgtccac gaaactcacg acctgatagt   1740
tgacctggga gatcaccgag aggtgctgtc atttgatgtg actcagtctc cattcttccc   1800
tgtcgtccta ggggttcgct ggctgagcac acatgatccc aatatcacat ggagcactcg   1860
atctatcgtc tttgattctg aatactgccg ctaccactgc cggatgtatt ctccaatacc   1920
accatcgctc ccaccaccag caccacaacc gccactctat tatccagtag atggatacag   1980
agtttaccaa ccagtgaggt attactatgt ccagaatgtg tacactccag tagatgagca   2040
cgtctaccca gatcaccgcc tggttgaccc tcacatagaa atgatacctg gagcacacag   2100
tattcccagt ggacatgtgt attcactgtc cgaacctgaa atggcagctc ttcgagattt   2160
tgtggcaaga aatgtaaaag atgggctaat tactccaacg attgcaccta atggagccca   2220
agttctccag gtgaagaggg ggtggaaact gcaagtttct tatgattgcc gagctccaaa   2280
caattttact atccagaatc agtatcctcg cctatctatt ccaaatttag aagaccaagc   2340
acacctggca acgtacactg aattcgtacc tcaaatacct ggataccaaa catacccccac   2400
atatgccgcg tacccgacct acccagtagg attcgcctgg tacccagtgg gacgagacgg   2460
acaaggaaga tcactatatg tacctgtgat gatcacttgg aatccacact ggtaccgcca   2520
gcctccggta ccacagtacc cgccgccaca gccgccgcct ccaccaccac caccgccgcc   2580
gcctccatct tacagtaccc tgtaaatacc tgtcatgtcc ttcaggatct ctgccctcaa   2640
aatttattcc tgttcagctt ctcaatcagt gactgtgtgc taaattttag gctactgtat   2700
cttcaggcca cctgaggcac atcctctctg aaacggctat ggaaggttag ggccactctg   2760
gactggcaca catcctaaag caccaaaaga ccttcaacat tttctgagag caacagagta   2820
tttgccaata aatgatctct catttttcca ccttgactgc caatctaact aaaataatta   2880
ataagtttac tttccagcca gtcctggaag tctgggtttt acctgccaaa acctccatca   2940
ccatctaaat tataggctgc caaatttgct gtttaacatt tacagagaag ctgatacaaa   3000
```

```
cgcaggaaat gctgatttct ttatggaggg ggagacgagg aggaggagga catgactttt   3060
cttgcggttt cggtaccctc tttttaaatc actggaggac tgaggcctta ttaaggaagc   3120
caaaattatc ggtgcagtgt ggaaaggctt ccgtgatcct ctcgctgcac ccttagaaac   3180
ttcaccgtct tcaaactcca tttccatggt tctgttaatt ctcaaggagc agcaactcga   3240
ctggttctcc caggagcagg aaaaaccctt gtgacatgaa acatctcagg cctgaaaaga   3300
aagtgctctc tcagatggac tcttgcatgt taagactatg tcttcacatc atggtgcaaa   3360
tcacatgtac ccaatgactc cggctttgac acaacacctt accatcatca tgccatgatg   3420
gcttccacaa agcattaaac ctggtaacca gagattactg gtggctccag cgttgttaga   3480
tgttcatgaa atgtgaccac ctctcaatca cctttgaggg ctaaagagta gcacatcaaa   3540
aggactccaa aatcccatac ccaactctta agagatttgt cctggtactt cagaaagaat   3600
tttcatgagt gttcttaatt ggctggaaaa gcaccagctg acgttttgga agaatctatc   3660
catgtgtctg cctccatatg catctgggca tttcatcttc agtcccctca ttagactgta   3720
gcattaggat gtgtggagag aggagaaatg atttagcacc cagattcaca ctcctatgcc   3780
tggaaggggg acatctttga agaagaggaa ttagggctgt ggacactgtc ttgaggatgt   3840
ggacttcctt agtgagctcc acattacttg atggtaacca cttcaaaagg atcagaatcc   3900
acgtaatgaa aaaggtccct ctagaggatg gagctgatgt gaagctgcca atggatgaaa   3960
agcctcagaa agcaactcaa aggactcaaa gcaacggaca acacaagagt tgtcttcagc   4020
ccagtgacac ctctgatgtc ccctggaagc tttgtgctaa cctgggactg cctgacttcc   4080
tttagcctgg tcccttgcta ctaccttgaa ctgttttatc taacctctct ttttctgttt   4140
aattctttgc tactgccatt gaccctgctg caggatttgt gtcattttcc tgcctggttg   4200
ctgagactcc attttgctgc cacacacaga gatgtaagag gcaggcttta attgccaaag   4260
cacagtttga gcagtagaaa acaacatggt gtatatctca aattgcctga catgaagagg   4320
agtctaacgg tgaagtttca cttttcatca gcatcatctt tcacatgttc attatcatct   4380
gctcttattc ttgcatgttt aaacacttaa aatttttagt ataattttta gtgtgttttg   4440
aagtggtgac taggctttca aaaacttcca ttgaattaca aagcactatc cagttcttat   4500
tgttaaacta agtaaaaatg ataagtaaca tagtgtaaaa tattccttta ctgtgaactt   4560
cttacaatgc tgtgaatgag aggctcctca gaactggagc atttgtataa taattcatcc   4620
tgttcatctt caattttaac atcatatata atttcaattc tatcaattgg gcctttaaaa   4680
atcatataaa aggatataaa atttgaaaag agaaacctaa ttggctattt aatccaaaac   4740
aacttttttt ttccttcaat ggaatcagaa agcttgtcaa tcactcatgt gttttagagt   4800
aattactttt aaaatggtgc atttgtgctt ctgaactatt ttgaagagtc acttctgttt   4860
acctcaagta tcaattcatc ctccatacat ttgaattcaa gttgtttttt tgtcaaattt   4920
acagttgtca attgatcttc aagctgcagg gtgcctagaa atgggccgtt gtctgtagcc   4980
ctggcatgtg cacacggaca tttgccacca ctgcaagcaa aagtctggag aagttcacca   5040
acgacaagaa cgattaggga aaatatgctg ctgtgggtta acaactcaga aagtccctga   5100
tccacatttg gctgtttact aaagcttgtg attaactttt tggcagtgtg tactatgctc   5160
tattgctata tatgctatct ataaatgtag atgttaagga taagtaattc taaatttatt   5220
attctatagt tttgaagttt ggttaagttt cctttcactc aattgattta ttttgttgtt   5280
aatcaaattt atgttaattg gatcctttaa attttttttg gcattttcca acaaaaatgg   5340
ctttattcat aagaaaggaa aaaaatcaat ggaatttgat atctaaagaa gttagaaagg   5400
```

```
gagcaaaata aaaaacataa aggagataga tgaattagta agcaaatcag tagtcgagtt   5460
tttcaaactg gcaaaattaa ttaattgact tttagcccaa atttacattg ttaattaaat   5520
caagaaggaa gaagatctaa gagctcccat tgataggcaa gcctagagag aactagctaa   5580
atttatcatg ctaggatatt gaaacacaga aagtttacat acatttatga agggtcaatt   5640
tagtttggac agtgaggtat ttgtcttagt ggaaaaaagg agaattagtc tgatcaaatc   5700
gtgaagtaat acagtgaact tgcaggtgca caaaataaga gggccacatc tatatggtgc   5760
agtctggaat tctgtttaag tttgtaggta cctcttggac ttctgaattg atccagttgt   5820
catccaccac agacatctca catcagatac agacagttcc aagattgaca acagagaaca   5880
acctgctgga aagacctggg cagaaatgga gagccctgcg ggaaccatgc tacattttca   5940
tctaaagaga gaatgcacat ctgatgagac tgaaagttct ttgttgtttt agattgtaga   6000
atggtattga attggtctgt ggaaaattgc attgctttta tttctttgtg taatcaagtt   6060
taagtaatag gggatatata atcataagca ttttagggtg ggagggacta ttaagtaatt   6120
ttaagtgggt ggggttattt agaatgttag aataatatta tgtattagat atcgctataa   6180
gtggacatgc gtacttactt gtaacccttt accctataat tgctatcctt aaagatttca   6240
aataaactcg gagggaactg cagggagacc aacttattta gagcgaattg gacatggata   6300
aaaaccccag tgggagaaag ttcaaaggtg attagattaa taatttaata gaggatgagt   6360
gacctctgat aaattactgc tagaatgaac ttgtcaatga tggatggtaa attttcatgg   6420
aagttataaa agtgataaat aaaaaccctt gcttttaccc ctgtcagtag ccctcctcct   6480
accactgaac cccattgccc ctacccctcc ttctaacttt attgctgtat tctcttcact   6540
ctatatttct ctctatttgc taatattgca ttgctgttac aataaaaatt caataaagat   6600
ttagtggtta agtgcaaaaa aaaaaaaa                                      6628
```

<210> SEQ ID NO 74
<211> LENGTH: 6287
<212> TYPE: DNA
<213> ORGANISM: Homo sapiens

<400> SEQUENCE: 74

```
ccggcttcca gcccagacac cagccagcca gtggcgttcc tggctcctcg ggattttcct     60
tttcctccga agctgctgat tcatccccag gctggagtca ggctcagctg tggggctggg    120
agcatgggct ctcaggctgc tgctgagtgg aggaactggg cctcctggga ggtgtcctcc    180
agcctctctg gatgctccat ggggtgcttc aaggatgacc gcatcgtctt ctggacttgg    240
atgttctcca cctacttcat ggagaaatgg gctccccggc aggacgacat gcttttctat    300
gtgcgccgga agctggcgta ctccggcagc gaaagcggtg cagacgggag gaaggcagct    360
gagcctgagg tggaggtgga ggtgtaccgg cgggactcca agaagctgcc aggcctggga    420
gaccctgaca tcgactggga ggagagcgtc tgcctgaatc tcatcctgca gaagctggac    480
tacatggtga cctgtgcggt gtgcacacgt gctgacggcg gggacattca catccataag    540
aagaaatctc agcaagtgtt cgcgtccccc agtaaacacc ccatggacag caagggggag    600
gagtccaaga tcagctaccc caacatcttc ttcatgattg acagcttcga ggaggtgttc    660
agcgacatga ccgtagggga aggagagatg gtctgtgtgg agctggtggc tagtgacaaa    720
accaacacgt tccagggggt catctttcag ggctccatcc gctacgaggc gctcaagaag    780
gtgtatgaca accgggtgag cgtggccgcc cgcatggcac agaagatgtc gtttggcttc    840
```

-continued

```
tacaagtaca gcaacatgga gtttgtgcgc atgaagggcc cccagggcaa gggccacgcc     900
gagatggcgg tcagccgagt gtctacaggt gacacatccc cctgtgggac tgaagaggac     960
tccagcccag cttcgcccat gcacgagcgg gtgacctcct tcagcacacc ccccacccca    1020
gaacggaaca accggcctgc cttcttctcc ccatccctca agaggaaggt gccccggaac    1080
cggatcgctg agatgaagaa gtcgcactcg gccaacgaca gcgaggagtt cttccgggag    1140
gacgacggtg gagccgatct gcacaatgca accaacctgc ggtctcggtc cctgtcgggc    1200
acaggacggt ccctggtcgg gtcctggctg aagctgaaca gagcagatgg aaacttcctt    1260
ctctatgcac acttaaccta cgtcacgttg ccgctgcatc ggattttaac agacatcctg    1320
gaagttcggc agaagcccat cctgatgacc tagccgcgtg cggagcctgc gcagagcccc    1380
ggccgggccc agccctcgga gtgctgccaa gtgcctacct gtccaccgcc accggggtct    1440
gcgatggcac gccagtgctg gagccgcagc caggcgaggc cactcgactc ccggggccgg    1500
ggccgactcc acgaacacca gcccaaactg aagtgcctct tccctcccct gctggcgctg    1560
ctccgccctg tgcccccgc ccatcgcccc ccacccatct ctggagagcc ctctgcaccc    1620
aaagaggact agagatgccg agcggccatg agagagagcg gaaggagcag ctgatgccca    1680
gagcggggcc agagcggcgg gtctatgttc acgtcccccc agcagcaggc ggaaccaccc    1740
agccagggca ctcagtgcat tggactgtcc acatgttctt gaggaaagcc ggtggaagat    1800
tctggaatgc cgtgcggatg aacttcagca cccgagtcag tcccagctca tcctccccag    1860
tttaccactt tgttctaata ggagatggga acacgagaag tttgatggct ttgccctggg    1920
ctgggaatac ctcacccacg cccagttcca gaaaggcctc cagctgagca gacggccccg    1980
atcccgccag aacggccttt tgcttccagc caaagaacac cgccaacacg cacacctcca    2040
acctgggaca tcccacgctg ggcctcgcac ggaggaacct gcagaatttg gattctgagg    2100
gtagtcggga ggcctcggta gccaggcaga acaggatatc tgccaaaggg tgtctgatgt    2160
ggggtggggc tggcatcctc ccaggaaggt tctaggtggg accccgtctt ctgggggcgg    2220
gggtgtcttt tcatcttccc tggtttccta gaactcactt cctttgacgg cgtgtgttgg    2280
tcccatctct cagaccagct cactgaggca gaggagttgc tcagaggctc acatgggcac    2340
ccccattggt tcgtgtgagc agctgcccag ccccaggcct gccctcggcc tggtccagca    2400
tgaaggcgtt tccatctgca aggatgcacg gtaccctccc cgagagcagg cctgtcccct    2460
acccaactgg gaataaactg gaagctgggt ctctttgttg ctatgttttt ttgtttgaag    2520
ttcccaggaa tatttgaggg gttccggtga tgtgtttagg gatcttctct gtgggggaaa    2580
aggaagagga gggtcttgtt ctcccatctg tttattcttt gggctctggg aacaggggac    2640
tactttgggg ctttctccag acttttgtat gttgttatta aaagcgagct attgcatttc    2700
attctgcctc agtttgccca cctgtgaaat ggggctgata ccacctacct cactgaagtc    2760
ccagggttca agtgtgtggc tgggtcaggg cgtggtcacc cgtcattctg cataggtcgg    2820
gttggatgtt agactcctgg gatgccctcc tccccctcgc cctttgtaat aacctaatct    2880
gagaccgtgc ttggtggggg gatgtgaact ttctctctcc cccagcagtg tctgctcagg    2940
cctgacagct cagctctgca cgatttcatg ttcctaaacc catgtcttag ggcagcacag    3000
agccaggtca tgtcatgccc caaagtgtgg ggacagagcc tcagggagcc ccgagcatgg    3060
tccagcccca tttgagtgct ctccggggat gccaaatgct gcttccaagt ttgagtccat    3120
gtggctaaaa tacacccatt tcttcaggaa ctcttcccct ggttgttctg gggatcttgg    3180
gagaaacaca gccctgacag ctcgtccgtg ggaagatgag gcagtccagg ttgtgaggag    3240
```

```
cacagcggcc cgccctctgt tctcagaggt gaggggcggg agaaggttgt ctcctctggg   3300
gccagcattt ggccaagctc ggaggcttgg ccagcactgc tggatggctc agagcaagct   3360
gggctccccg tctgtaagat ggcaaaaatg ctgcccccct cacagggtga ccatgaggac   3420
cagtcacagt gatgtgtgaa agggctcgct ggtcacagaa acgtgtacaa atcatgctat   3480
tttagagatc agccctcaat ttgtaaggca tgtgaacagg gcacgcggtg ggctggtggt   3540
ttcatagccg acacacagcg cctaccatgt gcagctgcct gtccgacccc atcttacaga   3600
cgagaaaacc agcacacagg caccaaggaa ctgtccggaa ctaacagcag gggccggcga   3660
tgggagtcaa acccaggcac gcggcctggc ctgcatgctg agccacatgg tgctgtccgg   3720
acagatggac agacactcgg tggagtctgc ctttctcagg ccctaaatcc ctctccaaag   3780
ggtacttgcg atgccggatt taaaacttgc tcagagccac ttagccactt gagaaccaga   3840
cagtaaggtg ttactcccag gtttgttttt ccaaagtaac agatgacatg tggaataaag   3900
taatagagta acaagtggca gggccagaac cagggtcccc aaagtcctgg tgttggcaca   3960
tttgtacttc ttgtaagacc atctttaatt tttctgggaa cacacctgcc ttttgtgtaa   4020
tgcggggaag actaatgcat ggtgacacct agttttcctc aacaggacac ttgatcccaa   4080
aaccccttta agaccttagg tttcctcagc ggaaaactgt actttaatcc caaacccccct   4140
ttaagacata ttggggctgg gcgcagtggc tcacgcctgt aatcccagca ctttgggagg   4200
ctgagatggg tggatcacct gagatcagga gttcaagacc agcctgacta acatgctgaa   4260
accccatgtc tactaaagat agaaaaatta gctggacatg gtggcaggca cctgtaatcc   4320
cagctactcg gaaggctgag gaaggagaat cacttgaacc tagtaggcag aggttgcagt   4380
gagccgagat cacgccattg cattctagcc tgggcaacga gagcgaaact ctgtctcaaa   4440
aaaaaaaaaa aaaaaaaaaa aaaaaaaaaa aaaaaagata cattggtctt taaacccaaa   4500
ccccctttaa ggcatgttgg tctcaagggg atttgggatt gaagcacagc tttctgttga   4560
ggaaacctag gtgtcacttt ttagaacatt aaaaagaaag ttgtagggtg ggcttttcca   4620
tttaaaggaa tgtgatgatc ctaggttctg atgagtgata ggtggtctcc gtttataccc   4680
tttcttcttt tggcacctgt aagttccggt agtggccatc ttacattctc atgtcctgct   4740
ggaagtgcct agttgcctgc aaagccagct aaggcttatt atttcaaaag aagattattt   4800
aaaacatgag tgacaggtag tcagaagaga acaaaaggac gcaagatact ctatagccaa   4860
gtcagcttgg aggcaggatg ggttgctgag tgaagtcgcc gctcactttt ggattcttat   4920
ggactgtgag ttagtcttcc ctctacacgg agtcacagga agggtataaa tgcatgttcc   4980
tgaggtgccc tcccccaaag aatgtacctg cactcaaacc aggatctgtt tttgctgttt   5040
taatcataaa tagactagtt agtagaagac ttttgaagaa caaagtaaaa cttttttttt   5100
tcattaaaag atgtcccaga ggaaaggccc tgtgcagcca gtatattcta atgactgcct   5160
ggaccatgtc ctaatatggt ggttttaagt tgttggccaa aatcctttaa agacatacga   5220
aacatctgcc aactttttag cgaacttaac aggtttcact gacgttttcc tcaatttttg   5280
aatttaggtg ggatttgctt tcatgtcctg tttcaaaaac caagtgtctc ttgacagccc   5340
actggttctt cctgtcctct tgctctagtc tgtatcagaa agcagaatga ctgtactttt   5400
gttttacaaa caaccacctg ataggacgga cactccacga gataaggaaa ggcacgtgcc   5460
cttgagcttg aatggaagca gcctctggag gggcagccca ctgcccttcg agggagagca   5520
gctcttcagc agtggccaga gtgccacgtg actctgcaga tgacccctgg gagccgggtg   5580
```

atgggcacct gctggggctt ttgttttttc tttttcactg gctggcttga tcctcagtgg 5640
caaaaggacc cctgagcccc ttctccgagc cctggagcac tcctcgggac accgagtggc 5700
ctcagggctg ggttcagagc tcctcccgca gggggagcct cagaagtgga ggcagctgct 5760
gatgggtgag tttacaactt cttatcctgc ctaaggcgag taggcgtttt tattccgttt 5820
ccagtccttg agctcagcag atcaaaataa cagtgaccct gcaaccccac agagcccgcg 5880
acacgctcgc tttcttcccc gccctgcccc tttagtcccc gctctggaag gccaggcagt 5940
ttaggtgtaa ataggtatct tttatggttt ccaaatgaat tatttgtgtg agagtaatta 6000
aatctgtaag aaaacctgtt gagattcttc actatgaatt atgacttcta caacatgtat 6060
tttagcaaaa acacgatgct ggcctccact ggatagctca gtatgctgat tgccagtgat 6120
agttctgtac gcgttaccaa cagcgtcttt attaaccctc ttccacatcc agtggaaatc 6180
attgctaggc ggtatttgtt ggttggctgt tagctttgct ttatgatttc atgtttcttt 6240
taaaggttgt tttgcatgtt gaatattaaa ttttttttt ctgtgtc 6287

<210> SEQ ID NO 75
<211> LENGTH: 6264
<212> TYPE: DNA
<213> ORGANISM: Homo sapiens

<400> SEQUENCE: 75
gagtgtggct gcagtgcgcc gggacaccag ggctccgcgc tccgcactca agaggctccc 60
gcgtcccaac ccctcgcgcc cgcgcgttcg cggatccagg ccgaggaccg aaaggggccg 120
cccgagcccc cggggccggc gcccagagag cccagcaagg ccggccgccc tgccggtgtg 180
ccgccggcgg gtgcttctgg aagggccaat gcgttcgggc agcagcccct gaagccgagc 240
ccgaggctaa gtgggactga ccggggccca gagtggacga accgccagca tggggagaga 300
ccagcgcgcg gtggccggcc ctgccctacg gcggtggctg ctgctgggga cagtgaccgt 360
ggggttcctc gcccagagcg tcttggcggg tgtgaagaag tttgatgtgc cgtgtggagg 420
aagagattgc agtgggggct gccagtgcta ccctgagaaa ggtggacgtg gtcagcctgg 480
gccagtgggc ccccaggggt acaatgggcc accaggatta caaggattcc cgggactgca 540
gggacgtaaa ggagacaagg gtgaaagggg agccccccgga gtaacgggac ccaagggcga 600
cgtgggagca agaggcgttt ctggattccc tggtgccgat ggaattcctg gacacccggg 660
gcaaggtggg cccaggggaa ggccgggcta cgatggctgc aacggaaccc agggagactc 720
aggtccacag gggcccccccg gctctgaggg gttcaccggg cctcccgggc cccaaggacc 780
aaaagggcag aaaggtgagc cttatgcact gcctaaagag gagcgcgaca gatatcgggg 840
tgaacctgga gagcctggat tggtcggttt ccagggacct cccggccgcc ctggcatgt 900
gggacagatg ggtccagttg gagctccagg gagaccagga ccacctggac cccctggacc 960
aaaaggacag caaggcaaca gaggacttgg tttctacgga gttaagggtg aaaagggtga 1020
cgtagggcag ccgggaccca acgggattcc atcagacacc ctccacccca tcatcgcgcc 1080
cacaggagtc accttccacc cagatcagta caagggtgaa aaaggcagtg agggggaacc 1140
aggaataaga ggcatttcct tgaagggaga agaaggaatc atgggctttc ctggactgag 1200
gggttaccct ggcttgagtg gtgaaaaagg atcaccagga cagaagggaa gccgaggcct 1260
ggatggctat caagggcctg atggaccccg gggacccaag ggagaagccg gagacccagg 1320
gcccccctgga ctacctgcct actcccctca cccttcccta gcaaaaggtg ccagaggtga 1380
cccgggattc ccaggggccc aaggggagcc aggaagccag ggtgagccag gagacccggg 1440

```
cctcccaggt cccccctggcc tctccatcgg agatggagat cagaggagag gcctgccggg   1500
tgagatggga cccaagggct tcatcggaga ccccggcatc cctgcgctct acgggggccc   1560
acctggacct gatggaaagc gagggcctcc aggacccccc gggctccctg gaccacctgg   1620
acctgatggc ttcctgtttg ggctgaaagg agcaaaagga agagcaggct tccctgggct   1680
tcccggctcc cctggagccc gcggaccaaa ggggtggaaa ggtgacgctg ggaatgcag    1740
atgtacagaa ggcgacgaag ctatcaaagg tcttccggga ctgccaggac ccaagggctt   1800
cgcaggcatc aacggggagc cggggaggaa aggggacaga ggagaccccg gccaacacgg   1860
cctccctggg ttcccagggc tcaagggagt gcctggcaac attggtgctc ccggacccaa   1920
aggagcaaaa ggagattcca gaacaatcac aaccaaaggt gagcggggac agcccggcgt   1980
cccaggtgtg cccgggatga aaggtgacga tggcagccca ggccgcgatg ggctcgatgg   2040
attccccggc ctcccaggcc ctcccggtga tggcatcaag ggccctccag ggacccagg    2100
ctatccagga atacctggaa cgaagggtac tccaggagaa atgggccccc caggactggg   2160
ccttcccggc ctcaaaggcc aacgtggttt ccctggagac gccggcttac ctggaccacc   2220
aggcttcctg ggccctcctg gccccgcagg gaccccagga caaatagatt gtgacacaga   2280
tgtgaaaagg gccgttggag gtgacagaca ggaggccatc cagccaggtt gcataggagg   2340
gcccaaggga ttgccaggcc tgccaggacc cccaggcccc acaggtgcca aaggcctccg   2400
aggaatccca ggcttcgcag gagctgatgg aggaccaggg cccaggggct tgccaggaga   2460
cgcaggtcgt gaagggttcc caggaccccc agggttcata ggaccccgag gatccaaagg   2520
tgcagtgggc ctccctggcc cagatggatc cccaggtccc atcggcctgc cagggccaga   2580
tgggccccct ggggaaaggg gcctccctgg agaagtcctg ggagctcagc ccgggccacg   2640
gggagatgct ggtgtgcctg gacagcctgg gcttaaaggc cttcccggag acagaggccc   2700
ccctggattc agaggaagcc aagggatgcc tgggatgcca gggctgaagg gccagccagg   2760
cctcccagga ccttccggcc agccaggcct gtatgggcct ccaggactgc atggattccc   2820
aggagctcct ggccaagagg ggcccttggg gctgccagga atcccaggcc gtgaaggtct   2880
gcctggtgat agaggggacc ctggggacac aggcgctcct ggccctgtgg gcatgaaagg   2940
tctctctggt gacagaggag atgctggctt cacaggggag caaggccatc caggaagccc   3000
tggatttaaa ggaattgatg gaatgcctgg gacccccggg ctaaaaggag atagaggctc   3060
acctgggatg gatggtttcc aaggcatgcc tggactcaaa gggagacccg ggtttccagg   3120
gagcaaaggc gaggctggat tttcggaat acccggtctg aagggtctgg ctggtgagcc    3180
aggttttaaa ggcagccgag gggaccctgg gcccccagga ccacctcctg tcatcctgcc   3240
aggaatgaaa gacattaaag gagagaaagg agatgaaggg cctatggggc tgaaaggata   3300
cctgggcgca aaaggtatcc aaggaatgcc aggcatccca gggctgtcag gaatccctgg   3360
gctgcctggg aggcccggcc acatcaaagg agtcaaggga gacatcggag tccccggcat   3420
ccccggtttg ccaggattcc ctggggtggc tggcccccct ggaattacgg gattcccagg   3480
attcatagga agccggggtg acaaaggtgc cccagggaga gcaggcctgt atggcgagat   3540
tggcgcgact ggtgatttcg gtgacatcgg ggacactata aatttaccag gaagaccagg   3600
cctgaagggg gagcggggca ccactggaat accaggtctg aagggattct ttggagagaa   3660
gggaacagaa ggtgacatcg gcttccctgg gataacaggc gtgactggag tccaaggccc   3720
tcctggactt aaaggacaaa caggctttcc agggctgact gggcctccag ggtcgcaggg   3780
```

```
agagctgggg cggattggac tgcctggtgg caaaggagat gatggctggc cgggagctcc   3840
gggcttacca ggttttccgg gactccgtgg gatccgcggc ttacacggct tgccaggcac   3900
caagggcttt ccaggatccc caggttctga catccacgga gacccaggct tcccaggccc   3960
tcctggggaa agaggtgacc caggagaggc caacaccctt ccaggccctg tgggagtccc   4020
aggacagaaa ggagaccaag gagctccagg ggaacgaggc ccacctggga gcccaggact   4080
tcaggggttc ccaggcatca cacccccttc caacatctct ggggcacctg gtgacaaagg   4140
ggcgccaggg atatttggcc tgaaaggtta tcggggccca ccagggccac caggttctgc   4200
tgctcttcct ggaagcaaag gtgacacagg gaacccagga gctccaggaa ccccagggac   4260
caaaggatgg gccggggact ccgggcccca gggcaggcct ggtgtgtttg gtctcccagg   4320
agaaaaaggg cccaggggtg aacaaggctt catggggaac actggaccca ccggggcggt   4380
gggcgacaga ggccccaagg gacccaaggg agacccagga ttccctggtg cccccgggac   4440
tgtgggagcc cccgggattg caggaatccc ccagaagatt gccgtccaac cagggacagt   4500
gggtccccag gggaggcgag gcccccctgg ggcaccgggg gagatggggc cccagggccc   4560
ccccggagaa ccaggttttc gtggggctcc agggaaagct gggccccaag gaagaggtgg   4620
tgtgtctgct gttcccggct tccggggaga tgaaggaccc ataggccacc aggggccgat   4680
tggccaagaa ggtgcaccag gccgtccagg gagcccgggc ctgccgggta tgccaggccg   4740
cagcgtcagc atcggctacc tcctggtgaa gcacagccag acggaccagg agcccatgtg   4800
cccagtgggc atgaacaaac tctggagtgg atacagcctg ctgtacttcg agggccagga   4860
gaaggcgcac aaccaggacc tggggctggc gggctcctgc ctggcgcggt tcagcaccat   4920
gcccttcctg tactgcaacc ctggtgatgt ctgctactat gccagccgga acgacaagtc   4980
ctactggctc tctaccactg cgccgctgcc catgatgccc gtggccgagg acgagatcaa   5040
gccctacatc agccgctgtt ctgtgtgtga ggccccggcc atcgccatcg cggtccacag   5100
tcaggatgtc tccatcccac actgcccagc tgggtggcgg agtttgtgga tcggatattc   5160
cttcctcatg cacacggcgg cgggagacga aggcggtggc caatcactgg tgtcaccggg   5220
cagctgtcta gaggacttcc gcgccacacc attcatcgaa tgcaatggag gccgcggcac   5280
ctgccactac tacgccaaca agtacagctt ctggctgacc accattcccg agcagagctt   5340
ccagggctcg ccctccgccg acacgctcaa ggccggcctc atccgcacac acatcagccg   5400
ctgccaggtg tgcatgaaga acctgtgagc cggcgcgtgc caggaagggc cattttggtg   5460
cttattctta acttattacc tcaggtgcca acccaaaaat tggttttatt tttttcttaa   5520
aaaaaaaaaa gtctaccaaa ggaatttgca tccagcagca gcacttagac ctgccagcca   5580
ctgtcaccga gcgggtgcaa gcactcgggg tccctggagg gcaagccctg cccacagaaa   5640
gccaggagca gccctggccc ccatcagccc tgctagacgc accgcctgaa ggcacagcta   5700
accacttcgc acacacccat gtaaccactg cactttccaa tgccacagac aactcacatt   5760
gttcaactcc cttctcgggg tgggacagac gagacaacag cacacaggca gccagccgtg   5820
gccagaggct cgaggggctc agggcctcag gcacccgtcc ccacacgagg gccccgtggg   5880
tgggcctggc cctgctttct acgccaatgt tatgccagct ccatgttctc ccaaataccg   5940
ttgatgtgaa ttattttaaa ggcaaaaccg tgctctttat tttaaaaaac actgataatc   6000
acactgcggt aggtcattct tttgccacat ccctatagac cactgggttt ggcaaaactc   6060
aggcagaagt ggagaccttt ctagacatca ttgtcagcct tgctacttga aggtacaccc   6120
catagggtcg gaggtgctgt ccccactgcc ccacgttgtc cctgagattt aacccctcca   6180
```

ctgctggggg tgagctgtac tcttctgact gccccctcct gtgtaacgac tacaaaataa 6240
aacttggttc tgaatatttt taaa 6264

<210> SEQ ID NO 76
<211> LENGTH: 3859
<212> TYPE: DNA
<213> ORGANISM: Homo sapiens

<400> SEQUENCE: 76
ttgtgtcgcc atggcggcgg cagcggcgac gagaacggcg agcgaggggt cgagcgcggc 60
cggggcctga ggaggctacg cgaccatggt ggcacgcagc actgacagcc tggatggccc 120
aggggagggc tcggtgcagc ctctacccac tgctgggggg cccagtgtga aggggaagcc 180
tgggaagagg ctctcagctc ctcgaggccc cttcccgcgg ctggctgact gcgcccattt 240
ccactacgag aacgttgact ttggccacat tcagctcctg ctgtctccag accgtgaagg 300
gcccagcctc tctggagaga atgagctggt gttcggggtg caggtgacct gtcagggccg 360
ttcctggccg gttctccgga gttacgatga ctttcgttcc ctggatgccc acctccaccg 420
gtgcatattt gaccggaggt tctcctgcct tccggagctt cccccgcccc ccgagggtgc 480
cagggctgcc cagatgctgg tgccactgct gctgcagtac ctggagacac tgtcaggact 540
ggtggacagt aacctcaact gcgggcctgt gctcacctgg atggagctgg acaatcacgg 600
ccggcgactg ctcctcagtg aggaggcgtc actcaatatc cctgcagtgg cggccgccca 660
tgtgatcaaa cggtatacag cccaggcgcc agatgagctg tcctttgagg tgggagacat 720
tgtctcggtg atcgacatgc cacccacaga ggatcggagc tggtggcggg gcaagcgagg 780
cttccaggtc gggttcttcc ccagtgagtg tgtggaactc ttcacagagc ggccaggtcc 840
gggcctgaag gcggatgccg atggcccccc atgtggcatc ccggctcccc agggtatctc 900
gtctctgacc tcagctgtgc cacggcctcg tgggaagctg gccggcctgc tccgcacctt 960
catgcgctcc cgcccttctc ggcagcggct gcggcagcgg ggaatcctgc gacagagggt 1020
gtttggctgc gatcttggcg agcacctcag caactcaggc caggatgtgc cccaggtgct 1080
gcgctgctgc tccgagttca ttgaggccca cggggtggtg gatgggatct accggctctc 1140
aggcgtgtct tccaacatcc agaggcttcg gcacgagttt gacagtgaga ggatcccgga 1200
gctgtctggc cctgcattcc tgcaggacat ccacagcgtg tcctccctct gcaagctcta 1260
cttccgagag cttccgaacc ctctgctcac ctaccagctc tatgggaagt tcagtgaggc 1320
catgtcagtg cctggggagg aggagcgtct ggtgcgggtg cacgatgtca tccagcagct 1380
gcccccacca cattacagga ccctggagta cctgctgagg cacctggccc gcatggcgag 1440
acacagtgcc aacaccagca tgcatgcccg caacctggcc attgtctggg cacccaacct 1500
gctacggtcc atggagctgg agtcagtggg aatgggtggc gcggcggcgt tccgggaagt 1560
tcgggtgcag tcggtggtgg tggagtttct gctcacccat gtggacgtcc tgttcagcga 1620
caccttcacc tccgccggcc tcgaccctgc aggccgctgc ctgctcccca ggcccaagtc 1680
ccttgcgggc agctgcccct ccacccgcct gctgacgctg gaggaagccc aggcacgcac 1740
ccagggccgg ctggggacgc ccacggagcc cacaactccc aaggccccgg cctcacctgc 1800
ggaaaggagg aaaggggaga gaggggagaa gcagcggaag ccagggggca gcagctggaa 1860
gacgttcttt gcactgggcc ggggccccag tgtccctcga aagaagcccc tgccctggct 1920
ggggggcacc cgtgccccac cgcagccttc aggcagcaga cccgacaccg tcacactgag 1980

-continued

```
atctgccaag agcgaggagt ctctgtcatc gcaggccagc ggggctgaac tgctgggggc   2040

tgggggagca cctgcctcag ccaccccaac accagctctc agccccggcc ggagcctgcg   2100

cccccatctc ataccccctgc tgctgcgagg agccgaggcc ccgctgactg acgcctgcca   2160

gcaggagatg tgcagcaagc tccggggagc ccagggccca ctcggtcctg atatggagtc   2220

accactgcca ccccctcccc tgtctctcct gcgccctggg ggtgccccac ccccgccccc   2280

taagaaccca gcacgcctca tggccctggc cctggctgag cgggctcagc aggtggccga   2340

gcaacagagc cagcaggagt gtgggggcac ccccacctgct tcccaatccc ccttccaccg   2400

ctcgctgtct ctggaggtgg gcggggagcc cctggggacc tcagggagtg ggccacctcc   2460

caactcccta gcacacccgg gtgcctgggt cccgggaccc ccaccctact taccaaggca   2520

acaaagtgat gggagcctgc tgaggagcca gcggcccatg ggacctcaa ggaggggact   2580

ccgaggccct gcccaggtca gtgcccagct cagggcaggt ggcgggggca gggatgcgcc   2640

agaggcagca gcccagtccc catgttctgt cccctcacag gttcctaccc ccggcttctt   2700

ctccccagcc cccagggagt gcctgccacc cttcctcggg gtccccaagc caggcttgta   2760

ccccctgggc cccccatcct tccagcccag ttccccagcc ccagtctgga ggagctctct   2820

gggcccccct gcaccactcg acaggggaga gaacctgtac tatgagatcg gggcaagtga   2880

ggggtccccc tattctggcc ccacccgctc ctggagtccc tttcgctcca tgccccccga   2940

caggctcaat gcctcctacg gcatgcttgg ccaatcaccc ccactccaca ggtcccccga   3000

cttcctgctc agctacccgc cagccccctc ctgctttccc cctgaccacc ttggctactc   3060

agccccccag caccctgctc ggcgccctac accgcctgag cccctctacg tcaacctagc   3120

tctagggccc aggggtccct cacctgcctc ttcctcctcc tcttcccctc ctgcccaccc   3180

ccgaagccgt tcagatcccg gtcccccagt cccccgcctt ccccagaaac aacgggcacc   3240

ctggggaccc cgtacccctc atagggtgcc gggtccctgg ggccctcctg agcctctcct   3300

gctctacagg gcagccccgc cagcctacgg aaggggggc gagctccacc gagggtcctt   3360

gtacagaaat ggagggcaaa gaggggaggg ggctggtccc ccaccccctt accccactcc   3420

cagctggtcc ctccactctg agggccagac ccgaagctac tgctgagcac cagctgggag   3480

gggccgtcct tccttccctt caccctcact ggatcttggc ccaaccaaat cccttgtttt   3540

gtattttctt gaaccccgac cactacccca ggtttctaac tttgtaactt gcttctgatg   3600

tgggtcccta acctataatc tcagcttccc taccctggac tgaagggtct gcccatcccc   3660

ccaccaccct ccatcctggg ggccctcgca caaatctggg gtgggagggg ctaggctgac   3720

cccatcctcc tctccctcca ggagccccca gcatgtcctg acctgtgcac ggggatgggg   3780

ggacaactcc taccccttctt tccccacatg ccccactaaa ccatctgaca acattaatga   3840

ataaaatggt gaaaatgtg                                                 3859
```